(12) United States Patent
Eggenweiler et al.

(10) Patent No.: US 8,791,129 B2
(45) Date of Patent: Jul. 29, 2014

(54) PHENYLQUINAZOLINE DERIVATIVES

(75) Inventors: Hans-Michael Eggenweiler, Darmstadt (DE); Christian Sirrenberg, Darmstadt (DE); Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/819,109

(22) PCT Filed: Aug. 31, 2011

(86) PCT No.: PCT/EP2011/004397
§ 371 (c)(1),
(2), (4) Date: Feb. 26, 2013

(87) PCT Pub. No.: WO2012/041435
PCT Pub. Date: Apr. 5, 2012

(65) Prior Publication Data
US 2013/0178443 A1 Jul. 11, 2013

(30) Foreign Application Priority Data
Sep. 29, 2010 (DE) .......................... 10 2010 046 837

(51) Int. Cl.
*A01N 43/54* (2006.01)
*A61K 31/517* (2006.01)
*C07D 239/72* (2006.01)
*C07D 401/00* (2006.01)

(52) U.S. Cl.
USPC ..................... 514/266.2; 514/266.1; 544/283; 544/284

(58) Field of Classification Search
USPC ..................... 514/266.1, 266.2; 544/283, 284
See application file for complete search history.

(56) References Cited

U.S. PATENT DOCUMENTS

| 2010/0234324 A1 | 9/2010 | Eggenweiler et al. |
| 2011/0245225 A1 | 10/2011 | Eggenweiler et al. |

FOREIGN PATENT DOCUMENTS

| WO | WO-2009 101139 | | 1/2009 | |
| WO | WO 2009001039 | * | 1/2009 | ........... C07D 437/00 |
| WO | WO-2010 066324 | | 6/2010 | |
| WO | WO 2010066324 | * | 6/2010 | ........... C07D 437/00 |

OTHER PUBLICATIONS

International Search Report for PCT/EP2011/004397, Date of actual completion of the international search: Oct. 25, 2011, Date of mailing of the international search report: Nov. 4, 2011.

* cited by examiner

*Primary Examiner* — Paul V. Ward
(74) *Attorney, Agent, or Firm* — Millen, White, Zelano & Branigan, P.C.

(57) ABSTRACT

Novel quinazolinamide derivatives of the formula (I), in which R1-R43 and X have the meanings indicated in Claim 1, are HSP90 inhibitors and can be used for the preparation of a medicament for the treatment of diseases in which the inhibition, regulation and/or modulation of HSP90 plays a role.

2 Claims, No Drawings

PHENYLQUINAZOLINE DERIVATIVES

BACKGROUND OF THE INVENTION

The invention was based on the object of finding novel compounds having valuable properties, in particular those which can be used for the preparation of medicaments.

The present invention relates to compounds in which the inhibition, regulation and/or modulation of HSP90 plays a role, furthermore to pharmaceutical compositions which comprise these compounds, and to the use of the compounds for the treatment of diseases in which HSP90 plays a role.

The correct folding and conformation of proteins in cells is ensured by molecular chaperones and is critical for the regulation of the equilibrium between protein synthesis and degradation. Chaperones are important for the regulation of many central functions of cells, such as, for example, cell proliferation and apoptosis (Jolly and Morimoto, 2000; Smith et al., 1998; Smith, 2001).

Heat Shock Proteins (HSPs)

The cells of a tissue react to external stress, such as, for example, heat, hypoxia, oxidative stress, or toxic substances, such as heavy metals or alcohols, with activation of a number of chaperones which are known under the term "heat shock proteins" (HSPs).

The activation of HSPs protects the cell against damage initiated by such stress factors, accelerates the restoration of the physiological state and results in a stress-tolerant state of the cell.

Besides this originally discovered protective mechanism promoted by HSPs against external stress, further important chaperone functions have also been described in the course of time for individual HSPs under normal stress-free conditions. Thus, various HSPs regulate, for example, correct folding, intracellular localisation and function or regulated degradation of a number of biologically important proteins of cells.

HSPs form a gene family with individual gene products whose cellular expression, function and localisation differs in different cells. The naming and classification within the family is carried out on the basis of their molecular weight, for example HSP27, HSP70, and HSP90.

Some human diseases are based on incorrect protein folding (see review, for example, Tytell et al., 2001; Smith et al., 1998). The development of therapies which engages in the mechanism of the chaperone-dependent protein folding could therefore be useful in such cases. For example, incorrectly folded proteins result in aggregation of protein with neurodegenerative progression in the case of Alzheimer's disease, prion diseases or Huntington's syndrome. Incorrect protein folding may also result in loss of wild-type function, which can have the consequence of incorrectly regulated molecular and physiological function.

HSPs are also ascribed great importance in tumour diseases. There are, for example, indications that the expression of certain HSPs correlates with the stage of progression of tumours (Martin et al., 2000; Conroy et al., 1996; Kawanishi et al., 1999; Jameel et al., 1992; Hoang et al., 2000; Lebeau et al., 1991).

The fact that HSP90 plays a role in a number of central oncogenic signalling pathways in the cell and certain natural products having cancer-inhibiting activity target HSP90 has led to the concept that inhibition of the function of HSP90 would be sensible in the treatment of tumour diseases. An HSP90 inhibitor, 17-allylamino-17-demethoxygeldanamycin (17AAG), a derivative of geldanamycin, is currently undergoing clinical trials.

HSP90

HSP90 represents approximately 1-2% of the total cellular protein mass. It is usually in the form of a dimer in the cell and is associated with a multiplicity of proteins, so-called co-chaperones (see, for example, Pratt, 1997). HSP90 is essential for the vitality of cells (Young et al., 2001) and plays a key role in the response to cellular stress by interaction with many proteins whose native folding has been modified by external stress, such as, for example, heat shock, in order to restore the original folding or to prevent aggregation of the proteins (Smith et al., 1998).

There are also indications that HSP90 is of importance as buffer against the effects of mutations, presumably through correction of incorrect protein folding caused by the mutation (Rutherford and Lindquist, 1998).

In addition, HSP90 also has a regulatory importance. Under physiological conditions, HSP90, together with its homologue in the endoplasmatic reticulum, GRP94, plays a role in the cell balance for ensuring the stability of the conformation and maturing of various client key proteins. These can be divided into three groups: receptors for steroid hormones, Ser/Thr or tyrosine kinases (for example ERBB2, RAF-1, CDK4 and LCK) and a collection of various proteins, such as, for example, mutated p53 or the catalytic subunit of telomerase hTERT. Each of these proteins takes on a key role in the regulation of physiological and biochemical processes of cells. The preserved HSP90 family in humans consists of four genes, cytosolic HSP90α, the inducible HSP90β isoform (Hickey et al., 1989), GRP94 in the endoplasmatic reticulum (Argon et al., 1999) and HSP75/TRAP1 in the mitochondrial matrix (Felts et al., 2000). It is assumed that all members of the family have a similar mode of action, but, depending on their localisation in the cell, bind to different client proteins. For example, ERBB2 is a specific client protein of GRP94 (Argon et al., 1999), while the type 1 receptor of tumour necrosis factor (TNFR1) or the retinoblastoma protein (Rb) have been found to be clients of TRAP1 (Song et al., 1995; Chen et al., 1996).

HSP90 is involved in a number of complex interactions with a large number of client proteins and regulatory proteins (Smith, 2001). Although precise molecular details have not yet been clarified, biochemical experiments and investigations with the aid of X-ray crystallography in recent years have increasingly been able to decipher details of the chaperone function of HSP90 (Prodromou et al., 1997; Stebbins et al., 1997). Accordingly, HSP90 is an ATP-dependent molecular chaperone (Prodromou et al, 1997), with dimerisation being important for ATP hydrolysis. The binding of ATP results in the formation of a toroidal dimer structure, in which the two N-terminal domains come into close contact with one another and act as a switch in the conformation. (Prodromou and Pearl, 2000).

Known HSP90 Inhibitors

The first class of HSP90 inhibitors to be discovered were benzoquinone ansamycins with the compounds herbimycin A and geldanamycin. Originally, the reversion of the malignant phenotype in fibroblasts which had been induced by transformation with the v-Src oncogene was detected with them (Uehara et al., 1985).

Later, a strong antitumoural activity was demonstrated in vitro (Schulte et al., 1998) and in vivo in animal models (Supko et al., 1995).

Immune precipitation and investigations on affinity matrices then showed that the principal mechanism of action of geldanamycin involves binding to HSP90 (Whitesell et al., 1994; Schulte and Neckers, 1998). In addition, X-ray crystallographic studies have shown that geldanamycin competes for the ATP binding site and inhibits the intrinsic ATPase activity of HSP90 (Prodromou et al., 1997; Panaretou et al., 1998). This prevents the formation of the multimeric HSP90 complex, with its property of functioning as chaperone for client proteins. As a consequence, client proteins are degraded via the ubiquitin-proteasome pathway.

The geldanamycin derivative 17-allylamino-17-demethoxygeldanamycin (17AAG) showed an unchanged property in the inhibition of HSP90, the degradation of client proteins and antitumoural activity in cell cultures and in xenograft tumour models (Schulte et al, 1998; Kelland et al, 1999), but had significantly lower liver cytotoxicity than geldanamycin (Page et al. 1997). 17AAG is currently undergoing phase I/II clinical trials.

Radicicol, a macrocyclic antibiotic, likewise exhibited revision of the v-Src and v-Ha-Ras-induced malignant phenotype of fibroblasts (Kwon et all 1992; Zhao et al, 1995). Radicicol degrades a large number of signal proteins as a consequence of HSP90 inhibition (Schulte et al., 1998). X-ray crystallographic studies have shown that radicicol likewise binds to the N-terminal domain of HSP90 and inhibits the intrinsic ATPase activity (Roe et al., 1998).

As is known, antibiotics of the coumarine type bind to the ATP binding site of the HSP90 homologue DNA gyrase in bacteria. The coumarine, novobiocin, binds to the carboxy-terminal end of HSP90, i.e. to a different site in HSP90 than the benzoquinone-ansamycins and radicicol, which bind to the N-terminal end of HSP90. (Marcu et al., 2000b).

The inhibition of HSP90 by novobiocin results in degradation of a large number of HSP90-dependent signal proteins (Marcu et al., 2000a).

The degradation of signal proteins, for example ERBB2, was demonstrated using PU3, an HSP90 inhibitor derived from purines. PU3 causes cell cycle arrest and differentiation in breast cancer cell lines (Chiosis et al., 2001).

HSP90 as Therapeutic Target

Due to the participation of HSP90 in the regulation of a large number of signalling pathways which are of crucial importance in the phenotype of a tumour, and the discovery that certain natural products exert their biological effect through inhibition of the activity of HSP90, HSP90 is currently being tested as a novel target for the development of a tumour therapeutic agent (Neckers et al., 1999).

The principal mechanism of action of geldanamycin, 17AAG, and radicicol includes the inhibition of the binding of ATP to the ATP binding site at the N-terminal end of the protein and the resultant inhibition of the intrinsic ATPase activity of HSP90 (see, for example, Prodromou et al., 1997; Stebbins et al., 1997; Panaretou et al., 1998). Inhibition of the ATPase activity of HSP90 prevents the recruitment of co-chaperones and favours the formation of an HSP90 hetero-complex, which causes client proteins to undergo degradation via the ubiquitin-proteasome pathway (see, for example, Neckers et al., 1999; Kelland et al., 1999). The treatment of tumour cells with HSP90 inhibitors results in selective degradation of important proteins having fundamental importance for processes such as cell proliferation, regulation of the cell cycle and apoptosis. These processes are frequently deregulated in tumours (see, for example, Hostein et al., 2001).

An attractive rationale for the development of an inhibitor of HSP90 is that a strong tumour-therapeutic action can be achieved by simultaneous degradation of a plurality of proteins which are associated with the transformed phenotype.

In detail, the present invention relates to compounds which inhibit, regulate and/or modulate HSP90, to compositions which comprise these compounds, and to methods for the use thereof for the treatment of HSP90-induced diseases, such as tumour diseases, viral diseases, such as, for example, hepatitis B (Waxman, 2002); immunosuppression in transplants (Bijlmakers, 2000 and Yorgin, 2000); inflammation-induced diseases (Bucci, 2000), such as rheumatoid arthritis, asthma, multiple sclerosis, type 1 diabetes, lupus erythematosus, psoriasis and inflammatory bowel disease; cystic fibrosis (Fuller, 2000); diseases associated with angiogenesis (Hur, 2002 and Kurebayashi, 2001), such as, for example, diabetic retinopathy, haemangiomas, endometriosis and tumour angiogenesis; infectious diseases; autoimmune diseases; ischaemia; promotion of nerve regeneration (Rosen et al., WO 02/09696; Degranco et al., WO 99/51223; Gold, U.S. Pat. No. 6,210,974 B1); fibrogenetic diseases, such as, for example, scleroderma, polymyositis, systemic lupus, cirrhosis of the liver, keloid formation, interstitial nephritis and pulmonary fibrosis (Strehlow, WO 02/02123).

The invention also relates to the use of the compounds according to the invention for the protection of normal cells against toxicity caused by chemotherapy, and to the use in diseases where incorrect protein folding or aggregation is a principal causal factor, such as, for example, scrapie, Creutzfeldt-Jakob disease, Huntington's or Alzheimer's (Sittler, Hum. Mol. Genet., 10, 1307, 2001; Tratzelt et al., Proc. Nat. Acad. Sci., 92, 2944, 1995; Winklhofer et al., J. Biol. Chem., 276, 45160, 2001).

WO 01/72779 describes purine compounds and the use thereof for the treatment of GRP94 (homologue or paralogue of HSP90)-induced diseases, such as tumour diseases, where the cancerous tissue includes a sarcoma or carcinoma selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenstrom's macroglobulinaemia and heavy chain disease.

WO 01/72779 furthermore discloses the use of the compounds mentioned therein for the treatment of viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type 1 (HIV-1) and human immunodeficiency virus type II (HIV-II).

WO 01/72779 furthermore describes the use of the compounds mentioned therein for GRP94 modulation, where the modulated biological GRP94 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

Finally, WO 01/72779 describes the use of an effective amount of a GRP94 protein modulator for the preparation of a medicament for changing a subsequent cellular reaction to an ischaemic state in a tissue site in an individual, by treatment of the cells at the tissue site with the GRP94 protein modulator in order that the GRP94 activity in cells is increased to such an extent that a subsequent cellular reaction to an ischaemic state is changed, where the subsequent ischaemic condition is preferably the consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress, or where the tissue site is the donor tissue for a transplant.

A. Kamal et al. in Trends in Molecular Medicine, Vol. 10 No. 6 Jun. 2004, describe therapeutic and diagnostic applications of HSP90 activation, inter alia for the treatment of diseases of the central nervous system and of cardiovascular diseases.

The identification of small compounds which specifically inhibit, regulate and/or modulate HSP90 is therefore desirable and an aim of the present invention.

It has been found that the compounds according to the invention and salts thereof have very valuable pharmacological properties while being well tolerated.

In particular, they exhibit HSP90-inhibiting properties.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammalian species, for example a primate species, particularly humans; rodents, including mice, rats and hamsters; rabbits; horses, cows, dogs, cats, etc. Animal models are of interest for experimental investigations, where they provide a model for the treatment of a human disease.

PRIOR ART

Other quinazoline derivatives are described as HSP90 inhibitors in EP 2 164 833 and in WO 2010/066324.

WO 00/53169 describes HSP90 inhibition using coumarin or a coumarin derivative.

WO 03/041643 A2 discloses HSP90-inhibiting zearalanol derivatives. HSP90-inhibiting indazole derivatives are known from WO 06/010595 and WO 02/083648.

FURTHER LITERATURE

Argon Y and Simen B B. 1999 "Grp94, an ER chaperone with protein and peptide binding properties", Semin. Cell Dev. Biol., Vol. 10, pp. 495-505.

Bijlmakers M-JJE, Marsh M. 2000 "Hsp90 is essential for the synthesis and subsequent membrane association, but not the maintenance, of the Srckinase p56Ick", Mol. Biol. Cell, Vol. 11 (5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", Brit. J. Pharmacol., Vol 131(1), pp. 13-16.

Carreras C W, Schirmer A, Zhong Z, Santi VS. 2003 "Filter binding assay for the geldanamycin-heat shock protein 90 interaction", Analytical Biochem., Vol 317, pp 40-46.

Chen C-F, Chen Y, Dai K D, Chen P-L, Riley DJ and Lee W—H.1996 "A new member of the hsp90 family of molecular chaperones interacts with the retinoblastoma protein during mitosis and after heat shock", Mol. Cell. Biol., Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", Chem. Biol., Vol. 8, pp. 289-299.

Chiosis G, Lucas B, Shtil A, Huezo H, Rosen N 2002 "Development of a purine-scaffold novel class of HSP90 binders that inhibit the proliferation of cancer cells and induce the degradation of her2 tyrosine kinase". Bioorganic Med. Chem., Vol 10, pp 3555-3564.

Conroy S E and Latchman D S. 1996 "Do heat shock proteins have a role in breast cancer?", Brit. J. Cancer, Vol. 74, pp. 717-721.

Felts S J, Owen BAL, Nguyen P, Trepel J, Donner D B and Toft D O. 2000 "The HSP90-related protein TRAP1 is a mitochondrial protein with distinct functional properties", J. Biol. Chem., Vol. 5, pp. 3305-331 2.

Fuller W, Cuthbert A W. 2000 "Post-translational disruption of the delta F508 cystic fibrosis transmembrane conductance regulator (CFTR)-molecular Chaperone complex with geldanamycin stabilises delta F508 CFTR in the rabbit reticulocyte lysate", J. Biol. Chem., Vol. 275(48), pp. 37462-37468.

Hickey E, Brandon S E, Smale G, Lloyd D and Weber L A. 1999 "Sequence and regulation of a gene encoding a human 89-kilodalton heat shock protein", Mol. Cell. Biol., Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor 1 (HSF1) and prostate adenocarcinoma, Am. J. Pathol., Vol. 156, pp. 857-864.

Hostein I, Robertson D, Di Stefano F, Workman P and Clarke P A. 2001 "Inhibition of signal transduction by the HSP90 inhibitor 17-allylamino-1 7-demethoxygeldanamycin results in cytostasis and apoptosis", Cancer Res., Vol. 61, pp. 4003-4009.

Hur E, Kim H-H, Choi S M, Kim J H, Yim S, Kwon H J, Choi Y, Kim D K, Lee M-0, Park H.2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", Mol. Pharmacol., Vol 62(5), pp. 975-982.

Jameel A, Skilton R A, Campbell T A, Chander S K, Coombes R C and Luqmani Y A. 1992 "Clinical Jolly C and Morimoto R I. 2000 "Role of the heat shock response and molecular chaperones in oncogenesis and cell death", J. Natl. Cancer Inst., Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", Cancer, Vol. 85, pp. 1649-1657.

Kelland L R, Abel G, McKeage M J, Jones M, Goddard P M, Valenti M, Murrer B A, and Harrap K R. 1993 "Preclinical antitumour evaluation of bis-acetalo-amino-dichloro-cyclohexylamine platinum (IV): an orally active platinum drug", Cancer Research, Vol. 53, pp. 2581-2586.

Kelland L R, Sharp SY, Rogers P M, Myers TG and Workman P. 1999 "DT-diaphorase expression and tumour cell sensitivity to 17-allylamino, 17-demethoxygeldanamycin, an inhibitor of heat shock protein 90", J. Natl. Cancer Inst., Vol. 91, pp. 1940-1949.

Kurebayashi J, Otsuki T, Kurosumi M, Soga S, Akinaga S, Sonoo, H.2001 "A radicicol derivative, KF58333, inhibits expression of hypoxia-inducible factor-1α and vascular endothelial growth factor, angiogenesis and growth of human breast cancer xenografts", Jap. J. Cancer Res., Vol. 92(12), 1342-1351.

Kwon H J, Yoshida M, Abe K, Horinouchi S and Bepple T. 1992 "Radicicol, an agent inducing the reversal of transformed phentoype of src-transformed fibroblasts, Biosci., Biotechnol., Biochem., Vol. 56, pp. 538-539. Lebeau J, Le Cholony C, Prosperi M T and Goubin G. 1991 "Constitutive overexpression of 89 kDa heat shock protein gene in the HBL100 mammary cell line converted to a tumourigenic phenotype by the EJE24 Harvey-ras oncogene", Oncogene, Vol. 6, pp. 1125-1132.

Marcu M G, Chadli A, Bouhouche I, Catelli M and Neckers L. 2000a "The heat shock protein 90 antagonist novobiocin interacts with a previously unrecognised ATP-binding domain in the carboxyl terminus of the chaperone", J. Biol. Chem., Vol. 275, pp. 37181-37186.

Marcu M G, Schulte TW and Neckers L. 2000b "Novobiocin and related coumarins and depletion of heat shock protein 90-dependent signaling proteins", J. Natl. Cancer Inst., Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", Cancer Res., Vol. 60, pp. 2232-2238.

Neckers L, Schulte T W and Momnaaugh E. 1999 "Geldanamycin as a potential anti-cancer agent: its molecular target and biochemical activity", Invest. New Drugs, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", Proc. Am. Assoc. Cancer Res., Vol. 38, pp. 308.

Panaretou B, Prodromou C, Roe S M, OBrien R, Ladbury J E, Piper P W and Pearl L H. 1998 "ATP binding and hydrolysis are essential to the function of the HSP90 molecular chaperone in vivo", EMBO J., Vol. 17, pp. 4829-4836.

Pratt W B. 1997 "The role of the HSP90-based chaperone system in signal transduction by nuclear receptors and receptors signalling via MAP kinase", Annu. Rev. Pharmacol. Toxicol., Vol. 37, pp. 297-326.

Prodromou C, Roe SM, O'Brien R, Ladbury J E, Piper P W and Pearl L H. 1997 "Identification and structural characterisation of the ATP/ADP-binding site in the HSP90 molecular chaperone", Cell, Vol. 90, pp. 65-75.

Prodromou C, Panaretou B, Chohan S, Siligardi G, O'Brien R, Ladbury J E, Roe S M, Piper P W and Pearl L H. 2000 "The ATPase cycle of HSP90 drives a molecular "clamp" via transient dimerisation of the N-terminal domains", EMBO J., Vol. 19, pp. 4383-4392.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", J. Med. Chem., Vol. 42, pp. 260-266.

Rutherford S L and Lindquist S. 1998 "HSP90 as a capacitor for morphological evolution. Nature, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", Mol. Endocrinology, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", Cell Stress and Chaperones, Vol. 3, pp. 100-108.

Schulte T W and Neckers L M. 1998 "The benzoquinone ansamycin 17-allylamino-17-demethoxygeldanamcyin binds to HSP90 and shares important biologic activities with geldanamycin", Cancer Chemother. Pharmacol., Vol. 42, pp. 273-279.

Smith D F. 2001 "Chaperones in signal transduction", in: Molecular chaperones in the cell (P Lund, ed.; Oxford University Press, Oxford and NY), pp. 165-178.

Smith D F, Whitesell L and Katsanis E. 1998 "Molecular chaperones: Biology and prospects for pharmacological intervention", Pharmacological Reviews, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", J. Biol. Chem., Vol. 270, pp. 3574-3581.

Stebbins C E, Russo A, Schneider C, Rosen N, Hartl FU and Pavletich NP. 1997 "Crystal structure of an HSP90-geldanamcyin complex: targeting of a protein chaperone by an antitumour agent", Cell, Vol. 89, pp. 239-250.

Supko J G, Hickman R L, Greyer M R and Malspeis L. 1995 "Preclinical pharmacologic evaluation of geldanamycin as an antitumour agent", Cancer Chemother. Pharmacol., Vol. 36, pp. 305-315.

Tytell M and Hooper P L. 2001 "Heat shock proteins: new keys to the development of cytoprotective therapies", Emerging Therapeutic Targets, Vol. 5, pp. 267-287.

Uehara U, Hori M, Takeuchi T and Umezawa H.1986 "Phenotypic change from transformed to normal induced by benzoquinoid ansamycins accompanies inactivation of p60src in rat kidney cells infected with Rous sarcoma virus", Mol. Cell. Biol., Vol. 6, pp. 21 98-2206.

Waxman, Lloyd H. Inhibiting hepatitis C virus processing and replication. (Merck & Co., Inc., USA). PCT Int. Appl. (2002), WO 0207761 Whitesell L, Mimnaugh E G, De Costa B, Myers C E and Neckers L M. 1994 "Inhibition of heat shock protein HSP90-pp 60v-src heteroprotein complex form ation by benzoquinone ansamycins: essential role for stress proteins in oncogenic transformation", Proc. Natl. Acad. Sci. USA., Vol. 91, pp. 8324-8328.

Yorgin et al. 2000 "Effects of geldanamycin, a heat-shock protein 90-binding agent, on T cell function and T cell nonreceptor protein tyrosine kinases", J. Immunol., Vol 164(6), pp. 2915-2923.

Young J C, Moarefi I and Hartl F U. 2001 "HSP90: a specialised but essential protein-folding tool", J. Cell. Biol., Vol. 154, pp. 267-273.

Zhao J F, Nakano H and Sharma S. 1995 "Suppression of RAS and MOS transformation by radicicol", Oncogene, Vol. 11, pp. 161-173.

SUMMARY OF THE INVENTION

The invention relates to compounds of the formula I in which
$R^1$ denotes H, Hal or A",
$R^2, R^3$ each, independently of one another, denote H, Hal, OH or OA,
$R^2$ and $R^3$ together also denote $OCH_2O$,
X denotes $OR^4$, $O(CO)R^4$, $O(CO)OR^4$, $O(CO)NR^4R^5$, $ONR^4R^5$, $OP(=O)(OH)_2$, $OP(=O)(OA")_2$, $NR^4OR^5$, $NR^4R^5$, $NR^4(CO)R^5$, $NR^4(CO)NR^5$ or $NR^4(CO)OR^5$,
$R^4, R^5, R^6$ each, independently of one another, denote H, A, Y-Het or Y—Ar,
$R^4$ and $R^5$ or
$R^5$ and $R^6$, together with the heteroatom to which they are bonded, also denote a saturated, unsaturated or aromatic mono- or bicyclic heterocycle which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA', $OC(=O)(CH_2)_nNH_2$ and/or =O (carbonyl oxygen) and which may contain a further 1 to 3 N, O and/or S atoms, and in which, in addition, an N atom may be oxidised,
Ar denotes phenyl, naphthyl, tetrahydronaphthyl or biphenyl, each of which is unsubstituted or mono-, di-, tri-, tetra- or pentasubstituted by A, Hal, $(CH_2)_nOA$, $(CH_2)_nOH$, $(CH_2)_nCN$, SA, SOA, $SO_2A$, $NO_2$, C≡CH, $(CH_2)_nCOOH$, CHO, $(CH_2)_nCOOA$, $CONH_2$, CONHA, CONAA', NHCOA, CH(OH)A, $(CH_2)_nNH_2$, $(CH_2)_nNHA$, $(CH_2)_nNAA'$, $(CH_2)_nNHSO_2A$, $SO_2NH(CH_2)_nNH_2$, $SO_2NH_2$, $SO_2NHA$, $SO_2NAA'$, $CONH(CH_2)_nCOOA$, $CONH(CH_2)_nCOOH$, $NHCO(CH_2)_nCOOA$, $NHCO(CH_2)_n$ COOH, $CONH(CH_2)_nNH_2$, $CONH(CH_2)_nNHA$, CONH $(CH_2)_nNAA'$, $CONH(CH_2)_nCN$ and/or $(CH_2)_nCH(NH_2)$ COOH, Het denotes a mono- or bicyclic saturated, unsaturated or aromatic heterocycle having 1 to 4 N, O and/or S atoms, which may be unsubstituted or mono-, di- or trisubstituted by A, OA, OH, phenyl, SH, $S(O)_mA$, Hal, $NO_2$, CN, COA, COOA, COObenzyl, $CONH_2$, CONHA, CONAA', $SO_2NH_2$, $NH_2$, NHA, NAA', NHCOA, $NHSO_2A$ and/or =O (carbonyl oxygen), A, A' each, independently of one another, denote unbranched or branched alkyl having 1-16C atoms, in which 1-6 non-adjacent $CH_2$ groups may be replaced by O, NH, NMe, NEt, NZ, S, SO, $SO_2$, NHCO, CONH, NHCOO, NA'COO, $NHSO_2$, $SO_2NH$ and/or CH groups may be replaced by N and/or, in addition, 1-7H atoms may be replaced by F, Cl, OH, OZ, $NH_2$, SH and/or SZ, or cyclic alkyl having 3-8C atoms, A" denotes unbranched or branched alkyl having 1-6C atoms, Y denotes unbranched or branched alkylene having 1-10C atoms, in which 1-3 non-adjacent $CH_2$ groups may be replaced by O, NH, NMe, NEt, S, SO, $SO_2$ and/or CH groups may be replaced by N and/or, in addition, 1-5H atoms may be replaced by F, Cl, OH and/or $NH_2$, W, W' denote unbranched or branched alkyl having 1-10C atoms, in which 1-3 non-adjacent $CH_2$ groups may be replaced by O, NH, NMe, NEt, S, SO, $SO_2$ and/or CH groups may be replaced by N and/or, in addition, 1-5H atoms may be replaced by Ar, Het, F, Cl, OH and/or $NH_2$, or cyclic alkyl having 3-8C atoms, Z denotes —COW, —COOW, —CONWW', —SOW or —$SO_2$W, Hal denotes F, Cl, Br or I,
m denotes 0, 1 or 2,
n denotes 0, 1, 2, 3 or 4,
and pharmaceutically usable salts and stereoisomers thereof, including mixtures thereof in all ratios.

The invention relates to the compounds of the formula I and salts thereof and to a process for the preparation of compounds of the formula I and pharmaceutically usable salts, tautomers and stereoisomers thereof, characterised in that
a)
a compound of the formula II in which
$R^1, R^2, R^3$ and X have the meanings indicated in claim 1,
R denotes an amino-protecting group, and
A" has the meaning indicated in claim 1,
is reacted with a compound of the formula III $$Y_3Si—N=C=N—SiY_3 \qquad III$$

in which
Y denotes alkyl having 1-4C atoms,
or
b)
a compound of the formula IV

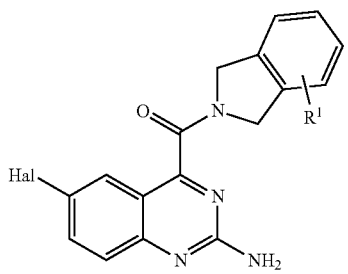

IV in which R¹ has the meaning indicated in claim 1,
and Hal denotes bromine or iodine,
is reacted with a compound of the formula V

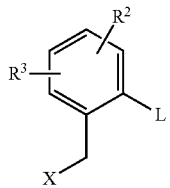

V in which X, R² and R³ have the meanings indicated in claim 1,
and L denotes a boronic acid or boronic acid ester radical,
and/or a base or acid of the formula I is converted into one of its salts.

Compounds of the formula I are also taken to mean the hydrates and solvates of these compounds, furthermore pharmaceutically usable derivatives. The invention also relates to the stereoisomers (E, Z isomers) and the hydrates and solvates of these compounds. Solvate of the compounds are taken to mean adductions of inert solvent molecules onto the compounds which form owing to their mutual attractive force. Solvate are, for example, mono- or dihydrates or alcoholates.

The compounds of the formula I are of course also taken to mean the solvates of the salts.

Pharmaceutically usable derivatives are taken to mean, for example, the salts of the compounds according to the invention and also so-called prodrug compounds.

Prodrug derivatives are taken to mean compounds of the formula I which have been modified with, for example, alkyl or acyl groups, sugars or oligo-peptides and which are rapidly cleaved in the organism to give the effective compounds according to the invention.

These also include biodegradable polymer derivatives of the compounds according to the invention, as described, for example, in Int. J. Pharm. 115, 61-67 (1995).

The expression "effective amount" means the amount of a medicament or pharmaceutical active ingredient that causes a biological or medical response which is sought or desired, for example, by a researcher or physician in a tissue, system, animal or human.

In addition, the expression "therapeutically effective amount" means an amount which, compared with a corresponding subject who has not received this amount, has the following consequence:
improved healing treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, their meanings are independent of one another.

Above and below, the radicals and parameters $R^1$, $R^2$, $R^3$ and X have the meanings indicated the formula I, unless expressly indicated otherwise.

Carbamoyl denotes aminocarbonyl.

BOC or Boc denotes tert-butyloxycarbonyl.

A or A' preferably denotes alkyl, is unbranched (linear) or branched, and has 1, 2, 3, 4, 5, 6, 7, 8, 9, 10, 11, 12, 13, 14, 15 or 16C atoms. A or A' particularly preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

A or A' very particularly preferably denotes alkyl having 1, 2, 3, 4, 5 or 6C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A, A' also each denote, independently of one another, unbranched or branched alkyl having 1-16C atoms, in which 1-6 non-adjacent $CH_2$ groups may be replaced by O, NH, NMe, NEt, NHCO, CONH, NHCOO, NA'COO and/or CH groups may be replaced by N and/or, in addition, 1-7H atoms may be replaced by F, Cl, OH and/or $NH_2$, such as, for example, 2-methoxyethyl or 3-methylaminopropyl.

A or A' also denotes cyclic alkyl (cycloalkyl). Cycloalkyl or cyclic alkyl preferably denotes cyclopropyl, cyclobutyl, cylopentyl, cyclohexyl or cycloheptyl.

A" preferably denotes alkyl having 1, 2, 3, 4, 5 or 6C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

$R^4$, $R^5$, $R^6$ preferably denote, in each case independently of one another, H or A.

$R^4$ and $R^5$ or $R^5$ and $R^6$, together with the heteroatom to which they are bonded, also denote a saturated, unsaturated or aromatic mono- or bicyclic heterocycle which is unsubstituted or mono-, di- or trisubstituted by Hal, A, $(CH_2)_n OH$, $(CH_2)_n OA$, $(CH_2)_n NH_2$, $(CH_2)_n COOH$, $(CH_2)_n COOA$, NHCOA, NA'COA, $CONH_2$, CONHA, CONAA', $OC(=O)(CH_2)_n NH_2$ and/or =O (carbonyl oxygen) and which may contain a further 1 to 3 N, O and/or S atoms, and in which, in addition, an N atom may be oxidised.

The heterocycle is preferably selected from the group piperidine, pyrrolidine, piperazine, 1,2-oxazinane, 1,2,5-oxadiazinane, 1,3-oxazinane, hexahydropyrimidinyl, morpholinyl, imidazolidine, oxazolidine, dihydroindole, isoindoline, tetrahydroquinoline, tetrahydroisoquinoline, tetrahydroquinoxaline.

X preferably denotes $OR^4$, $O(CO)R^4$, $O(CO)OR^4$, $O(CO)NR^4R^5$, $ONR^4R^5$, $OP(=O)(OH)_2$, $OP(=O)(OA'')_2$, $NR^4OR^5$, $NR^4R^5$, $NR^4(CO)R^5$, $NR^4(CO)NR^5$, $NR^4(CO)OR^5$, 1-A-piperazin-4-yl-COO, piperidin-1-yl, pyrrolidin-1-yl, piperazin-1-yl, 1,2-oxazinan-2-yl, 1,2,5-oxa-diazinan-2-yl, 1,3-oxazinan-3-yl, hexahydropyrimidinyl or morpholinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA' and/or =O.

Y preferably denotes methylene, ethylene or propylene.

W, W' preferably denote, in each case independently of one another, alkyl having 1, 2, 3, 4, 5 or 6C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Z preferably denotes acetyl, propionyl, methoxycarbonyl, ethoxycarbonyl, dimethylaminocarbonyl, diethylaminocarbonyl, $SOCH_3$ or $SO_2CH_3$.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes phenyl which is unsubstituted or mono-, di-, tri-, tetra- or pentasubstituted by A, Hal and/or OA.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-,-3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, isoindolinyl, 3,4-(difluoromethylenedioxy)-phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes pyridyl, pyrimidinyl, furyl, thienyl, pyrrolyl, imidazolyl, pyrazolyl, triazolyl, oxazolyl, isoxazolyl, thiazolyl, benzothiazolyl, benzo-1,4-dioxanyl, quinolyl, isoquinolyl, quinazolinyl, benzimidazolyl, indazolyl, indolyl, 1,3-dihydroisoindolyl, benzofuranyl, dihydrobenzofuranyl, benzo-1,3-dioxolyl, piperazinyl, pyrazinyl, pyridazinyl, morpholinyl, azepanyl, azetidinyl, pyrrolidinyl or piperidinyl, each of which is unsubstituted or mono-, di- or trisubstituted by A, OA, OH, Hal, CN and/or =O (carbonyl oxygen).

n preferably denotes 0, 1 or 2.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to If, which conform to the formula I and in which the radicals not designated in greater detail have the meaning indicated for the formula I, but in which in Ia $R^2$, $R^3$ each, independently of one another, denote H, Hal or OA'';

in Ib $R^4$, $R^5$, $R^6$ each, independently of one another, denote H or A;

in Ic $R^3$ and $R^4$, together with the C atom to which they are bonded, also denote an unsubstituted saturated monocyclic C3-C6-carbocycle, which may contain a further 1 to 3 N, O and/or S atoms;

in Id X denotes OR⁴, O(CO)R⁴, O(CO)OR⁴, O(CO)NR⁴R⁵, ONR⁴R⁵, OP(=O)(OH)₂, OP(=O)(OA")₂, NR⁴OR⁵, NR⁴R⁵, NR⁴(CO)R⁵, NR⁴(CO)NR⁵, NR⁴(CO)OR⁵, 1-A-piperazin-4-yl-COO, piperidin-1-yl, pyrrolidin-1-yl, piperazin-1-yl, 1,2-oxazinan-2-yl, 1,2,5-oxadiazinan-2-yl, 1,3-oxazinan-3-yl, hexahydropyrimidinyl or morpholinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, CONH₂, CONHA, CONAA' and/or =O;

in Ie A, A' each, independently of one another, denote unbranched or branched alkyl having 1-16C atoms, in which 1-6 non-adjacent CH₂ groups may be replaced by O, NH, NMe, NEt, NHCO, CONH, NHCOO, NA'COO, and/or CH groups may be replaced by N and/or, in addition, 1-7H atoms may be replaced by F, Cl, OH and/or NH₂, or cyclic alkyl having 3-8C atoms;

in If R¹ denotes H, Hal or A",

R², R³ each, independently of one another, denote H, Hal or OA",

X denotes OR⁴, O(CO)R⁴, O(CO)OR⁴, O(CO)NR⁴R⁵, ONR⁴R⁵, OP(=O)(OH)₂, OP(=O)(OA")₂, NR⁴OR⁵, NR⁴R⁵, NR⁴(CO)R⁵, NR⁴(CO)NR⁵, NR⁴(CO)OR⁵, 1-A-piperazin-4-yl-COO, piperidin-1-yl, pyrrolidin-1-yl, piperazin-1-yl, 1,2-oxazinan-2-yl, 1,2,5-oxadiazinan-2-yl, 1,3-oxazinan-3-yl, hexahydropyrimidinyl or morpholinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, CONH₂, CONHA, CONAA' and/or =O, R⁴, R⁵ each, independently of one another, denote H or A, A, A' each, independently of one another, denote unbranched or branched alkyl having 1-16C atoms, in which 1-6 non-adjacent CH₂ groups may be replaced by O, NH, NMe, NEt, NHCO, CONH, NHCOO, NA'COO and/or CH groups may be replaced by N and/or, in addition, 1-7H atoms may be replaced by F, Cl, OH and/or NH₂, or cyclic alkyl having 3-8C atoms, A" denotes unbranched or branched alkyl having 1-6C atoms, Hal denotes F, Cl, Br or I, n denotes 0, 1, 2, 3 or 4;

and pharmaceutically usable salts, tautomers and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

Compounds of the formula I can preferably be obtained by reacting a compound of the formula II with a compound of the formula III.

In the compounds of the formula II, R denotes an aminoprotecting group, preferably tert-butyloxycarbonyl (BOC).

In the 1,3-bis(trialkylsilyl)carbodiimides of the formula III, alkyl preferably denotes C1, C2, C3 or C4 alkyl, such as, for example, N,N'-bis(trimethylsilyl)carbodiimide.

Suitable solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The reaction is carried out in a suitable solvent, preferably THF or acetonitrile, and at temperatures between 10 and 50° C.

Depending on the conditions used, the reaction time is between a few minutes and 14 days, the reaction temperature is between about 0° and 150°, normally between 15° and 120°, particularly preferably between 20° and 60° C.

The term "aminoprotecting group" is known in general terms and relates to groups which are suitable for protecting (blocking) an amino group against chemical reactions, but which are easily removable after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are, in addition, not crucial; however, preference is given to those having 1-20, in particular 1-8, C atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or toluoyl; aryloxyalkanoyl, such as POA; alkoxycarbonyl, such as methoxycarbonyl, ethoxycarbonyl, 2,2,2-trichloroethoxycarbonyl, BOC (tert-butyloxycarbonyl), 2-iodoethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

The compounds of the formula I are liberated from their functional derivatives using—depending on the protecting group used—for example, strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid in the form of a mixture of acetic acid and 70% perchloric acid in the ratio 9:1. The reaction temperatures for the cleavage are advantageously between about 0 and about 50°, work preferably being carried out between 15 and 30° (room temperature).

The BOGC, OBut and Mtr groups can, for example, preferably be cleaved off using TFA in dichloromethane or using approximately 3 to 5N HCl in dioxane at 15-30°, the FMOC group using an approximately 5 to 50% solution of dimethylamine, diethylamine or piperidine in DMF at 15-30°.

Hydrogenolytically removable protecting groups (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Compounds of the formula I can furthermore preferably be obtained by reacting a compound of the formula IV with a compound of the formula V.

The reaction is carried out under conditions as are known to the person skilled in the art for a Suzuki reaction.

The starting compounds of the formulae IV and V are generally known. If they are novel, however, they can be prepared by methods known per se.

In the compounds of the formula V, L preferably denotes

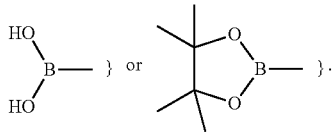

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane and/or water.

It is furthermore possible to convert a compound of the formula I into another compound of the formula I by, for example, reducing nitro groups to amino groups, for example by hydrogenation on Raney nickel or Pd/carbon in an inert solvent, such as methanol or ethanol, and/or converting an ester group into a carboxyl group or esterifying carboxyl groups by reaction with alcohols and/or converting carboxyl groups or acid chlorides into an acid amide by reaction with an amine.

Ester can be saponified, for example, using acetic acid or using NaOH or KOH in water, water/THF or water/dioxane at temperatures between 0 and 100°.

Furthermore, free amino and/or hydroxyl groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

Ether cleavages are carried out by methods which are known to the person skilled in the art.

The reaction is carried out in a suitable solvent, as indicated above, preferably by addition of boron tribromide.

The reaction is particularly preferably carried out in dichloromethane at a reaction temperature between about −30° and 500, normally between −20° and 20°, in particular between about −15° and about 0°.

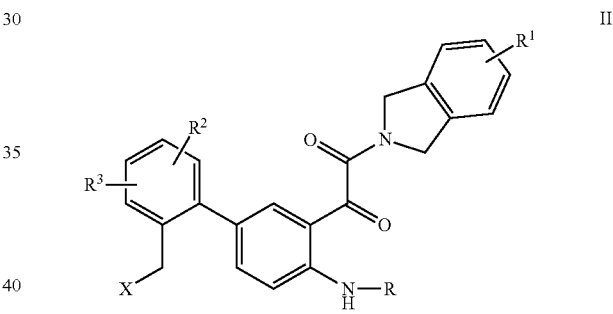

The invention also relates to the compounds of the formula II
in which
$R^1$ denotes H, Hal or A",
$R^2$, $R^3$ each, independently of one another, denote H, Hal or OA",
X denotes $OR^4$, $O(CO)R^4$, $O(CO)OR^4$, $O(CO)NR^4R^5$, $ONR^4R^5$, $NR^4OR^5$, $NR^4R^5$, $NR^4(CO)R^5$, $NR^4(CO)NR^5$, $NR^4(CO)OR^5$, 1-A-piperazin-4-yl-COO,
piperidin-1-yl, pyrrolidin-1-yl, piperazin-1-yl, 1,2-oxazinan-2-yl, 1,2,5-oxadiazinan-2-yl, 1,3-oxazinan-3-yl, hexahydropyrimidinyl or morpholinyl, each of which is unsubstituted or mono-, di- or trisubstituted by Hal, A, $(CH_2)_nOH$, $(CH_2)_nOA$, $(CH_2)_nNH_2$, $(CH_2)_nCOOH$, $(CH_2)_nCOOA$, NHCOA, NA'COA, $CONH_2$, CONHA, CONAA' and/or =O,
R denotes an amino-protecting group,
$R^4$, $R^5$ each, independently of one another, denote H or A,
A, A' each, independently of one another, denote unbranched or branched alkyl having 1-16C atoms, in which 1-6 non-adjacent $CH_2$ groups may be replaced by O, NH, NMe, NEt, NHCO, CONH, NHCOO, NA'COO and/or CH groups may be replaced by N and/or, in addition, 1-7H atoms may be replaced by F, Cl, OH and/or $NH_2$,
or cyclic alkyl having 3-8C atoms, A″ denotes unbranched or branched alkyl having 1-6C atoms,
Hal denotes F, Cl, Br or I,
n denotes 0, 1, 2, 3 or 4,
and salts thereof.

The meanings and the preferred meanings of the radicals indicated are those as indicated above for the compounds of the formula I.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.1 mg to 3 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition requiring treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

Further medicament active ingredients are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

Particular preference is given in the said classes to, for example, caminomycin, daunorubicin, aminopterin, methotrexate, methopterin, dichloromethotrexate, mitomycin C, porfiromycin, 5-fluorouracil, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

The invention also relates to a set (kit) consisting of separate packs of (a) an effective amount of a compound according to the invention and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of diseases in which HSP90 plays a role.

The invention thus relates to the use of the compounds according to the invention, and pharmaceutically usable derivatives, solvates and stereoisomers thereof, including mixtures thereof in all ratios, for the preparation of a medicament for the treatment of diseases in which the inhibition, regulation and/or modulation of HSP90 plays a role.

The present invention encompasses the use of the compounds according to the invention and/or physiologically acceptable salts and solvates thereof for the preparation of a medicament for the treatment of tumour diseases, such as, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumour, leiosarcoma, rhabdomyosarcoma, colon carcinoma, pancreatic cancer, breast cancer, ovarian cancer, prostate cancer, squamous cell carcinoma, basal cell carcinoma, adenocarcinoma, syringocarcinoma, sebaceous gland carcinoma, papillary carcinoma, papillary adenocarcinomas, cystadenocarcinomas, bone marrow carcinoma, bronchogenic carcinoma, renal cell carcinoma, hepatoma, bile duct carcinoma, choriocarcinoma, seminoma, embryonic carcinoma, Wilm's tumour, cervical cancer, testicular tumour, lung carcinoma, small-cell lung carcinoma, bladder carcinoma, epithelial carcinoma, glioma, astrocytoma, medulloblastoma, craniopharyngioma, ependymoma, pinealoma, haemangioblastoma, acoustic neuroma, oligodendroglioma, meningioma, melanoma, neuroblastoma, retinoblastoma, leukaemia, lymphoma, multiple myeloma, Waldenström's macroglobulinaemia and heavy chain disease; viral diseases, where the viral pathogen is selected from the group consisting of hepatitis type A, hepatitis type B, hepatitis type C, influenza, varicella, adenovirus, herpes simplex type I (HSV-I), herpes simplex type II (HSV-II), cattle plague, rhinovirus, echovirus, rotavirus, respiratory syncytial virus (RSV), papillomavirus, papovavirus, cytomegalovirus, echinovirus, arbovirus, huntavirus, Coxsackie virus, mumps virus, measles virus, rubella virus, polio virus, human immunodeficiency virus type I (HIV-1) and human immunodeficiency virus type II (HIV-II); for immunosuppression in transplants; inflammation-induced diseases, such as rheumatoid arthritis, asthma, sepsis, multiple sclerosis, type 1 diabetes, lupus erythematosus, psoriasis and inflammatory bowel disease; cystic fibrosis; diseases associated with angiogenesis, such as, for example, diabetic retinopathy, haemangiomas, endometriosis, tumour angiogenesis; infectious diseases; autoimmune diseases; ischaemia; promotion of nerve regeneration; fibrogenetic diseases, such as, for example, scleroderma, polymyositis, systemic lupus, cirrhosis of the liver, keloid formation, interstitial nephritis and pulmonary fibrosis;

The compounds according to the invention can inhibit, in particular, the growth of cancer, tumour cells and tumour metastases and are therefore suitable for tumour therapy.

The present invention furthermore encompasses the use of the compounds according to the invention and/or physiologically acceptable salts and solvates thereof for the preparation of a medicament for the protection of normal cells against toxicity caused by chemotherapy, and for the treatment of diseases in which incorrect protein folding or aggregation is a principal causal factor, such as, for example, scrapie, Creutzfeldt-Jakob disease, Huntington's or Alzheimer's.

The invention also relates to the use of the compounds according to the invention and/or physiologically acceptable salts and solvates thereof for the preparation of a medicament for the treatment of diseases of the central nervous system, of cardiovascular diseases and cachexia.

In a further embodiment, the invention also relates to the use of the compounds according to the invention and/or physiologically acceptable salts and solvates thereof for the preparation of a medicament for HSP90 modulation, where the modulated biological HSP90 activity causes an immune reaction in an individual, protein transport from the endoplasmatic reticulum, recovery from hypoxic/anoxic stress, recovery from malnutrition, recovery from heat stress, or combinations thereof, and/or where the disorder is a type of cancer, an infectious disease, a disorder associated with disrupted protein transport from the endoplasmatic reticulum, a disorder associated with ischaemia/reperfusion, or combinations thereof, where the disorder associated with ischaemia/reperfusion is a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

In a further embodiment, the invention also relates to the use of the compounds according to the invention and/or physiologically acceptable salts and solvates thereof for the preparation of a medicament for the treatment of ischaemia as a consequence of cardiac arrest, asystolia and delayed ventricular arrhythmia, heart operation, cardiopulmonary bypass operation, organ transplant, spinal cord trauma, head trauma, stroke, thromboembolic stroke, haemorrhagic stroke, cerebral vasospasm, hypotonia, hypoglycaemia, status epilepticus, an epileptic fit, anxiety, schizophrenia, a neurodegenerative disorder, Alzheimer's disease, Huntington's disease, amyotrophic lateral sclerosis (ALS) or neonatal stress.

The invention relates to the compounds of the formula I and pharmaceutically usable salts, tautomers and stereoisomers thereof, including mixtures thereof in all ratios, for use for the treatment or prevention of tumour diseases, viral diseases, for immunosuppression in transplants, inflammation-induced diseases, cystic fibrosis, diseases associated with angiogenesis, infectious diseases, autoimmune diseases, ischaemia, fibrogenetic diseases,
for the promotion of nerve regeneration,
for inhibiting the growth of cancer, tumour cells and tumour metastases,
for the protection of normal cells against toxicity caused by chemotherapy,
for the treatment of diseases in which incorrect protein folding or aggregation is a principal causal factor.

The invention furthermore relates to the compounds of the formula I and pharmaceutically usable salts, tautomers and stereoisomers thereof, including mixtures thereof in all ratios, for use for the treatment or prevention of tumours, viral infections, malaria, transplant-rejection reactions, inflammatory diseases, multiple sclerosis, Alzheimer's, rheumatoid arthritis, asthma, COPD, type 1 diabetes, lupus, psoriasis, cystic fibrosis, diabetic retinopathy, haemangioma, endometritis, angiogenesis-induced diseases, and for the treatment of cardiovascular diseases or cachexia.

Test Method for the Measurement of HSP90 Inhibitors

The binding of geldanamycin or 17-allylamino-17-demethoxygeldanamycin (17AAG) to HSP90 and competitive inhibition thereof can be utilised in order to determine the inhibitory activity of the compounds according to the invention (Carreras et al. 2003, Chiosis et al. 2002).

In the specific case, a radioligand filter binding test is used. The radioligand used here is tritium-labelled 17-allylaminogeldanamycin, [3H]17AAG. This filter binding test allows a targeted search for inhibitors which interfere with the ATP binding site.

Material

Recombinant human HSP90α (E. coli expressed, 95% purity);
[3H]17AAG (17-allylaminogeldanamycin, [allylamino-2,3-$^3$H. Specific activity: $1.11 \times 10^{12}$ Bq/mmol (Moravek, MT-1717);
HEPES filter buffer (50 mM HEPES, pH 7.0, 5 mM MgCl2, BSA 0.01%)
Multiscreen FB (1 µm) filter plate (Millipore, MAFBNOB 50).

Method

The 96-well microtitre filter plates are firstly irrigated and coated with 0.1% of polyethyleneimine.
The test is carried out under the following conditions:
Reaction temperature 22° C.
Reaction time: 30 min., shaking at 800 rpm
Test volume: 50 µl
Final concentrations:
50 mM HEPES HCl, pH 7.0, 5 mM MgCl2, 0.01% (w/v) of BSA
HSP90: 1.5 µg/assay
[3H]17AAG: 0.08 µM.

At the end of the reaction, the supernatant in the filter plate is removed by suction with the aid of a vacuum manifold (Multiscreen Separation System, Millipore), and the filter is washed twice.

The filter plates are then measured in a beta counter (Microbeta, Wallac) with scintillator (Microscint 20, Packard).

"% of control" is determined from the "counts per minutes" values, and the IC-50 value of a compound is calculated therefrom.

TABLE I

HSP90 inhibition by compounds of the formula I according to the invention

| Compound No. | IC$_{50}$ |
|---|---|
| [2-Amino-6-(2-{[(2-hydroxyethyl)methylamino]methyl}phenyl)-quinazolin-4-yl]-(1,3-dihydroisoindol-2-yl)methanone | A |

TABLE I-continued

HSP90 inhibition by compounds of the formula I according to the invention

| Compound No. | IC$_{50}$ |
|---|---|
| [2-Amino-6-(2-{[ethyl-(2-hydroxyethyl)amino]methyl}phenyl)-quinazolin-4-yl]-(1,3-dihydroisoindol-2-yl)methanone | A |
| {2-Amino-6-[2-(4-hydroxypiperidin-1-ylmethyl)phenyl]quinazolin-4-yl}-(1,3-dihydroisoindol-2-yl)methanone | A |
| {2-Amino-6-[2-(tert-butylaminomethyl)phenyl]quinazolin-4-yl}-(1,3-dihydroisoindol-2-yl)methanone | A |
| [2-Amino-6-(2-pyrrolidin-1-ylmethylphenyl)quinazolin-4-yl]-(1,3-dihydroisoindol-2-yl)methanone | A |

TABLE I-continued

HSP90 inhibition by compounds of the formula I according to the invention

| Compound No. | IC$_{50}$ |
|---|---|
| {2-Amino-6-[2-(2-methylpyrrolidin-1-ylmethyl)phenyl]quinazolin-4-yl}-(1,3-dihydroisoindol-2-yl)methanone | A |
| {2-Amino-6-[2-(3-hydroxymethylpyrrolidin-1-ylmethyl)phenyl]-quinazolin-4-yl}-(1,3-dihydroisoindol-2-yl)methanone | A |
| {2-Amino-6-[2-(3-hydroxypyrrolidin-1-ylmethyl)phenyl]quinazolin-4-yl}-(1,3-dihydroisoindol-2-yl)methanone | A |
| {2-Amino-6-[2-(3-aminopyrrolidin-1-ylmethyl)phenyl]quinazolin-4-yl}-(1,3-dihydroisoindol-2-yl)methanone | A |

TABLE I-continued

HSP90 inhibition by compounds of the formula I according to the invention

| Compound No. | IC$_{50}$ |
|---|---|
| (2-Amino-6-{2-[(ethylmethylamino)methyl]phenyl}quinazolin-4-yl)-(1,3-dihydroisoindol-2-yl)methanone | A |
| [2-Amino-6-(2-diethylaminomethylphenyl)quinazolin-4-yl]-(1,3-dihydroisoindol-2-yl)methanone | A |
| N-Methyl-1-{2-[2-amino-4-(1,3-dihydroisoindole-2-carbonyl)-quinazolin-6-yl]benzyl}pyrrolidine-2-carboxamide | A |
| N-(2-Hydroxyethyl)-1-{2-[2-amino-4-(1,3-dihydroisoindole-2-carbonyl)-quinazolin-6-yl]benzyl}pyrrolidine-2-carboxamide | A |

TABLE I-continued

HSP90 inhibition by compounds of the formula I according to the invention

| Compound No. | $IC_{50}$ |
|---|---|
| [2-Amino-6-(2-cyclopropylaminomethylphenyl)quinazolin-4-yl]-(1,3-dihydroisoindol-2-yl)methanone | A |
| [2-Amino-6-(2-cyclopropylaminomethylphenyl)quinazolin-4-yl]-(1,3-dihydroisoindol-2-yl)methanone | A |
| {2-Amino-6-[2-(3,3-difluoropyrrolidin-1-ylmethyl)phenyl]quinazolin-4-yl}-(1,3-dihydroisoindol-2-yl)methanone | A |
| {2-Amino-6-[2-(2,5-dimethylpyrrolidin-1-ylmethyl)phenyl]quinazolin-4-yl}-(1,3-dihydroisoindol-2-yl)methanone | A |

TABLE I-continued

HSP90 inhibition by compounds of the formula I according to the invention

| Compound No. | IC$_{50}$ |
| --- | --- |
| {2-Amino-6-[2-((S)-3-fluoropyrrolidin-1-ylmethyl)phenyl]quinazolin-4-yl}-(1,3-dihydroisoindol-2-yl)methanone | A |
| {2-Amino-6-[2-((R)-2-methylpyrrolidin-1-ylmethyl)phenyl]quinazolin-4-yl}-(1,3-dihydroisoindol-2-yl)methanone | A |
| {2-Amino-6-[2-(tert-butylaminomethyl)-4-flourophenyl]quinazolin-4-yl}-(1,3-dihydroisoindol-2-yl)methanone | A |
| {2-Amino-6-[4-fluoro-2-(2-methylpyrrolidin-1-ylmethyl)phenyl]-quinazolin-4-yl}-(1,3-dihydroisoindol-2-yl)methanone | A |

TABLE I-continued

HSP90 inhibition by compounds of the formula I according to the invention

| Compound No. | IC$_{50}$ |
|---|---|
| {2-Amino-6-[5-fluoro-2-(2-methylpyrrolidin-1-ylmethyl)phenyl]-quinazolin-4-yl}-(1,3-dihydroisoindol-2-yl)methanone | A |
| {2-Amino-6-[2-(tert-butylaminomethyl)-5-fluorophenyl]quinazolin-4-yl}-(1,3-dihydroisoindol-2-yl)methanone | A |
| 2-{2-[2-Amino-4-(1,3-dihydroisoindole-2-carbonyl)quinazolin-6-yl]-benzylamino}acetamide | A |
| [2-Amino-6-(2-{[bis-(2-hydroxyethyl)amino]methyl}phenyl)quinazolin-4-yl]-(1,3-dihydroisoindol-2-yl)methanone | A |

TABLE I-continued

HSP90 inhibition by compounds of the formula I according to the invention

| Compound No. | IC$_{50}$ |
|---|---|
| {2-Amino-6-[2-((S)-2-methylpyrrolidin-1-ylmethyl)phenyl]quinazolin-4-yl}-(1,3-dihydroisoindol-2-yl)methanone | A |
| (2-Amino-6-{2-[(cyclopropylmethylamino)methyl]phenyl}quinazolin-4-yl)-(1,3-dihydroisoindol-2-yl)methanone | A |
| {2-Amino-6-{2-[(ethylmethylamino)methyl]-5-fluorophenyl}quinazolin-4-yl)-(1,3-dihydroisoindol-2-yl)methanone | A |
| {2-Amino-6-[5-fluoro-2-(4-methylpiperazin-1-ylmethyl)phenyl]quinazolin-4-yl}-(1,3-dihydroisoindol-2-yl)methanone | A |

TABLE I-continued

HSP90 inhibition by compounds of the formula I according to the invention

| Compound No. | IC$_{50}$ |
|---|---|
| {2-Amino-6-[4-fluoro-2-(4-methylpiperazin-1-ylmethyl)phenyl]-quinazolin-4-yl}-(1,3-dihydroisoindol-2-yl)methanone | A |
| [2-Amino-6-(2-{[ethyl-(2-hydroxyethyl)amino]methyl}-5-fluorophenyl)-quinazolin-4-yl]-(1,3-dihydroisoindol-2-yl)methanone | A |
| {2-Amino-6-[2-(tert-butylaminomethyl)-4,5-difluorophenyl]quinazolin-4-yl}-(1,3-dihydroisoindol-2-yl)methanone | A |

TABLE I-continued

HSP90 inhibition by compounds of the formula I according to the invention

| Compound No. | IC$_{50}$ |
| --- | --- |
| (2-Amino-6-{2-[(ethylmethylamino)methyl]-4,5-difluorophenyl}-quinazolin-4-yl)-(1,3-dihydroisoindol-2-yl)methanone | A |
| [2-Amino-6-(2-diethylaminomethyl-4,5-difluorophenyl)quinazolin-4-yl]-(1,3-dihydroisoindol-2-yl)methanone | A |
| [2-Amino-6-(4,5-difluoro-2-pyrrolidin-1-ylmethylphenyl)quinazolin-4-yl]-(1,3-dihydroisoindol-2-yl)methanone | A |

TABLE I-continued

HSP90 inhibition by compounds of the formula I according to the invention

| Compound No. | IC$_{50}$ |
|---|---|
| {2-Amino-6-[2-(2,5-dimethylpyrrolidin-1-ylmethyl)-4,5-difluorophenyl]-quinazolin-4-yl}-(1,3-dihydroisoindol-2-yl)methanone 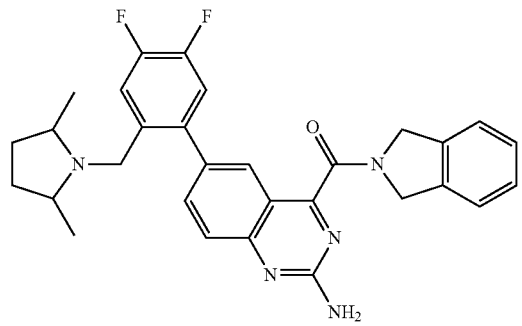 | A |
| {2-Amino-6-[4,5-difluoro-2-(2-methylpyrrolidin-1-ylmethyl)phenyl]-quinazolin-4-yl}-(1,3-dihydroisoindol-2-yl)methanone 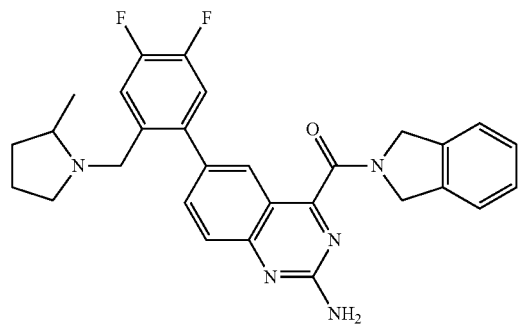 | A |
| (2-Amino-6-{2-[(tert-butylmethylamino)methyl]-4,5-difluorophenyl}-quinazolin-4-yl)-(1,3-dihydroisoindol-2-yl)methanone 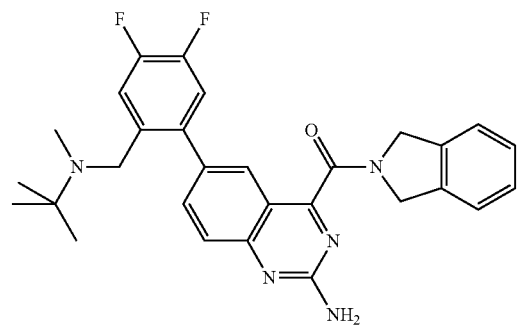 | A |

TABLE I-continued

HSP90 inhibition by compounds of the formula I according to the invention

| Compound No. | IC$_{50}$ |
|---|---|
| {2-Amino-6-[4,5-difluoro-2-(4-methylpiperazin-1-ylmethyl)phenyl]-quinazolin-4-yl}-(1,3-dihydroisoindol-2-yl)methanone | A |
| [2-Amino-6-(2-diethylaminomethyl-5-fluorophenyl)quinazolin-4-yl]-(1,3-dihydroisoindol-2-yl)methanone | A |
| {2-Amino-6-[5-fluoro-2-(4-hydroxypiperidin-1-ylmethyl)phenyl]-quinazolin-4-yl}-(1,3-dihydroisoindol-2-yl)methanone | A |
| {2-Amino-6-[6-(tert-butylaminomethyl)benzo-1,3-dioxol-5-yl]-quinazolin-4-yl}-(1,3-dihydroisoindol-2-yl)methanone | A |

TABLE I-continued

HSP90 inhibition by compounds of the formula I according to the invention

| Compound No. | IC$_{50}$ |
|---|---|
| [2-Amino-6-(2-hydroxymethyl-4,5-dimethoxyphenyl)quinazolin-4-yl]-(1,3-dihydroisoindol-2-yl)methanone | B |
| [2-Amino-6-(2-aminomethyl-4,5-difluorophenyl)quinazolin-4-yl]-(1,3-dihydroisoindol-2-yl)methanone | A |
| 3-Amino-N-{2-[2-amino-4-(1,3-dihydroisoindole-2-carbonyl)quinazolin-6-yl]-4,5-difluorobenzyl}propionamide | A |
| N-{2-[2-Amino-4-(1,3-dihydroisoindole-2-carbonyl)quinazolin-6-yl]-4,5-difluorobenzyl}-3-dimethylaminopropionamide | A |

TABLE I-continued

HSP90 inhibition by compounds of the formula I according to the invention

| Compound No. | IC$_{50}$ |
|---|---|
| 2-[2-Amino-4-(1,3-dihydroisoindole-2-carbonyl)quinazolin-6-yl]-4,5-difluorobenzyl 3-aminopropionate | A |

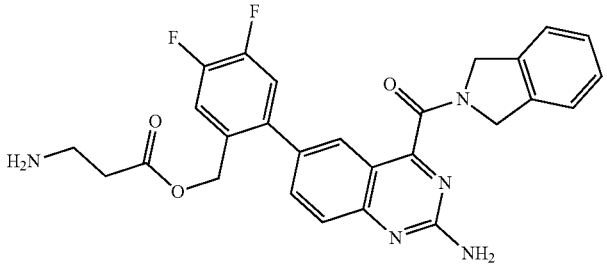

| {2-Amino-6-[2-(3-dimethylaminopropoxymethyl)-4,5-difluorophenyl]-quinazolin-4-yl}-(1,3-dihydroisoindol-2-yl)methanone | A |

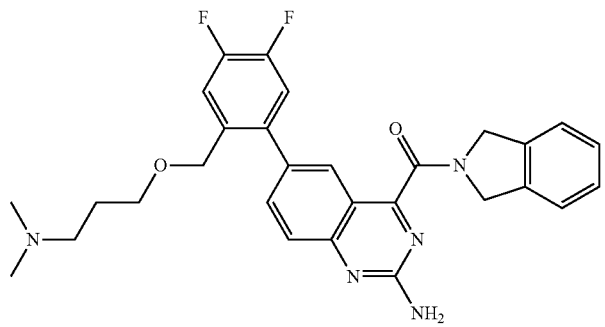

| {2-Amino-6-[2-(2-dimethylaminoethoxymethyl)-4,5-difluorophenyl]-quinazolin-4-yl}-(1,3-dihydroisoindol-2-yl)methanone | A |

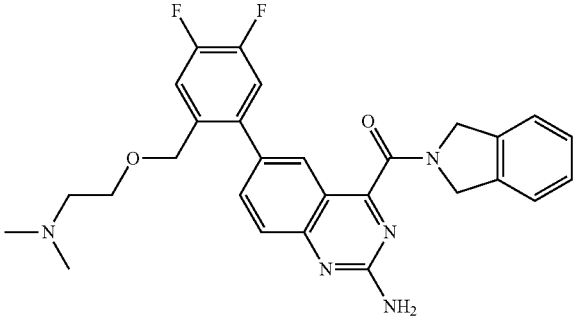

| {2-Amino-6-[2-(3-aminopropoxymethyl)-4,5-difluorophenyl]-quinazolin-4-yl}-(1,3-dihydroisoindol-2-yl)methanone | A |

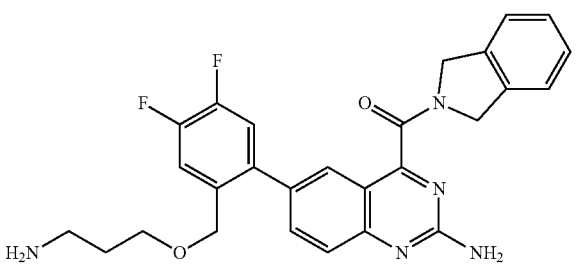

TABLE I-continued

HSP90 inhibition by compounds of the formula I according to the invention

| Compound No. | IC$_{50}$ |
|---|---|
| {2-Amino-6-[4,5-difluoro-2-(2-hydroxyethoxymethyl)phenyl]quinazolin-4-yl}-(1,3-dihydroisoindol-2-yl)methanone | A |

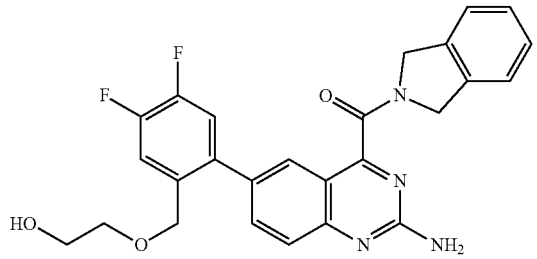

| [2-Amino-6-(4,5-difluoro-2-{2-[2-(2-hydroxyethoxy)ethoxy]ethoxymethyl}phenyl)quinazolin-4-yl]-(1,3-dihydroisoindol-2-yl)methanone | A |

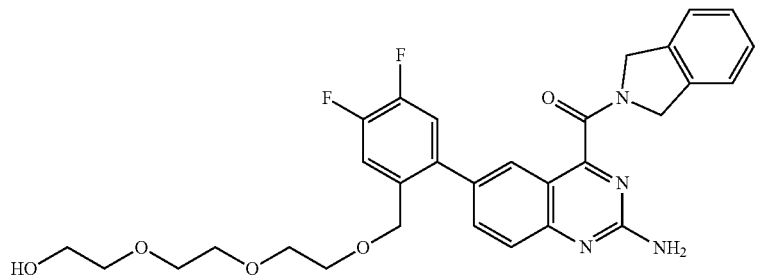

| 2-[2-Amino-4-(1,3-dihydroisoindole-2-carbonyl)quinazolin-6-yl]-4,5-difluorobenzyl (S)-2,5-diaminopentanoate | A |

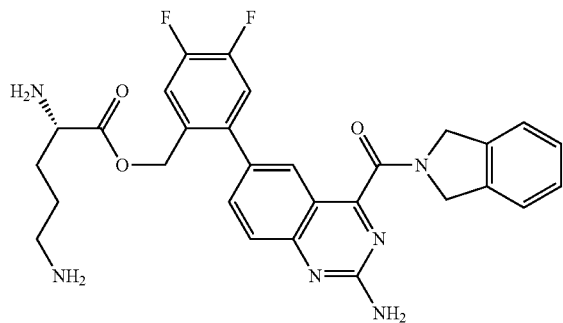

| 2-[2-Amino-4-(1,3-dihydroisoindole-2-carbonyl)quinazolin-6-yl]-4,5-difluorobenzyl 3-dimethylaminopropionate | A |

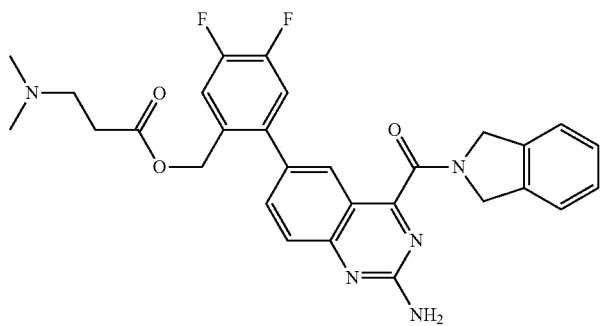

TABLE I-continued

HSP90 inhibition by compounds of the formula I according to the invention

| Compound No. | IC$_{50}$ |
| --- | --- |
| 2-[2-Amino-4-(1,3-dihydroisoindole-2-carbonyl)quinazolin-6-yl]-4,5-difluorobenzyl 2,6-diaminohexanoate | A |

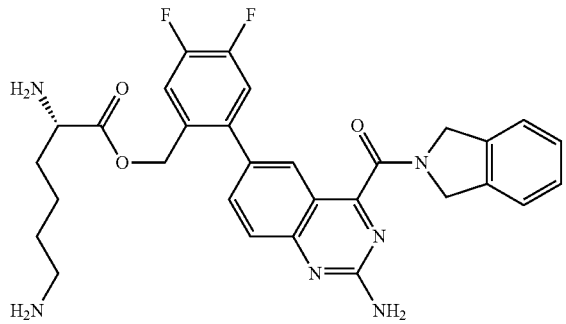

| [2-Amino-6-(2-aminooxymethyl-4,5-difluorophenyl)quinazolin-4-yl]-(1,3-dihydroisoindol-2-yl)methanone | A |
| --- | --- |

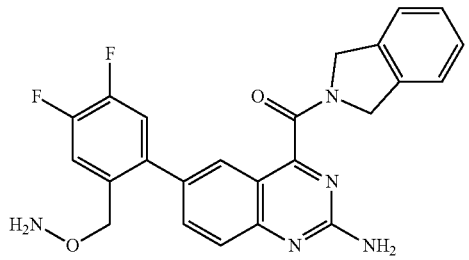

| Mono-{2-[2-amino-4-(1,3-dihydroisoindole-2-carbonyl)quinazolin-6-yl]-4,5-difluorobenzyl}phosphate | A |
| --- | --- |

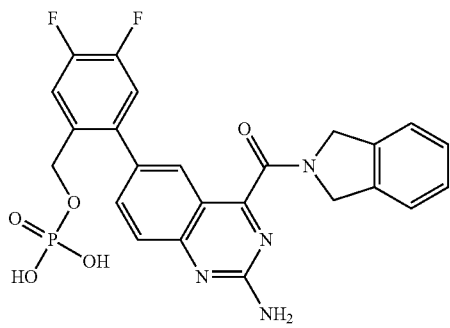

| 2-[2-Amino-4-(1,3-dihydroisoindole-2-carbonyl)quinazolin-6-yl]-4-fluorobenzyl 2,6-diaminohexanoate | A |
| --- | --- |

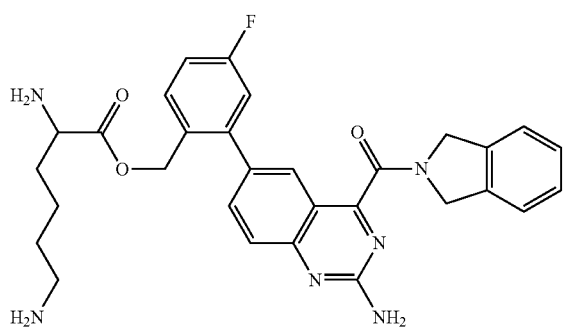

TABLE I-continued

HSP90 inhibition by compounds of the formula I according to the invention

| Compound No. | IC$_{50}$ |
|---|---|
| 2-[2-Amino-4-(1,3-dihydroisoindole-2-carbonyl)quinazolin-6-yl]-4,5-difluorobenzyl di-tert-butyl phosphate | A |
| 2-[2-Amino-4-(1,3-dihydroisoindole-2-carbonyl)quinazolin-6-yl]-4,5-difluorobenzyl 2-amino-4-methylpentanoate | A |
| 2-[2-Amino-4-(1,3-dihydroisoindole-2-carbonyl)quinazolin-6-yl]-4,5-difluorobenzyl 2,2-dimethylpropionate | A |

TABLE I-continued

HSP90 inhibition by compounds of the formula I according to the invention

| Compound No. | IC$_{50}$ |
| --- | --- |
| 2-[2-Amino-4-(1,3-dihydroisoindole-2-carbonyl)quinazolin-6-yl]-4,5-difluorobenzyl 6-tert-butoxycarbonylaminohexanoate | A |
| 2-{2-[2-Amino-4-(1,3-dihydroisoindole-2-carbonyl)quinazolin-6-yl]-4,5-difluorobenzyl} 1-tert-butyl (S)-pyrrolidine-1,2-dicarboxylate | A |
| 2-[2-Amino-4-(1,3-dihydroisoindole-2-carbonyl)quinazolin-6-yl]benzyl (S)-2,6-diaminohexanoate | A |
| 2-[2-Amino-4-(1,3-dihydroisoindole-2-carbonyl)quinazolin-6-yl]-4,5-difluorobenzyl (S)-pyrrolidine-2-carboxylate | A |

IC$_{50}$: 10 nM-1 μM = A
1 μM-10 μM = B
>10 μM = C

Above and below, all temperatures are indicated in ° C. In the following examples, "conventional work-up" means: water is added if necessary, the pH is adjusted, if necessary, depending on the constitution of the final product, to values between 2 and 10, the mixture is extracted with ethyl acetate or dichloromethane, the phases are separated, the organic phase is dried over sodium sulfate, evaporated and purified by chromatography on silica gel and/or by crystallisation.

LC-MS Conditions

The LC/MS measurements are carried out using an HP 1200 series Hewlett Packard system having the following features: ion source: electrospray (positive mode); scan: 100-1000 m/e; fragmentation voltage: 60 V; gas temperature: 300° C., UV: 220 nm.

Flow rate: 2.4 ml/min.

Column: Chromolith SpeedROD RP-18e 50-4.6

Solvent: LiChrosolv grade from Merck KGaA

Solvent A: $H_2O$ (0.05% of formic acid)

Solvent B: ACN (0.04% of formic acid)

"Standard" Gradient:

4% of B→100% of B: 0 min to 2.8 min

100% of B: 2.8 min to 3.3 min

100% of B→4% of B: 3.3 min to 3.4 min

"Polar" Gradient:

0% of B: 0 min to 0.5 min

0% of B→100% of B: 0.5 min to 2.6 min

100% of B: 2.6 min to 3 min

100% of B→10% of B: 3 min to 3.1 min

"Nonpolar" Gradient:

20% of B→100% of B: 0 min to 2.8 min

100% of B: 2.8 min to 3.3 min

100% of B→20% of B: 3.3 min to 3.4 min

If nothing further is stated regarding the retention time, "standard" gradient is used.

General Synthesis Schemes:

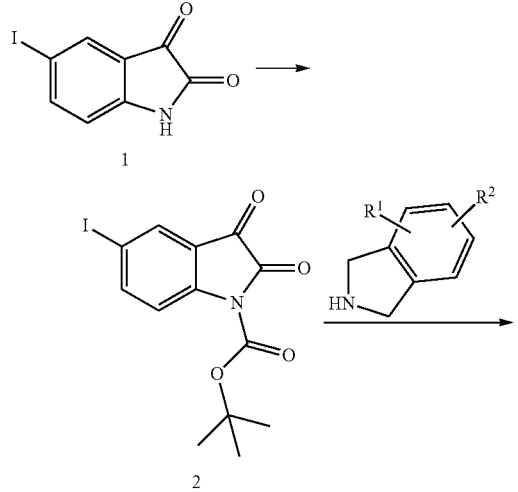

Scheme 1

Scheme 2: Phenylquinazoline syntheses method A

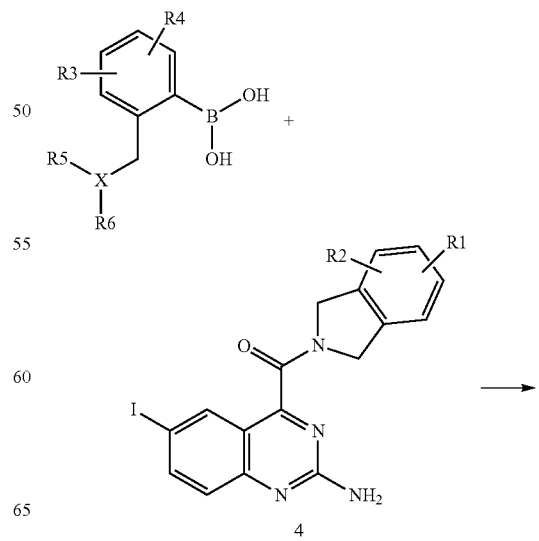

-continued

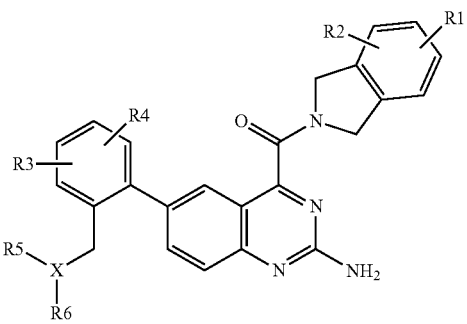

method B

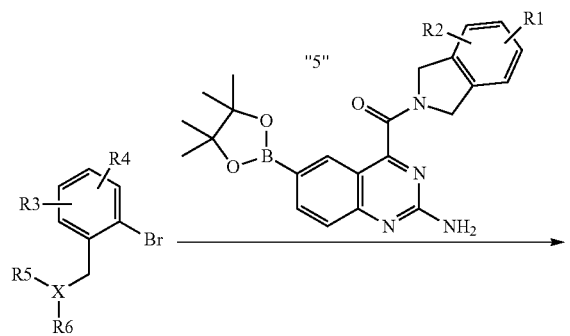

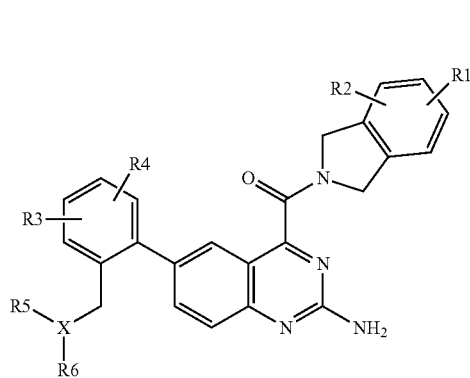

Synthesis in Accordance with Scheme 1 tert-Butyl
5-iodo-2,3-dioxo-2,3-dihydroindole-1-carboxylate
("2")

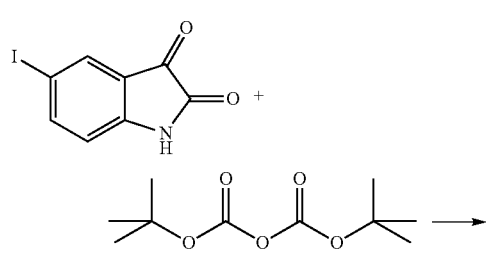

-continued

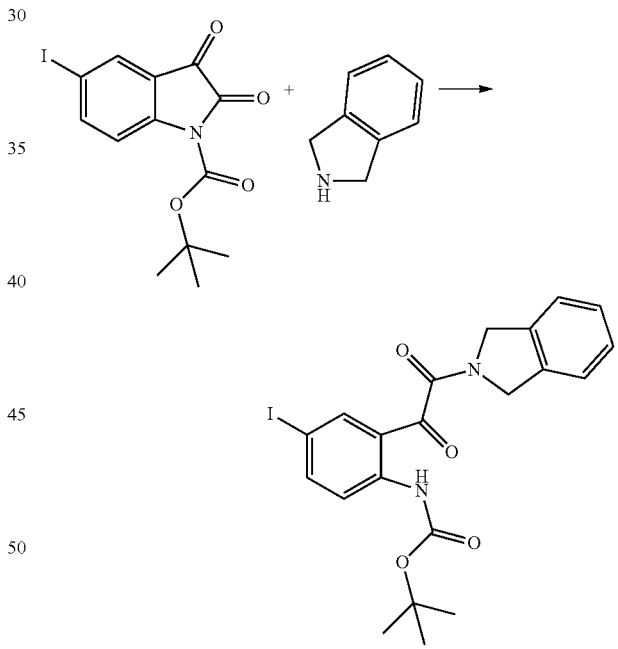

50 g of 5-iodo-1H-indole-2,3-dione are dissolved in 500 ml of THF, cooled to 10° C., and 43.97 g of di-tert-butyl dicarbonate are added. The mixture is stirred at 23° C. for 16 h and subsequently evaporated to dryness in vacuo. The residue is taken up in petroleum ether and THF and crystallised at −20° C. The resultant yellow solid is filtered and dried at 30° C. in a drying cabinet. Yield: 62.41 g of tert-butyl 5-iodo-2,3-dioxo-2,3-dihydroindole-1-carboxylate; LC-MS retention time: 2.11 min.

tert-Butyl {2-[2-(1,3-dihydroisoindol-2-yl)-2-oxoacetyl]-4-iodophenyl}carbamate ("3")

62.41 g of tert-butyl 5-iodo-2,3-dioxo-2,3-dihydroindole-1-carboxylate are dissolved in dried THF, and 18.98 ml of 2,3-dihydro-1H-isoindole are added. The mixture is stirred at 25° C. for 30 min, evaporated to dryness in vacuo, and the residue is triturated with petroleum ether, filtration gives 82.3 g of tert-butyl {2-[2-(1,3-dihydroisoindol-2-yl)-2-oxoacetyl]-4-iodophenyl}carbamate (beige solid); LC-MS retention time: 2.63 min;

$^1$H NMR (500 MHz, DMSO-$d_6$/TFA-$d_1$): δ [ppm] 8.014 (d, 1H), 7.962 (dd, 1H), 7.913 (d, 1H), 7.391 (d, 1H), 7.326-7.292 (m, 3H), 4.901 (s, 2H), 4.872 (s, 2H), 1.398 (s, 9H).

(2-Amino-6-iodoquinazolin-4-yl)-(1,3-dihydroisoindol-2-yl)methanone ("4")

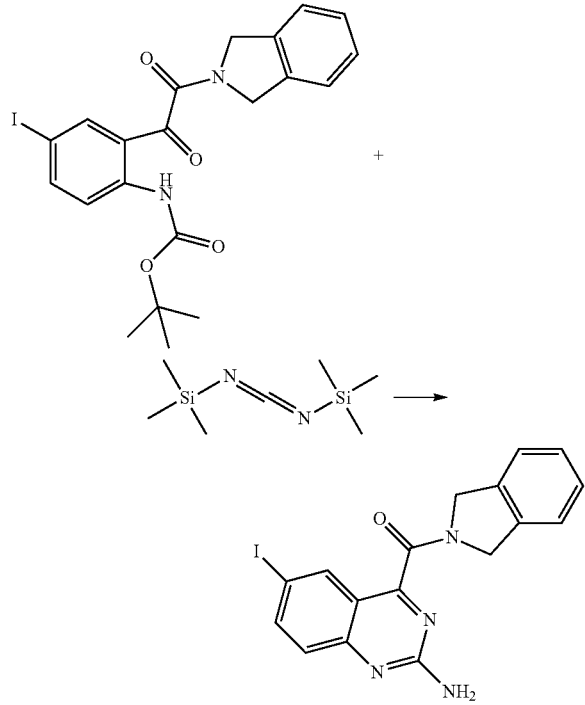

24.50 g of tert-butyl {2-[2-(1,3-dihydroisoindol-2-yl)-2-oxoacetyl]-4-iodophenyl}carbamate are dissolved in 500 ml of acetonitrile under argon. 0.756 g of caesium fluoride is added, and 16.887 ml of bis(trimethylsilyl)carbodiimide are added dropwise to the solution over the course of 5 min. The mixture is stirred at room temperature for 15 min, and 400 ml of dichloromethane are added. After addition of 400 ml of hydrochloric acid (1N), the product precipitates out as white solid; yield: 14 g of (2-amino-6-iodoquinazolin-4-yl)-(1,3-dihydroisoindol-2-yl)methanone; LC-MS retention time: 1.66 min;

¹H NMR (500 MHz, DMSO) 8.143 (d, 1H), 7.957 (dd, 1H), 7.451 (d, 1H), 7.361-7.256 (m, 4H), 7.213 (s, 2H), 4.993 (s, 2H), 4.745 (s, 2H).

[2-Amino-6-(4,4,5,5-tetramethyl-1,3,2-dioxaborolan-2-yl)quinazolin-4-yl]-(1,3-dihydroisoindol-2-yl)methanone ("5")

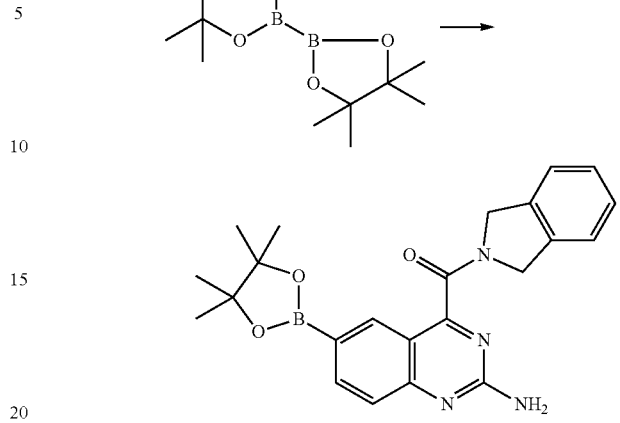

10 g of (2-amino-6-iodoquinazolin-4-yl)-(1,3-dihydroisoindol-2-yl)methanone ("4") are dissolved in 500 ml of dimethyl sulfoxide under argon atmosphere. 6.1 g of bis(pinacolato)diboron, 8.017 g of potassium acetate and 981 mg of [1,1'-bis(diphenylphosphino)ferrocene]palladium(II) dichloride are added to this solution, and the mixture is heated at 80° C. for 60 min. After cooling, 250 ml of diethyl ether are added to the mixture, which is then extracted four times against 100 ml of water each time. The combined organic phases are dried over sodium sulfate, filtered, and the filtrate is evaporated until a red oil is present. This oil is triturated with acetonitrile, with pale-beige crystals being formed. The precipitate is filtered and dried at 50° C. in a drying cabinet for 12 h. The resultant product is reacted further without further purification.

Yield: 6.45 g (65%) of [2-amino-6-(4,4,5,5-tetramethyl-1,3,2-dioxaborolan-2-yl)quinazolin-4-yl]-(1,3-dihydroisoindol-2-yl)methanone;

LC-MS retention time: 2.08 min;

¹H NMR (400 MHz, DMSO-$d_6$/TFA-$d_1$) δ [ppm] 8.38 (d, J=0.6, 1H), 8.29 (dd, J=8.4, 1.2, 1H), 7.78 (d, J=8.5, 1H), 7.45 (d, J=7.3, 1H), 7.33 (dt, J=15.1, 6.5, 2H), 7.24 (d, J=7.2, 1H), 5.11 (s, 2H), 4.92 (s, 2H), 1.33 (s, 12H).

Scheme 2, Method A

2-[2-Amino-4-(1,3-dihydroisoindole-2-carbonyl)quinazolin-6-yl]benzaldehyde

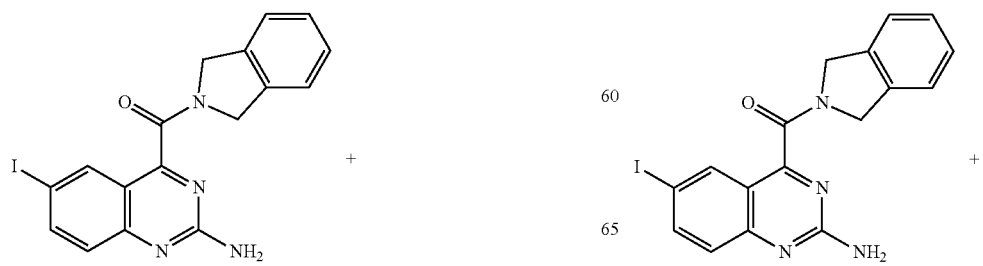

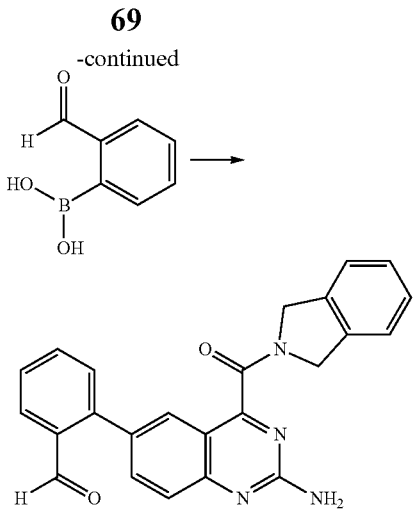

1 g of (2-amino-6-iodoquinazolin-4-yl)-(1,3-dihydroisoindol-2-yl)methanone are dissolved in 10 ml of ethanol. 468.3 mg of 2-formylphenylboronic acid, 664 mg of potassium carbonate, 58.9 mg of [1,1'-bis(diphenylphosphino)ferrocene]palladium(II) dichloride and 3 ml of water are added to this solution, and the mixture is heated at 130° C. under argon for 30 min. During this time, a precipitate forms, which is filtered and dried at 50° C. in a drying cabinet for 12 h. The resultant product is reacted further without further purification. Yield 910 mg of 2-[2-amino-4-(1,3-dihydroisoindole-2-carbonyl)quinazolin-6-yl]benzaldehyde; LC-MS retention time: 1.86 min.

[2-Amino-6-[2-(hydroxymethyl)phenyl]quinazolin-4-yl]isoindolin-2-ylmethanone ("A1")

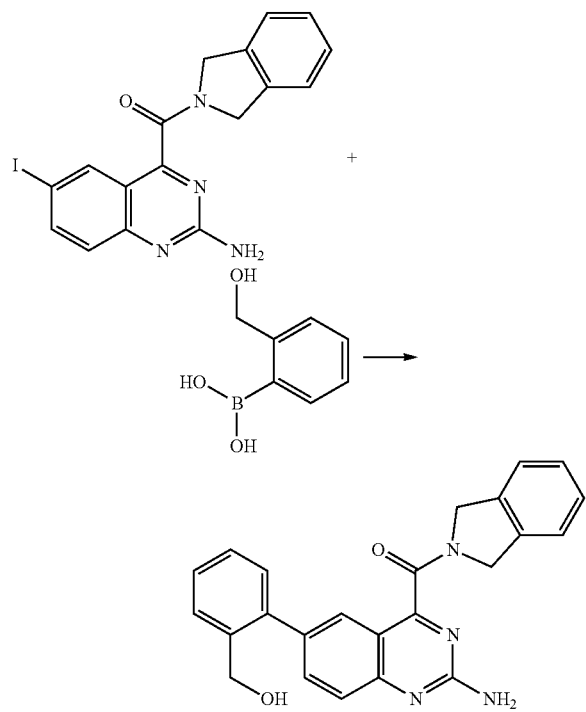

100 mg of (2-amino-6-iodoquinazolin-4-yl)-(1,3-dihydroisoindol-2-yl)methanone are dissolved in 2 ml of ethylene glycol dimethyl ether. 48 mg of 2-hydroxymethylphenylboronic acid, 66 mg of potassium carbonate, 14 mg of [1,1'-bis(diphenylphosphino)ferrocene]palladium(II) dichloride and 50 µl of water are added to this solution, and the mixture is heated at 130° C. under argon for 30 min. The hot mixture is filtered off through Celite, and the solution is evaporated to dryness under reduced pressure. The reddish residue obtained is triturated with acetonitrile, during which a beige solid precipitates out. This is filtered, washed with acetonitrile and dried overnight at 40° C. in a drying cabinet.

Yield: 16 mg (17%) of [2-amino-6-[2-(hydroxymethyl)phenyl]quinazolin-4-yl]isoindolin-2-ylmethanone; HPLC retention time: 1.83 min;

$^1$H NMR (400 MHz, DMSO-d$_6$/TFA-d$_1$) δ [ppm] 8.18-8.11 (m, 2H), 7.87 (d, J=9.2, 1H), 7.61 (d, J=7.5, 1H), 7.48-7.28 (m, 6H), 7.26 (d, J=7.0, 1H), 5.04 (s, 2H), 4.87 (s, 2H), 4.40 (s, 2H).

[2-Amino-6-[5-fluoro-2-(hydroxymethyl)phenyl]quinazolin-4-yl]isoindolin-2-ylmethanone ("A2")

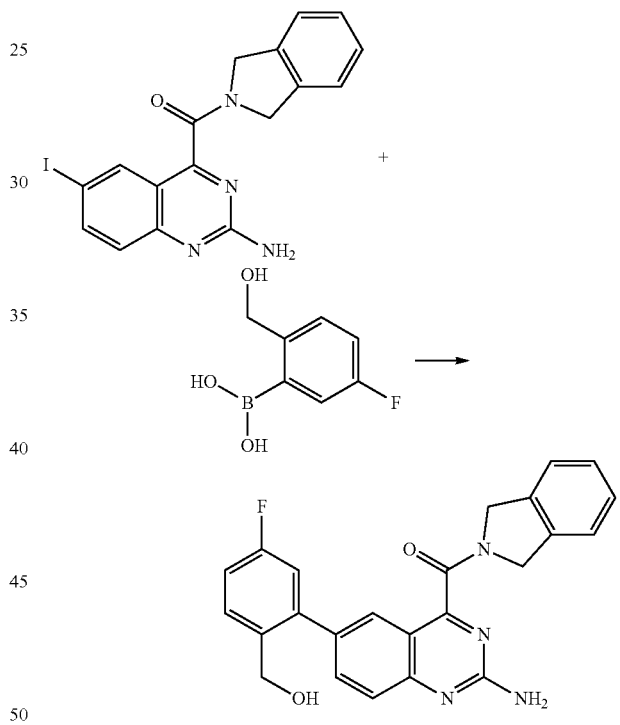

10.405 g of (2-amino-6-iodoquinazolin-4-yl)-(1,3-dihydroisoindol-2-yl)methanone are dissolved in 450 ml of ethanol. 5 g of 5-fluoro-2-hydroxymethylphenylboronic acid, 10.4 g of potassium carbonate, 1 g of [1,1'-bis(diphenylphosphino)ferrocene]palladium(II) dichloride and 450 µl of water are added to this solution, and the mixture is heated at 100° C. under argon for 1 h. The hot mixture is filtered off through Celite, and the filter cake is rinsed with 500 ml of hot ethanol. The filtrate is evaporated to dryness in vacuo, and the reddish residue obtained is triturated with 50 ml of acetonitrile, during which a beige solid precipitates out. This is filtered, washed with 20 ml of acetonitrile and dried at 40° C. in a drying cabinet for 16 h Yield: 9.7 g (94%) of [2-amino-6-[5-fluoro-2-(hydroxymethyl)phenyl]quinazolin-4-yl]isoindolin-2-ylmethanone; HPLC retention time: 1.92 min;

¹H NMR (500 MHz, DMSO-d₆/TFA-d₁) δ [ppm] 8.14-8.08 (m, 2H), 7.82 (dd, J=7.8, 1.6, 1H), 7.58 (dd, J=8.6, 6.1, 1H), 7.41 (d, J=7.2, 1H), 7.33-7.25 (m, 2H), 7.24-7.18 (m, 2H), 7.13 (dd, J=9.6, 2.7, 1H), 4.99 (s, 2H), 4.82 (s, 2H), 4.31 (s, 2H).

[2-Amino-6-[2-(methylaminomethyl)phenyl]quinazolin-4-yl]isoindolin-2-ylmethanone ("A3")

a)

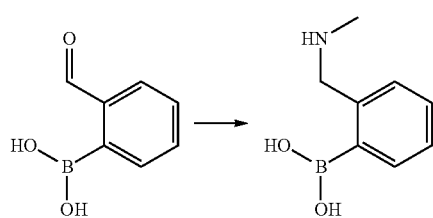

500 mg of 2-formylphenylboronic acid are dissolved in 5 ml of methanol. 628 µl of methylamine (33% in ethanol) are added to this solution, the mixture is cooled to 0° C., and 63 of sodium borohydride are added. The mixture is stirred at 22° C. for 1 h, 10 ml of water are added, and the mixture is washed 3 times with 10 ml of ethyl acetate each time. The combined organic phases are dried over sodium sulfate, filtered, and the filtrate is evaporated to dryness. The solid obtained is employed in the following reaction without further purification.

Yield: 400 mg (73%) of 2-methylaminomethylphenylboronic acid; LC-MS retention time: 0.34 min ("polar" gradient).

b)

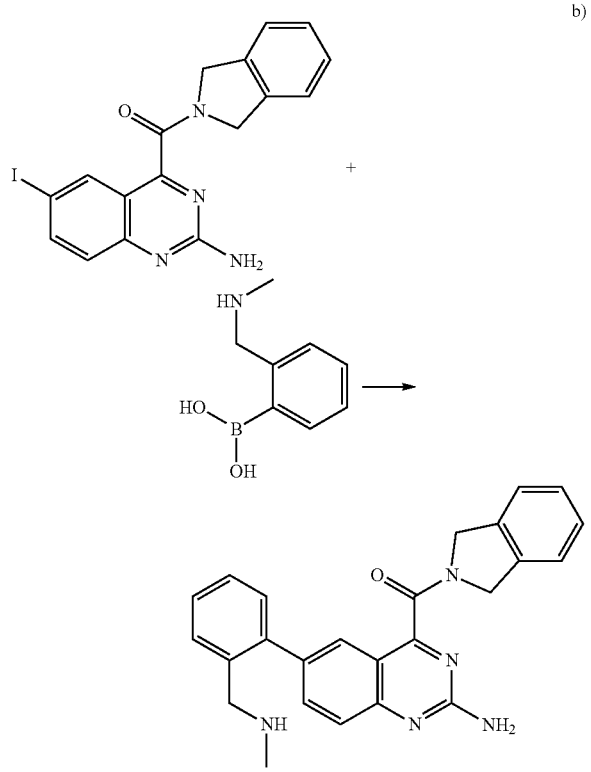

100 mg of (2-amino-6-iodoquinazolin-4-yl)-(1,3-dihydroisoindol-2-yl)methanone are dissolved in 2 ml of ethanol. 79 mg of 2-methylaminomethylphenylboronic acid, 66 mg of potassium carbonate, 6 mg of [1,1'-bis(diphenylphosphino)ferrocene]palladium(II) dichloride and 450 µl of water are added to this solution, and the mixture is heated at 100° C. under argon for 1 h. The hot mixture is filtered off through Celite and rinsed with 500 ml of hot ethanol. The reaction mixture is evaporated to dryness under reduced pressure, dissolved in 2 ml of DMSO, filtered and chromatographed by means of preparative HPLC (Agilent). The product fractions obtained are subsequently evaporated and freeze-dried. Yield: 20 mg (21%) of [2-amino-6-[2-(methylaminomethyl)phenyl]quinazolin-4-yl]isoindolin-2-ylmethanone; HPLC retention time: 1.42 min;

¹H NMR (500 MHz, DMSO-d₆/TFA-d₁) δ [ppm] 8.08-8.05 (m, 1H), 8.03 (dd, J=8.6, 2.0, 1H), 7.85 (d, J=8.6, 1H), 7.69-7.65 (m, 1H), 7.54-7.46 (m, 2H), 7.41-7.36 (m, 2H), 7.28 (dt, J=19.8, 7.1, 2H), 7.21 (d, J=7.3, 1H), 5.00 (s, 2H), 4.82 (s, 2H), 4.02 (s, 2H), 2.46 (s, 3H).

Scheme 2, Method B

2-[2-Amino-4-(isoindoline-2-carbonyl)quinazolin-6-yl]-4-fluorobenzaldehyde

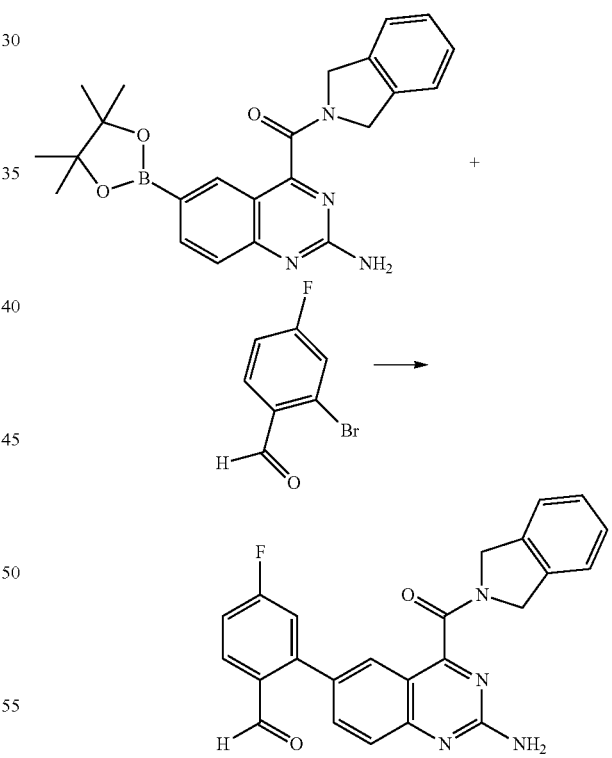

244 mg of 2-bromo-4-fluorobenzaldehyde, 0.35 g of potassium carbonate, 4 µl of water and 98 mg of [1,1'-bis(diphenylphosphino)ferrocene]palladium(II) dichloride are added to a solution of 500 mg of [2-amino-6-(4,4,5,5-tetramethyl-1,3,2-dioxaborolan-2-yl)quinazolin-4-yl]-(1,3-dihydroisoindol-2-yl)methanone in 12 ml of ethanol under argon. The mixture is heated at 120° C. for 4 h; then allowed to cool, during which a precipitate deposits. The precipitate is filtered off, taken up in 10 ml of ethyl acetate and washed 3 times with 10 ml of water each time. After drying over sodium sulfate, the mixture is filtered off and evaporated to dryness in vacuo; yield: 495 mg (91%) of 2-[2-amino-4-(isoindoline-2-carbonyl)quinazolin-6-yl]-4-fluorobenzaldehyde; HPLC retention time: 1.73 min;

$^1$H NMR (500 MHz, DMSO-d$_6$/TFA-d$_1$) δ [ppm] 9.78 (s, 1H), 8.13 (d, J=1.7, 1H), 8.08 (dd, J=8.7, 2.0, 1H), 8.02 (dd, J=8.6, 6.0, 1H), 7.82 (d, J=8.7, 1H), 7.42-7.31 (m, 3H), 7.26 (dt, J=12.8, 6.8, 2H), 7.19 (d, J=6.9, 1H), 4.97 (s, 2H), 4.82 (s, 2H).

2-[2-Amino-4-(isoindoline-2-carbonyl)quinazolin-6-yl]-5-fluorobenzaldehyde

2-[2-Amino-4-(isoindoline-2-carbonyl)quinazolin-6-yl]-5-hydroxybenzaldehyde

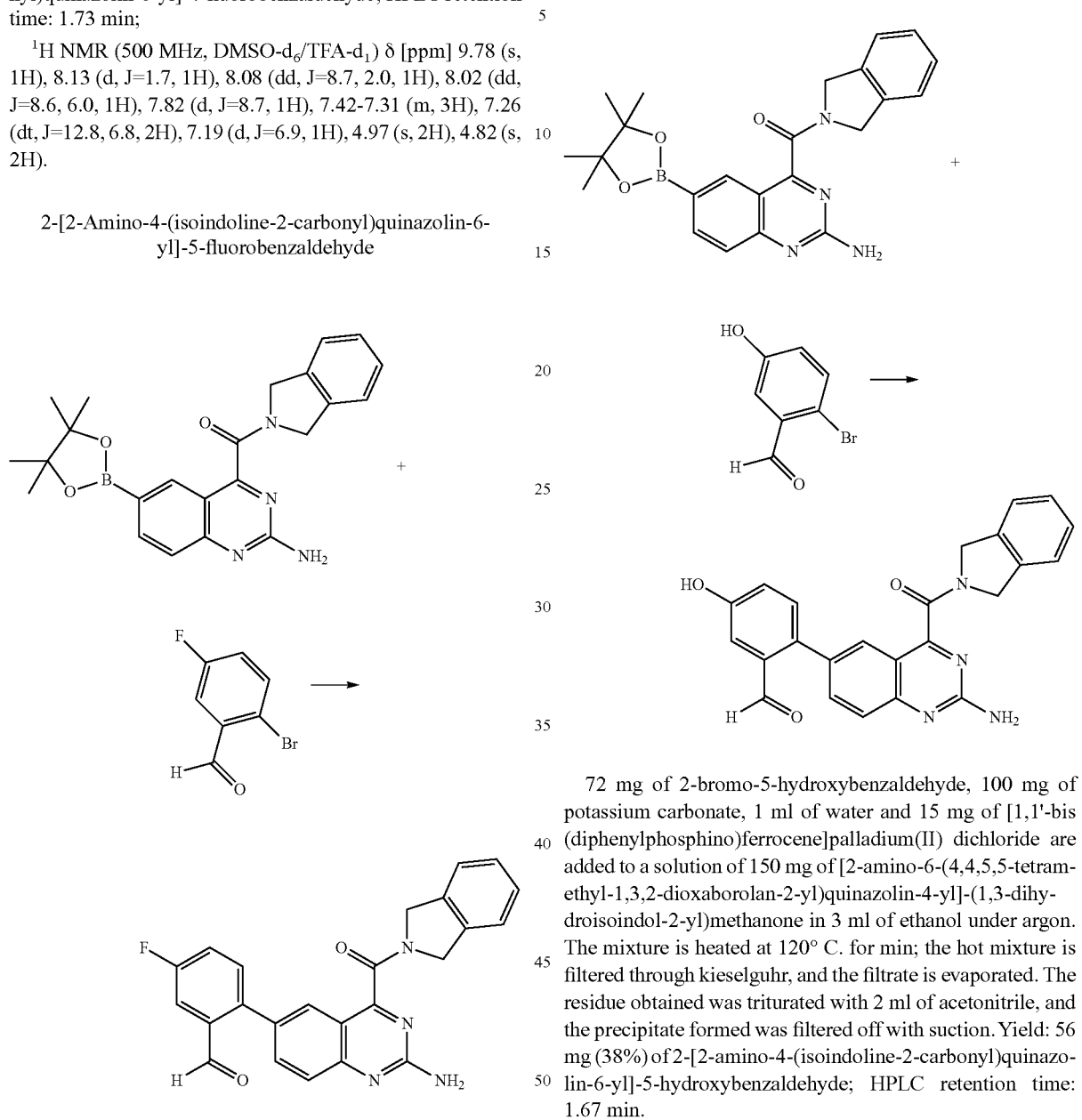

244 mg of 2-bromo-5-fluorobenzaldehyde, 1.7 g of potassium carbonate, 87 μl of water and 196 mg of [1,1'-bis(diphenylphosphino)ferrocene]palladium(II) dichloride are added to a solution of 2 g of [2-amino-6-(4,4,5,5-tetramethyl-1,3,2-dioxaborolan-2-yl)quinazolin-4-yl]-(1,3-dihydroisoindol-2-yl)methanone in 200 ml of ethanol under argon. The mixture is heated at 120° C. for 30 min; the hot mixture is filtered through kieselguhr, and the filtrate is evaporated. The residue obtained is triturated with 2 ml of acetonitrile, and the precipitate formed is filtered off with suction.

Yield: 1.9 mg (95%) of 2-[2-amino-4-(isoindoline-2-carbonyl)quinazolin-6-yl]-5-fluorobenzaldehyde; HPLC retention time: 2.74 min ("polar" gradient).

72 mg of 2-bromo-5-hydroxybenzaldehyde, 100 mg of potassium carbonate, 1 ml of water and 15 mg of [1,1'-bis(diphenylphosphino)ferrocene]palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 3 ml of ethanol under argon. The mixture is heated at 120° C. for min; the hot mixture is filtered through kieselguhr, and the filtrate is evaporated. The residue obtained was triturated with 2 ml of acetonitrile, and the precipitate formed was filtered off with suction. Yield: 56 mg (38%) of 2-[2-amino-4-(isoindoline-2-carbonyl)quinazolin-6-yl]-5-hydroxybenzaldehyde; HPLC retention time: 1.67 min.

2-[2-Amino-4-(isoindoline-2-carbonyl)quinazolin-6-yl]-5-(2-dimethylaminoethoxy)benzaldehyde a)

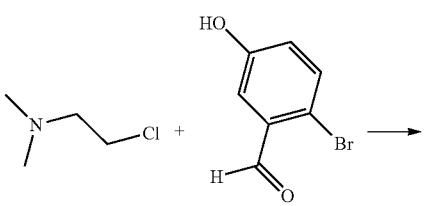

-continued

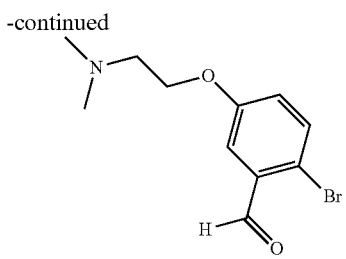

143 mg of (2-chloroethyl)dimethylamine hydrochloride together with 5 mg of tetrabutylammonium iodide are added to a solution of 200 mg of 2-bromo-5-hydroxybenzaldehyde and 648 mg of caesium carbonate in 5 ml of toluene, and the mixture is heated under reflux for 1 h. After cooling to 22° C., the residue is filtered off, 5 ml of ethyl acetate are added, and the mixture is washed 3 times with 5 ml of 2N sodium hydroxide solution each time. After drying over sodium sulfate, the solid is filtered off and the filtrate is evaporated to dryness in vacuo. The residue is purified by reverse-phase column chromatography.

Yield: 116 mg (43%) of 2-bromo-5-(2-dimethylaminoethoxy)benzaldehyde; HPLC retention time: 1.18 min.

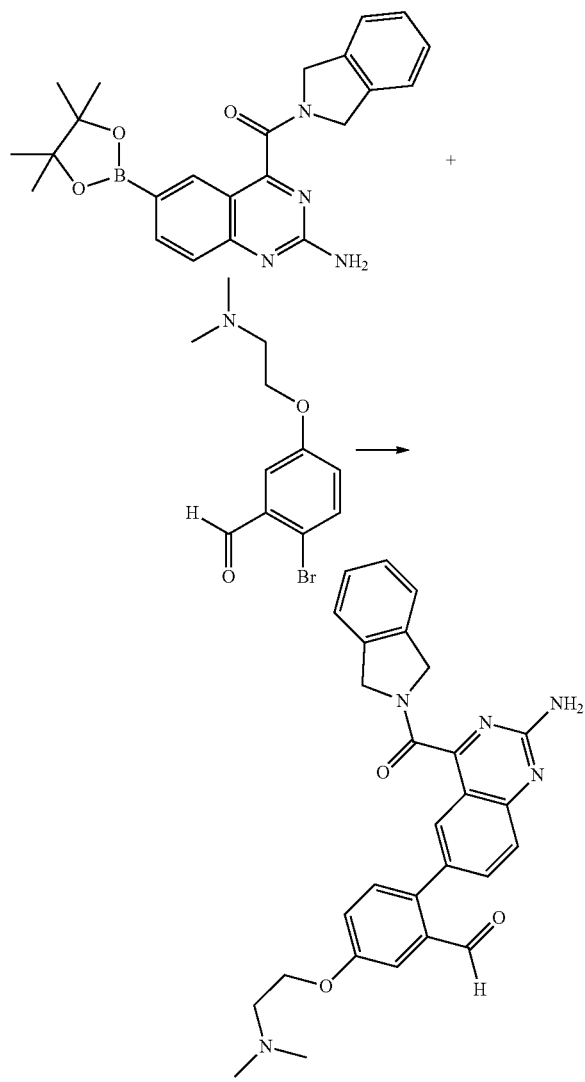

98 mg of 2-bromo-5-(2-dimethylaminoethoxy)benzaldehyde, 100 mg of potassium carbonate, 1 ml of water and 15 mg of [1,1'-bis(diphenylphosphino)ferrocene]palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 3 ml of ethanol under argon. The mixture is heated at 120° C. for 30 min; the hot mixture is filtered through kieselguhr, and the filtrate is evaporated. The residue obtained is triturated with 2 ml of acetonitrile, and the precipitate formed is filtered off with suction.

Yield: 150 mg (86%) of 2-[2-amino-4-(isoindoline-2-carbonyl)quinazolin-6-yl]-5-(2-dimethylaminoethoxy)benzaldehyde; HPLC retention time: 1.37 min.

6-[2-Amino-4-(isoindoline-2-carbonyl)quinazolin-6-yl]-1,3-benzodioxole-5-carbaldehyde

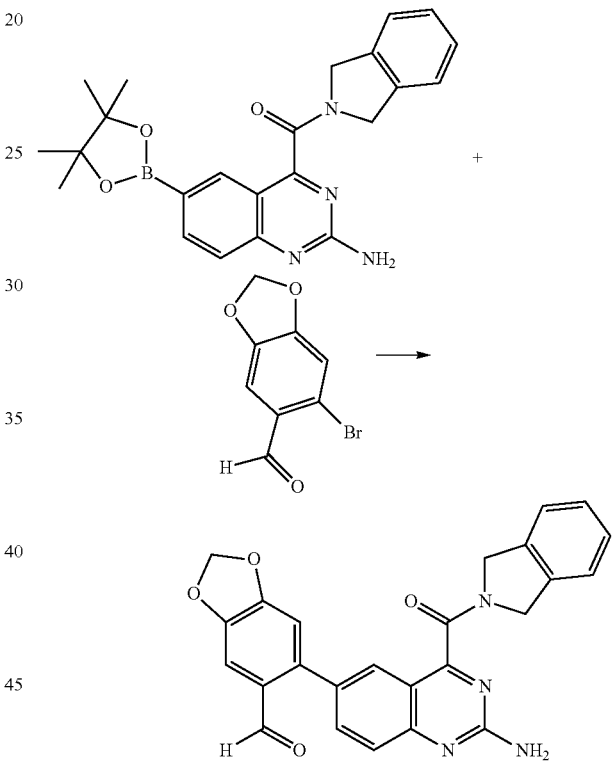

280 mg of 6-bromo-1,3-benzodioxole-5-carbaldehyde, 331 mg of potassium carbonate, 22 µl of water and 49 mg of [1,1'-bis(diphenylphosphino)ferrocene]-palladium(II) dichloride are added to a solution of 500 mg of [2-amino-6-(4,4,5,5-tetramethyl-1,3,2-dioxaborolan-2-yl)quinazolin-4-yl]-(1,3-dihydroisoindol-2-yl)methanone in 50 ml of ethanol under argon. The mixture is heated at 120° C. for 4 h; the hot mixture is filtered through kieselguhr, and the filtrate is evaporated. The residue obtained was triturated with 2 ml of acetonitrile, and the precipitate formed was filtered off with suction.

Yield: 370 mg (70%) of 6-[2-amino-4-(isoindoline-2-carbonyl)quinazolin-6-yl]-1,3-benzodioxole-5-carbaldehyde; HPLC retention time: 2.57 min ("polar" gradient);
$^1$H NMR (500 MHz, DMSO-$d_6$/TFA-$d_1$) δ [ppm] 9.64 (s, 1H), 8.11-8.06 (m, 2H), 7.82 (d, J=8.4, 1H), 7.44 (d, J=7.3, 1H), 7.40 (s, 1H), 7.36-7.28 (m, 2H), 7.26 (d, J=7.3, 1H), 7.11 (s, 1H), 6.21 (s, 2H), 5.00 (s, 2H), 4.85 (s, 2H).

[2-Amino-6-[4-fluoro-2-(hydroxymethyl)phenyl] quinazolin-4-yl]isoindolin-2-ylmethanone ("A4")

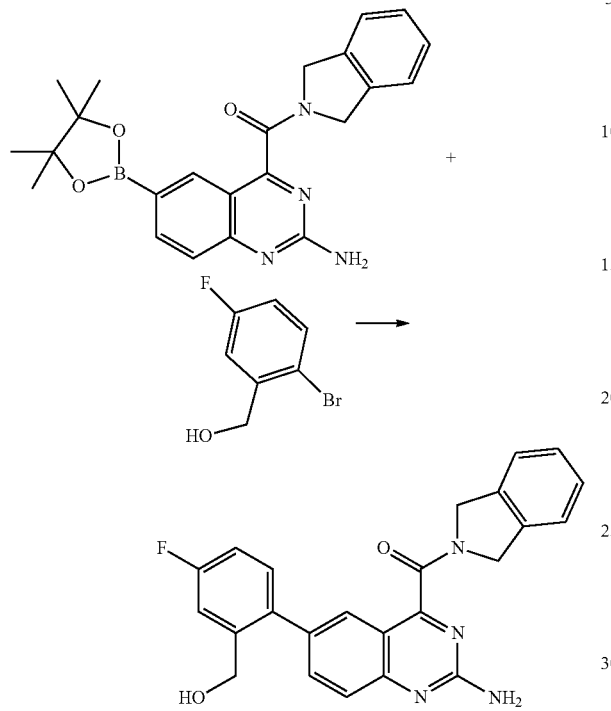

74 mg of (2-bromo-5-fluorophenyl)methanol, 100 mg of potassium carbonate, 1 ml of water and 15 mg of [1,1'-bis (diphenylphosphino)ferrocene]palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 3 ml of ethanol under argon. The mixture is heated at 120° C. for min; the hot mixture is filtered through kieselguhr, and the filtrate is evaporated in vacuo. The residue is purified by reverse-phase column chromatography.

Yield: 8 mg (5%) of [2-amino-6-[4-fluoro-2-(hydroxymethyl)phenyl]quinazolin-4-yl]isoindolin-2-ylmethanone; HPLC retention time: 1.51 min;

$^1$H NMR (400 MHz, DMSO-$d_6$/TFA-$d_1$) δ [ppm] 8.08-8.02 (m, 2H), 7.81 (d, J=8.7, 1H), 7.42 (d, J=7.2, 1H), 7.39-7.25 (m, 4H), 7.24 (d, J=6.9, 1H), 7.16 (td, J=8.5, 2.8, 1H), 4.99 (s, 2H), 4.82 (s, 2H), 4.36 (s, 2H).

[2-Amino-6-[5-fluoro-2-(hydroxymethyl)phenyl] quinazolin-4-yl]isoindolin-2-ylmethanone ("A5")

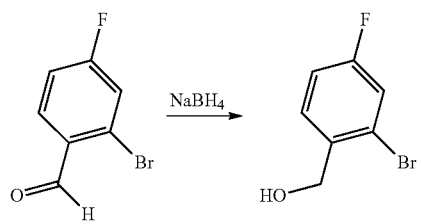

304 mg of 2-bromo-4-fluorobenzaldehyde are added at 22° C. in portions with stirring to a solution of 28 mg of sodium borohydride and 5 ml of methanol and stirred at 22° C. for 1 h. The mixture is poured into water, extracted three times with dichloromethane, and the combined organic phases are dried over sodium sulfate. After filtration, the filtrate is evaporated to dryness and purified by chromatography (reversed phase HPLC).

Yield 250 mg (81%) of (2-bromo-4-fluorophenyl)methanol;

LC-MS retention time: 1.39 min.

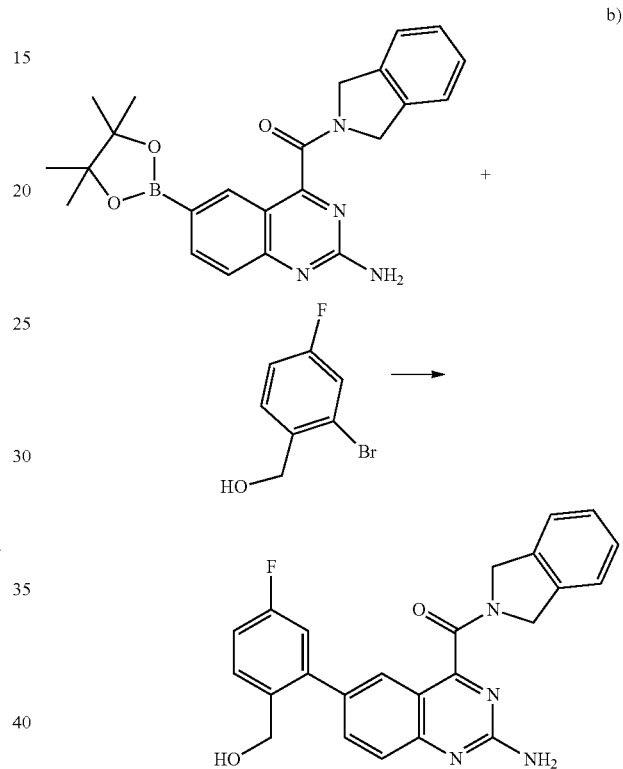

150 mg of [2-amino-6-(4,4,5,5-tetramethyl-1,3,2-dioxaborolan-2-yl)quinazolin-4-yl]-(1,3-dihydroisoindol-2-yl) methanone, 80 mg of (2-bromo-4-fluorophenyl)methanol and 15 mg of [1,1'-bis(diphenylphosphino)ferrocene]palladium(II) dichloride are weighed out into a microwave vial and blanketed with argon. 1 ml of DMF and 500 µl of 2N soda solution are added through the septum using a syringe under argon atmosphere. The mixture is subsequently treated in the microwave at 50 W and 120° C. over 30 min. The olive-green suspension formed is taken up in ethyl acetate and washed with water, dried over sodium sulfate, filtered and evaporated in vacuo. The residue obtained is triturated with 2 ml of acetonitrile, and the precipitate formed is filtered off with suction.

Yield: 56 mg (38%) of [2-amino-6-[5-fluoro-2-(hydroxymethyl)phenyl]quinazolin-4-yl]isoindolin-2-ylmethanone; HPLC retention time: 1.51 min;

$^1$H NMR (500 MHz, DMSO-$d_6$/TFA-$d_1$) δ [ppm] 8.14-8.08 (m, 2H), 7.82 (dd, J=7.8, 1.6, 1H), 7.58 (dd, J=8.6, 6.1, 1H), 7.41 (d, J=7.2, 1H), 7.33-7.25 (m, 2H), 7.24-7.18 (m, 2H), 7.13 (dd, J=9.6, 2.7, 1H), 4.99 (s, 2H), 4.82 (s, 2H), 4.31 (s, 2H).

79
[2-Amino-6-[4,5-difluoro-2-(hydroxymethyl)phenyl]quinazolin-4-yl]isoindolin-2-ylmethanone ("A6")

80
[2-Amino-6-[2-(hydroxymethyl)-4,5-dimethoxyphenyl]quinazolin-4-yl]isoindolin-2-ylmethanone ("A7")

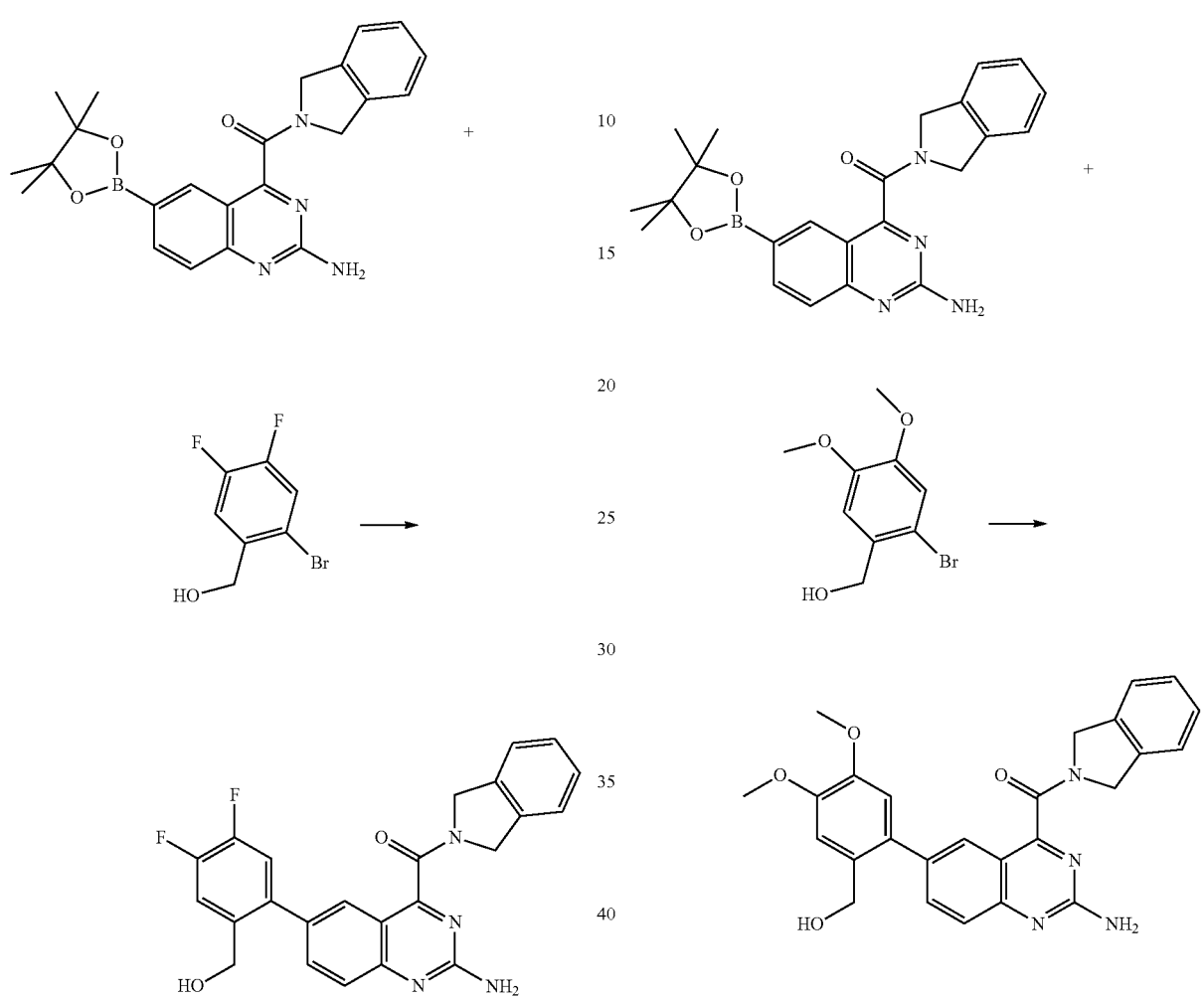

43 mg of (2-bromo-4,5-difluorophenyl)methanol, 80 mg of potassium carbonate, 4 μl of water and 16 mg of [1,1'-bis(diphenylphosphino)ferrocene]palladium(II) dichloride are added to a solution of 100 mg of [2-amino-6-(4,4,5,5-tetramethyl-1,3,2-dioxaborolan-2-yl)quinazolin-4-yl]-(1,3-dihydroisoindol-2-yl)methanone in 10 ml of ethanol under argon. The mixture is heated at 120° C. for 30 min; during which a precipitate forms. After cooling to 22° C., 10 ml of water are added, and the precipitate is filtered off. The residue is washed 3 times with 25 ml of ethanol each time and dried at 40° C. in vacuo.

Yield: 52 mg (63%) of [2-amino-6-[4,5-difluoro-2-(hydroxymethyl)phenyl]quinazolin-4-yl]isoindolin-2-ylmethanone; HPLC retention time: 1.98 min;

$^1$H NMR (500 MHz, DMSO-$d_6$/TFA-$d_1$) δ [ppm] 8.09-8.04 (m, 2H), 7.83-7.79 (m, 1H), 7.52 (dd, J=11.8, 8.3, 1H), 7.41 (d, J=7.3, 1H), 7.37 (dd, J=11.1, 8.0, 1H), 7.30 (dt, J=14.9, 7.0, 2H), 7.23 (d, J=7.3, 1H), 4.99 (s, 2H), 4.82 (s, 2H), 4.31 (s, 2H).

48 mg of (2-bromo-4,5-dimethoxyphenyl)methanol, 80 mg of potassium carbonate, 7 μl of water and 8 mg of [1,1'-bis(diphenylphosphino)ferrocene]palladium(II) dichloride are added to a solution of 100 mg of [2-amino-6-(4,4,5,5-tetramethyl-1,3,2-dioxaborolan-2-yl)quinazolin-4-yl]-(1,3-dihydroisoindol-2-yl)methanone in 10 ml of ethanol under argon. The mixture is heated at 120° C. for 30 min. The solid is filtered off through kieselguhr with suction, and the filtrate is evaporated to dryness in vacuo. The residue is dissolved in 1 ml of DMSO and chromatographed by means of prep. HPLC (Agilent). The product fractions obtained are subsequently evaporated and freeze-dried.

Yield: 54 mg (62%) of [2-amino-6-[2-(hydroxymethyl)-4,5-dimethoxyphenyl]-quinazolin-4-yl]isoindolin-2-ylmethanone; HPLC retention time: 1.71 min;

$^1$H NMR (500 MHz, DMSO-$d_6$/TFA-$d_1$) δ [ppm] 8.13 (dd, J=8.6, 1.8, 1H), 8.11 (s, 1H), 7.83 (d, J=8.6, 1H), 7.45 (d, J=7.3, 1H), 7.33 (dt, J=18.7, 7.2, 2H), 7.26 (d, J=7.3, 1H), 7.15 (s, 1H), 6.86 (s, 1H), 5.02 (s, 2H), 4.84 (s, 2H), 4.30 (s, 2H), 3.82 (s, 3H), 3.77 (s, 3H).

[2-Amino-6-[2-(2-dimethylaminoethoxymethyl)-4,5-difluorophenyl]quinazolin-4-yl]isoindolin-2-yl-methanone ("A8")

a)

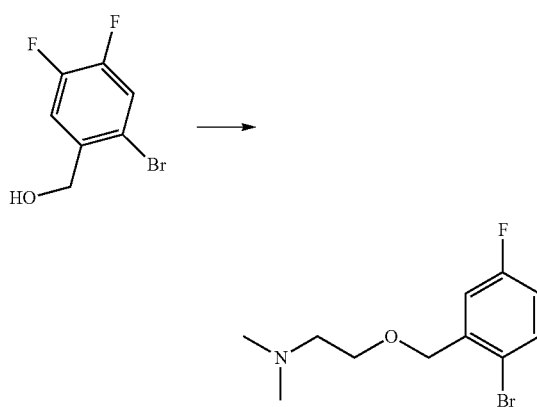

2 ml of sodium hydroxide solution (32%) and 5 mg of tetrabutylammonium iodide are added to a solution of 100 mg of (2-bromo-4,5-difluorophenyl)methanol and 78 mg of (2-chloroethyl)dimethylamine hydrochloride in 3 ml of tetrahydrofuran. The mixture is stirred at 80° C. for 14 h and cooled to 22° C. The mixture is washed 3 times with 5 ml of ethyl acetate, dried over sodium sulfate, the solid is filtered off, and the filtrate is evaporated to dryness in vacuo. The oil obtained is employed in the next step without further purification.

Yield: 102 mg (77%) of [2-(2-bromo-4,5-difluorobenzyloxy)ethyl]dimethylamine; HPLC retention time: 1.29 min b)

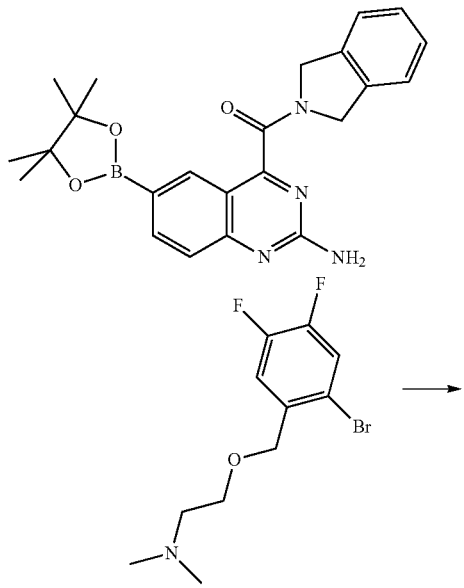

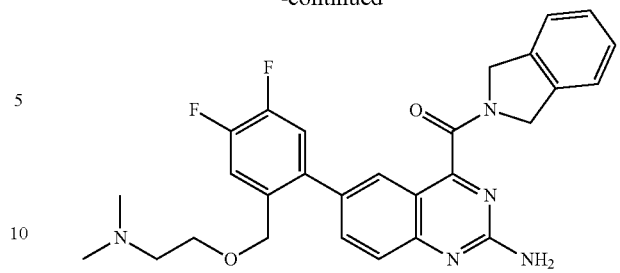

85 mg of [2-(2-bromo-4,5-difluorobenzyloxy)ethyl]dimethylamine, 80 mg of potassium carbonate, 5 µl of water and 12 mg of [1,1'-bis(diphenylphosphino)ferrocene]palladium (II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 2 ml of ethanol under argon. The mixture is heated at 120° C. for 60 min. The solid is subsequently filtered off through kieselguhr with suction, and the filtrate is evaporated to dryness in vacuo. The residue is dissolved in 1 ml of DMSO and chromatographed by means of preparative HPLC (Agilent). The product fractions obtained were subsequently evaporated and freeze-dried.

Yield: 54 mg (62%) of [2-amino-6-[2-(2-dimethylamino-ethoxymethyl)-4,5-difluorophenyl]quinazolin-4-yl]isoindolin-2-ylmethanone; HPLC retention time: 1.67 min;

$^1$H NMR (500 MHz, DMSO-$d_6$/TFA-$d_1$) δ [ppm] 8.08 (dd, J=6.4, 2.0, 2H), 7.88-7.83 (m, 1H), 7.70 (dd, J=11.4, 8.6, 1H), 7.46 (dd, J=11.1, 8.3, 2H), 7.34 (dt, J=19.3, 6.9, 2H), 7.26 (d, J=7.3, 1H), 5.04 (s, 2H), 4.85 (s, 2H), 4.38 (s, 2H), 3.67-3.60 (m, 2H), 3.33-3.25 (m, 2H), 2.80 (s, 6H).

[2-Amino-6-[2-(3-dimethylaminopropoxymethyl)-4,5-difluorophenyl]quinazolin-4-yl]isoindolin-2-yl-methanone ("A9")

a)

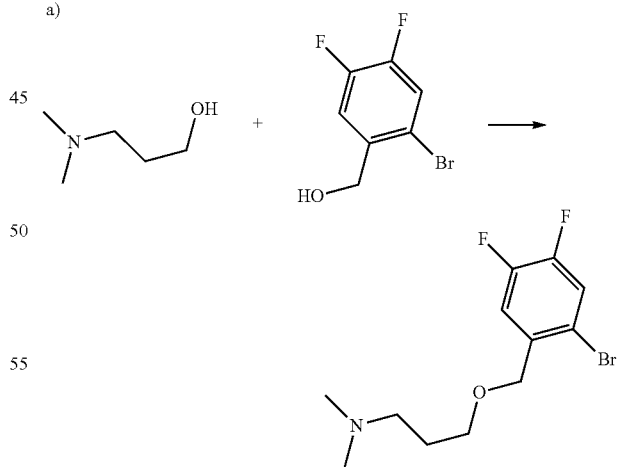

4 ml of sodium hydroxide solution (32%) and 5 mg of tetrabutylammonium iodide are added to a solution of 200 mg of (2-bromo-4,5-difluorophenyl)methanol and 170 mg of (3-chloropropyl)dimethylamine hydrochloride in 4 ml of tetrahydrofuran. The mixture is stirred at 80° C. for 14 h and cooled to 22° C. The mixture is washed 3 times with 5 ml of ethyl acetate, dried over sodium sulfate, the solid is filtered off, and the filtrate is evaporated to dryness in vacuo. the oil obtained is employed in the next step without further purification.

Yield: 230 mg (83%) of [2-(2-bromo-4,5-difluorobenzyloxy)ethyl]dimethylamine; HPLC retention time: 1.32 min b)

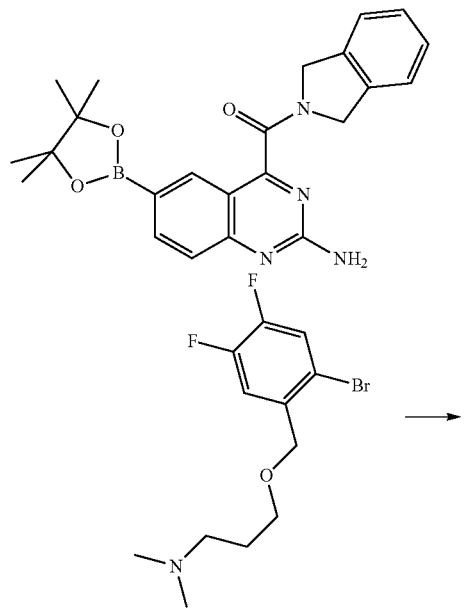

88 mg of [3-(2-bromo-4,5-difluorobenzyloxy)propyl]dimethylamine, 80 mg of potassium carbonate, 5 μl of water and 12 mg of [1,1'-bis(diphenylphosphino)ferrocene]palladium (II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 2 ml of ethanol under argon. The mixture is heated at 120° C. for 60 min. The solid is subsequently filtered off through kieselguhr with suction, and the filtrate is evaporated to dryness in vacuo. The residue is dissolved in 1 ml of DMSO and chromatographed by means of preparative HPLC (Agilent). The product fractions obtained are subsequently evaporated and freeze-dried.

Yield: 54 mg (62%) of [2-amino-6-[2-(2-dimethylaminoethoxymethyl)-4,5-difluorophenyl]quinazolin-4-yl]isoindolin-2-ylmethanone; HPLC retention time: 1.67 min;

$^1$H NMR (500 MHz, DMSO-$d_6$/TFA-$d_1$) δ [ppm] 8.07 (s, 2H), 7.86 (d, J=7.7, 1H), 7.58 (s, 1H), 7.45 (s, 2H), 7.40-7.29 (m, 2H), 7.27 (s, 1H), 5.04 (s, 2H), 4.87 (s, 2H), 4.32 (s, 2H), 3.37 (t, 2H), 3.07 (t, 2H), 2.80 (s, 6H), 1.86 (m, 2H).

Synthesis of Benzylamines Via Reductive Amination

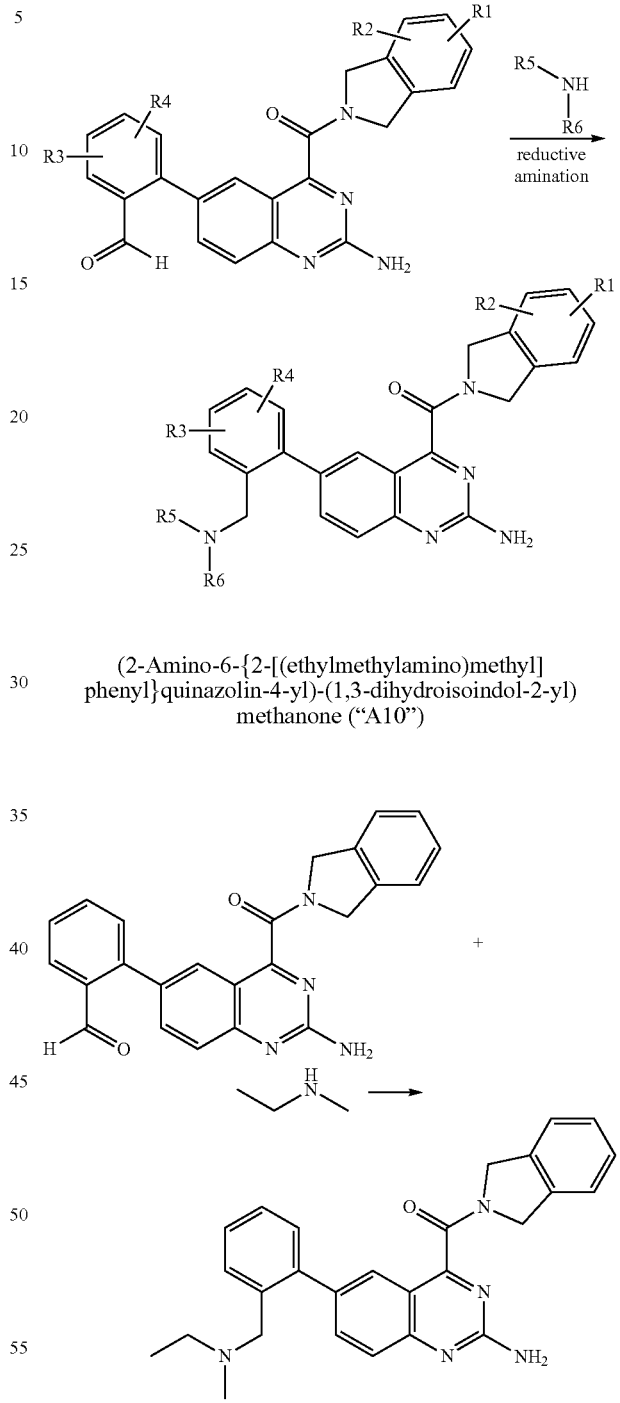

(2-Amino-6-{2-[(ethylmethylamino)methyl]phenyl}quinazolin-4-yl)-(1,3-dihydroisoindol-2-yl)methanone ("A10")

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 44 μl of methylethylamine and 15 μl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 36 mg (33%) of (2-amino-6-{2-[(ethylmethylamino)methyl]phenyl}quinazolin-4-yl)-(1,3-dihydroisoindol-2-yl)methanone;

LC-MS retention time: 1.41 min;

$^1$H NMR (500 MHz, DMSO-d$_6$/TFA-d$_1$) δ [ppm] 8.101 (s, 1H), 8.050 (d, 1H), 7.888 (d, 1H), 7.708-7.554 (m, 1H), 7.574-7.507 (m, 2H), 7.442-7.424 (m, 2H), 7.347 (t, 1H), 7.285 (t, 1H), 7.296 (d, 1H), 5.028 (s, 2H), 4.356-4.163 (m, 2H), 3.056-2.794 (m, 2H), 2.508 (s, 3H), 0.992 (t, 3H).

(2-Amino-6-{2-[(ethylmethylamino)methyl]-5-fluorophenyl}quinazolin-4-yl)-(1,3-dihydroisoindol-2-yl)methanone ("A11")

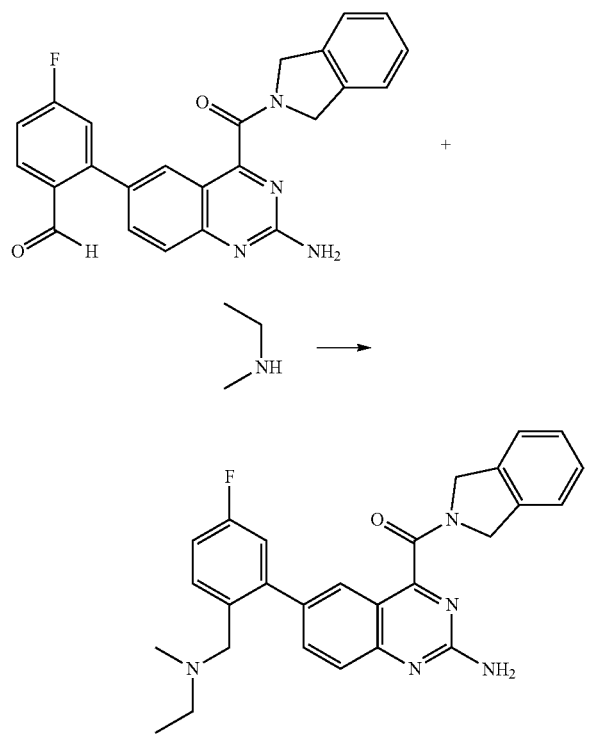

114 mg of 2-[2-amino-4-(1,3-dihydroisoindole-2-carbonyl)quinazolin-6-yl]-4-fluorobenzaldehyde are dissolved in 2 ml of 1,2-dichloroethane and 2 ml of tetrahydrofuran. 48 µl of methylethylamine and 32 µl of glacial acetic acid are added, and the mixture is stirred at 60° C. for 6 h. After cooling to 25° C., 185 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 24 mg (19%) of (2-amino-6-{2-[(ethylmethylamino)methyl]-5-fluorophenyl}quinazolin-4-yl)-(1,3-dihydroisoindol-2-yl)methanone;

LC-MS retention time: 1.53 min;

$^1$H NMR (500 MHz, DMSO-d$_6$/TFA-d$_1$) δ [ppm] 8.12 (d, J=1.8, 1H), 8.06 (dd, J=1.9, 8.6, 1H), 7.89 (d, J=8.7, 1H), 7.81 (dd, J=5.7, 8.7, 1H), 7.43 (dd, J=4.5, 12.7, 2H), 7.38-7.28 (m, 3H), 7.25 (d, J=7.3, 1H), 5.03 (s, 2H), 4.84 (s, 2H), 4.23 (dd, J=13.7, 82.8, 2H), 3.01 (dq, J=7.2, 14.5, 1H), 2.90-2.73 (m, 1H), 2.49 (s, 3H), 0.98 (t, J=7.3, 3H).

[2-Amino-6-(2-diethylaminomethylphenyl)quinazolin-4-yl]-(1,3-dihydroisoindol-2-yl)methanone ("A12")

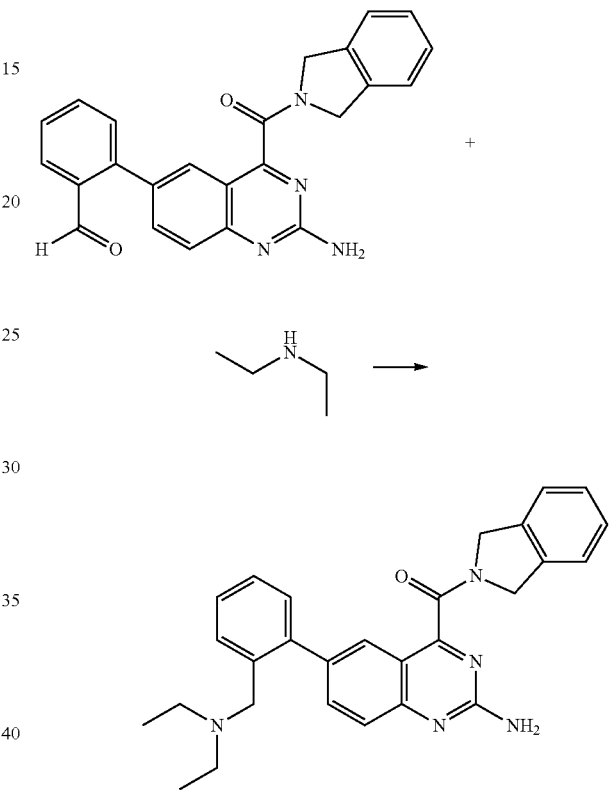

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 54 µl of diethylamine and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 30 mg (26%) of [2-amino-6-(2-diethylaminomethylphenyl)quinazolin-4-yl]-(1,3-dihydroisoindol-2-yl)methanone;

LC-MS retention time: 1.43 min;

$^1$H NMR (500 MHz, DMSO-d$_6$/TFA-d$_1$) δ [ppm] 8.084 (s, 1H), 8.010 (d, 1H), 7.851 (d, 1H), 7.729-7.710 (m, 1H), 7.551-7.503 (m, 2H), 7383 (d, 2H), 7.292 (t, 1H), 7.254 (t, 1H), 7.192 (d, 1H), 4.989 (s, 2H), 4.806 (s, 2H), 4.218 (s, 2H), 2.963-2.892 (m, 2H), 2.855-2.785 (m, 2H), 0.904 (t, 6H).

87

[2-Amino-6-(2-{[(2-hydroxyethyl)methylamino]methyl}phenyl)quinazolin-4-yl]-(1,3-dihydroisoindol-2-yl)methanone ("A13")

88

[2-Amino-6-(2-{[(2-hydroxyethyl)ethylamino]methyl}phenyl)quinazolin-4-yl]-(1,3-dihydroisoindol-2-yl)methanone ("A14")

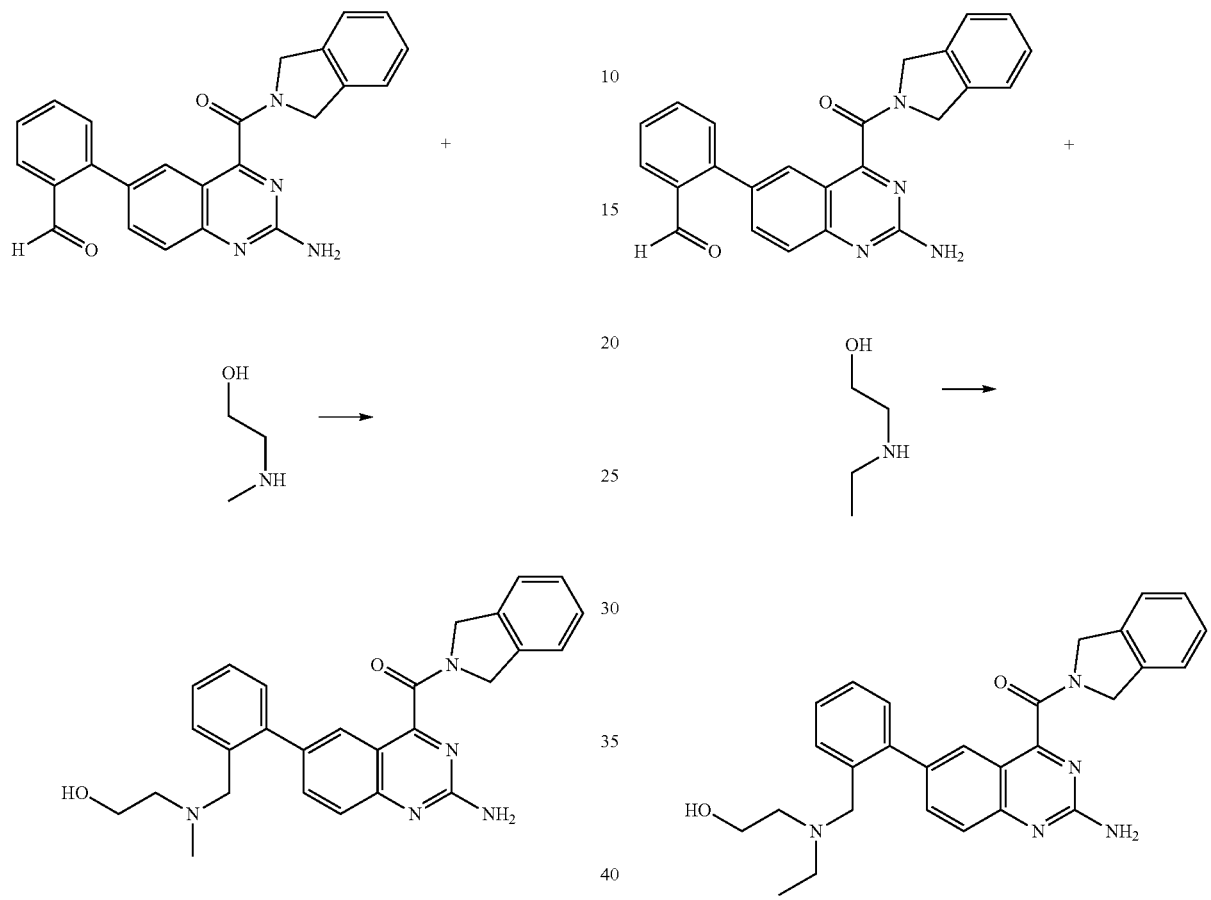

200 mg of 2-[2-amino-4-(1,3-dihydroisoindole-2-carbonyl)quinazolin-6-yl]benzaldehyde are dissolved in 10 ml of 1,2-dichloroethane and 10 ml of tetrahydrofuran. 85 μl of 2-(methylamino)ethanol and 29 μl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 90 mg (39%) of [[2-amino-6-(2-{[(2-hydroxyethyl)methylamino]methyl}-phenyl)quinazolin-4-yl]-(1,3-dihydroisoindol-2-yl)methanone;

LC-MS retention time: 1.37 min;

$^1$H NMR (500 MHz, DMSO-$d_6$/TFA-$d_1$) δ [ppm] 8.070 (s, 1H), 8.039 (d, 1H), 7.863 (d, 1H), 7.778 (d, 1H), 7.537-7.550 (m, 2H), 7.430 (t, 2H), 7.347 (t, 1H), 7.310 (t, 1H), 7.248 (d, 1H), 5.014 (s, 2H), 4.835 (s, 2H), 4.389-4.240 (m, 2H), 3.518 (s, 2H), 3.000-2.863 (m, 2H), 2.579 (s, 3H).

200 mg of 2-[2-amino-4-(1,3-dihydroisoindole-2-carbonyl)quinazolin-6-yl]benzaldehyde are dissolved in 10 ml of 1,2-dichloroethane and 10 ml of tetrahydrofuran. 99 μl of 2-(ethylamino)ethanol and 29 μl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 52 mg (22%) of [2-amino-6-(2-{[(2-hydroxyethyl)ethylamino]methyl}-phenyl)quinazolin-4-yl]-(1,3-dihydroisoindol-2-yl)methanone;

$^1$H NMR (500 MHz, DMSO-$d_6$/TFA-$d_1$) δ [ppm] 8.123 (s, 1H), 8.064 (d, 1H), 7.895 (d, 1H), 7.819 (d, 1H), 7.605-7.550 (m, 2H), 7.447-7.452 (m, 2H), 7.349 (t, 1H), 7.311 (t, 1H), 7.250 (d, 1H), 5.038 (s, 2H), 4.854 (s, 2H), 4.362 (d, 2H), 3.549 (s, 2H), 3.019-2.957 (m, 4H), 0.981 (t, 3H).

89

[2-Amino-6-(2-{[ethyl-(2-hydroxyethyl)amino]methyl}-5-fluorophenyl)quinazolin-4-yl]-(1,3-dihydroisoindol-2-yl)methanone ("A15")

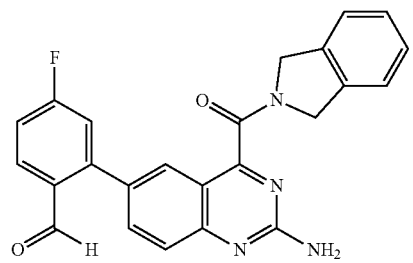

+

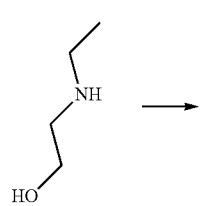

→

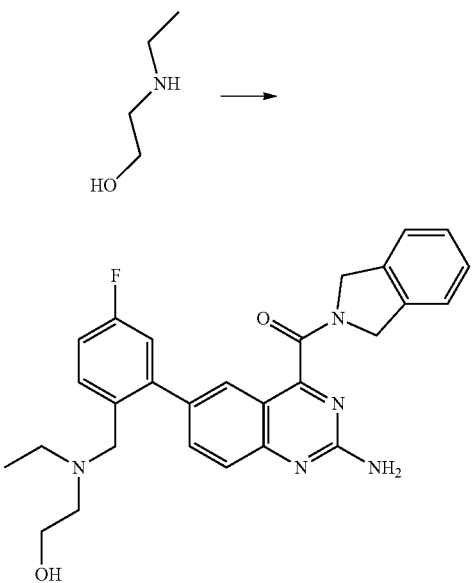

114 mg of 2-[2-amino-4-(1,3-dihydroisoindole-2-carbonyl)quinazolin-6-yl]-4-fluorobenzaldehyde are dissolved in 2 ml of 1,2-dichloroethane and 2 ml of tetrahydrofuran. 57 µl of 2-(ethylamino)ethanol and 28 µl of glacial acetic acid are added, and the mixture is stirred at 60° C. for 6 h. After cooling to 25° C., 216 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 35 mg (21%) of [2-amino-6-(2-{[ethyl-(2-hydroxyethyl)amino]methyl}-5-fluorophenyl)quinazolin-4-yl]-(1,3-dihydroisoindol-2-yl)methanone LC-MS retention time: 1.52 min;

$^1$H NMR (500 MHz, DMSO-$d_6$/TFA-$d_1$) δ [ppm] 8.15 (d, J=1.7, 1H), 8.07 (dd, J=1.9, 8.7, 1H), 7.92-7.85 (m, 2H), 7.47-7.39 (m, 2H), 7.38-7.27 (m, 3H), 7.25 (d, J=7.3, 1H), 5.04 (s, 2H), 4.86 (s, 2H), 4.33 (d, J=18.5, 2H), 3.53 (s, 2H), 3.09-2.86 (m, 4H), 0.97 (t, J=7.2, 3H).

90

[2-Amino-6-(2-{[ethyl-(2-hydroxyethyl)amino]methyl}-4-fluorophenyl)quinazolin-4-yl]-(1,3-dihydroisoindol-2-yl)methanone ("A16")

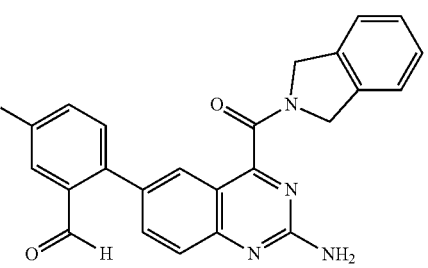

+

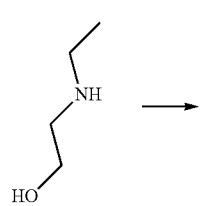

→

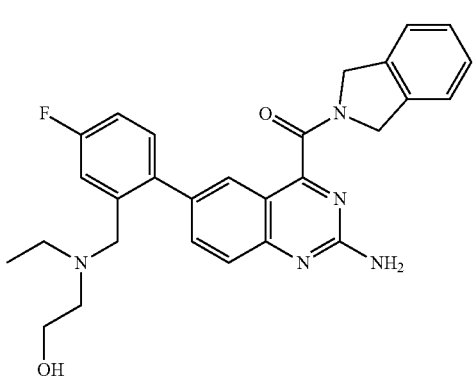

114 mg of 2-[2-amino-4-(1,3-dihydroisoindole-2-carbonyl)quinazolin-6-yl]-5-fluorobenzaldehyde are dissolved in 2 ml of 1,2-dichloroethane and 2 ml of tetrahydrofuran. 57 µl of 2-(ethylamino)ethanol and 28 µl of glacial acetic acid are added, and the mixture is stirred at 60° C. for 6 h. After cooling to 25° C., 216 mg of sodium triacetoxyborohydride are added, and the mixture is stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 53 mg (23%) of [2-amino-6-(2-{[ethyl-(2-hydroxyethyl)amino]methyl}-4-fluorophenyl)quinazolin-4-yl]-(1,3-dihydroisoindol-2-yl)methanone LC-MS retention time: 1.50 min.

91

[2-Amino-6-(2-{[bis-(2-hydroxyethyl)amino]methyl}phenyl)quinazolin-4-yl]-(1,3-dihydroisoindol-2-yl)methanone ("A17")

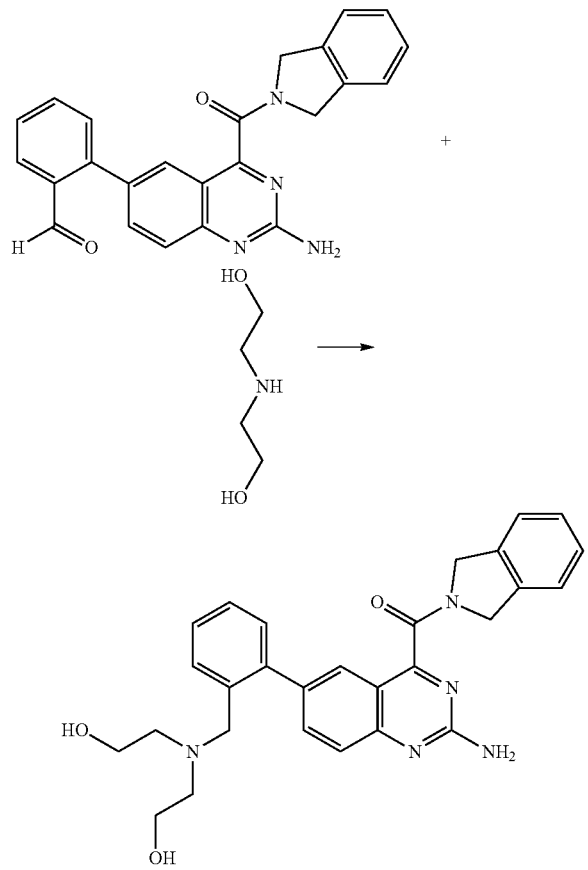

100 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 35 µl of diethanolamine and 20 µl of glacial acetic acid are added, and the mixture is stirred at 60° C. for 6 h. After cooling to 25° C., 113 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 61 mg (50%) of [2-amino-6-(2-{[bis-(2-hydroxyethyl)amino]methyl}-phenyl)quinazolin-4-yl]-(1,3-dihydroisoindol-2-yl)methanone;

LC-MS retention time: 1.42 min;

$^1$H NMR (500 MHz, DMSO-d$_6$/TFA-d$_1$) δ [ppm] 8.07 (s, 1H), 8.00 (d, J=8.6, 1H), 7.83 (d, J=8.6, 1H), 7.79-7.73 (m, 1H), 7.56-7.49 (m, 2H), 7.38 (d, J=6.0, 2H), 7.33-7.22 (m, 2H), 7.20 (d, J=7.4, 1H), 4.98 (s, 2H), 4.80 (s, 2H), 4.45 (s, 2H), 3.47 (bs, 4H), 3.02 (bs, 4H).

92

{2-Amino-6-[2-(tert-butylaminomethyl)phenyl]quinazolin-4-yl}-(1,3-dihydroisoindol-2-yl)methanone ("A18")

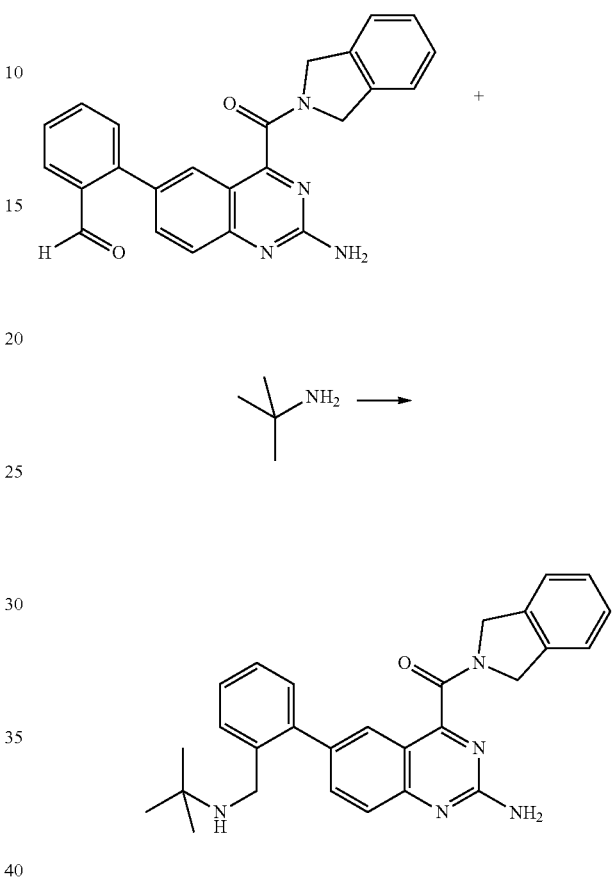

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 55 µl of tert-butylamine and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 25 mg (22%) of {2-amino-6-[2-(tert-butylaminomethyl)phenyl]quinazolin-4-yl}-(1,3-dihydroisoindol-2-yl)methanone;

LC-MS retention time: 1.43 min;

$^1$H NMR (500 MHz, DMSO-d$_6$/TFA-d$_1$) δ [ppm] 8.070 (s, 1H), 8.038 (d, 1H), 7.843 (d, 1H), 7.736 (d, 1H), 7.574-7.507 (m, 2H), 7426 (d, 1H), 7.373 (d, 1H), 7.323 (t, 1H), 7.285 (t, 1H), 7.215 (d, 1H), 5.004 (s, 2H), 4.792 (s, 2H), 3.980 (s, 2H), 1.036 (s, 9H).

93

{2-Amino-6-[2-(tert-butylaminomethyl)-4-fluorophenyl]quinazolin-4-yl}-(1,3-dihydroisoindol-2-yl)methanone ("A19")

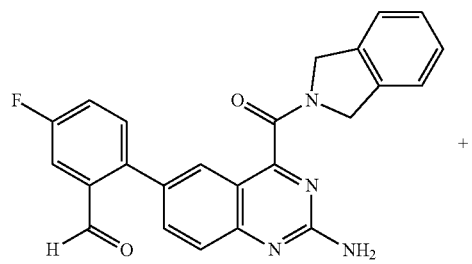

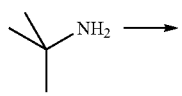

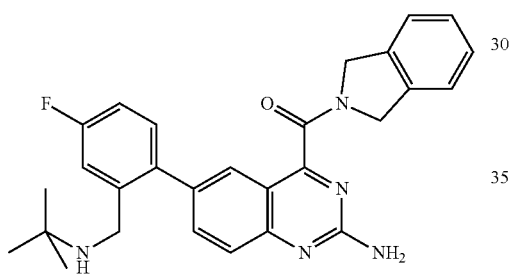

95 mg of 2-[2-amino-4-(1,3-dihydroisoindole-2-carbonyl)quinazolin-6-yl]-5-fluorobenzaldehyde are dissolved in 2 ml of 1,2-dichloroethane and 2 ml of tetrahydrofuran. 34 µl of tert-butylamine and 18 µl of glacial acetic acid are added, and the mixture is stirred at 60° C. for 6 h. After cooling to 25° C., 103 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 15 mg (14%) of {2-amino-6-[2-(tert-butylaminomethyl)-4-fluorophenyl]-quinazolin-4-yl}-(1,3-dihydroisoindol-2-yl)methanone;

LC-MS retention time: 2.18 min ("polar" gradient);

$^1$H NMR (400 MHz, DMSO-$d_6$/TFA-$d_1$) δ [ppm] 8.06 (t, J=2.2, 1H), 7.98 (dd, J=1.9, 8.7, 1H), 7.82 (d, J=8.7, 1H), 7.59 (dd, J=2.6, 9.9, 1H), 7.39 (dd, J=6.1, 8.5, 2H), 7.33-7.21 (m, 3H), 7.17 (d, J=7.3, 1H), 4.99 (s, 2H), 4.77 (s, 2H), 4.02-3.86 (m, 2H), 1.02 (s, 9H).

94

{2-Amino-6-[2-(tert-butylaminomethyl)-5-fluorophenyl]quinazolin-4-yl}-(1,3-dihydroisoindol-2-yl)methanone ("A20")

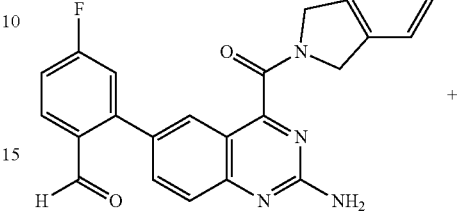

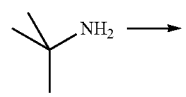

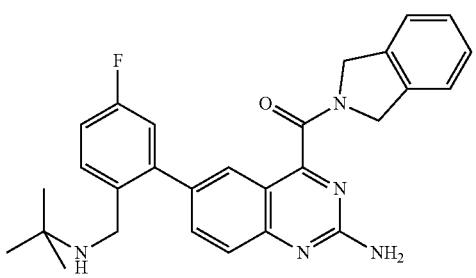

150 mg of 2-[2-amino-4-(1,3-dihydroisoindole-2-carbonyl)quinazolin-6-yl]-4-fluorobenzaldehyde are dissolved in 2 ml of 1,2-dichloroethane and 2 ml of tetrahydrofuran. 53 µl of tert-butylamine and 40 µl of glacial acetic acid are added, and the mixture is stirred at 60° C. for 6 h. After cooling to 25° C., 161 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 44 mg (26%) of {2-amino-6-[2-(tert-butylaminomethyl)-5-fluorophenyl]-quinazolin-4-yl}-(1,3-dihydroisoindol-2-yl)methanone;

LC-MS retention time: 2.21 min ("polar" gradient);

$^1$H NMR (500 MHz, DMSO-$d_6$/TFA-$d_1$) δ [ppm] 8.13 (d, 1H), 8.08 (dd, J=1.9, 8.6, 1H), 7.87 (d, J=8.6, 1H), 7.83 (dd, J=5.8, 8.7, 1H), 7.49-7.40 (m, 2H), 7.38-7.26 (m, 3H), 7.24 (d, J=7.4, 1H), 5.03 (s, 2H), 4.82 (s, 2H), 3.98 (s, 2H), 1.06 (s, 9H).

95

{2-Amino-6-[6-(tert-butylaminomethyl)benzo-1,3-dioxol-5-yl]quinazolin-4-yl}-(1,3-dihydroisoindol-2-yl)methanone ("A21")

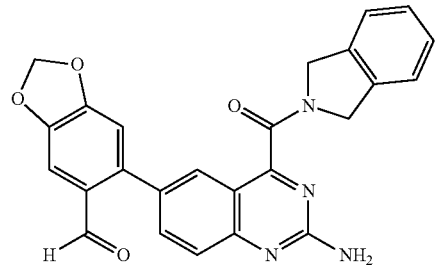

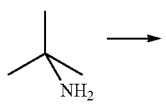

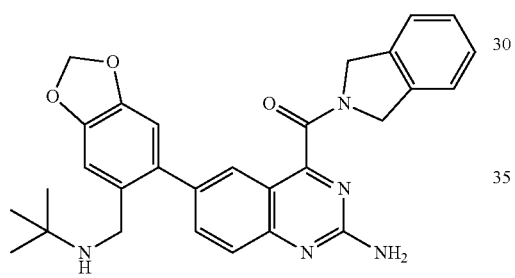

100 mg of 6-[2-amino-4-(1,3-dihydroisoindole-2-carbonyl)quinazolin-6-yl]-benzo-1,3-dioxole-5-carbaldehyde are dissolved in 2 ml of 1,2-dichloroethane and 2 ml of tetrahydrofuran. 30 µl of tert-butylamine and 13 µl of glacial acetic acid are added, and the mixture is stirred at 60° C. for 6 h. After cooling to 25° C., 102 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 50 mg (44%) of {2-amino-6-[6-(tert-butylaminomethyl)benzo-1,3-dioxol-5-yl]quinazolin-4-yl}-(1,3-dihydroisoindol-2-yl)methanone;

LC-MS retention time: 1.53 min;

$^1$H NMR (500 MHz, DMSO-$d_6$) δ [ppm] 8.10 (d, J=1.8, 1H), 8.03 (dd, J=1.9, 8.6, 1H), 7.87 (d, J=8.6, 1H), 7.45 (d, J=7.5, 1H), 7.24 (d, J=7.4, 1H), 6.95 (s, 1H), 6.12 (s, 2H), 5.06 (s, 2H), 4.84 (s, 2H), 3.90 (s, 2H), 1.06 (s, 9H).

96

2-{2-[2-Amino-4-(1,3-dihydroisoindole-2-carbonyl)quinazolin-6-yl]benzylamino}acetamide ("A22")

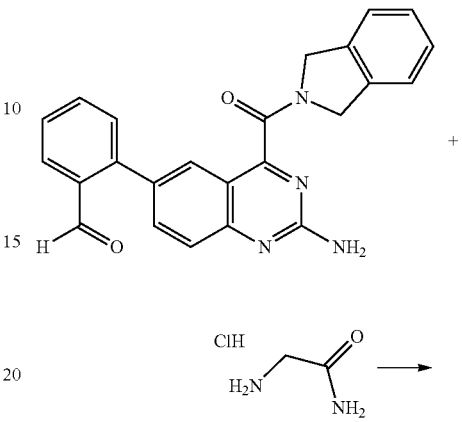

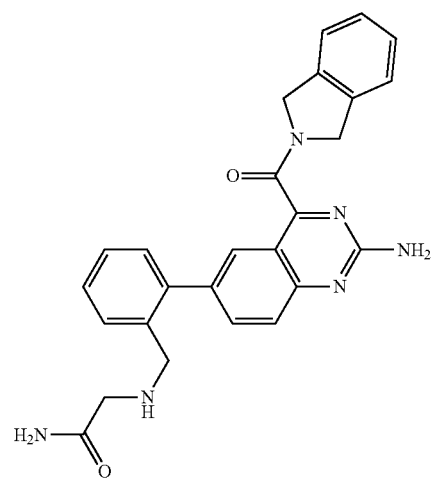

100 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 39 mg of aminoacetamide hydrochloride are added, and the mixture is stirred at 60° C. for 6 h. After cooling to 25° C., 113 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 13 mg (11%) of 2-{2-[2-amino-4-(1,3-dihydroisoindole-2-carbonyl)quinazolin-6-yl]benzylamino}acetamide; LC-MS retention time: 1.46 min;

$^1$H NMR (500 MHz, DMSO-$d_6$/TFA-$d_1$) δ [ppm] 8.08-8.03 (m, 2H), 7.83 (d, J=9.1, 1H), 7.75 (d, J=7.4, 1H), 7.56-7.47 (m, 2H), 7.39 (dd, J=7.3, 10.9, 2H), 7.34-7.25 (m, 2H), 7.24 (d, J=7.2, 1H), 4.99 (s, 2H), 4.84 (s, 2H), 4.10 (s, 2H), 3.56 (s, 2H).

97

[2-Amino-6-(2-cyclopropylaminomethylphenyl)quinazolin-4-yl]-(1,3-dihydroisoindol-2-yl)methanone ("A23")

98

[2-Amino-6-(2-cyclobutylaminomethylphenyl)quinazolin-4-yl]-(1,3-dihydroisoindol-2-yl)methanone ("A24")

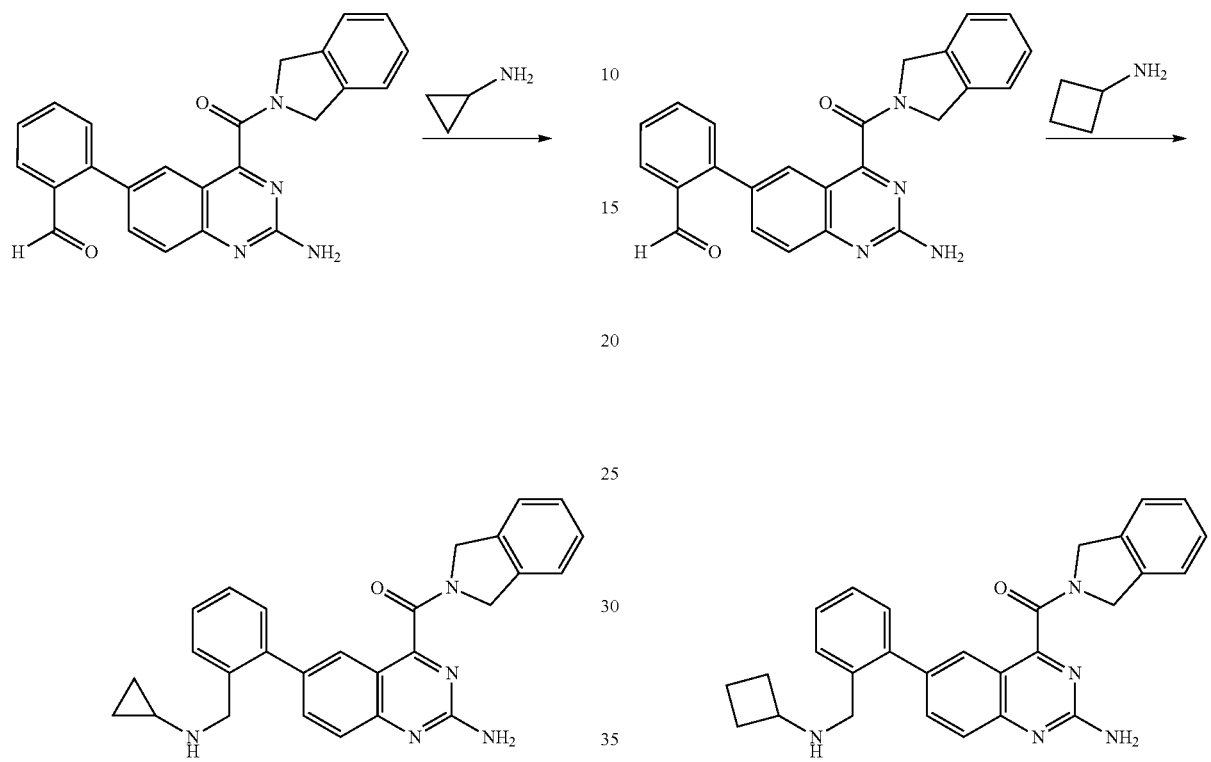

200 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 81 µl of cyclopropylamine and 35 µl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 62 mg (25%) of [2-amino-6-(2-cyclopropylaminomethylphenyl)quinazolin-4-yl]-(1,3-dihydroisoindol-2-yl)methanone;

LC-MS retention time: 2.12 min ("polar" gradient);

$^1$H NMR (500 MHz, DMSO-$d_6$/TFA-$d_1$) δ [ppm] 8.10 (d, J=1.6, 1H), 8.08 (dd, J=1.9, 8.6, 1H), 7.90 (d, J=8.6, 1H), 7.73-7.70 (m, 1H), 7.59-7.51 (m, 2H), 7.45 (d, J=7.4, 1H), 7.41 (dd, J=1.6, 7.3, 1H), 7.33 (dt, J=7.3, 20.3, 2H), 7.25 (d, J=7.4, 1H), 5.04 (s, 2H), 4.86 (s, 2H), 4.17 (s, 2H), 0.69-0.64 (m, 2H), 0.54 (q, J=7.0, 2H).

200 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 106 µl of cyclobutylamine and 35 µl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 60 mg (24%) of [2-amino-6-(2-cyclobutylaminomethylphenyl)quinazolin-4-yl]-(1,3-dihydroisoindol-2-yl)methanone;

LC-MS retention time: 2.17 min ("polar" gradient);

$^1$H NMR (500 MHz, DMSO-$d_6$/TFA-$d_1$) δ [ppm] 8.11 (d, J=1.6, 1H), 8.06 (dd, J=1.9, 8.6, 1H), 7.89 (d, J=8.6, 1H), 7.73-7.70 (m, 1H), 7.60-7.52 (m, 2H), 7.47-7.39 (m, 2H), 7.37-7.29 (m, 2H), 7.26 (d, J=7.3, 1H), 5.04 (s, 2H), 4.86 (s, 2H), 3.93 (s, 2H), 3.53 (p, J=8.1, 1H), 2.01-1.88 (m, 4H), 1.65-1.48 (m, 2H).

[2-Amino-6-(2-pyrrolidin-1-ylmethylphenyl) quinazolin-4-yl]-(1,3-dihydroisoindol-2-yl)methanone ("A25")

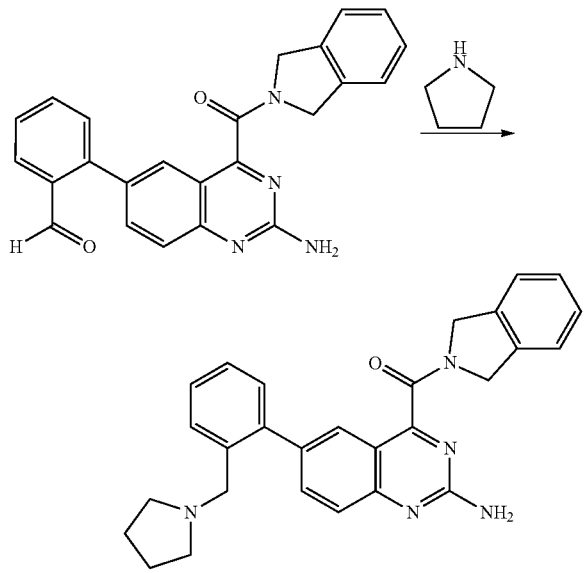

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 36 µl of pyrrolidine and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC). Yield: 30 mg (26%) of [2-amino-6-(2-pyrrolidin-1-ylmethylphenyl)quinazolin-4-yl]-(1,3-dihydroisoindol-2-yl)methanone; LC-MS retention time: 1.45 min;

$^1$H NMR (500 MHz, DMSO-d$_6$/TFA-d$_1$) δ [ppm] 8.071 (s, 1H), 8.004 (d, 1H), 7.855 (d, 1H), 7.716 (d, 1H), 7.547-7.498 (m, 2H), 7404-7.377 (m, 2H), 7.303 (t, 1H), 7.264 (t, 1H), 7.205 (d, 1H), 4.988 (s, 2H), 4.803 (s, 2H), 4.274 (s, 2H), 3.360 (s, 2H), 2.798 (bs, 2H), 1.750 (m, 4H).

{2-Amino-6-[2-(2-methylpyrrolidin-1-ylmethyl) phenyl]quinazolin-4-yl}-(1,3-dihydroisoindol-2-yl)methanone ("A26")

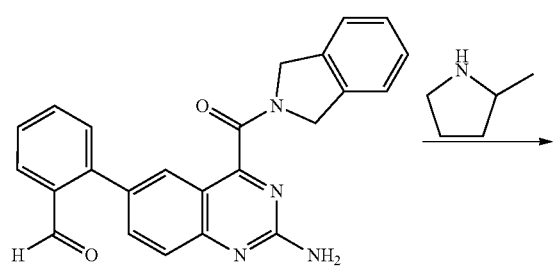

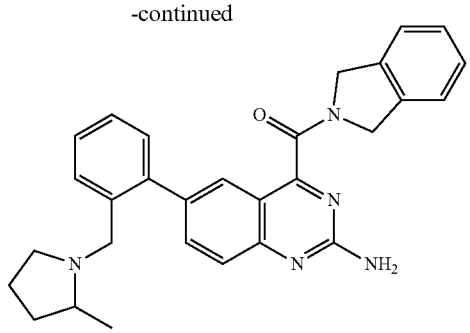

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 56 µl of 2-methylpyrrolidine and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 46 mg (39%) of {2-amino-6-[2-(2-methylpyrrolidin-1-ylmethyl)phenyl]-quinazolin-4-yl}-(1,3-dihydroisoindol-2-yl)methanone;

LC-MS retention time: 1.46 min;

$^1$H NMR (500 MHz, DMSO-d$_6$/TFA-d$_1$) δ [ppm] 8.062 (s, 1H), 8.036-8.015 (m, 1H), 7.871-7.846 (m, 1H), 7.735-7.699 (m, 1H), 7.555-7.502 (m, 2H), 7403-7.366 (m, 2H), 7.305 (t, 1H), 7.267 (t, 1H), 7.207 (d, 1H), 5.031 (m, 2H), 4.810 (s, 2H), 4.510-4.070 (m, 2H), 3.290-3.186 (m, 2H), 2.850-2.793 (m, 1H), 2.032-1.964 (m, 1H), 1.737-1.676 (m, 2H), 1.470-1.392 (m, 1H), 1.034-0.965 (m, 3H).

{2-Amino-6-[2-(2-hydroxymethylpyrrolidin-1-ylmethyl)phenyl]quinazolin-4-yl}-(1,3-dihydroisoindol-2-yl)methanone ("A27")

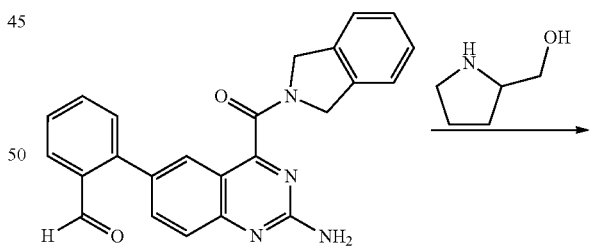

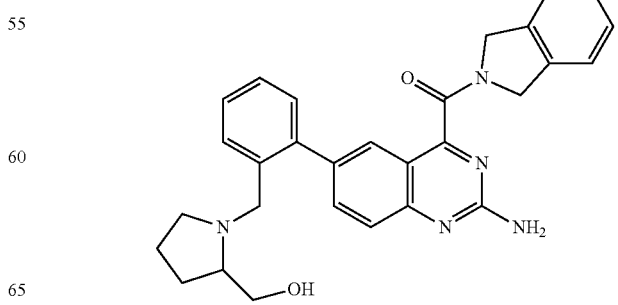

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 51 mg of pyrrolidin-2-ylmethanol and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 35 mg (29%) of {2-amino-6-[2-(2-hydroxymethylpyrrolidin-1-ylmethyl)phenyl]quinazolin-4-yl}-(1,3-dihydroisoindol-2-yl)methanone;

LC-MS retention time: 1.39 min;

$^1$H NMR (500 MHz, DMSO-$d_6$/TFA-$d_1$) δ [ppm] 8.070 (s, 1H), 8.012 (d, 1H), 7.855 (d, 1H), 7.735 (t, 1H), 7.555-7.507 (m, 2H), 7411-7.383 (m, 2H), 7.308 (t, 1H), 7.270 (t, 1H), 7.215 (d, 1H), 4.995 (s, 2H), 4.814 (s, 2H), 4.295 (d, 2H), 3.347-2.661 (m, 6H), 2.353-2.299 (m, 1H), 1.864-1.804 (m, 1H), 1.643-1.453 (m, 1H).

{2-Amino-6-[2-(3-hydroxypyrrolidin-1-ylmethyl)phenyl]quinazolin-4-yl}-(1,3-dihydroisoindol-2-yl)methanone ("A28")

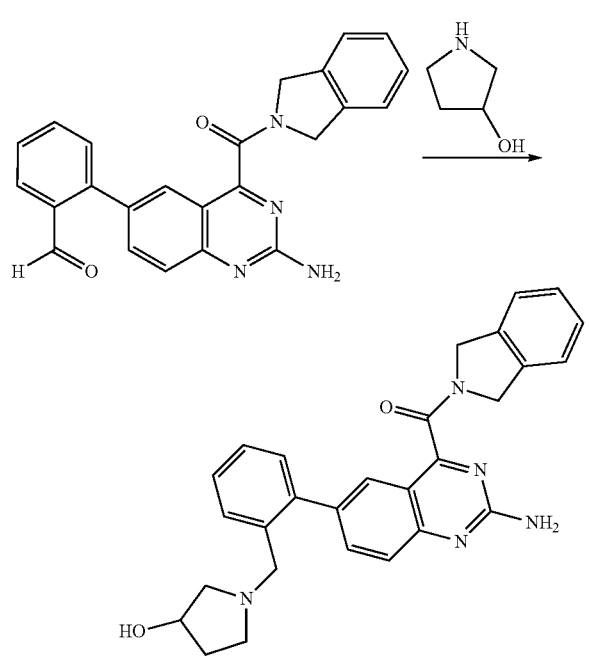

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 94 mg of pyrrolidin-3-ol and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 37 mg (31%) of {2-amino-6-[2-(3-hydroxypyrrolidin-1-ylmethyl)phenyl]-quinazolin-4-yl}-(1,3-dihydroisoindol-2-yl)methanone;

LC-MS retention time: 1.40 min;

$^1$H NMR (500 MHz, DMSO-$d_6$/TFA-$d_1$) δ [ppm] 8.067 (s, 1H), 8.025 (d, 1H), 7.848 (d, 1H), 7.792-7.728 (m, 1H), 7.567-7.507 (m, 2H), 7422-7.382 (m, 2H), 7.321 (t, 1H), 7.283 (t, 1H), 7.226 (d, 1H), 4.998 (s, 2H), 4.807 (s, 2H), 4.395-4.236 (m, 3H), 3.481-2.781 (m, 4H), 2.085-1.837 (m, 1H), 1.711-1.638 (m, 1H).

{2-Amino-6-[2-(3-aminopyrrolidin-1-ylmethyl)phenyl]quinazolin-4-yl}-(1,3-dihydroisoindol-2-yl)methanone ("A29")

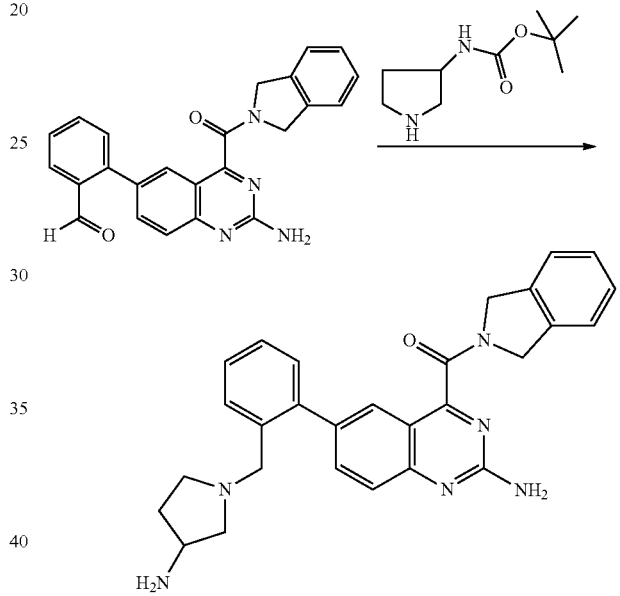

100 mg of 2-[2-amino-4-(1,3-dihydroisoindole-2-carbonyl)quinazolin-6-yl]benzaldehyde are dissolved in 2 ml of 1,2-dichloroethane and 2 ml of tetrahydrofuran. 94 mg of tert-butyl pyrrolidin-3-ylcarbamate and 15 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC). Yield: 60 mg (51%) of {2-amino-6-[2-(3-aminopyrrolidin-1-ylmethyl)phenyl]quinazolin-4-yl}-(1,3-dihydroisoindol-2-yl)methanone;

LC-MS retention time: 1.25 min;

$^1$H NMR (500 MHz, DMSO-$d_6$/TFA-$d_1$) δ [ppm] 8.074 (s, 1H), 8.030 (d, 1H), 7.855 (d, 1H), 7.740 (d, 1H), 7.575-7.526 (m, 2H), 7418-7.403 (m, 2H), 7.321 (t, 1H), 7.285 (t, 1H), 7.229 (d, 1H), 4.997 (s, 2H), 4.839 (s, 2H), 4.390-4.295 (m, 2H), 3.855 (bs, 1H), 3.554-2.873 (m, 4H), 2.207 (bs, 1H), 1.909 (bs, 1H).

{2-Amino-6-[2-(2,5-dimethylpyrrolidin-1-ylmethyl) phenyl]quinazolin-4-yl}-(1,3-dihydroisoindol-2-yl) methanone ("A30")

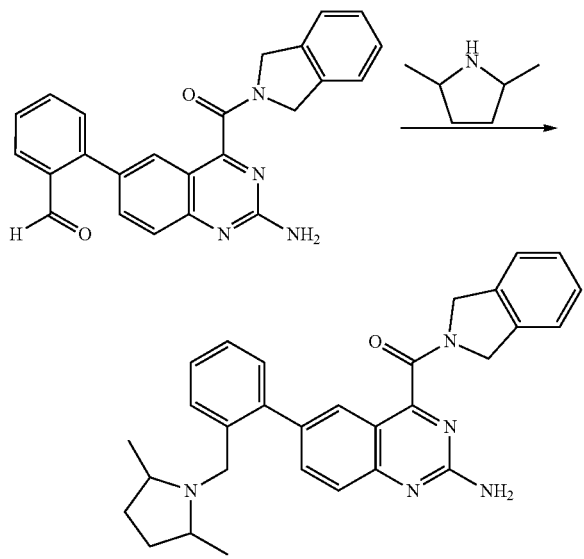

150 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 65 µl of 2,5-dimethylpyrrolidine and 22 µl of glacial acetic acid are added, and the mixture is stirred at 60° C. for 6 h. After cooling to 25° C., 170 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 92 mg (51%) of {2-amino-6-[2-(2,5-dimethylpyrrolidin-1-ylmethyl)phenyl]-quinazolin-4-yl}-(1,3-dihydroisoindol-2-yl)methanone;

LC-MS retention time: 2.15 min ("polar" gradient);

$^1$H NMR (500 MHz, DMSO-d$_6$/TFA-d$_1$) δ [ppm] 8.06-8.00 (m, 2H), 7.86 (dd, J=2.7, 9.1, 1H), 7.79-7.69 (m, 1H), 7.59-7.49 (m, 2H), 7.43-7.38 (m, 2H), 7.30 (dt, J=7.3, 17.9, 2H), 7.22 (dd, J=3.5, 7.2, 1H), 5.06-4.94 (m, 2H), 4.86-4.76 (m, 2H), 4.44-4.04 (m, 2H), 3.82-3.26 (m, 1H), 3.20 (dd, J=6.1, 12.4, 1H), 2.09-1.84 (m, 2H), 1.55-1.38 (m, 2H), 1.07-0.82 (m, 6H).

{2-Amino-6-[2-(3,3-difluoropyrrolidin-1-ylmethyl) phenyl]quinazolin-4-yl}-(1,3-dihydroisoindol-2-yl) methanone ("A31")

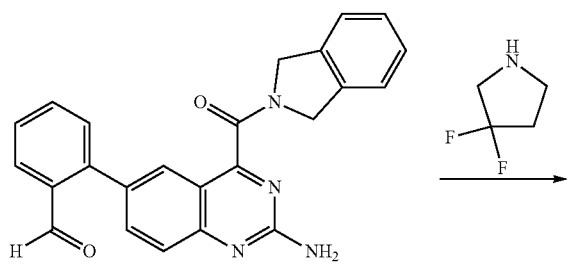

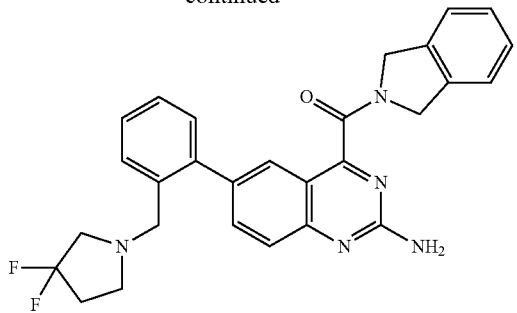

200 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 104 mg of 3,3-difluoropyrrolidine hydrochloride are added, and the mixture is stirred at 40° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 92 mg (51%) of {2-amino-6-[2-(3,3-difluoropyrrolidin-1-ylmethyl)phenyl]-quinazolin-4-yl}-(1,3-dihydroisoindol-2-yl)methanone;

LC-MS retention time: 2.39 min ("polar" gradient);

$^1$H NMR (500 MHz, DMSO-d$_6$/TFA-d$_1$) δ [ppm] 8.061 (d, 1H), 7.932 (dd, 1H), 7.812 (d, 1H), 7.693-7.674 (m, 1H), 7.477-7.459 (m, 2H), 7342-7.305 (m, 2H), 7.236 (t, 1H), 7.198 (t, 1H), 7.127 (d, 1H), 4.952 (s, 2H), 4.781 (s, 2H), 4.388 (s, 2H), 3.727 (t, 2H), 3.409 (t, 2H), 2.355 (dt, 2H).

{2-Amino-6-[2-((S)-3-fluoropyrrolidin-1-ylmethyl) phenyl]quinazolin-4-yl}-(1,3-dihydroisoindol-2-yl) methanone ("A32")

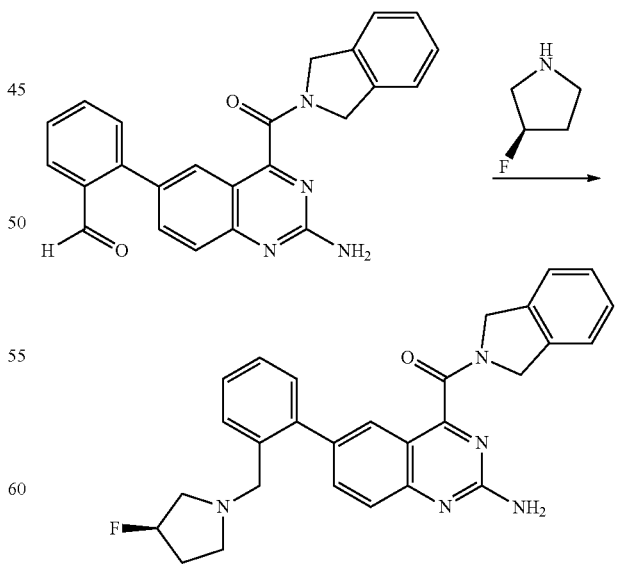

200 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 92 mg of (S)-(+)-3-fluoropyrrolidine hydrochloride are added, and the mixture is stirred at 40° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 70 mg (30%) of {2-amino-6-[2-((R)-3-fluoropyrrolidin-1-ylmethyl)phenyl]-quinazolin-4-yl}-(1,3-dihydroisoindol-2-yl)methanone;

LC-MS retention time: 1.57 min;

$^1$H NMR (500 MHz, DMSO-d$_6$/TFA-d$_1$) δ [ppm] 8.13 (s, 1H), 8.06 (dd, J=1.8, 8.6, 1H), 7.89 (d, J=8.6, 1H), 7.79 (d, J=6.4, 1H), 7.62-7.54 (m, 2H), 7.44 (d, J=7.1, 2H), 7.33 (dt, J=7.2, 18.1, 2H), 7.25 (d, J=7.4, 1H), 5.28 (d, J=53.4, 1H), 5.03 (s, 2H), 4.84 (s, 2H), 4.51-4.31 (m, 2H), 3.87-3.45 (m, 2H).

{2-Amino-6-[2-((S)-2-methylpyrrolidin-1-ylmethyl)phenyl]quinazolin-4-yl}-(1,3-dihydroisoindol-2-yl)methanone ("A33")

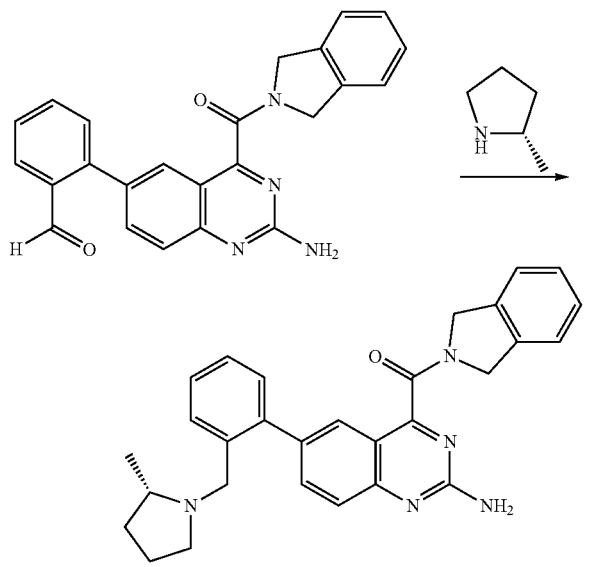

100 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 43 mg of (S)-2-methylpyrrolidine hydrochloride are added, and the mixture is stirred at 40° C. for 6 h. After cooling to 25° C., 113 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 62 mg (53%) of {2-amino-6-[2-((S)-2-methylpyrrolidin-1-ylmethyl)phenyl]quinazolin-4-yl}-(1,3-dihydroisoindol-2-yl)methanone;

LC-MS retention time: 1.50 min;

$^1$H NMR (500 MHz, DMSO-d$_6$/TFA-d$_1$) δ [ppm] 8.08-7.99 (m, 2H), 7.85 (d, J=8.6, 1H), 7.71 (d, J=6.6, 1H), 7.58-7.50 (m, 2H), 7.40 (t, J=7.0, 2H), 7.34-7.25 (m, 2H), 7.22 (d, J=7.4, 1H), 5.00 (d, J=4.9, 2H), 4.81 (s, 2H), 4.29 (dd, J=13.8, 207.4, 2H), 3.26 (s, 2H), 2.82 (d, J=11.4, 1H), 2.00 (d, J=6.5, 1H), 1.77-1.64 (m, 2H), 1.43 (s, 1H), 1.03 (d, J=6.4, 3H).

{2-Amino-6-[2-((R)-2-methylpyrrolidin-1-ylmethyl)phenyl]quinazolin-4-yl}-(1,3-dihydroisoindol-2-yl)methanone ("A34")

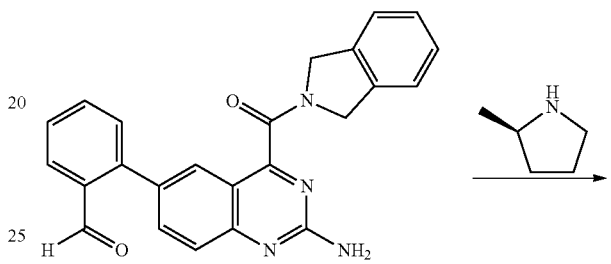

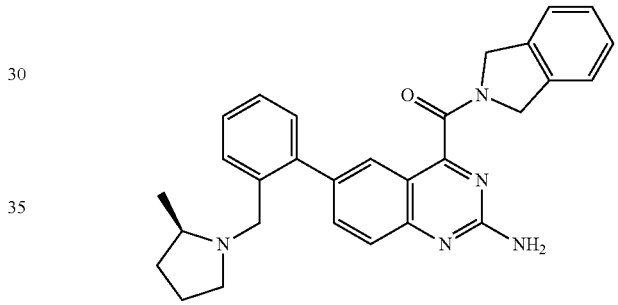

200 mg of 2-[2-amino-4-(1,3-dihydroisoindole-2-carbonyl)quinazolin-6-yl]benzaldehyde are dissolved in 3 ml of 1,2-dichloroethane and 3 ml of tetrahydrofuran. 71 µl of R-(−)-2-methylpyrrolidine and 41 µl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 81 mg (35%) of {2-amino-6-[2-((R)-2-methylpyrrolidin-1-ylmethyl)phenyl]quinazolin-4-yl}-(1,3-dihydroisoindol-2-yl)methanone;

LC-MS retention time: 1.61 min;

$^1$H NMR (500 MHz, DMSO-d$_6$/TFA-d$_1$) δ [ppm] 8.09-8.02 (m, 2H), 7.87 (dd, J=5.1, 8.5, 1H), 7.77-7.70 (m, 1H), 7.61-7.53 (m, 2H), 7.42 (ddd, J=5.9, 8.4, 10.3, 2H), 7.33 (dt, J=7.3, 18.1, 2H), 7.25 (d, J=7.4, 1H), 5.07-4.95 (m, 2H), 4.83 (s, 2H), 4.53 (d, J=13.8, 1H), 4.11 (d, J=13.9, 1H), 3.34-3.20 (m, 2H), 2.88-2.78 (m, 1H), 2.08 (dt, J=7.1, 13.7, 1H), 1.79-1.66 (m, 2H), 1.45 (dq, J=8.8, 13.1, 1H), 1.11-0.97 (m, 3H).

{2-Amino-6-[4-fluoro-2-(2-methylpyrrolidin-1-ylmethyl)phenyl]quinazolin-4-yl}-(1,3-dihydroisoindol-2-yl)methanone ("A35")

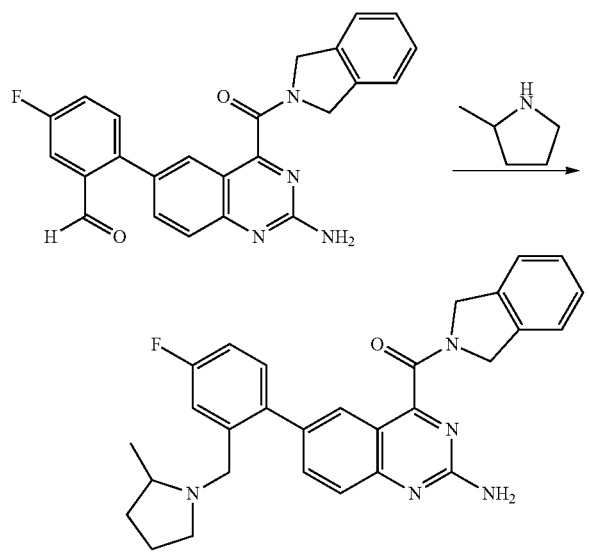

95 mg of 2-[2-amino-4-(1,3-dihydroisoindole-2-carbonyl)quinazolin-6-yl]-5-fluorobenzaldehyde are dissolved in 2 ml of 1,2-dichloroethane and 2 ml of tetrahydrofuran. 34 µl of 2-methylpyrrolidine and 18 µl of glacial acetic acid are added, and the mixture is stirred at 60° C. for 6 h. After cooling to 25° C., 103 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 20 mg (14%) of {2-amino-6-[4-fluoro-2-(2-methylpyrrolidin-1-ylmethyl)phenyl]quinazolin-4-yl}-(1,3-dihydroisoindol-2-yl)methanone;

LC-MS retention time: 2.19 min ("polar" gradient);

$^1$H NMR (500 MHz, DMSO-d$_6$/TFA-d$_1$) δ [ppm] 8.04 (d, J=1.6, 1H), 7.99 (dd, J=1.8, 8.6, 1H), 7.85 (d, J=8.6, 1H), 7.63-7.56 (m, 1H), 7.43 (dd, J=5.9, 8.6, 1H), 7.39 (d, J=7.4, 1H), 7.36-7.23 (m, 4H), 7.20 (d, J=7.4, 1H), 5.06-4.92 (m, 2H), 4.86-4.74 (m, 2H), 4.56-4.45 (m, 1H), 4.09-4.00 (m, 1H), 3.37-3.17 (m, 2H), 2.82-2.72 (m, 1H), 2.05-1.94 (m, 1H), 1.80-1.64 (m, 2H), 1.50-1.37 (m, 1H), 1.10-0.90 (m, 3H).

{2-Amino-6-[5-fluoro-2-(2-methylpyrrolidin-1-ylmethyl)phenyl]quinazolin-4-yl}-(1,3-dihydroisoindol-2-yl)methanone ("A36")

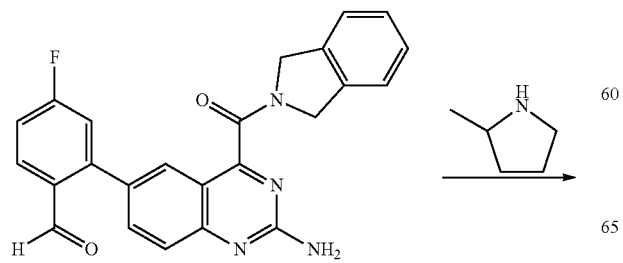

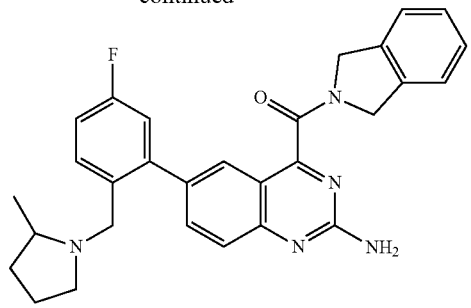

150 mg of 2-[2-amino-4-(1,3-dihydroisoindole-2-carbonyl)quinazolin-6-yl]-4-fluorobenzaldehyde are dissolved in 2 ml of 1,2-dichloroethane and 2 ml of tetrahydrofuran. 53 µl of 2-methylpyrrolidine and 40 µl of glacial acetic acid are added, and the mixture is stirred at 60° C. for 6 h. After cooling to 25° C., 161 mg of sodium triacetoxyborohydride are added, and the mixture is stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 37 mg (21%) of {2-amino-6-[5-fluoro-2-(2-methylpyrrolidin-1-ylmethyl)phenyl]quinazolin-4-yl}-(1,3-dihydroisoindol-2-yl)methanone;

LC-MS retention time: 1.53 min;

$^1$H NMR (500 MHz, DMSO-d$_6$/TFA-d$_1$) δ [ppm] 8.14-8.10 (m, 1H), 8.07 (dd, J=1.8, 8.6, 1H), 7.89 (d, J=8.6, 1H), 7.80 (dd, J=5.7, 8.7, 1H), 7.48-7.40 (m, 2H), 7.39-7.27 (m, 3H), 7.25 (d, J=7.4, 1H), 5.11-4.96 (m, 2H), 4.90-4.78 (m, 2H), 4.51 (d, J=13.9, 1H), 4.14-4.04 (m, 1H), 3.34-3.18 (m, 2H), 2.85-2.76 (m, 1H), 2.10-1.97 (m, 1H), 1.73 (dt, J=7.8, 15.4, 2H), 1.47 (dq, J=8.8, 13.0, 1H), 1.12-0.97 (m, 3H).

Methyl 1-{2-[2-amino-4-(1,3-dihydroisoindole-2-carbonyl)quinazolin-6-yl]-benzyl}pyrrolidine-2-carboxylate ("A37")

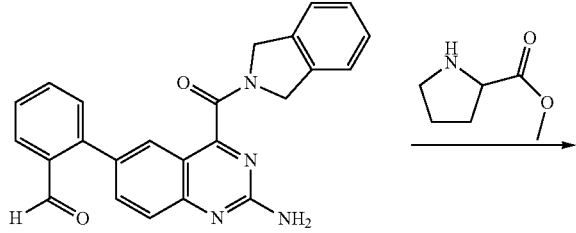

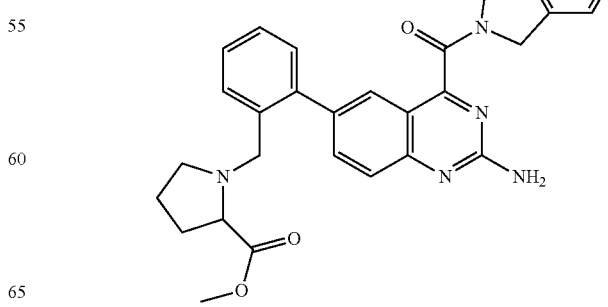

500 mg of 2-[2-amino-4-(1,3-dihydroisoindole-2-carbonyl)quinazolin-6-yl]benzaldehyde are dissolved in 5 ml of 1,2-dichloroethane and 5 ml of tetrahydrofuran. 314 mg of methylpyrrolidine-2-carboxylate hydrochloride are added, and the mixture is stirred at 60° C. for 6 h. After cooling to 25° C., 566 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 310 mg (55%) of methyl 1-{2-[2-amino-4-(1,3-dihydroisoindole-2-carbonyl)quinazolin-6-yl]benzyl}pyrrolidine-2-carboxylate;

LC-MS retention time: 2.40 min ("polar" gradient).

1-{2-[2-Amino-4-(1,3-dihydroisoindole-2-carbonyl)quinazolin-6-yl]benzyl}-pyrrolidine-2-carboxylic acid ("A38")

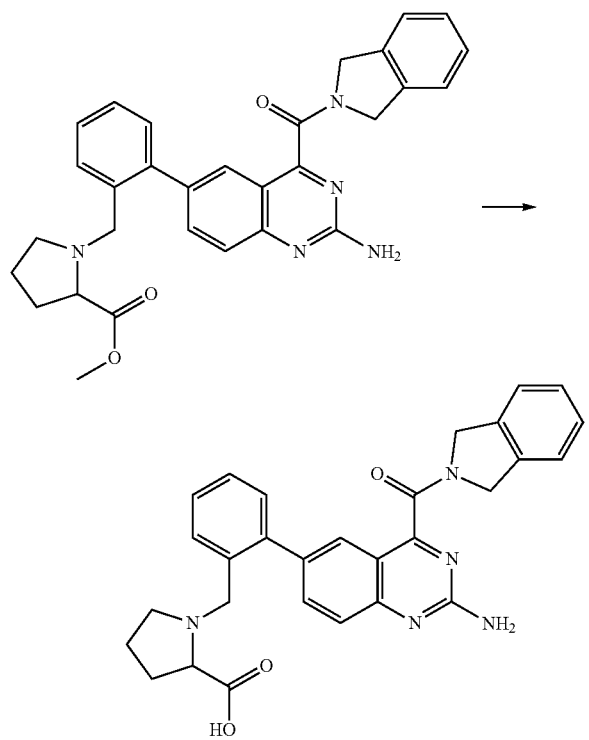

280 mg of methyl 1-{2-[2-amino-4-(1,3-dihydroisoindole-2-carbonyl)quinazolin-6-yl]benzyl}pyrrolidine-2-carboxylate are dissolved in 5 ml of tetrahydrofuran. 5 ml of 2N sodium hydroxide solution are added, and the mixture is stirred at 25° C. for 16 h. The mixture is evaporated in vacuo and acidified using 2N hydrochloric acid, during which the product precipitates out. Filtration and drying at 40° C. in vacuo gives 1-{2-[2-amino-4-(1,3-dihydroisoindole-2-carbonyl)quinazolin-6-yl]benzyl}pyrrolidine-2-carboxylic acid.

Yield: 310 mg (55%) of 1-{2-[2-amino-4-(1,3-dihydroisoindole-2-carbonyl)quinazolin-6-yl]benzyl}pyrrolidine-2-carboxylic acid;

LC-MS retention time: 2.14 min ("polar" gradient).

N-Methyl-1-{2-[2-amino-4-(1,3-dihydroisoindole-2-carbonyl)quinazolin-6-yl]-benzyl}pyrrolidine-2-carboxamide ("A39")

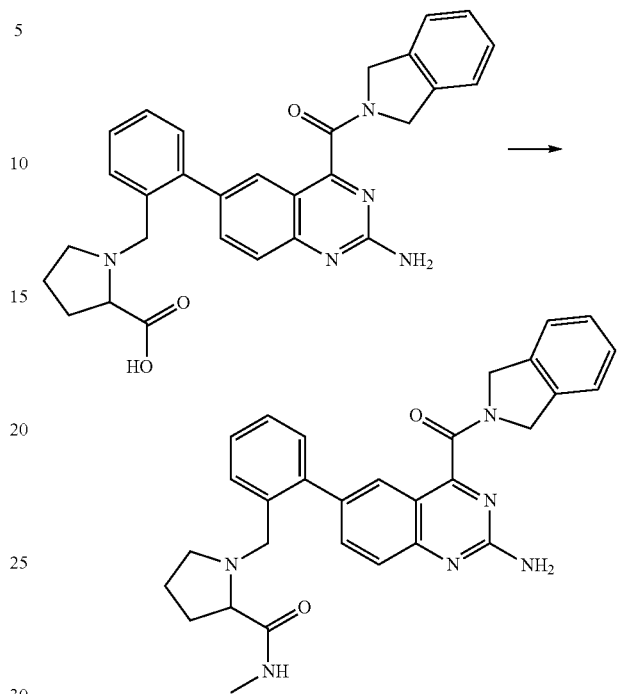

107 mg of TBTU (O-(benzotriazol-1-yl)-N,N,N',N'-tetramethyluronium tetrafluoroborate), 123 µl of 4-methylmorpholine and 334 µl of methylamine (2 M in THF) are added to a solution of 110 mg of 1-{2-[2-amino-4-(1,3-dihydroisoindole-2-carbonyl)quinazolin-6-yl]benzyl}pyrrolidine-2-carboxylic acid in 1 ml of DMF. The mixture is stirred at 22° C. for 16 h, and the product is isolated directly by column chromatography. Yield: 32 mg (28%) of N-methyl-1-{2-[2-amino-4-(1,3-dihydroisoindole-2-carbonyl)quinazolin-6-yl]benzyl}pyrrolidine-2-carboxamide; LC-MS retention time: 2.19 min ("polar" gradient);

$^1$H NMR (500 MHz, DMSO-d$_6$/TFA-d$_1$) δ [ppm] 8.06 (dd, J=2.5, 11.2, 2H), 7.87 (d, J=8.5, 1H), 7.75-7.68 (m, 1H), 7.54 (dd, J=3.4, 5.6, 2H), 7.44 (d, J=7.4, 1H), 7.39 (dd, J=3.3, 5.6, 1H), 7.32 (dt, J=7.2, 19.0, 2H), 7.25 (d, J=7.3, 1H), 5.08-4.97 (m, 2H), 4.93-4.78 (m, 2H), 4.43-4.22 (m, 2H), 3.92 (t, J=8.2, 1H), 3.45-3.30 (m, 2H), 2.95-2.80 (m, 2H), 2.26 (dd, J=9.1, 15.7, 2H), 1.90-1.64 (m, 3H).

N-(2-Hydroxyethyl)-1-{2-[2-amino-4-(1,3-dihydroisoindole-2-carbonyl)quinazolin-6-yl]benzyl}pyrrolidine-2-carboxamide ("A40")

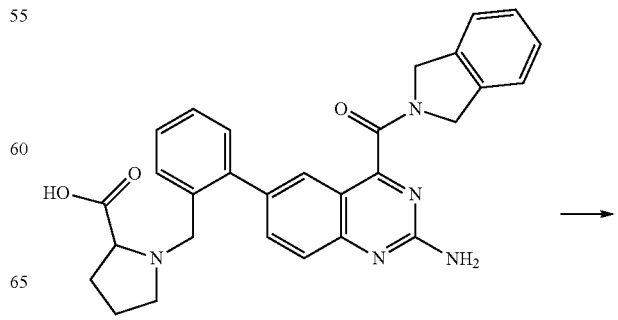

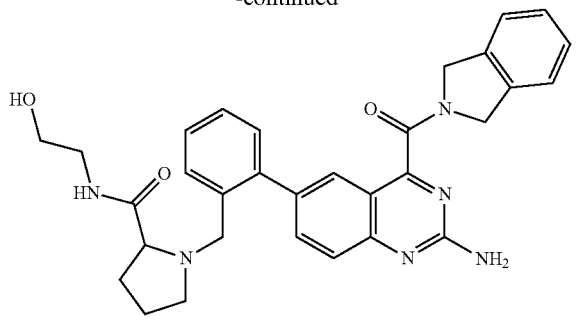

107 mg of TBTU (O-(benzotriazol-1-yl)-N,N,N',N'-tetramethyluronium tetrafluoroborate), 123 µl of 4-methylmorpholine and 223 µl of ethanolamine are added to a solution of 110 mg of 1-{2-[2-amino-4-(1,3-dihydroisoindole-2-carbonyl)quinazolin-6-yl]benzyl}pyrrolidine-2-carboxylic acid in 1 ml of DMF. The mixture is stirred at 22° C. for 16 h, and the product is isolated directly by column chromatography. Yield: 34 mg (28%) of N-(2-hydroxyethyl)-1-{2-[2-amino-4-(1,3-dihydroisoindole-2-carbonyl)quinazolin-6-yl]benzyl}pyrrolidine-2-carboxamide; LC-MS retention time: 2.15 min ("polar" gradient);

$^1$H NMR (500 MHz, DMSO-$d_6$/TFA-$d_1$) δ [ppm] 8.10-8.04 (m, 2H), 7.87 (d, J=8.5, 1H), 7.71 (dd, J=3.6, 5.5, 1H), 7.59-7.51 (m, 2H), 7.44 (d, J=7.3, 1H), 7.39 (dd, J=3.6, 5.5, 1H), 7.32 (dt, J=7.1, 18.0, 2H), 7.25 (d, J=7.3, 1H), 5.02 (s, 2H), 4.94-4.78 (m, 2H), 4.60 (t, J=5.6, 1H), 4.41-4.24 (m, 2H), 3.96 (t, J=8.2, 1H), 3.52 (t, J=5.7, 1H), 3.45-3.27 (m, 3H), 3.16-3.03 (m, 2H), 2.96-2.86 (m, 1H), 2.36-2.24 (m, 1H), 1.79-1.67 (m, 2H).

{2-Amino-6-[2-(4-hydroxypiperidin-1-ylmethyl)phenyl]quinazolin-4-yl}-(1,3-dihydroisoindol-2-yl)methanone ("A41")

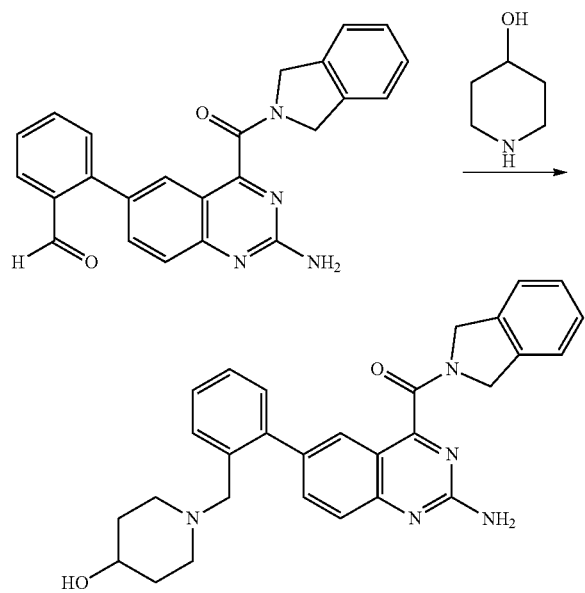

200 mg of 2-[2-amino-4-(1,3-dihydroisoindole-2-carbonyl)quinazolin-6-yl]benzaldehyde are dissolved in 10 ml of 1,2-dichloroethane and 10 ml of tetrahydrofuran. 103 mg of 4-piperidinol and 29 µl of glacial acetic acid are added, and the mixture is stirred at 60° C. for 6 h. After cooling to 25° C., 226 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 10 mg (4%) of {2-amino-6-[2-(4-hydroxypiperidin-1-ylmethyl)phenyl]-quinazolin-4-yl}-(1,3-dihydroisoindol-2-yl)methanone;

LC-MS retention time: 1.41 min.

{2-Amino-6-[5-fluoro-2-(4-methylpiperazin-1-ylmethyl)phenyl]quinazolin-4-yl}-(1,3-dihydroisoindol-2-yl)methanone ("A42")

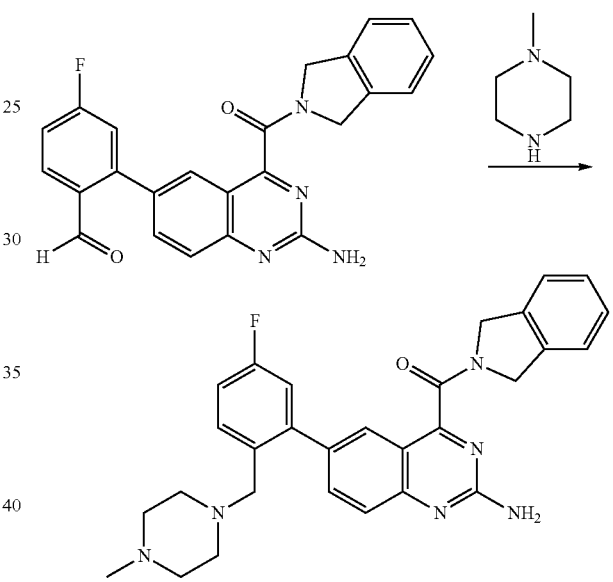

114 mg of 2-[2-amino-4-(1,3-dihydroisoindole-2-carbonyl)quinazolin-6-yl]-4-fluorobenzaldehyde are dissolved in 2 ml of 1,2-dichloroethane and 2 ml of tetrahydrofuran. 97 µl of 1-methylpiperazine and 50 µl of glacial acetic acid are added, and the mixture is stirred at 60° C. for 6 h. After cooling to 25° C., 195 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 27 mg (20%) of {2-amino-6-[5-fluoro-2-(4-methylpiperazin-1-ylmethyl)phenyl]quinazolin-4-yl}-(1,3-dihydroisoindol-2-yl)methanone;

LC-MS retention time: 1.62 min;

$^1$H NMR (500 MHz, DMSO-$d_6$/TFA-$d_1$) δ [ppm] 8.10 (d, J=1.7, 1H), 8.04 (dd, J=1.9, 8.6, 1H), 7.83 (d, J=8.6, 1H), 7.73 (dd, J=5.8, 8.6, 1H), 7.41 (d, J=7.3, 1H), 7.37 (td, J=2.8, 8.5, 1H), 7.35-7.19 (m, 4H), 5.00 (s, 2H), 4.80 (s, 2H), 4.11 (s, 2H), 3.26 (s, 8H), 2.82 (s, 3H).

{2-Amino-6-[4-fluoro-2-(4-methylpiperazin-1-ylmethyl)phenyl]quinazolin-4-yl}-(1,3-dihydroisoindol-2-yl)methanone ("A43")

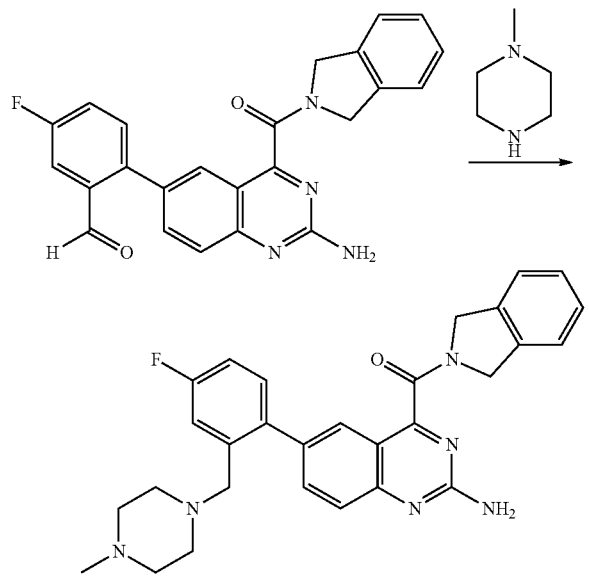

114 mg of 2-[2-amino-4-(1,3-dihydroisoindole-2-carbonyl)quinazolin-6-yl]-5-fluorobenzaldehyde are dissolved in 2 ml of 1,2-dichloroethane and 2 ml of tetrahydrofuran. 97 µl of 1-methylpiperazine and 50 µl of glacial acetic acid are added, and the mixture is stirred at 60° C. for 6 h. After cooling to 25° C., 195 mg of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 67 mg (31%) of {2-amino-6-[4-fluoro-2-(4-methylpiperazin-1-ylmethyl)phenyl]quinazolin-4-yl}-(1,3-dihydroisoindol-2-yl)methanone;

LC-MS retention time: 1.59 min;

$^1$H NMR (500 MHz, DMSO-$d_6$/TFA-$d_1$) δ [ppm] 8.06 (d, J=1.7, 1H), 7.96 (dd, J=1.9, 8.6, 1H), 7.82 (d, J=8.6, 1H), 7.55 (dd, J=2.7, 9.7, 1H), 7.42-7.34 (m, 2H), 7.32-7.22 (m, 3H), 7.18 (d, J=7.3, 1H), 4.98 (s, 2H), 4.79 (s, 2H), 4.14 (s, 2H), 3.30 (s, 8H), 2.78 (s, 3H).

Synthesis of Benzylamines Via Alkylation

1-Bromo-2-chloromethyl-4,5-difluorobenzene

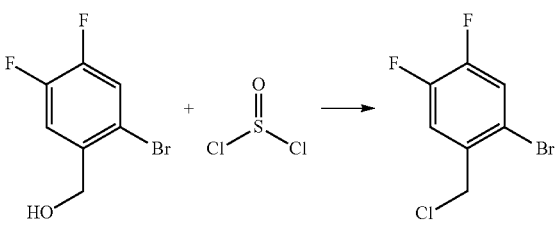

146 µl of thionyl chloride in 2.5 ml of dichloromethane are added dropwise to 300 mg of (2-bromo-4,5-difluorophenyl)methanol in 2.5 ml of dichloromethane, and the mixture is stirred at 25° C. The mixture is evaporated to dryness in vacuo, the residue is taken up in 10 ml of toluene, and the operation is repeated. The residue is employed in the subsequent reactions without further treatment.

Yield: 324 mg (99%) of 1-bromo-2-chloromethyl-4,5-difluorobenzene; HPLC retention time: 3.37 min.

(2-Bromo-4,5-difluorobenzyl)methylethylamine

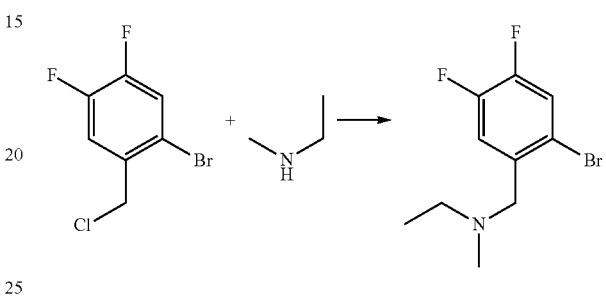

200 mg of 1-bromo-2-chloromethyl-4,5-difluorobenzene are dissolved in 5 ml of acetonitrile. 540 mg of caesium carbonate and 146 µl of methylethylamine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil.

Yield: 170 mg (78%) of (2-bromo-4,5-difluorobenzyl)methylethylamine;

LC-MS retention time: 1.00 min.

{2-Amino-6-[2-(methylethylaminomethyl)-4,5-difluorophenyl]quinazolin-4-yl}-(1,3-dihydroisoindol-2-yl)methanone ("A44")

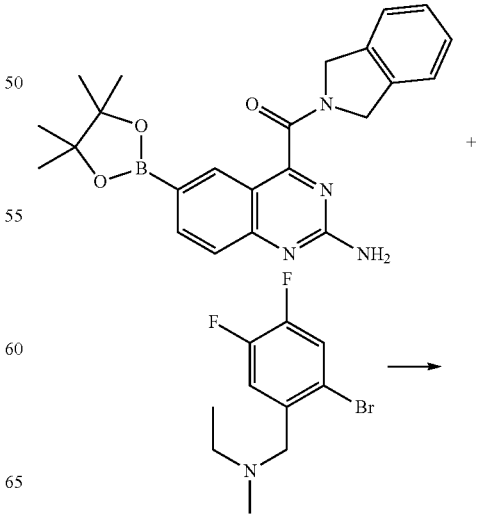

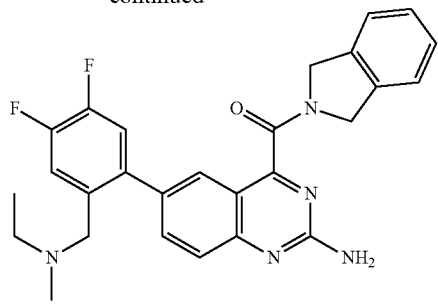

152 mg of (2-bromo-4,5-difluorobenzyl)methylethylamine, 133 mg of potassium carbonate, 9 μl of water and 20 mg of [1,1'-bis(diphenylphosphino)ferrocene]palladium(II) dichloride are added to a solution of 200 mg of [2-amino-6-(4,4,5,5-tetramethyl-1,3,2-dioxaborolan-2-yl)quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated. and purified by chromatography (reversed phase HPLC).

Yield: 83 mg (37%) of {2-amino-6-[2-(methylethylaminomethyl)-4,5-difluorophenyl]quinazolin-4-yl}-(1,3-dihydroisoindol-2-yl)methanone; LC-MS retention time: 1.59 min;

$^1$H NMR (500 MHz, DMSO-$d_6$/TFA-$d_1$) δ [ppm] 8.12 (d, J=1.9, 1H), 8.04 (dd, J=1.9, 8.7, 1H), 7.93-7.84 (m, 2H), 7.55 (dd, J=8.1, 10.9, 1H), 7.45 (d, J=7.4, 1H), 7.35 (t, J=7.2, 1H), 7.31 (t, J=7.2, 1H), 7.25 (d, J=7.4, 1H), 5.04 (s, 2H), 4.85 (s, 2H), 4.22 (s, 2H), 3.07-2.92 (m, 2H), 2.91-2.79 (m, 2H), 1.01 (t, J=7.2, 6H).

(2-Bromo-4,5-difluorobenzyl)diethylamine

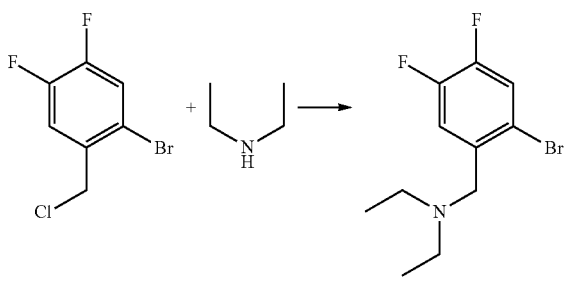

200 mg of 1-bromo-2-chloromethyl-4,5-difluorobenzene are dissolved in 5 ml of acetonitrile. 540 mg of caesium carbonate and 132 μl of diethylamine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil. Yield: 190 mg (83%) of (2-bromo-4,5-difluorobenzyl)diethylamine; LC-MS retention time: 1.59 min.

{2-Amino-6-[2-(diethylaminomethyl)-4,5-difluorophenyl]quinazolin-4-yl}-(1,3-dihydroisoindol-2-yl)methanone ("A45")

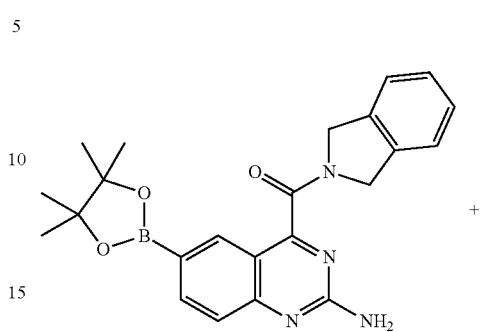

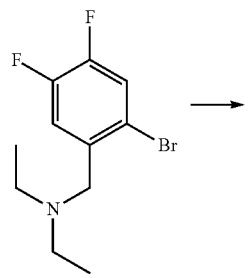

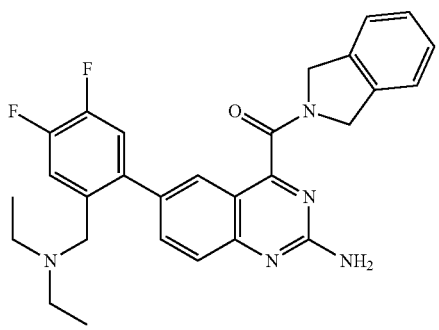

148 mg of (2-bromo-4,5-difluorobenzyl)diethylamine, 170 mg of potassium carbonate, 7 μl of water and 17 mg of [1,1'-bis(diphenylphosphino)ferrocene]-palladium(II) dichloride are added to a solution of 170 mg of [2-amino-6-(4,4,5,5-tetramethyl-1,3,2-dioxaborolan-2-yl)quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated and purified by chromatography (reversed phase HPLC).

Yield: 40 mg (20%) of {2-amino-6-[2-(diethylaminomethyl)-4,5-difluorophenyl]-quinazolin-4-yl}-(1,3-dihydroisoindol-2-yl)methanone;

LC-MS retention time: 1.56 min;

$^1$H NMR (500 MHz, DMSO-$d_6$/TFA-$d_1$) δ [ppm] 8.12 (d, J=1.9, 1H), 8.04 (dd, J=1.9, 8.7, 1H), 7.93-7.84 (m, 2H), 7.55 (dd, J=8.1, 10.9, 1H), 7.45 (d, J=7.4, 1H), 7.35 (t, J=7.2, 1H), 7.31 (t, J=7.2, 1H), 7.25 (d, J=7.4, 1H), 5.04 (s, 2H), 4.85 (s, 2H), 4.22 (s, 2H), 3.07-2.92 (m, 2H), 2.91-2.79 (m, 2H), 1.01 (t, J=7.2, 6H).

(2-Bromo-4,5-difluorobenzyl)-tert-butylamine

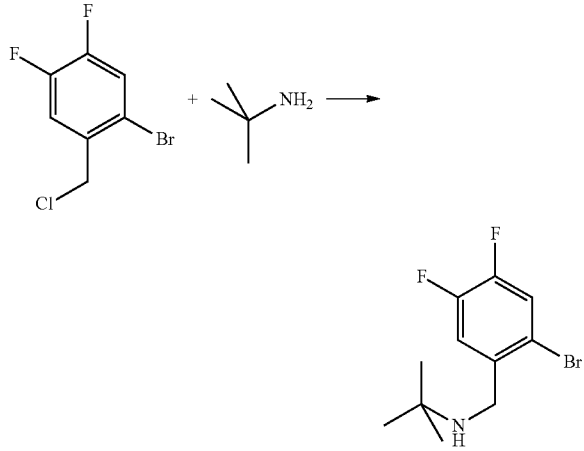

200 mg of 1-bromo-2-chloromethyl-4,5-difluorobenzene are dissolved in 5 ml of acetonitrile. 540 mg of caesium carbonate and 123 µl of tert-butylamine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil.

Yield: 210 mg (91%) of (2-bromo-4,5-difluorobenzyl)-tert-butylamine;

LC-MS retention time: 1.17 min.

{2-Amino-6-[2-(tert-butylaminomethyl)-4,5-difluorophenyl]quinazolin-4-yl}-(1,3-dihydroisoindol-2-yl)methanone ("A46")

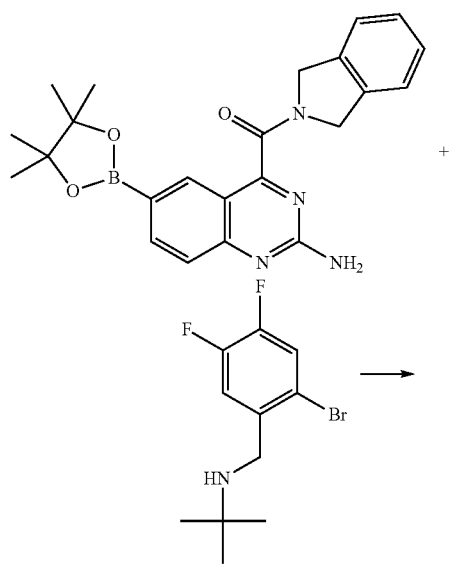

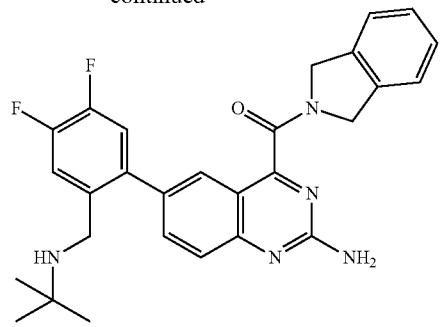

184 mg of (2-bromo-4,5-difluorobenzyl)-tert-butylamine, 166 mg of potassium carbonate, 11 µl of water and 25 mg of [1,1'-bis(diphenylphosphino)ferrocene]-palladium(II) dichloride are added to a solution of 250 mg of [2-amino-6-(4,4,5,5-tetramethyl-1,3,2-dioxaborolan-2-yl)quinazolin-4-yl]-(1,3-dihydroisoindol-2-yl)methanone in 10 ml of ethanol under argon. The mixture is heated at 120° C. for 30 min; the hot mixture is filtered through kieselguhr, and the filtrate is evaporated. and purified by chromatography (reversed phase HPLC).

Yield: 90 mg (31%) of {2-amino-6-[2-(tert-butylaminomethyl)-4,5-difluorophenyl]quinazolin-4-yl}-(1,3-dihydroisoindol-2-yl)methanone;

LC-MS retention time: 1.55 min;

$^1$H NMR (500 MHz, DMSO-d$_6$/TFA-d$_1$) δ [ppm] 8.16 (d, J=1.8, 1H), 8.07 (dd, J=1.7, 8.7, 1H), 7.92-7.81 (m, 2H), 7.51 (dd, J=8.1, 10.9, 1H), 7.45 (d, J=7.4, 1H), 7.36 (dd, J=5.1, 9.2, 1H), 7.31 (t, J=7.4, 1H), 7.24 (d, J=7.4, 1H), 5.06 (s, 2H), 4.84 (s, 2H), 3.99 (s, 2H), 1.09 (s, 9H).

(2-Bromo-4,5-difluorobenzyl)-tert-butylmethylamine

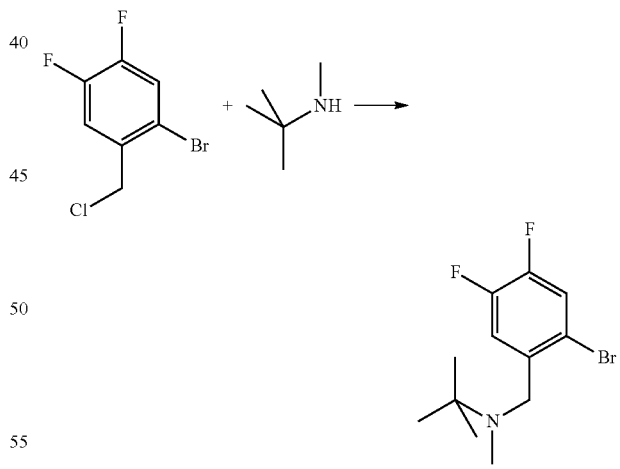

200 mg of 1-bromo-2-chloromethyl-4,5-difluorobenzene are dissolved in 5 ml of acetonitrile. 540 mg of caesium carbonate and 206 µl of tert-butylmethylamine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil.

Yield: 210 mg (87%) of (2-bromo-4,5-difluorobenzyl)-tert-butylmethylamine;

LC-MS retention time: 1.16 min.

(2-Amino-6-{2-[(tert-butylmethylamino)methyl]-4,5-difluorophenyl}quinazolin-4-yl)-(1,3-dihydroisoindol-2-yl)methanone ("A47")

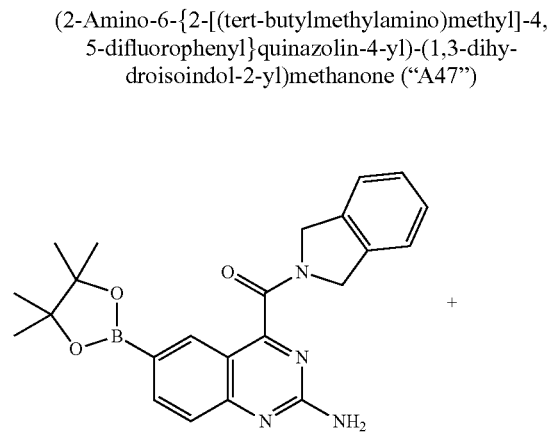

+

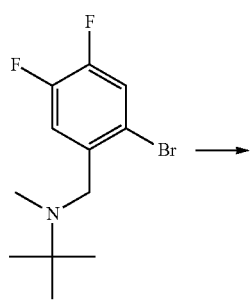

→

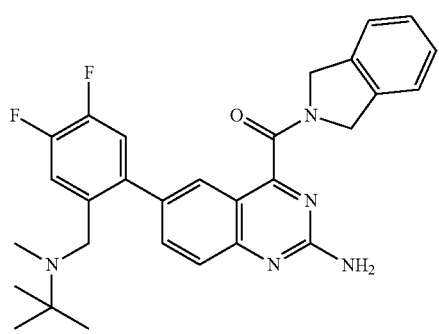

171 mg of (2-bromo-4,5-difluorobenzyl)-tert-butylmethylamine, 124 mg of potassium carbonate, 9 µl of water and 22 mg of [1,1'-bis(diphenylphosphino)ferrocene]palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated. and purified by chromatography (reversed phase HPLC).

Yield: 20 mg (9%) of (2-amino-6-{2-[(tert-butylmethylamino)methyl]-4,5-difluorophenyl}quinazolin-4-yl)-(1,3-dihydroisoindol-2-yl)methanone;

LC-MS retention time: 2.22 min.

1-(2-Bromo-4,5-difluorobenzyl)pyrrolidine

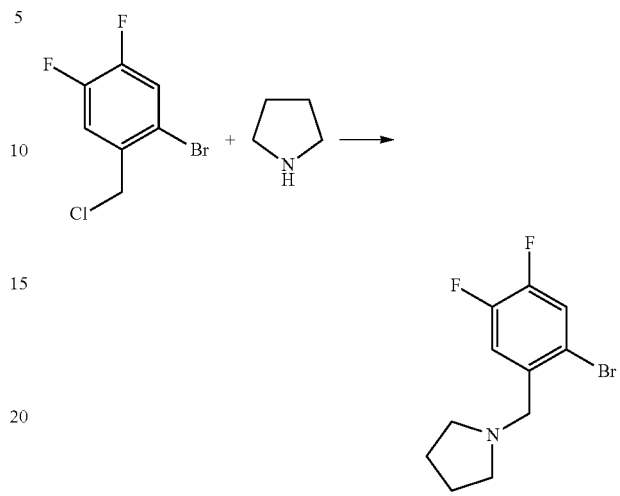

200 mg of 1-bromo-2-chloromethyl-4,5-difluorobenzene are dissolved in 5 ml of acetonitrile. 540 mg of caesium carbonate and 102 µl of pyrrolidine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil. Yield: 190 mg (83%) of 1-(2-bromo-4,5-difluorobenzyl)pyrrolidine; LC-MS retention time: 1.09 min.

[2-Amino-6-(4,5-difluoro-2-pyrrolidin-1-ylmethylphenyl)quinazolin-4-yl]-(1,3-dihydroisoindol-2-yl)methanone ("A48")

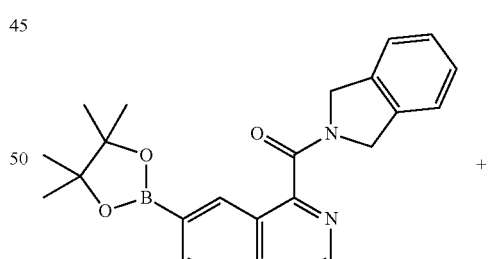

+

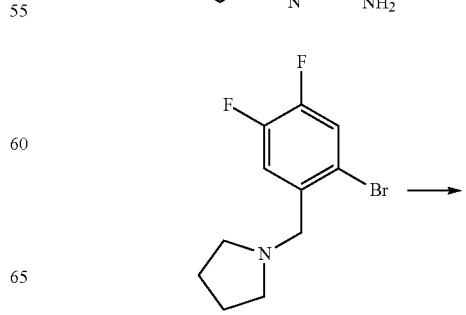

→

-continued

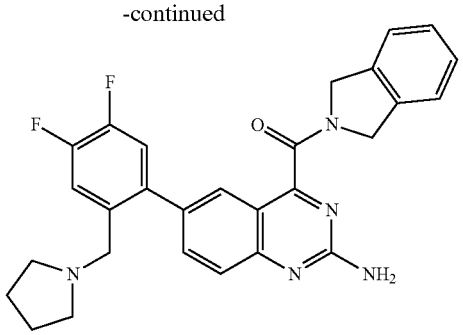

129 mg of 1-(2-bromo-4,5-difluorobenzyl)pyrrolidine, 100 mg of potassium carbonate, 7 μl of water and 17 mg of [1,1'-bis(diphenylphosphino)ferrocene]-palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated and purified by chromatography (reversed phase HPLC).

Yield: 90 mg (31%) of [2-amino-6-(4,5-difluoro-2-pyrrolidin-1-ylmethylphenyl)quinazolin-4-yl]-(1,3-dihydroisoindol-2-yl)methanone;

LC-MS retention time: 1.60 min;

$^1$H NMR (500 MHz, DMSO-d$_6$/TFA-d$_1$) δ [ppm] 8.11 (d, J=1.7, 1H), 8.03 (d, J=8.7, 1H), 7.87 (dd, J=8.4, 22.5, 2H), 7.54 (s, 1H), 7.45 (d, J=7.5, 1H), 7.33 (dt, J=7.2, 14.8, 2H), 7.25 (d, J=7.4, 1H), 5.03 (s, 2H), 4.84 (s, 2H), 4.28 (s, 2H), 3.41 (s, 2H), 2.77 (s, 2H), 1.79 (s, 4H).

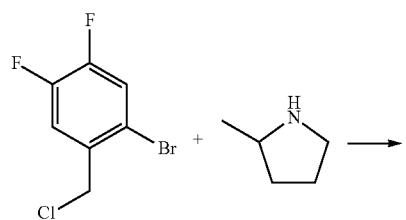

1-(2-Bromo-4,5-difluorobenzyl)-2-methylpyrrolidine 200 mg of 1-bromo-2-chloromethyl-4,5-difluorobenzene are dissolved in 5 ml of acetonitrile. 540 mg of caesium carbonate and 136 μl of 2-methylpyrrolidine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil. Yield: 190 mg (80%) of 1-(2-bromo-4,5-difluorobenzyl)-2-methylpyrrolidine; LC-MS retention time: 1.09 min.

{2-Amino-6-[4,5-difluoro-2-(2-methylpyrrolidin-1-ylmethyl)phenyl]quinazolin-4-yl}-(1,3-dihydroisoindol-2-yl)methanone ("A49")

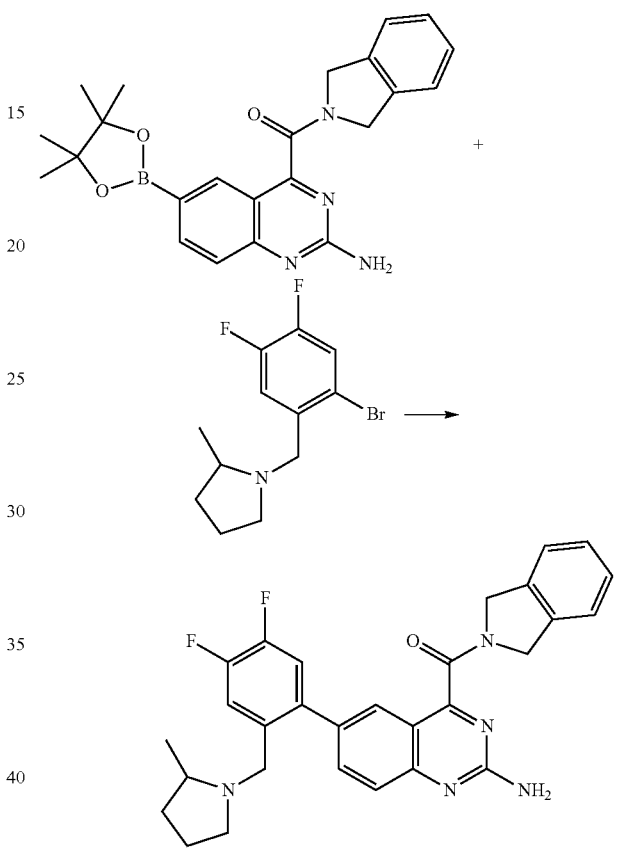

136 mg of 1-(2-bromo-4,5-difluorobenzyl)-2-methylpyrrolidine, 100 mg of potassium carbonate, 7 μl of water and 17 mg of [1,1'-bis(diphenylphosphino)ferrocene]palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated and purified by chromatography (reversed phase HPLC).

Yield: 25 mg (14%) of {2-amino-6-[4,5-difluoro-2-(2-methylpyrrolidin-1-ylmethyl)phenyl]quinazolin-4-yl}-(1,3-dihydroisoindol-2-yl)methanone;

LC-MS retention time: 1.65 min;

$^1$H NMR (500 MHz, DMSO-d$_6$/TFA-d$_1$) δ [ppm] 8.10 (d, J=1.7, 1H), 8.05 (dd, J=1.9, 8.6, 1H), 7.92-7.83 (m, 2H), 7.55 (dd, J=8.1, 10.9, 1H), 7.47 (d, J=7.5, 1H), 7.38-7.28 (m, 2H), 7.27 (d, J=7.4, 1H), 5.10-4.96 (m, 2H), 4.90 (d, J=12.2, 2H), 4.58 (d, J=13.9, 1H), 4.12 (d, J=13.9, 1H), 3.41-3.20 (m, 2H), 2.85 (dd, J=8.8, 20.0, 1H), 2.12-1.97 (m, 1H), 1.80-1.68 (m, 2H), 1.62-1.40 (m, 1H), 1.17 (d, J=6.4, 3H).

1-(2-Bromo-4,5-difluorobenzyl)-2,5-dimethylpyrrolidine

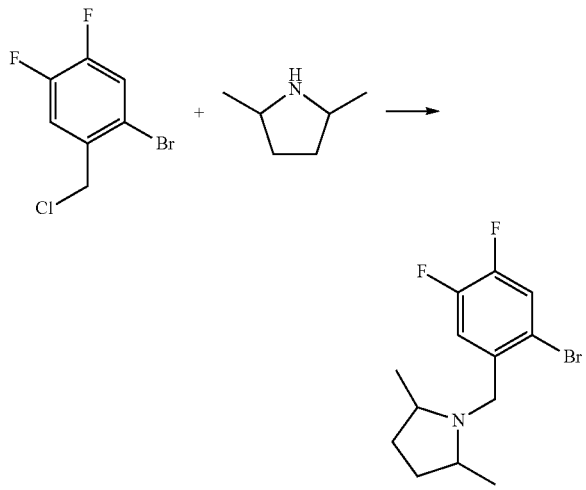

200 mg of 1-bromo-2-chloromethyl-4,5-difluorobenzene are dissolved in 5 ml of acetonitrile. 540 mg of caesium carbonate and 152 µl of 2,5-dimethylpyrrolidine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness, after which the product is isolated as oil.

Yield: 210 mg (83%) of 1-(2-bromo-4,5-difluorobenzyl)-2,5-dimethylpyrrolidine;

LC-MS retention time: 1.19 min.

{2-Amino-6-[2-(2,5-dimethylpyrrolidin-1-ylmethyl)-4,5-difluorophenyl]quinazolin-4-yl}-(1,3-dihydroisoindol-2-yl)methanone ("A50")

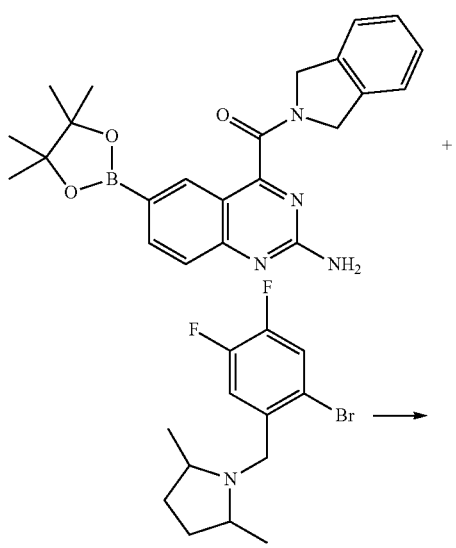

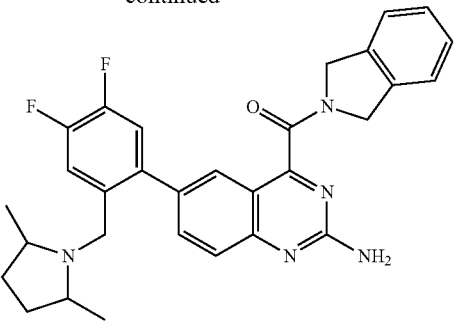

143 mg of 1-(2-bromo-4,5-difluorobenzyl)-2,5-dimethylpyrrolidine, 100 mg of potassium carbonate, 7 µl of water and 17 mg of [1,1'-bis(diphenylphosphino)ferrocene]palladium(II) dichloride are added to a solution of 150 mg of [2-amino-6-(4,4,5,5-tetramethyl-1,3,2-dioxaborolan-2-yl) quinazolin-4-yl]-(1,3-dihydroisoindol-2-yl)methanone in 4 ml of ethanol under argon. The mixture is heated at 120° C. for 30 min; the hot mixture is filtered through kieselguhr, and the filtrate is evaporated. and purified by chromatography (reversed phase HPLC).

Yield: 40 mg (22%) of {2-amino-6-[2-(2,5-dimethylpyrrolidin-1-ylmethyl)-4,5-difluorophenyl]quinazolin-4-yl}-(1,3-dihydroisoindol-2-yl)methanone;

LC-MS retention time: 1.65 min;

$^1$H NMR (500 MHz, DMSO-d$_6$/TFA-d$_1$) δ [ppm] 8.07 (d, J=1.6, 1H), 8.05 (d, J=8.8, 1H), 7.92 (d, J=8.6, 1H), 7.89 (dd, J=8.2, 11.1, 1H), 7.59-7.51 (m, 1H), 7.45 (d, J=7.3, 1H), 7.38 (dt, J=7.2, 18.5, 2H), 7.27 (d, J=7.0, 1H), 5.03 (s, 2H), 4.89 (s, 2H), 4.38 (s, 2H), 3.32 (q, J=6.1, 12.4, 2H), 2.02-1.89 (m, 2H), 1.57-1.45 (m, 2H), 1.05 (d, J=6.5, 6H).

(2-Bromobenzyl)cyclopropylamine

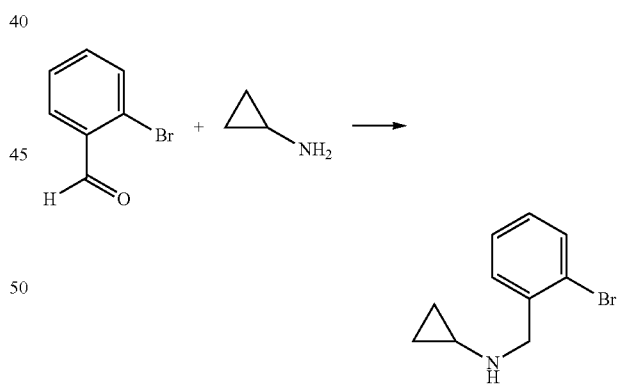

1 ml of 2-bromobenzaldehyde are dissolved in 20 ml of 1,2-dichloroethane and ml of tetrahydrofuran. 799 µl of cyclopropylamine and 643 µl of glacial acetic acid are added, and the mixture is stirred at 60° C. for 6 h. After cooling to 25° C., 5.3 g of sodium triacetoxyborohydride are added and stirred at 25° C. for a further 12 h. The mixture is poured into water, extracted three times with dichloromethane, and the combined organic phases are dried over sodium sulfate. After filtration, the filtrate is evaporated to dryness and purified by chromatography (reversed phase HPLC).

Yield: 1.5 g (77%) of (2-bromobenzyl)cyclopropylamine;

LC-MS retention time: 0.40 min.

(2-Bromobenzyl)cyclopropylmethylamine

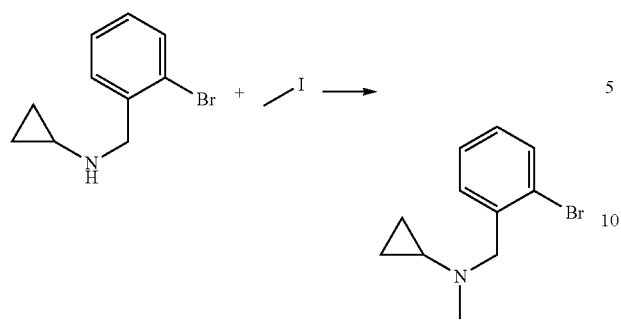

53 mg of sodium hydride in 3 ml of tetrahydrofuran are added to 300 mg of (2-bromobenzyl)cyclopropylamine in 2 ml of tetrahydrofuran with ice-cooling. 207 μl of iodomethane are subsequently added, and the mixture is heated at 600 for 1 h. The mixture is allowed to cool and poured onto 20 g of ice and 5 ml of 1N hydrochloric acid, washed 4 times with 10 ml of ethyl acetate each time, and the combined organic phases are dried over sodium sulfate. After filtration, the filtrate is evaporated to dryness.

Yield: 190 mg (60%) of (2-bromobenzyl)cyclopropylmethylamine;

LC-MS retention time: 1.32 min (high polar method).

(2-Amino-6-{2-[(cyclopropylmethylamino)methyl]phenyl}quinazolin-4-yl)-(1,3-dihydroisoindol-2-yl)methanone ("A51")

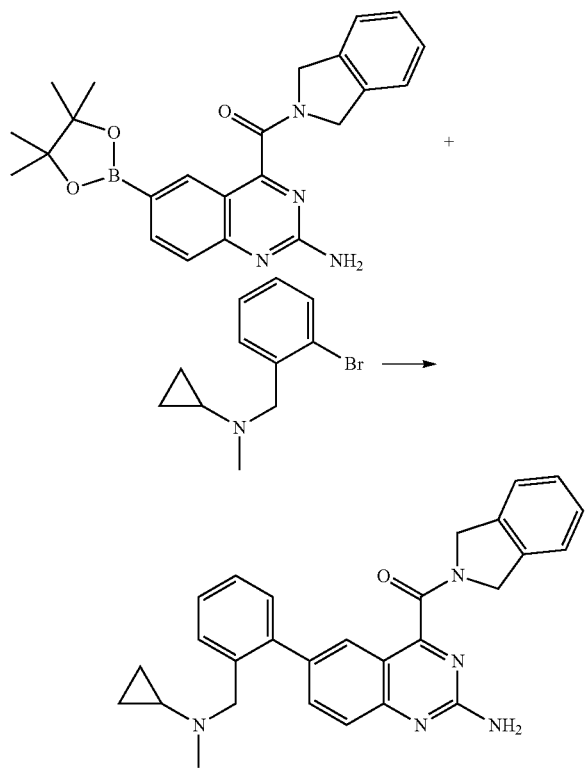

114 mg of (2-bromobenzyl)cyclopropylmethylamine, 100 mg of potassium carbonate, 7 μl of water and 29 mg of [1,1'-bis(diphenylphosphino)ferrocene]-palladium(II) dichloride are added to a solution of 150 mg of [2-amino-6-(4,4,5,5-tetramethyl-1,3,2-dioxaborolan-2-yl)quinazolin-4-yl]-(1,3-dihydroisoindol-2-yl)methanone in 5 ml of ethanol under argon. The mixture is heated at 120° C. for 30 min; the hot mixture is filtered through kieselguhr, the filtrate is evaporated and purified by chromatography (reversed phase HPLC).

Yield: 25 mg (15%) of (2-amino-6-{2-[(cyclopropylmethylamino)methyl]phenyl}-quinazolin-4-yl)-(1,3-dihydroisoindol-2-yl)methanone;

LC-MS retention time: 1.51 min;

$^1$H NMR (500 MHz, DMSO-d$_6$/TFA-d$_1$) δ [ppm] 8.01 (d, J=7.5, 2H), 7.87 (d, J=9.3, 1H), 7.69 (d, J=9.0, 1H), 7.54 (t, J=3.4, 2H), 7.40 (t, J=7.6, 2H), 7.35-7.25 (m, 2H), 7.22 (d, J=7.4, 1H), 4.98 (s, 2H), 4.86 (s, 2H), 4.45 (s, 2H), 2.63 (s, 3H), 2.52-2.51 (m, 4H).

[2-Amino-6-(2-chloromethyl-4,5-difluorophenyl)quinazolin-4-yl]-(1,3-dihydroisoindol-2-yl)methanone

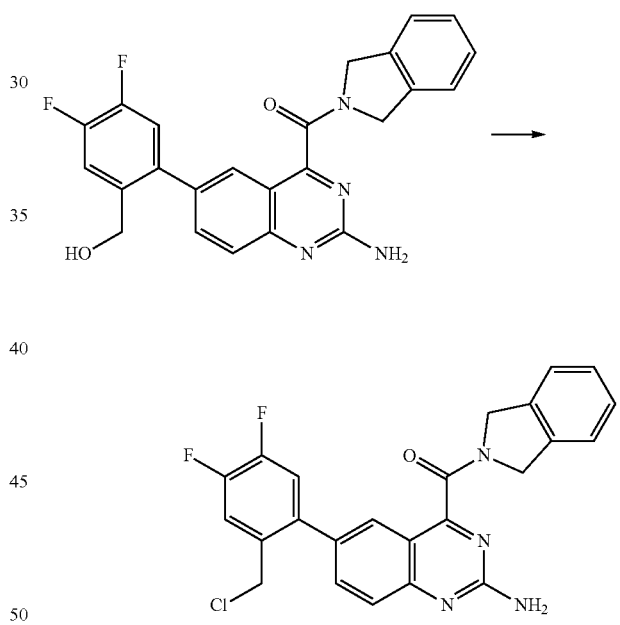

67 μl of thionyl chloride in 2 ml of dichloromethane are added dropwise to 200 mg of [2-amino-6-(2-hydroxymethyl-4,5-difluorophenyl)quinazolin-4-yl]-(1,3-dihydroisoindol-2-yl)methanone in 2 ml of dichloromethane, and the mixture is stirred at 25° C. for 2 h. The mixture is evaporated to dryness in vacuo, the residue is taken up in 10 ml of toluene, and the operation is repeated. The residue is employed in the subsequent reactions without further treatment.

Yield: 198 mg (95%) of [2-amino-6-(2-chloromethyl-4,5-difluorophenyl)quinazolin-4-yl]-(1,3-dihydroisoindol-2-yl)methanone;

LC-MS retention time: 2.31 min.

127

{2-Amino-6-[4,5-difluoro-2-(4-methylpiperazin-1-ylmethyl)phenyl]quinazolin-4-yl}-(1,3-dihydroisoindol-2-yl)methanone ("A52")

128 tert-Butyl{2-[2-amino-4-(1,3-dihydroisoindole-2-carbonyl)quinazolin-6-yl]-4,5-difluorobenzyl}biscarbamate ("A53")

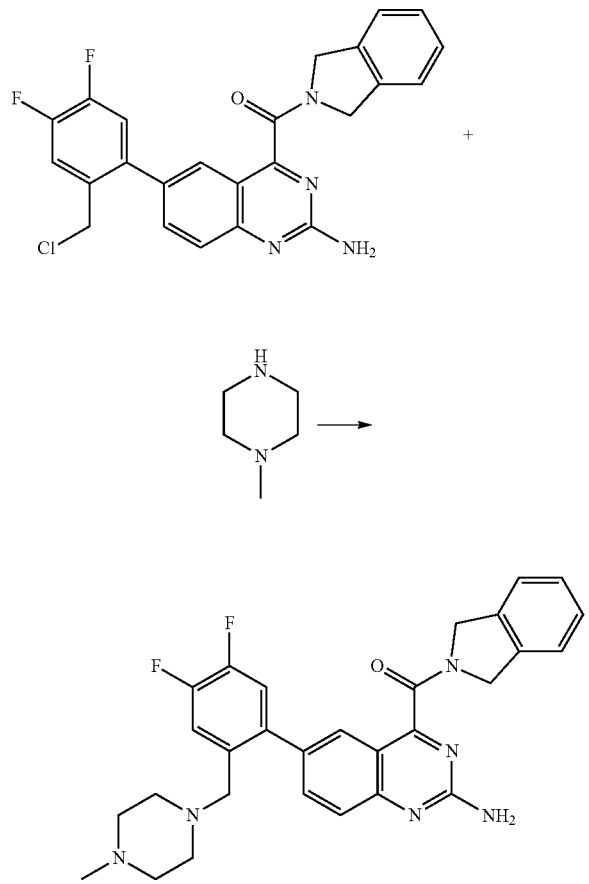

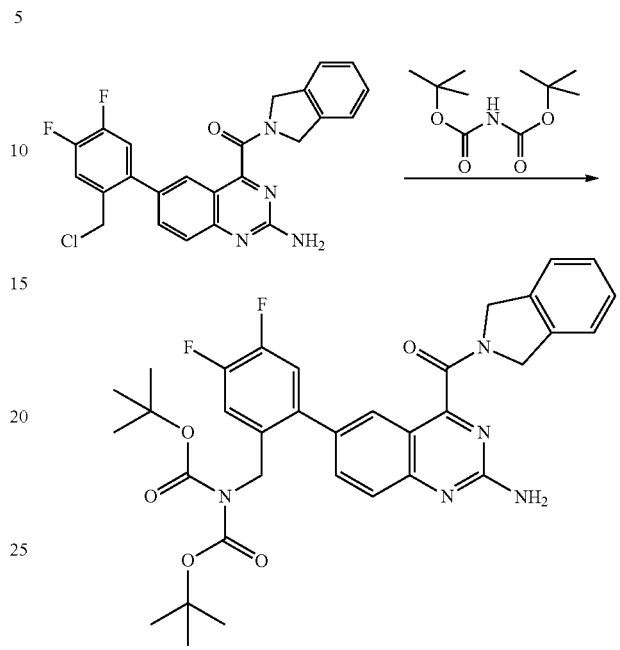

190 mg of [2-amino-6-(2-chloromethyl-4,5-difluorophenyl)quinazolin-4-yl]-(1,3-dihydroisoindol-2-yl)methanone are dissolved in 2 ml of ethyl methyl ketone. 381 mg of caesium carbonate, 4 mg of lithium iodide and 85 mgl of di-tert-butyl iminodicarboxylate are added, and the mixture is stirred at 70° C. for 3 h. The. precipitate is filtered, washed with ethyl acetate, and the mother liquor is evaporated. The oil formed is taken up in ethyl acetate and washed with saturated sodium hydrogencarbonate solution, before the combined organic phases are dried over sodium sulfate. After filtration, the filtrate is evaporated to dryness.

Yield: 250 mg (84%) of tert-butyl {2-[2-amino-4-(1,3-dihydroisoindole-2-carbonyl)quinazolin-6-yl]-4,5-difluorobenzyl}biscarbamate;

LC-MS retention time: 2.49 min (nonpolar method).

200 mg of [2-amino-6-(2-chloromethyl-4,5-difluorophenyl)quinazolin-4-yl]-(1,3-dihydroisoindol-2-yl)methanone are dissolved in 5 ml of acetonitrile. 289 mg of caesium carbonate and 84 µl of methylpiperazine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness and purified by chromatography (reversed phase HPLC).

Yield: 14 mg (6%) of {2-amino-6-[4,5-difluoro-2-(4-methylpiperazin-1-ylmethyl)phenyl]quinazolin-4-yl}-(1,3-dihydroisoindol-2-yl)methanone;

LC-MS retention time: 1.69 min;

$^1$H NMR (400 MHz, DMSO-$d_6$/TFA-$d_1$) δ [ppm] 8.10 (d, J=1.6, 1H), 8.06 (dd, J=1.8, 8.6, 1H), 7.85 (d, J=8.7, 1H), 7.76 (dd, J=8.3, 11.4, 1H), 7.52 (dd, J=8.1, 11.1, 1H), 7.45 (d, J=7.1, 1H), 7.34 (td, J=6.9, 13.2, 2H), 7.26 (d, J=6.9, 1H), 5.03 (s, 2H), 4.82 (s, 2H), 3.96 (s, 2H), 3.53-3.00 (m, 9H), 2.86 (s, 3H).

[2-Amino-6-(2-aminomethyl-4,5-difluorophenyl)quinazolin-4-yl]-(1,3-dihydroisoindol-2-yl)methanone ("A54")

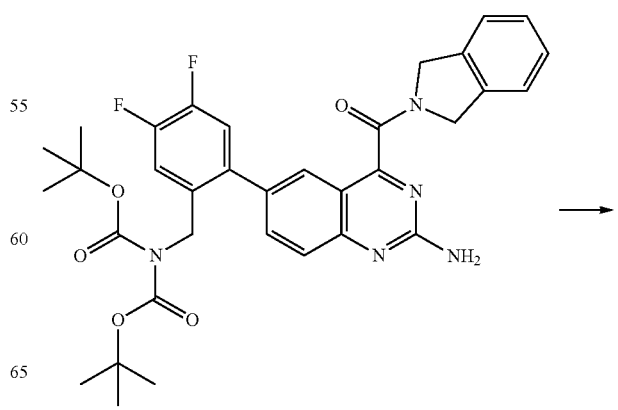

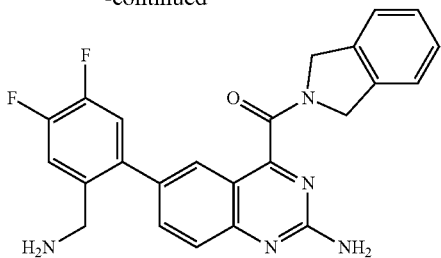

250 mg of tert-butyl {2-[2-amino-4-(1,3-dihydroisoindole-2-carbonyl)quinazolin-6-yl]-4,5-difluorobenzyl}biscarbamate are dissolved in 4 ml of dioxane/HCl (1 M). The mixture is stirred at 25° C. for 1 h and evaporated to dryness in vacuo.

Yield: 190 mg (100%) of [2-amino-6-(2-aminomethyl-4,5-difluorophenyl)quinazolin-4-yl]-(1,3-dihydroisoindol-2-yl)methanone;

LC-MS retention time: 1.55 min;

$^1$H NMR (400 MHz, DMSO-$d_6$/TFA-$d_1$) δ [ppm] 8.08 (dd, J=1.6, 10.1, 2H), 7.85 (d, J=8.5, 1H), 7.50-7.40 (m, 3H), 7.33 (s, 2H), 7.26 (d, J=7.2, 1H), 5.02 (s, 2H), 4.83 (s, 2H), 4.14 (s, 2H).

3-Amino-N-{2-[2-amino-4-(1,3-dihydroisoindole-2-carbonyl)quinazolin-6-yl]-4,5-difluorobenzyl}propionamide hydrochloride ("A55")

85 mg of TBTU (O-(benzotriazol-1-yl)-N,N,N',N'-tetramethyluronium tetrafluoroborate), 112 µl of 4-methylmorpholine and 88 mg of [2-amino-6-(2-aminomethyl-4,5-difluorophenyl)quinazolin-4-yl]-(1,3-dihydroisoindol-2-yl) methanone are added to a solution of 46 mg of 3-tert-butoxycarbonylaminopropionocarboxylic acid in 1 ml of DMF. The mixture is stirred at 22° C. for 16 h, and the product is isolated directly by column chromatography.

Yield: 25 mg (23%) of 3-amino-N-{2-[2-amino-4-(1,3-dihydroisoindole-2-carbonyl)quinazolin-6-yl]-4,5-difluorobenzyl}propionamide hydrochloride;

LC-MS retention time: 1.59 min;

$^1$H NMR (400 MHz, DMSO-$d_6$/TFA-$d_1$) δ [ppm] 8.12-8.04 (m, 2H), 7.85 (d, J=8.5, 1H), 7.50-7.39 (m, 3H), 7.39-7.29 (m, 2H), 7.26 (d, J=7.2, 1H), 5.02 (s, 2H), 4.83 (s, 2H), 4.14 (s, 2H), 2.94 (t, J=6.8, 2H), 2.48 (d, J=6.7, 2H).

N-{2-[2-Amino-4-(1,3-dihydroisoindole-2-carbonyl)quinazolin-6-yl]-4,5-difluorobenzyl}-3-dimethylaminopropionamide ("A56")

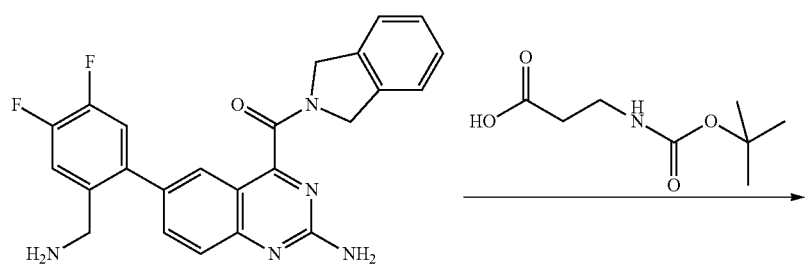

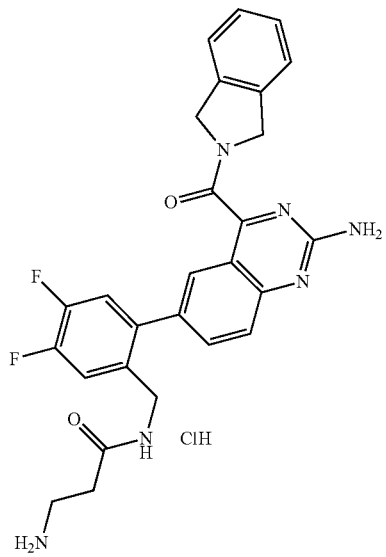

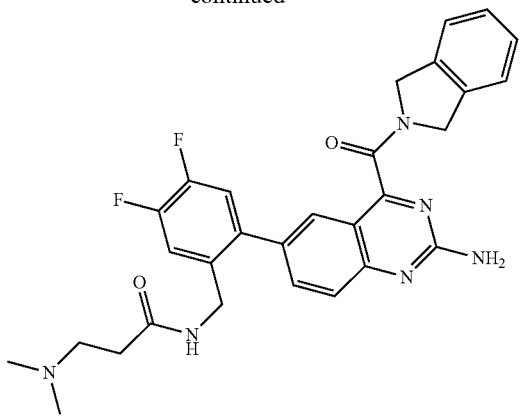

85 mg of TBTU (O-(benzotriazol-1-yl)-N,N,N',N'-tetramethyluronium tetrafluoroborate), 112 μl of 4-methylmorpholine and 100 mg of [2-amino-6-(2-aminomethyl-4,5-difluorophenyl)quinazolin-4-yl]-(1,3-dihydroisoindol-2-yl)methanone are added to a solution of 43 mg of 3-dimethylaminopropionocarboxylic acid hydrochloride in 1 ml of DMF. The mixture is stirred at 22° C. for 16 h, and the product is isolated directly by column chromatography.

Yield: 25 mg (23%) of N-{2-[2-amino-4-(1,3-dihydroisoindole-2-carbonyl)quinazolin-6-yl]-4,5-difluorobenzyl}-3-dimethylaminopropionamide;

LC-MS retention time: 1.60 min;

$^1$H NMR (500 MHz, DMSO-d$_6$/TFA-d$_1$) δ [ppm] 8.08 (dd, J=1.7, 7.6, 2H), 7.86 (d, J=9.4, 1H), 7.44 (ddd, J=8.1, 11.5, 19.1, 3H), 7.34 (dt, J=7.2, 18.5, 2H), 7.26 (d, J=7.5, 1H), 5.04 (s, 2H), 4.85 (s, 2H), 4.15 (s, 2H), 3.24 (t, J=7.1, 2H), 2.72 (s, 3H), 2.60 (t, J=4.7, 2H), 2.11 (s, 3H).

[2-Amino-6-(2-chloromethyl-5-fluorophenyl)quinazolin-4-yl]-(1,3-dihydroisoindol-2-yl)methanone

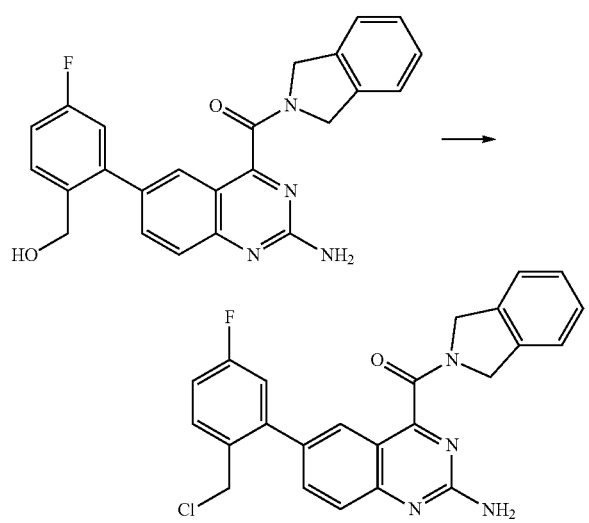

218 μl of thionyl chloride are added dropwise to 622 mg of [2-amino-6-(2-hydroxymethyl-5-fluorophenyl)quinazolin-4-yl]-(1,3-dihydroisoindol-2-yl)methanone in 50 ml of dichloromethane, and the mixture is stirred at 25° C. for 2 h. The mixture is evaporated to dryness in vacuo, the residue is taken up in 10 ml of toluene, and the operation is repeated. The residue is employed in the subsequent reactions without further treatment.

Yield: 649 mg (99%) of [2-amino-6-(2-chloromethyl-5-fluorophenyl)quinazolin-4-yl]-(1,3-dihydroisoindol-2-yl)methanone;

LC-MS retention time: 2.29 min.

[2-Amino-6-(2-diethylaminomethyl-5-fluorophenyl)quinazolin-4-yl]-(1,3-dihydroisoindol-2-yl)methanone ("A57")

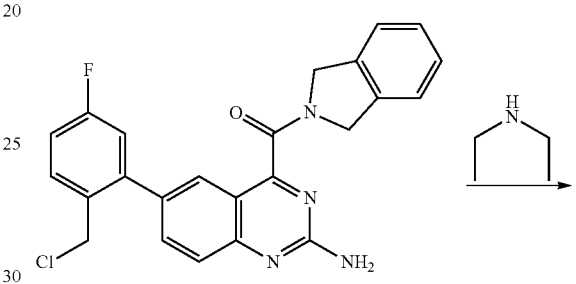

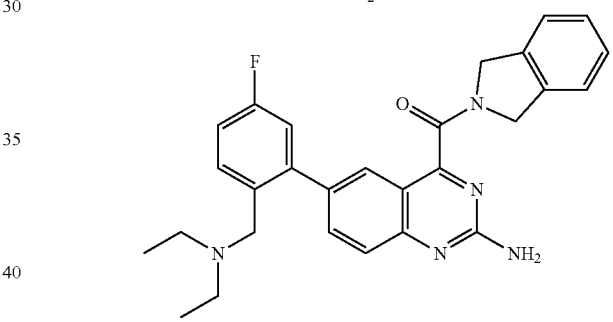

200 mg of [2-amino-6-(2-chloromethyl-5-fluorophenyl)quinazolin-4-yl]-(1,3-dihydroisoindol-2-yl)methanone are dissolved in 5 ml of acetonitrile. 301 mg of caesium carbonate and 73 μl of diethylamine are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness and purified by chromatography (reversed phase HPLC).

Yield: 35 mg (22%) of [2-amino-6-(2-diethylaminomethyl-5-fluorophenyl)quinazolin-4-yl]-(1,3-dihydroisoindol-2-yl)methanone;

LC-MS retention time: 1.57 min;

$^1$H NMR (500 MHz, DMSO-d$_6$) δ [ppm] 8.14 (d, J=1.7, 1H), 8.07 (dd, J=1.9, 8.6, 1H), 7.89 (d, J=8.6, 1H), 7.82 (dd, J=5.7, 8.7, 1H), 7.43 (dd, J=4.8, 13.1, 2H), 7.38-7.28 (m, 3H), 7.25 (d, J=7.4, 1H), 5.04 (s, 2H), 4.85 (s, 2H), 4.24 (s, 2H), 3.02-2.90 (m, 2H), 2.90-2.79 (m, 2H), 0.93 (t, J=7.2, 6H).

133

{2-Amino-6-[5-fluoro-2-(4-hydroxypiperidin-1-ylmethyl)phenyl]quinazolin-4-yl}-(1,3-dihydroisoindol-2-yl)methanone ("A58")

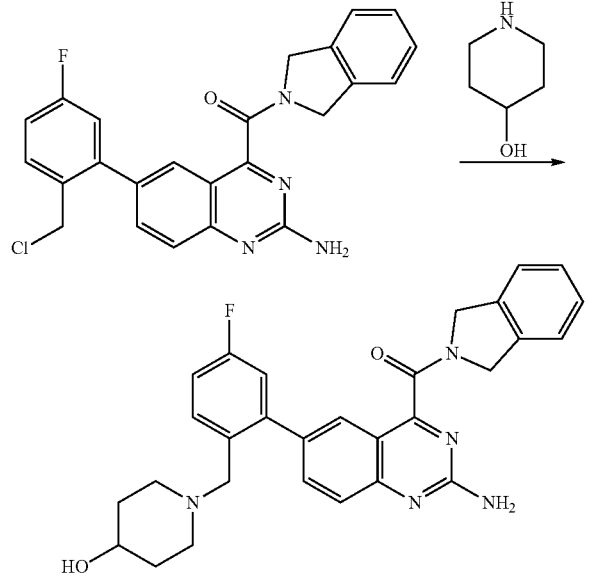

200 mg of [2-amino-6-(2-chloromethyl-5-fluorophenyl) quinazolin-4-yl]-(1,3-dihydroisoindol-2-yl)methanone are dissolved in 5 ml of acetonitrile. 301 mg of caesium carbonate and 57 µl of piperidin-4-ol are added, and the mixture is stirred at 80° C. for 16 h. After cooling to 25° C., the mixture is filtered, and the filtrate is evaporated to dryness. The residue is taken up in 5 ml of ethyl acetate, the solution is washed with 5 ml of 2N sodium hydroxide solution, and the combined organic phases are dried over sodium sulfate. After filtration, the filtrate is evaporated to dryness and purified by chromatography (reversed phase HPLC).

Yield: 70 mg (41%) of {2-amino-6-[5-fluoro-2-(4-hydroxypiperidin-1-ylmethyl)phenyl]quinazolin-4-yl}-(1,3-dihydroisoindol-2-yl)methanone;

LC-MS retention time: 1.48 min;

$^1$H NMR (500 MHz, DMSO-d$_6$) δ [ppm] 8.18-8.11 (m, 1H), 8.09-8.02 (m, 1H), 7.94-7.81 (m, 2H), 7.42 (ddd, J=5.0, 8.4, 9.4, 2H), 7.38-7.23 (m, 4H), 5.04 (s, 2H), 4.86 (d, J=6.6, 2H), 4.22 (d, J=24.6, 2H), 3.93-3.42 (m, 1H), 3.25 (d, J=12.1, 1H), 3.08 (d, J=11.9, 1H), 2.88 (t, J=11.5, 1H), 2.72-2.65 (m, 1H), 1.85-1.73 (m, 2H), 1.64-1.49 (m, 2H).

134

{2-Amino-6-[4,5-difluoro-2-(2-hydroxyethoxymethyl)phenyl]quinazolin-4-yl}-(1,3-dihydroisoindol-2-yl)methanone ("A59")

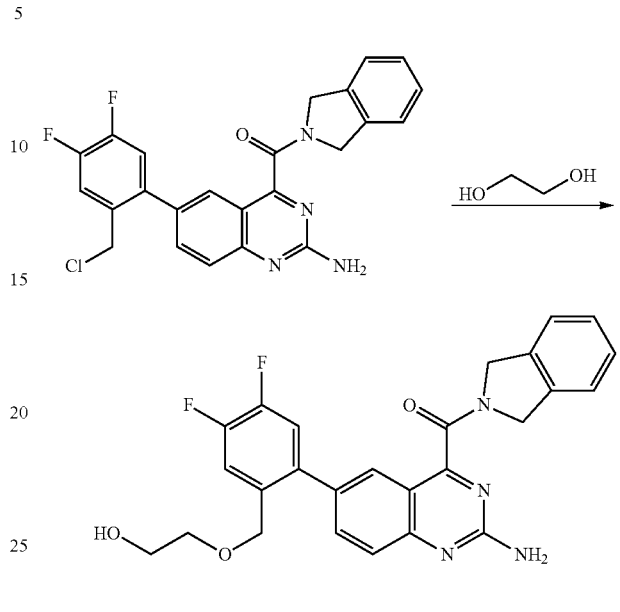

10 mg of sodium hydride (60% sodium hydride suspension in paraffin oil) are added in portions to 14 µl of ethylene glycol in 2 ml of THF, and the mixture is stirred at 25° C. for 1 h. A solution of 100 mg of [2-amino-6-(2-chloromethyl-5-fluorophenyl)quinazolin-4-yl]-(1,3-dihydroisoindol-2-yl)methanone together with 101 µl of triethylamine in 2 ml of tetrahydrofuran (dried) is added dropwise to this solution. The mixture is subsequently stirred at 70° C. overnight and evaporated to dryness. The residue is taken up in 1 ml of dimethyl sulfoxide and purified by chromatography (reversed phase HPLC).

Yield: 8 mg (8%) of {2-amino-6-[4,5-difluoro-2-(2-hydroxyethoxymethyl)phenyl]quinazolin-4-yl}-(1,3-dihydroisoindol-2-yl)methanone;

LC-MS retention time: 2.50 min;

$^1$H NMR (500 MHz, DMSO-d$_6$/TFA-d$_1$) δ [ppm] 8.13 (dd, J=8.7, 1.9, 1H), 8.09 (d, J=1.7, 1H), 7.85 (d, J=8.6, 1H), 7.62 (dd, J=11.6, 8.4, 1H), 7.44 (t, J=9.4, 2H), 7.33 (dt, J=18.2, 7.1, 2H), 7.26 (d, J=7.3, 1H), 5.04 (s, 2H), 4.86 (s, 2H), 4.32 (s, 2H), 3.47 (t, J=5.0, 2H), 3.36 (t, J=5.0, 2H).

[2-Amino-6-(4,5-difluoro-2-{2-[2-(2-hydroxyethoxy)ethoxy]ethoxymethyl}-phenyl)quinazolin-4-yl]-(1,3-dihydroisoindol-2-yl)methanone ("A60")

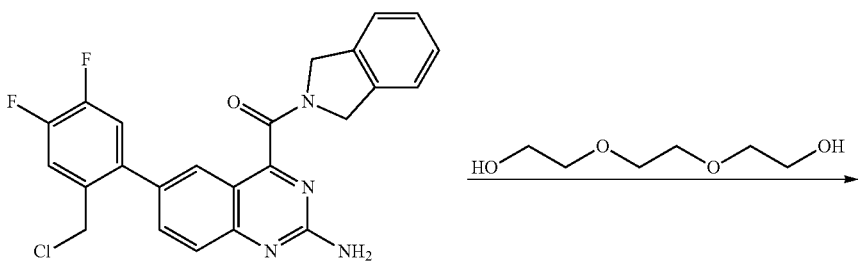

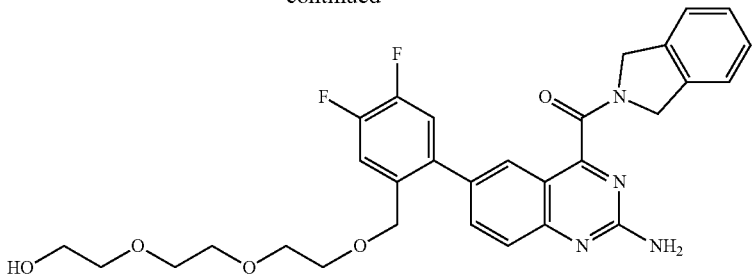

10 mg of sodium hydride (60% sodium hydride suspension in paraffin oil) are added in portions to 1 ml of triethylene glycol in 2 ml of THF, and the mixture is stirred at 25° C. for 1 h. A solution of 100 mg of [2-amino-6-(2-chloromethyl-5-fluorophenyl)quinazolin-4-yl]-(1,3-dihydroisoindol-2-yl) methanone together with 29 µl of triethylamine in 2 ml of tetrahydrofuran (dried) is added dropwise to this solution. The mixture is subsequently stirred at 70° C. overnight and evaporated to dryness. The residue is taken up in 1 ml of dimethyl sulfoxide and purified by chromatography (reversed phase HPLC).

Yield: 38 mg (33%) of [2-amino-6-(4,5-difluoro-2-{2-[2-(2-hydroxyethoxy)ethoxy]ethoxymethyl}phenyl)quinazolin-4-yl]-(1,3-dihydroisoindol-2-yl)methanone; LC-MS retention time: 2.00 min;

$^1$H NMR (500 MHz, DMSO-$d_6$/TFA-$d_1$) δ [ppm] 8.13 (dd, J=8.7, 1.9, 1H), 8.08 (d, J=1.8, 1H), 7.85 (d, J=8.6, 1H), 7.57 (dd, J=11.6, 8.4, 1H), 7.45 (dd, J=13.2, 5.9, 2H), 7.33 (dt, J=18.0, 7.2, 2H), 7.26 (d, J=7.3, 1H), 5.04 (s, 2H), 4.86 (s, 2H), 4.32 (s, 2H), 3.52-3.40 (m, 12H).

(2-Amino-6-{4,5-difluoro-2-[2-(2-hydroxyethoxy) ethoxymethyl]phenyl}quinazolin-4-yl)-(1,3-dihydroisoindol-2-yl)methanone ("A61")

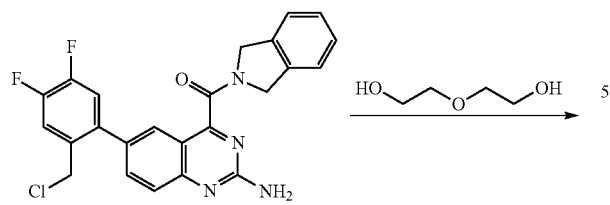

-continued

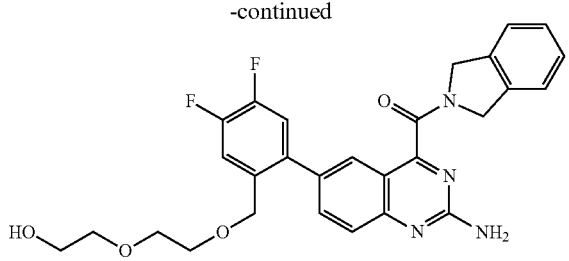

10 mg of sodium hydride (60% sodium hydride suspension in paraffin oil) are added in portions to 1 g of diethylene glycol in 2 ml of THF, and the mixture is stirred at 25° C. for 1 h. A solution of 100 mg of [2-amino-6-(2-chloromethyl-5-fluorophenyl)quinazolin-4-yl]-(1,3-dihydroisoindol-2-yl)methanone together with 29 µl of triethylamine in 2 ml of tetrahydrofuran (dried) is added dropwise to this solution. The mixture is subsequently stirred at 70° C. overnight and evaporated to dryness. The residue is taken up in 1 ml of dimethyl sulfoxide and purified by chromatography (reversed phase HPLC).

Yield: 30 mg (28%) of (2-amino-6-{4,5-difluoro-2-[2-(2-hydroxyethoxy)ethoxymethyl]phenyl}quinazolin-4-yl)-(1,3-dihydroisoindol-2-yl)methanone LC-MS retention time: 1.99 min;

$^1$H NMR (500 MHz, DMSO-$d_6$/TFA-$d_1$) δ [ppm] 8.12 (dd, J=8.6, 1.8, 1H), 8.07 (d, J=1.8, 1H), 7.85 (d, J=8.8, 1H), 7.57 (dd, J=11.5, 8.3, 1H), 7.45 (dd, J=13.1, 6.0, 2H), 7.33 (dt, J=18.2, 7.2, 2H), 7.26 (d, J=7.2, 1H), 5.04 (s, 2H), 4.86 (s, 2H), 4.32 (s, 2H), 3.49-3.43 (m, 6H), 3.38 (t, J=5.1, 2H).

{2-Amino-6-[4,5-difluoro-2-(2-{2-[2-(2-hydroxyethoxy)ethoxy]ethoxy}ethoxymethyl)phenyl] quinazolin-4-yl}-(1,3-dihydroisoindol-2-yl)methanone ("A62")

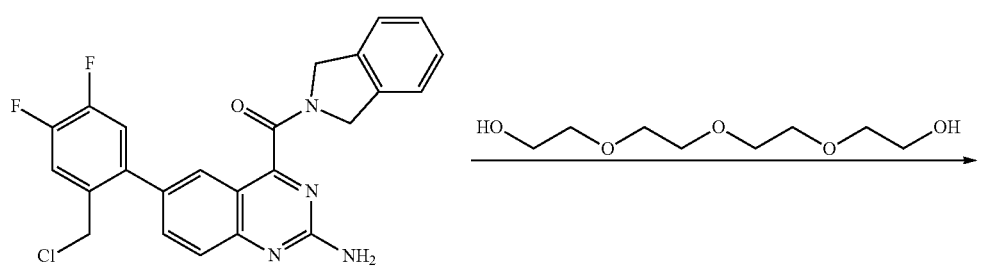

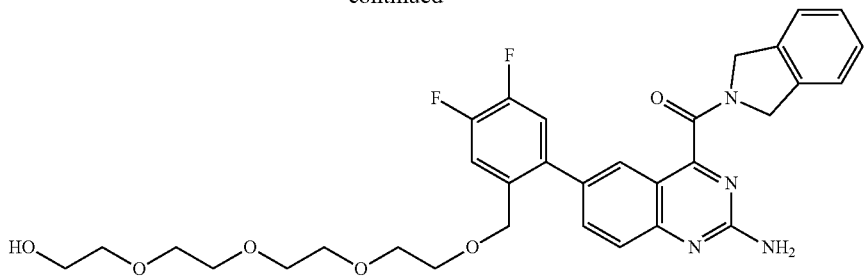

20 mg of sodium hydride (60% sodium hydride suspension in paraffin oil) are added in portions to 1 g of tetraethylene glycol in 2 ml of THF, and the mixture is stirred at 25° C. for 1 h. A solution of 200 mg of [2-amino-6-(2-chloromethyl-5-fluorophenyl)quinazolin-4-yl]-(1,3-dihydroisoindol-2-yl)methanone together with 57 µl of triethylamine in 2 ml of tetrahydrofuran (dried) is added dropwise to this solution. The mixture is subsequently stirred at 70° C. overnight and evaporated to dryness. The residue is taken up in 2 ml of dimethyl sulfoxide and purified by chromatography (reversed phase HPLC).

Yield: 80 mg (32%) of {2-amino-6-[4,5-difluoro-2-(2-{2-[2-(2-hydroxyethoxy)ethoxy]ethoxy}ethoxymethyl)phenyl]quinazolin-4-yl}-(1,3-dihydroisoindol-2-yl)methanone; LC-MS retention time: 2.05 min;

$^1$H NMR (500 MHz, DMSO-$d_6$/TFA-$d_1$) δ [ppm] 8.12 (dd, J=8.7, 1.6, 1H), 8.08 (d, J=1.7, 1H), 7.86 (d, J=8.6, 1H), 7.57 (dd, J=11.5, 8.3, 1H), 7.44 (t, J=9.4, 2H), 7.33 (dt, J=18.5, 7.4, 2H), 7.26 (d, J=7.5, 1H), 5.04 (s, 2H), 4.86 (s, 2H), 4.32 (s, 2H), 3.54-3.39 (m, 16H).

[2-Amino-6-(2-aminoxymethyl-4,5-difluorophenyl)quinazolin-4-yl]-(1,3-dihydroisoindol-2-yl)methanone ("A63")

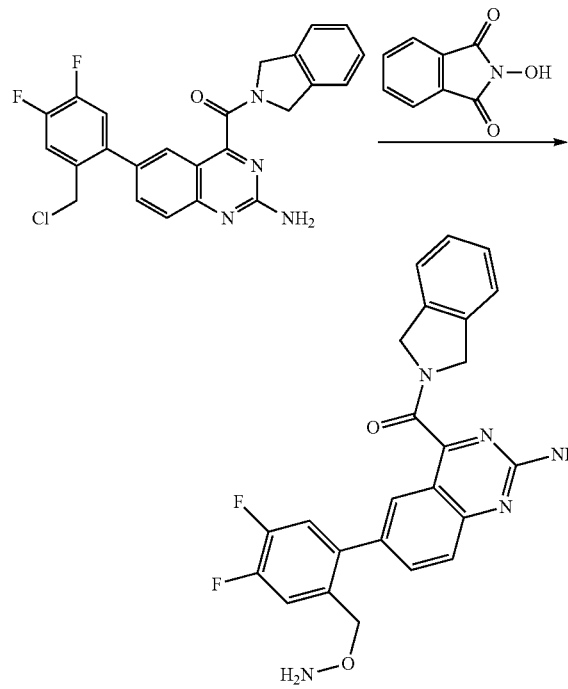

57 mg of potassium carbonate are added to 34 mg of N-hydroxyphthalimide in 1 ml of 1-methyl-2-pyrrolidone, and the mixture is stirred at 25° C. for 1 h. 100 mg of [2-amino-6-(2-chloromethyl-5-fluorophenyl)quinazolin-4-yl]-(1,3-dihydroisoindol-2-yl)methanone are added to this solution. The mixture is subsequently stirred at 25° C. overnight. 10 ml of ice-water are subsequently added, the precipitate formed is filtered off and suspended in 20 ml of dichloromethane. 20 µl of hydrazinium hydroxide are added, and the mixture is stirred at 25° C. for 4 h. The precipitate is filtered off, the filtrate is evaporated to dryness, the residue is taken up in 1 ml of dimethyl sulfoxide and purified by chromatography (reversed phase HPLC).

Yield: 29 mg (29%) of [2-amino-6-(2-aminoxymethyl-4,5-difluorophenyl)quinazolin-4-yl]-(1,3-dihydroisoindol-2-yl)methanone;

LC-MS retention time: 1.82 min.

[2-Amino-6-(4,5-difluoro-2-hydroxymethylphenyl)quinazolin-4-yl]-(1,3-dihydroisoindol-2-yl)methanone ("A64")

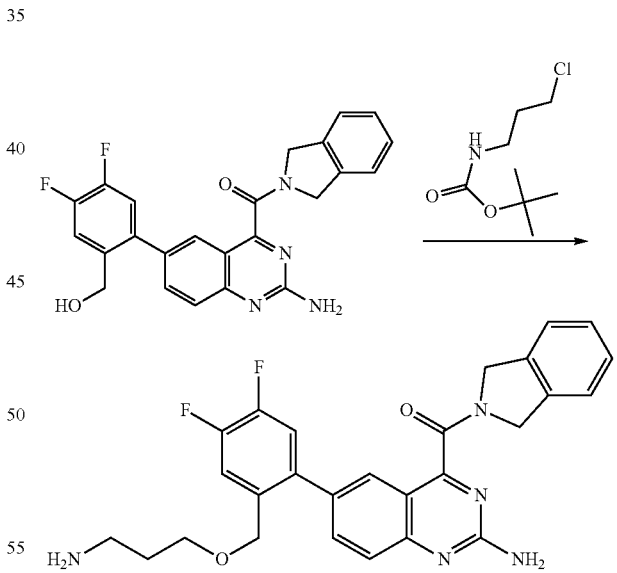

100 mg of [2-amino-6-(4,5-difluoro-2-hydroxymethylphenyl)quinazolin-4-yl]-(1,3-dihydroisoindol-2-yl)methanone are dissolved in 3 ml of tetrahydrofuran together with 90 mg of tert-butyl (3-chloropropyl)carbamate. 2 ml of sodium hydroxide solution (32%) and 2 mg of tetrabutylammonium iodide are added, and the mixture is stirred at 80° C. for 16 h. The mixture is extracted 3 times with 5 ml of ethyl acetate. The combined organic phases are dried over sodium sulfate. After filtration, the filtrate is evaporated to dryness, the residue is taken up in 3 ml of dichloromethane, and 1 ml of 4N HCl in dioxane is added. After 1 h at 25° C., the mixture is evaporated to dryness in vacuo and purified by chromatography (reversed phase HPLC).

Yield: 18 mg (16%) of {2-amino-6-[2-(3-aminopropoxymethyl)-4,5-difluorophenyl]quinazolin-4-yl}-(1,3-dihydroisoindol-2-yl)methanone;

LC-MS retention time: 1.66 min.

2-[2-Amino-4-(1,3-dihydroisoindole-2-carbonyl)quinazolin-6-yl]-4,5-difluorobenzyl 3-aminopropionate dihydrochloride ("A65")

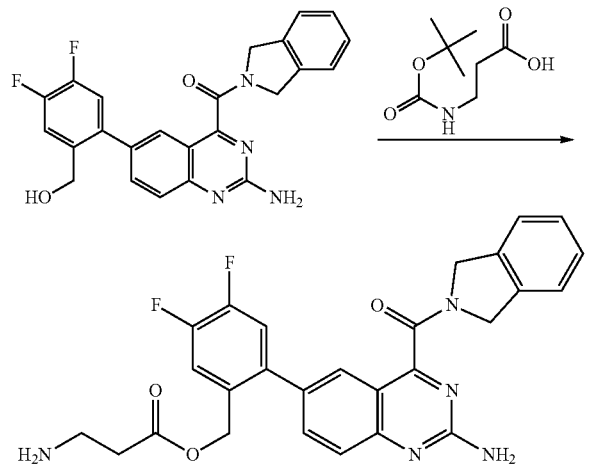

477 mg of dicyclohexylcarbodiimide are added to a solution of 875 mg of 3-tert-butoxycarbonylaminopropionic acid in 5 ml of dichloromethane, and the mixture is stirred at 25° C. for 1 h. The precipitate is filtered off, and the filtrate is added to a solution of 500 mg of [2-amino-6-(4,5-difluoro-2-hydroxymethylphenyl)quinazolin-4-yl]-(1,3-dihydroisoindol-2-yl)methanone and 70 mg of 4-(dimethylamino)pyridine (DMAP) in 10 ml of tetrahydrofuran. The mixture is stirred at 25° C. for 16 h and evaporated to dryness. Flash chromatography gives 480 mg of 2-[2-amino-4-(1,3-dihydroisoindole-2-carbonyl)quinazolin-6-yl]-4,5-difluorobenzyl 3-tert-butoxycarbonylaminopropionate. This material is dissolved in 10 ml of dichloromethane, and 5 ml of 4N HCl in dioxane are added with ice-cooling. The mixture is subsequently stirred at 25° C. for a further 1 h, during which a precipitate deposits. This is filtered off with suction and dried at 40° C. in vacuo.

Yield: 330 mg (50%) of 2-[2-amino-4-(1,3-dihydroisoindole-2-carbonyl)quinazolin-6-yl]-4,5-difluorobenzyl 3-aminopropionate dihydrochloride;

LC-MS retention time: 1.65 min;

$^1$H NMR (500 MHz, DMSO-$d_6$/TFA-$d_1$) δ [ppm] 8.11 (d, J=1.7, 1H), 8.07 (dd, J=1.9, 8.7, 1H), 7.89 (d, J=8.6, 1H), 7.63 (dd, J=8.2, 11.3, 1H), 7.49-7.43 (m, 2H), 7.34 (dt, J=7.2, 17.8, 2H), 7.26 (d, J=7.3, 1H), 5.05 (s, 2H), 4.99 (s, 2H), 4.88 (s, 2H), 3.06 (t, J=6.9, 2H), 2.73 (t, J=6.9, 2H).

2-[2-Amino-4-(1,3-dihydroisoindole-2-carbonyl)quinazolin-6-yl]-4,5-difluorobenzyl (S)-2,5-diaminopentanoate diformate ("A66")

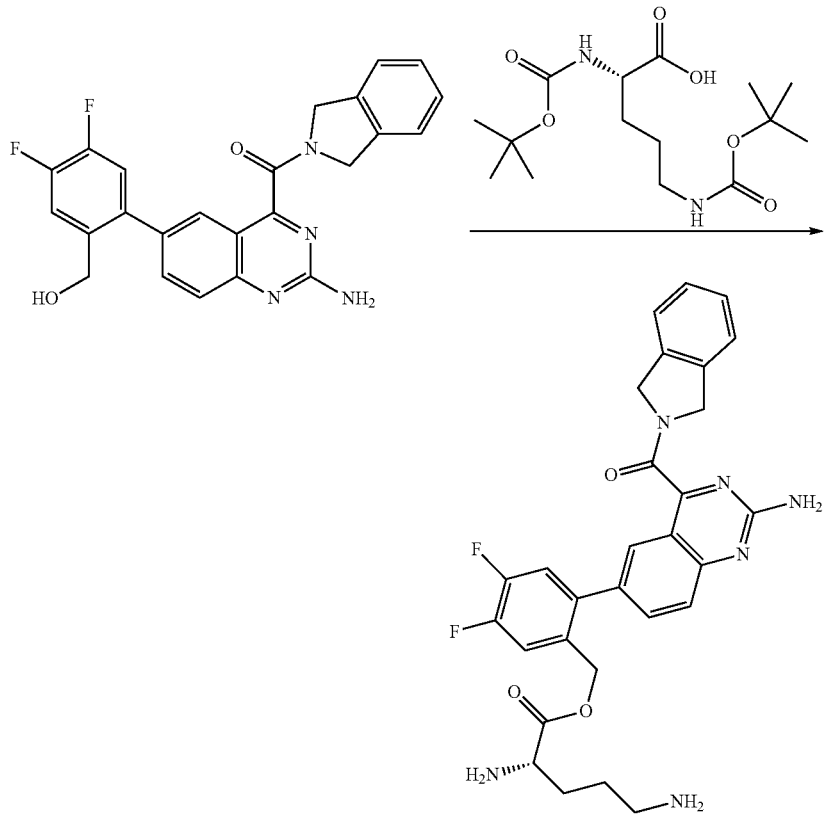

95 mg of dicyclohexylcarbodiimide are added to a solution of 308 mg of (S)-2,5-bis-tert-butoxycarbonylaminopentanoic acid in 2 ml of dichloromethane, and the mixture is stirred at 25° C. for 1 h. The precipitate is filtered off, and the filtrate is added to a solution of 100 mg of [2-amino-6-(4,5-difluoro-2-hydroxymethylphenyl)quinazolin-4-yl]-(1,3-dihydroisoindol-2-yl)methanone and 3 mg of 4-(dimethylamino)pyridine (DMAP) in 1 ml of tetrahydrofuran. The mixture is stirred at 25° C. for 16 h and evaporated to dryness. Trituration with petroleum ether gives 2-[2-amino-4-(1,3-dihydroisoindole-2-carbonyl)quinazolin-6-yl]-4,5-difluorobenzyl (S)-2,5-bis-tert-butoxycarbonylaminopentanoate as yellow solid. This material is dissolved in 2 ml of dichloromethane, and 4 ml of 4N HCl in dioxane are added with ice-cooling. The mixture is subsequently stirred at 25° C. for a further 3 h and subsequently evaporated to dryness in vacuo. The residue is dissolved in 2 ml of dimethyl sulfoxide and purified by chromatography (reversed phase HPLC).

Yield: 28 mg (22%) of 2-[2-amino-4-(1,3-dihydroisoindole-2-carbonyl)quinazolin-6-yl]-4,5-difluorobenzyl (S)-2,5-diaminopentanoate diformate;

LC-MS retention time: 1.45 min;

$^1$H NMR (500 MHz, DMSO-$d_6$/TFA-$d_1$) δ [ppm] 8.15-8.07 (m, 2H), 7.86 (d, J=8.8, 1H), 7.56 (dd, J=11.7, 8.4, 1H), 7.44 (d, J=7.3, 1H), 7.34 (dt, J=18.0, 9.4, 3H), 7.26 (d, J=7.5, 1H), 5.04 (s, 2H), 4.87 (s, 2H), 4.36 (s, 2H), 3.79 (dd, J=11.4, 6.2, 1H), 3.21 (dd, J=9.8, 4.5, 2H), 2.18 (s, 1H), 1.95-1.71 (m, 3H).

2-[2-Amino-4-(1,3-dihydroisoindole-2-carbonyl)quinazolin-6-yl]-4,5-difluorobenzyl 3-dimethylaminopropionate ("A67")

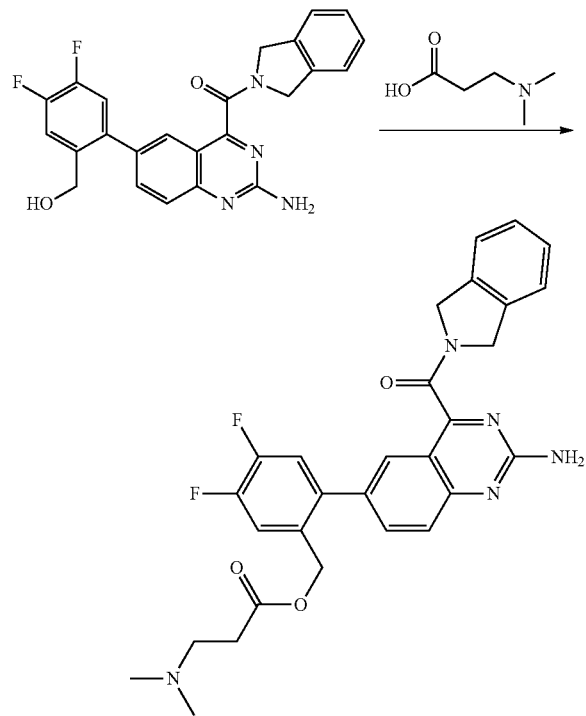

1.4 g of triethylamine and 1.431 g of dicyclohexylcarbodiimide are added to a solution of 2.131 g of 3-dimethylaminopropionic acid hydrochloride in 50 ml of dichloromethane, and the mixture is stirred at 25° C. for 1 h. The precipitate is filtered off, and the filtrate is added to a solution of 1.5 g of [2-amino-6-(4,5-difluoro-2-hydroxymethylphenyl)quinazolin-4-yl]-(1,3-dihydroisoindol-2-yl)methanone and 21 mg of 4-(dimethylamino)pyridine (DMAP) in 50 ml of tetrahydrofuran. The mixture is stirred at 25° C. for 16 h and evaporated to dryness. The residue is taken up in 50 ml of ethyl acetate, the solution is washed 3 times with 20 ml of water, and the combined organic phases are dried over sodium sulfate. After filtration, the filtrate is evaporated to dryness and purified by chromatography (reversed phase HPLC). The combined fractions are evaporated to dryness and recrystallised from 20 ml of acetonitrile.

Yield: 560 mg (30%) of 2-[2-amino-4-(1,3-dihydroisoindole-2-carbonyl)quinazolin-6-yl]-4,5-difluorobenzyl 3-dimethylaminopropionate;

LC-MS retention time: 1.67 min;

$^1$H NMR (500 MHz, DMSO-$d_6$/TFA-$d_1$) δ [ppm] 8.09 (d, J=1.7, 1H), 8.06 (dd, J=8.6, 2.0, 1H), 7.88 (d, J=8.6, 1H), 7.64 (dd, J=11.4, 8.3, 1H), 7.48 (dd, J=10.9, 8.0, 1H), 7.44 (d, J=7.5, 1H), 7.33 (dt, J=17.6, 7.3, 2H), 7.26 (d, J=7.3, 1H), 5.04 (s, 2H), 4.97 (s, 2H), 4.87 (s, 2H), 3.32 (t, J=7.4, 2H), 2.89 (t, J=7.3, 2H), 2.83 (s, 6H).

2-[2-Amino-4-(1,3-dihydroisoindole-2-carbonyl)quinazolin-6-yl]-4,5-difluorobenzyl (S)-2,6-bis-tert-butoxycarbonylaminohexanoate ("A68")

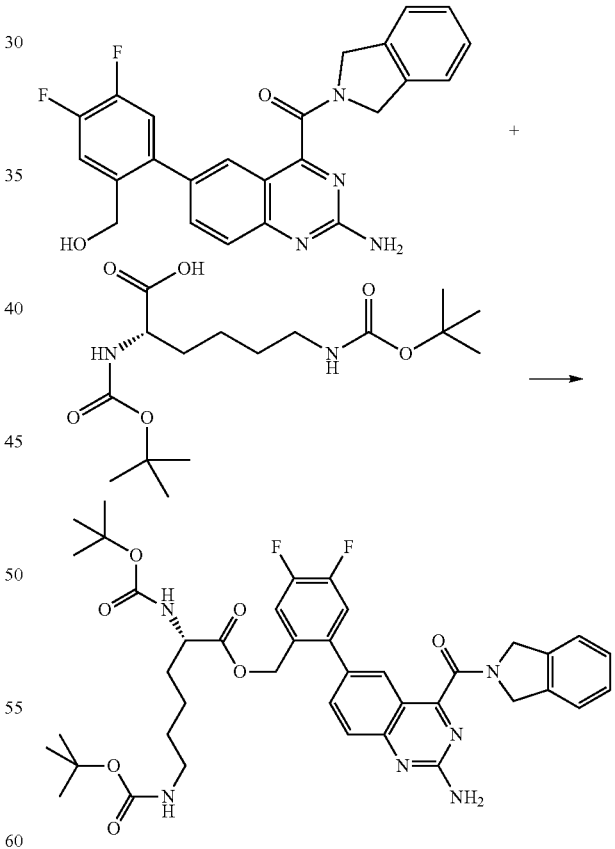

1.431 g of dicyclohexylcarbodiimide are added to a solution of 4.807 g of (S)-2,6-bis-tert-butoxycarbonylaminohexanoic acid in 50 ml of dichloromethane, and the mixture is stirred at 25° C. for 1 h. The precipitate is filtered off, and the filtrate is added to a solution of 1.5 g of [2-amino-6-(4,5-difluoro-2-hydroxymethylphenyl)quinazolin-4-yl]-(1,3-dihydroisoindol-2-yl)methanone and 21 mg of 4-(dimethylamino)pyridine (DMAP) in 100 ml of tetrahydrofuran. The mixture is stirred at 25° C. for 16 h, undissolved material is filtered, and the filtrate is evaporated to dryness. The residue is purified by normal-phase chromatography.

Yield: 1.85 g (70%) of 2-[2-amino-4-(1,3-dihydroisoindole-2-carbonyl)quinazolin-6-yl]-4,5-difluorobenzyl (S)-2,6-bis-tert-butoxycarbonylaminohexanoate;

LC-MS retention time: 2.67 min;

$^1$H NMR (500 MHz, DMSO-d$_6$) δ [ppm] 8.14 (d, J=1.7, 1H), 8.08 (dd, J=8.6, 1.9, 1H), 7.89 (d, J=8.6, 1H), 7.72 (dd, J=11.3, 8.2, 1H), 7.51 (dd, J=10.9, 8.0, 1H), 7.44 (d, J=7.4, 1H), 7.34 (dt, J=18.5, 7.2, 2H), 7.27 (d, J=7.3, 1H), 5.14-5.03 (m, 4H), 4.93-4.84 (m, 2H), 4.17 (t, J=6.5, 1H), 2.82-2.75 (m, 2H), 1.93-1.76 (m, 2H), 1.59 (dt, J=15.3, 7.5, 2H), 1.53-1.32 (m, 20H).

The following are obtained analogously:

2-[2-Amino-4-(1,3-dihydroisoindole-2-carbonyl)quinazolin-6-yl]benzyl (S)-2,6-bis-tert-butoxycarbonylaminohexanoate ("A69")

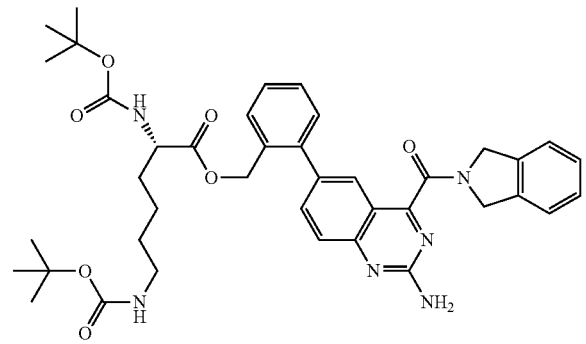 [SMILES: CC(C)(C)OC(=O)NCCCC[C@H](NC(=O)OC(C)(C)C)C(=O)OCc1ccccc1-c1ccc2nc(N)nc(C(=O)N3Cc4ccccc4C3)c2c1]

Yield: 3 g (33%) of 2-[2-amino-4-(1,3-dihydroisoindole-2-carbonyl)quinazolin-6-yl]benzyl (S)-2,6-bis-tert-butoxycarbonylaminohexanoate;

LC-MS retention time: 2.60 min;

$^1$H NMR (400 MHz, DMSO-d$_6$/TFA-d$_1$) δ [ppm] 8.15 (d, J=1.7, 1H), 8.10 (dd, J=8.7, 5.2, 1H), 7.90 (d, J=8.7, 1H), 7.68-7.62 (m, 1H), 7.55-7.47 (m, 2H), 7.42 (t, J=7.6, 2H), 7.33 (dt, J=14.3, 7.1, 2H), 7.26 (d, J=7.5, 1H), 5.15 (q, J=12.2, 2H), 5.05 (s, 2H), 4.90 (s, 2H), 4.16 (t, J=6.4, 1H), 2.85-2.72 (m, 2H), 1.84 (tt, J=13.9, 6.9, 2H), 1.60 (dt, J=15.3, 7.6, 2H), 1.54-1.29 (m, 20H).

2-[2-Amino-4-(1,3-dihydroisoindole-2-carbonyl)quinazolin-6-yl]-4-fluorobenzyl (S)-2,6-bis-tert-butoxycarbonylaminohexanoate ("A70")

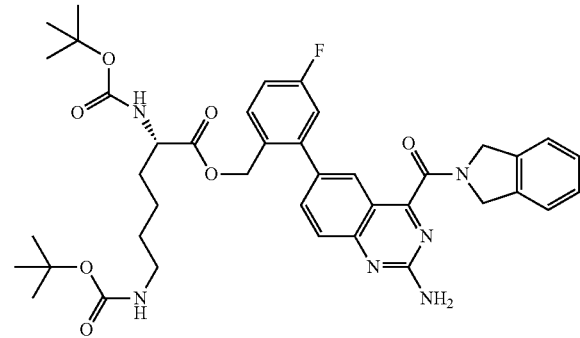 [SMILES: CC(C)(C)OC(=O)NCCCC[C@H](NC(=O)OC(C)(C)C)C(=O)OCc1ccc(F)cc1-c1ccc2nc(N)nc(C(=O)N3Cc4ccccc4C3)c2c1]

Yield: 5 g (99%) of 2-[2-amino-4-(1,3-dihydroisoindole-2-carbonyl)quinazolin-6-yl]-4-fluorobenzyl (S)-2,6-bis-tert-butoxycarbonylaminohexanoate;

LC-MS retention time: 2.38 min;

$^1$H NMR (500 MHz, DMSO-d$_6$) δ [ppm] 8.14 (d, J=1.7, 1H), 8.08 (dd, J=8.6, 1.9, 1H), 7.89 (d, J=8.6, 1H), 7.72 (dd, J=11.3, 8.2, 1H), 7.51 (dd, J=10.9, 8.0, 1H), 7.44 (d, J=7.4, 1H), 7.39-7.29 (m, 3H), 7.29-7.24 (m, 2H), 5.11 (q, J=12.3, 2H), 5.05 (s, 2H), 4.90 (s, 2H), 4.17 (t, J=6.5, 1H), 2.82-2.75 (m, 2H), 1.93-1.76 (m, 2H), 1.59 (dt, J=15.3, 7.5, 2H), 1.53-1.32 (m, 20H).

2-[2-Amino-4-(1,3-dihydroisoindole-2-carbonyl)quinazolin-6-yl]-4,5-difluorobenzyl (S)-2-tert-butoxycarbonylamino-6-dimethylaminohexanoate ("A70a")

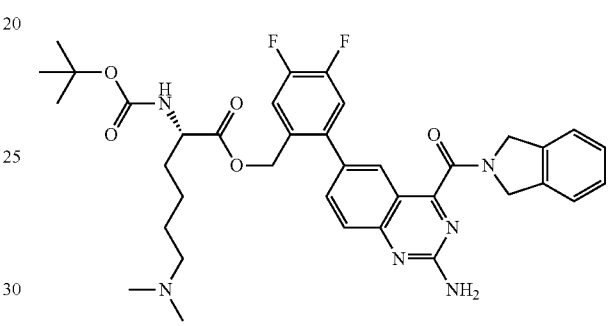

Yield: 1 g (63%) of 2-[2-amino-4-(1,3-dihydroisoindole-2-carbonyl)quinazolin-6-yl]-4,5-difluorobenzyl (S)-2-tert-butoxycarbonylamino-6-dimethylaminohexanoate;

LC-MS retention time: 1.87 min;

$^1$H NMR (500 MHz, DMSO-d$_6$/TFA-d$_1$) δ [ppm] 8.14 (1H, d, J 1.6), 8.06 (1H, dd, J 8.6, 1.7), 7.89 (1H, d, J 8.7), 7.56 (1H, dd, J 11.3, 8.1), 7.45-7.28 (4 H, m), 7.24 (1H, d, J 7.4), 5.07 (2H, s), 5.00 (2H, dd, J 25.8, 12.8), 4.89 (2H, s), 3.93 (1H, dd, J 9.6, 4.8), 3.21 (2H, s), 3.03 (2H, t, J 7.7), 2.61 (3H, t, J 3.5, 1.8), 1.71-1.56 (5H, m), 1.46-1.20 (11H, m).

2-[2-Amino-4-(1,3-dihydroisoindole-2-carbonyl)quinazolin-6-yl]-4,5-difluorobenzyl (S)-2,6-diaminohexanoate formate ("A71")

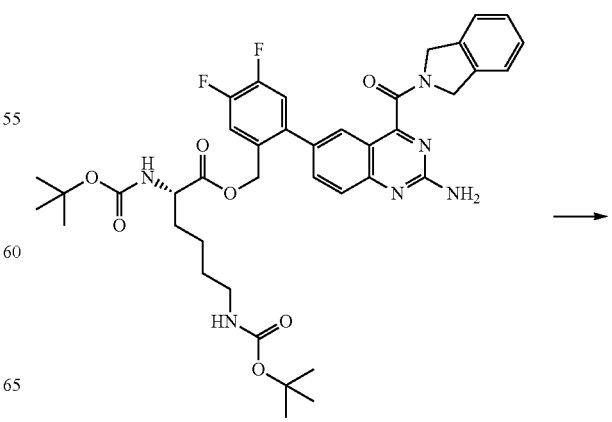

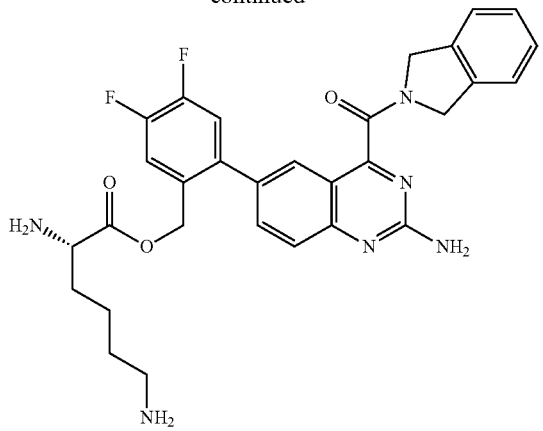

515 μl of trifluoroacetic acid are added to 1.8 g of 2-[2-amino-4-(1,3-dihydroisoindole-2-carbonyl)quinazolin-6-yl]-4,5-difluorobenzyl (S)-2,6-bis-tert-butoxycarbonylaminohexanoate in 50 ml of dichloromethane with ice-cooling. The mixture is subsequently stirred at 25° C. for a further 16 h, 20 ml of n-heptane are added, and the mixture is subsequently evaporated to dryness in vacuo. The residue is dissolved in 4 ml of acetonitrile and purified by chromatography (reversed phase HPLC).

Yield: 1.39 g (97%) of 2-[2-amino-4-(1,3-dihydroisoindole-2-carbonyl)quinazolin-6-yl]-4,5-difluorobenzyl (S)-2,6-diaminohexanoate formate;

LC-MS retention time: 1.45 min;

$^1$H NMR (500 MHz, DMSO-$d_6$) δ [ppm] 8.14 (d, J=1.7, 1H), 8.08 (dd, J=8.6, 1.9, 1H), 7.89 (d, J=8.6, 1H), 7.72 (dd, J=11.3, 8.2, 1H), 7.51 (dd, J=10.9, 8.0, 1H), 7.44 (d, J=7.4, 1H), 7.34 (dt, J=18.5, 7.2, 2H), 7.27 (d, J=7.3, 1H), 5.14-5.03 (m, 4H), 4.93-4.84 (m, 2H), 4.17 (t, J=6.5, 1H), 2.82-2.75 (m, 2H), 1.93-1.76 (m, 2H), 1.59 (dt, J=15.3, 7.5, 2H), 1.53-1.32 (m, 2H).

The following are obtained analogously:

2-[2-Amino-4-(1,3-dihydroisoindole-2-carbonyl)quinazolin-6-yl]-4-fluorobenzyl (S)-2,6-diaminohexanoate ("A72")

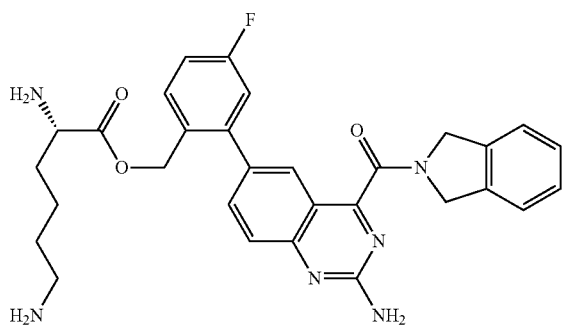 [SMILES: NCCCC[C@H](N)C(=O)OCc1ccc(F)cc1-c1ccc2nc(N)nc(C(=O)N3Cc4ccccc4C3)c2c1]

Yield: 5 g (99%) of 2-[2-amino-4-(1,3-dihydroisoindole-2-carbonyl)quinazolin-6-yl]-4-fluorobenzyl (S)-2,6-diaminohexanoate;

LC-MS retention time: 1.32 min;

$^1$H NMR (500 MHz, DMSO-$d_6$/TFA-$d_1$) δ [ppm] 8.16 (d, J=1.5, 1H), 8.13-8.08 (m, 1H), 7.89 (d, J=8.6, 1H), 7.70 (dd, J=8.6, 5.9, 1H), 7.43 (d, J=7.3, 1H), 7.39-7.29 (m, 3H), 7.29-7.24 (m, 2H), 5.11 (q, J=12.3, 2H), 5.05 (s, 2H), 4.90 (s, 2H), 4.14 (t, J=6.4, 1H), 2.82-2.74 (m, 2H), 1.91-1.74 (m, 2H), 1.58 (dt, J=15.2, 7.5, 2H), 1.53-1.30 (m, 2H).

2-[2-Amino-4-(1,3-dihydroisoindole-2-carbonyl)quinazolin-6-yl]benzyl (S)-2,6-diaminohexanoate ("A73")

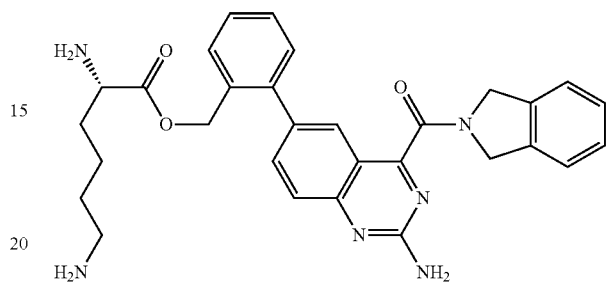

Yield: 2 g (85%) of 2-[2-amino-4-(1,3-dihydroisoindole-2-carbonyl)quinazolin-6-yl]benzyl (S)-2,6-diaminohexanoate; LC-MS retention time: 1.30 min;

$^1$H NMR (400 MHz, DMSO-$d_6$/TFA-$d_1$) δ [ppm] 8.15 (d, J=1.7, 1H), 8.10 (dd, J=8.7, 5.2, 1H), 7.90 (d, J=8.7, 1H), 7.68-7.62 (m, 1H), 7.55-7.47 (m, 2H), 7.42 (t, J=7.6, 2H), 7.33 (dt, J=14.3, 7.1, 2H), 7.26 (d, J=7.5, 1H), 5.15 (q, J=12.2, 2H), 5.05 (s, 2H), 4.90 (s, 2H), 4.16 (t, J=6.4, 1H), 2.85-2.72 (m, 2H), 1.84 (tt, J=13.9, 6.9, 2H), 1.60 (dt, J=15.3, 7.6, 2H), 1.54-1.29 (m, 2H).

2-[2-Amino-4-(1,3-dihydroisoindole-2-carbonyl)quinazolin-6-yl]-4,5-difluorobenzyl (S)-2-amino-6-dimethylaminohexanoate ("A73a")

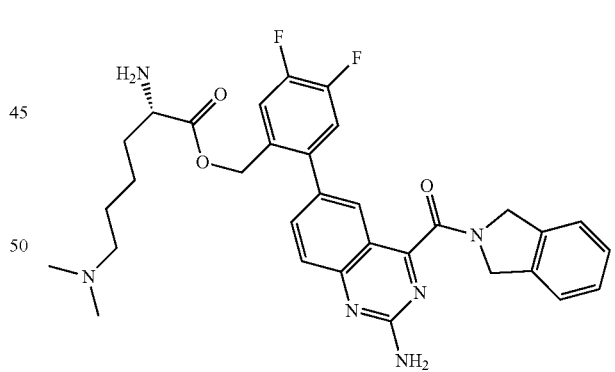

Yield: 1.99 g (98%) of 2-[2-amino-4-(1,3-dihydroisoindole-2-carbonyl)quinazolin-6-yl]-4,5-difluorobenzyl (S)-2-amino-6-dimethylaminohexanoate trihydrochloride;

LC-MS retention time: 1.43 min;

$^1$H NMR (500 MHz, DMSO-$d_6$/TFA-$d_1$) δ [ppm] 8.17 (1H, d, J1.8), 8.06 (1H, dd, J 8.7, 1.9), 7.93 (1H, d, J 8.6), 7.68 (1H, dd, J 11.2, 8.1), 7.42 (2H, t, J 9.3), 7.34 (2H, dt, J 18.2, 7.2), 7.26 (1H, d, J 7.3), 5.17-5.02 (4H, m), 4.90 (2H, d, J 14.1), 4.18 (1H, t, J 6.5), 3.07 (2H, t, J 8.1), 2.62 (3H, dt, J 3.6, 1.7), 1.96-1.83 (2H, m), 1.77-1.66 (2H, m), 1.56-1.37 (2H, m).

147

2-[2-Amino-4-(1,3-dihydroisoindole-2-carbonyl)quinazolin-6-yl]-4,5-difluorobenzyl 2-amino-4-methylpentanoate ("A74")

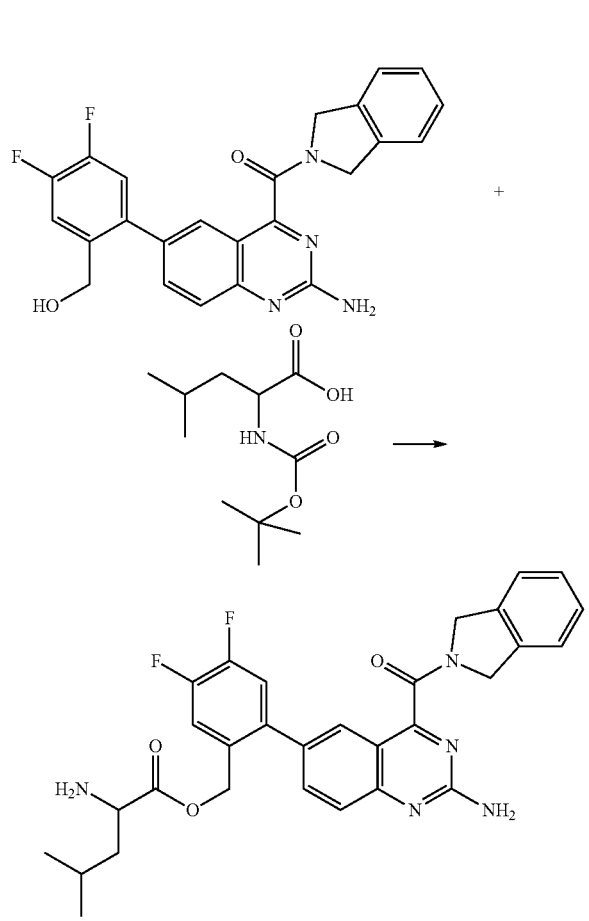

143 mg of dicyclohexylcarbodiimide are added to a solution of 321 mg of 2-tert-butoxycarbonylamino-4-methylpentanoic acid in 2 ml of dichloromethane, and the mixture is stirred at 25° C. for 1 h. The precipitate is filtered off, and the filtrate is added to a solution of 150 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 2 ml of tetrahydrofuran. The mixture is stirred at 25° C. for 16 h, undissolved material is filtered, and the filtrate is evaporated to dryness. The residue is taken up in 2 ml of dichloromethane, 100 µl of trifluoroacetic acid are added, and the mixture is stirred at 2500 for 16 h. 3 ml of n-heptane are subsequently added, and the mixture is evaporated to dryness in vacuo. The residue is dissolved in 4 ml of acetonitrile/water (1:1) and purified by chromatography (reversed phase HPLC).

Yield: 94 mg (50%) of 2-[2-amino-4-(1,3-dihydroisoindole-2-carbonyl)quinazolin-6-yl]-4,5-difluorobenzyl 2-amino-4-methylpentanoate;

LC-MS retention time: 1.77 min;

$^1$H NMR (500 MHz, DMSO-$d_6$/TFA-$d_1$) δ [ppm] 8.10 (d, J=1.5, 1H), 8.08 (dd, J=8.6, 2.0, 1H), 7.85 (d, J=8.6, 1H), 7.71 (dd, J=11.4, 8.1, 1H), 7.53 (dd, J=10.8, 8.1, 1H), 7.44 (d, J=7.3, 1H), 7.34 (dt, J=18.3, 7.2, 2H), 7.27 (d, J=7.3, 1H), 5.09 (s, 2H), 5.02 (s, 2H), 4.86 (s, 2H), 4.08 (t, J=7.1, 1H), 1.67 (td, J=13.4, 6.7, 1H), 1.56 (t, J=7.2, 2H), 0.86 (t, J=6.7, 6H).

148

2-[2-Amino-4-(1,3-dihydroisoindole-2-carbonyl)quinazolin-6-yl]-4,5-difluorobenzyl (S)-2-tert-butoxycarbonylaminopropionate ("A75")

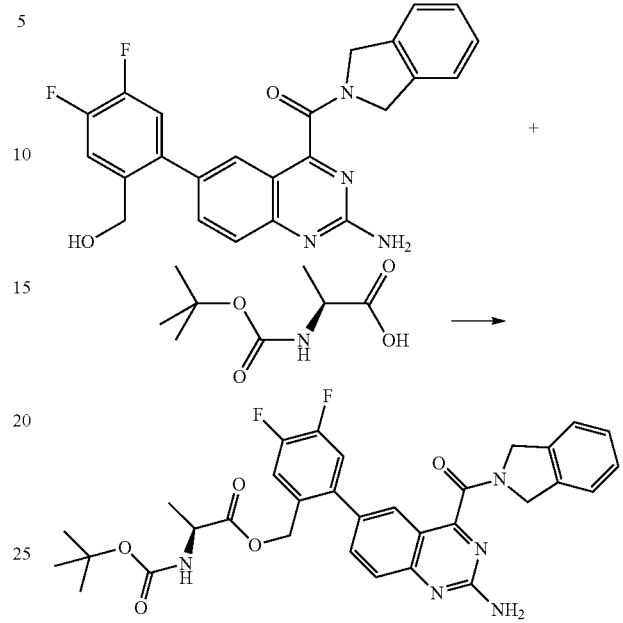

143 mg of dicyclohexylcarbodiimide are added to a solution of 263 mg of (S)-2-tert-butoxycarbonylaminopropanoic acid in 2 ml of dichloromethane, and the mixture is stirred at 25° C. for 1 h. The precipitate is filtered off, and the filtrate is added to a solution of 200 mg of [2-amino-6-(4,5-difluoro-2-hydroxymethylphenyl)quinazolin-4-yl]-(1,3-dihydroisoindol-2-yl)methanone and 3 mg of 4-(dimethylamino)pyridine (DMAP) in 2 ml of tetrahydrofuran. The mixture is stirred at 25° C. for 16 h, undissolved material is filtered, and the filtrate is evaporated to dryness. The residue is purified by normal-phase chromatography.

Yield: 270 mg (97%) of 2-[2-amino-4-(1,3-dihydroisoindole-2-carbonyl)quinazolin-6-yl]-4,5-difluorobenzyl (S)-2-tert-butoxycarbonylaminopropionate;

LC-MS retention time: 2.46 min;

$^1$H NMR (500 MHz, DMSO-$d_6$/TFA-$d_1$) δ [ppm] 8.14 (d, J=1.7, 1H), 8.07 (dd, J=8.6, 1.8, 1H), 7.89 (d, J=8.6, 1H), 7.69 (dd, J=11.4, 8.3, 1H), 7.47 (dt, J=13.9, 7.0, 1H), 7.44 (d, J=7.3, 1H), 7.34 (dt, J=18.0, 7.2, 2H), 7.26 (d, J=7.3, 1H), 5.07 (s, 2H), 4.98 (d, J=5.9, 2H), 4.89 (s, 2H), 3.54-3.43 (m, 1H), 1.42 (s, 9H), 1.40 (d, J=7.2, 3H).

2-[2-Amino-4-(1,3-dihydroisoindole-2-carbonyl)quinazolin-6-yl]-4,5-difluorobenzyl (S)-2-aminopropionate dihydrochloride ("A76")

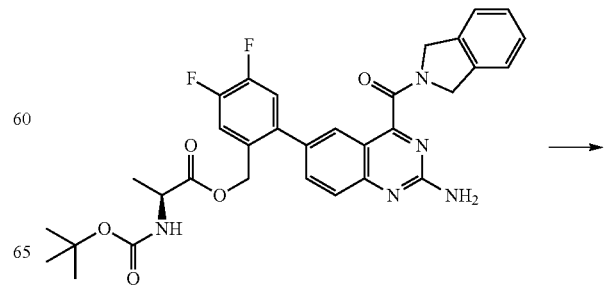

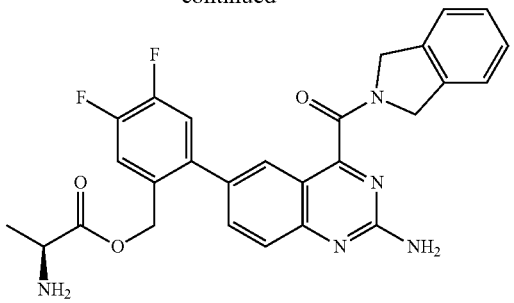

911 μl of 4N HCl in dioxane are added to 220 mg of 2-[2-amino-4-(1,3-dihydroisoindole-2-carbonyl)quinazolin-6-yl]-4,5-difluorobenzyl (S)-2-tert-butoxycarbonylaminopropionate in 4 ml of dichloromethane with ice-cooling. The mixture is subsequently stirred at 25° C. for a further 1 h, the precipitate is filtered off with suction and washed with 4 ml of dichloromethane. The residue is recrystallised from ethanol.

Yield: 60 mg (29%) of 2-[2-amino-4-(1,3-dihydroisoindole-2-carbonyl)quinazolin-6-yl]-4,5-difluorobenzyl (S)-2-aminopropionate dihydrochloride;

LC-MS retention time: 1.63 min;

$^1$H NMR (500 MHz, DMSO-d$_6$/TFA-d$_1$) δ [ppm] 8.14 (d, J=1.7, 1H), 8.07 (dd, J=8.6, 1.8, 1H), 7.89 (d, J=8.6, 1H), 7.69 (dd, J=11.4, 8.3, 1H), 7.47 (dt, J=13.9, 7.0, 1H), 7.44 (d, J=7.3, 1H), 7.34 (dt, J=18.0, 7.2, 2H), 7.26 (d, J=7.3, 1H), 5.08 (d, J=1.3, 2H), 5.04 (s, 2H), 4.89 (s, 2H), 4.20 (q, J=7.2, 1H), 1.40 (d, J=7.2, 3H).

2-[2-Amino-4-(1,3-dihydroisoindole-2-carbonyl)quinazolin-6-yl]-4,5-difluorobenzyl 2,2-dimethylpropionate ("A77")

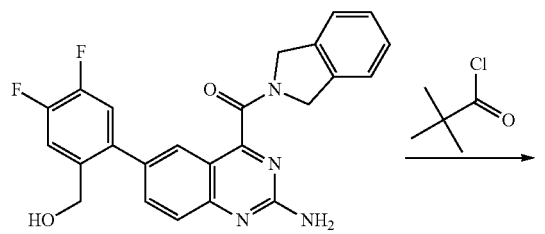

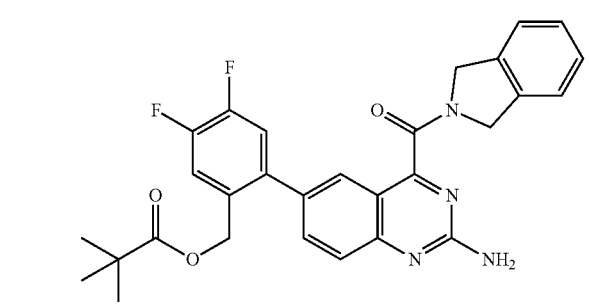

47 μl of pivaloyl chloride are added to a solution of 200 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 4 ml of dimethylformamide, and the mixture is stirred at 80° C. for 16 h. 8 ml of ethyl acetate and 8 ml of water are added, the organic phase is separated off and evaporated to dryness in vacuo. The residue is dissolved in 1 ml of dimethyl sulfoxide and purified by chromatography (reversed phase HPLC).

Yield: 26 mg (15%) of 2-[2-amino-4-(1,3-dihydroisoindole-2-carbonyl)quinazolin-6-yl]-4,5-difluorobenzyl 2,2-dimethylpropionate;

LC-MS retention time: 2.59 min;

$^1$H NMR (500 MHz, DMSO-d$_6$/TFA-d$_1$) δ [ppm] 8.11 (d, J=1.8, 1H), 8.06 (dd, J=8.6, 1.8, 1H), 7.88 (d, J=8.6, 1H), 7.54-7.47 (m, 1H), 7.43 (t, J=8.7, 2H), 7.33 (dt, J=19.1, 7.2, 2H), 7.25 (d, J=7.5, 1H), 5.04 (s, 2H), 4.95 (s, 2H), 4.87 (s, 2H), 1.06 (s, 9H).

2-[2-Amino-4-(1,3-dihydroisoindole-2-carbonyl)quinazolin-6-yl]-4,5-difluorobenzyl isobutyrate ("A78")

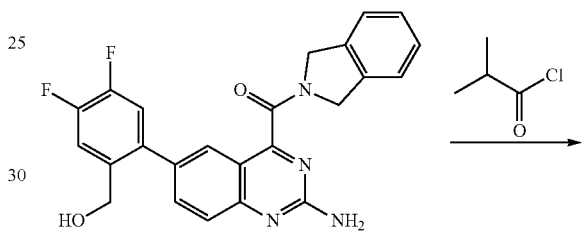

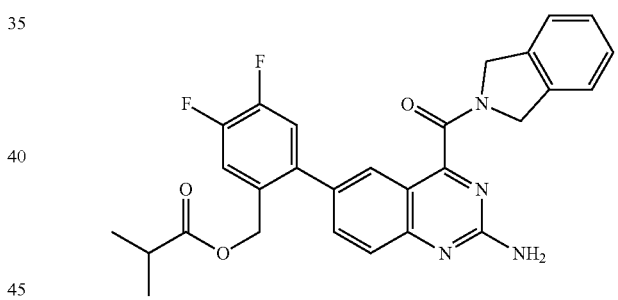

40 μl of isobutyryl chloride are added to a solution of 150 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 5 ml of dimethylformamide, and the mixture is stirred at 80° C. for 16 h. 8 ml of ethyl acetate and 8 ml of water are added, the organic phase is separated off and evaporated to dryness in vacuo. The residue is dissolved in 1 ml of dimethyl sulfoxide and purified by chromatography (reversed phase HPLC).

Yield: 48 mg (28%) of 2-[2-amino-4-(1,3-dihydroisoindole-2-carbonyl)quinazolin-6-yl]-4,5-difluorobenzyl isobutyrate;

LC-MS retention time: 2.49 min;

$^1$H NMR (500 MHz, DMSO-d$_6$/TFA-d$_1$) δ [ppm] 8.09-8.04 (m, 2H), 7.85 (d, J=8.6, 1H), 7.57 (dd, J=11.4, 8.3, 1H), 7.46 (dd, J=13.2, 7.7, 2H), 7.33 (dt, J=18.9, 7.1, 2H), 7.25 (d, J=7.2, 1H), 5.02 (s, 2H), 4.92 (s, 2H), 4.85 (s, 2H), 2.51-2.44 (m, 1H), 0.99 (d, J=7.0, 6H).

2-[2-Amino-4-(1,3-dihydroisoindole-2-carbonyl)quinazolin-6-yl]-4,5-difluorobenzyl propionate ("A79")

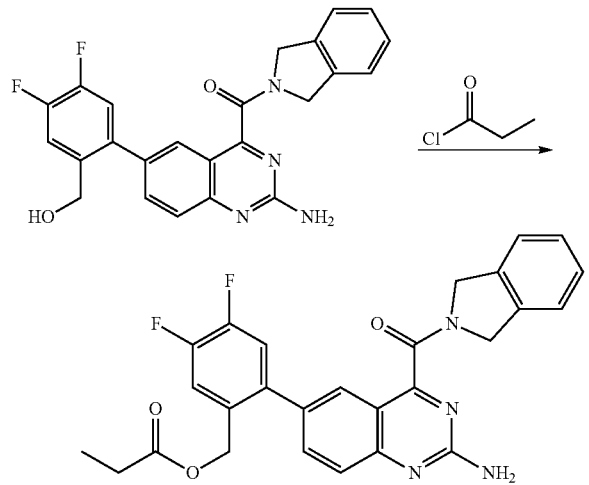

33 µl of propionyl chloride are added to a solution of 150 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 5 ml of dimethylformamide, and the mixture is stirred at 80° C. for 16 h. 8 ml of ethyl acetate and 8 ml of water are added, the organic phase is separated off and evaporated to dryness in vacuo. The residue is dissolved in 1 ml of dimethyl sulfoxide and purified by chromatography (reversed phase HPLC).

Yield: 30 mg (18%) of 2-[2-amino-4-(1,3-dihydroisoindole-2-carbonyl)quinazolin-6-yl]-4,5-difluorobenzyl propionate;

LC-MS retention time: 2.37 min;

$^1$H NMR (500 MHz, DMSO-d$_6$) δ [ppm] 8.09-8.03 (m, 2H), 7.86 (d, J=8.4, 1H), 7.58 (dd, J=11.4, 8.3, 1H), 7.48-7.42 (m, 2H), 7.33 (dt, J=19.1, 7.2, 2H), 7.25 (d, J=7.5, 1H), 5.03 (s, 2H), 4.90 (s, 2H), 4.86 (s, 2H), 2.27 (q, J=7.5, 2H), 0.95 (t, J=7.5, 3H).

2-[2-Amino-4-(1,3-dihydroisoindole-2-carbonyl)quinazolin-6-yl]-4,5-difluorobenzyl 2-tert-butoxycarbonylamino-2-methylpropionate ("A80")

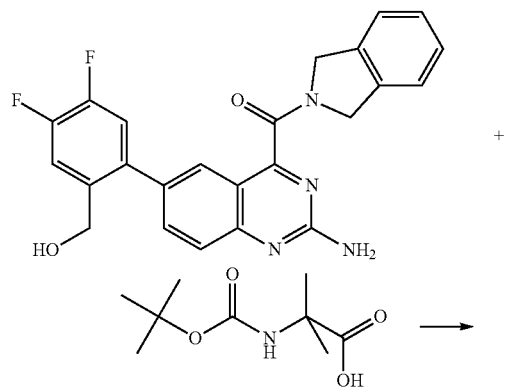

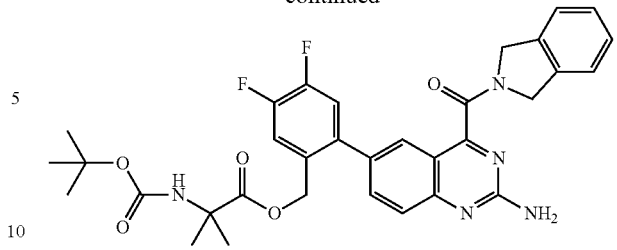

2.2 g of dicyclohexylcarbodiimide are added to a solution of 4.2 g of 2-tert-butoxycarbonylamino-2-methylpropionic acid in 100 ml of dichloromethane, and the mixture is stirred at 25° C. for 1 h. The precipitate is filtered off, and the filtrate is added to a solution of 1.5 g of [2-amino-6-(4,5-difluoro-2-hydroxymethylphenyl)quinazolin-4-yl]-(1,3-dihydroisoindol-2-yl)methanone and 20 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 1.3 g (61%) of 2-[2-amino-4-(1,3-dihydroisoindole-2-carbonyl)quinazolin-6-yl]-4,5-difluorobenzyl 2-tert-butoxycarbonylamino-2-methylpropionate; LC-MS retention time: 2.53 min;

$^1$H NMR (500 MHz, DMSO-d$_6$/TFA-d$_1$) δ [ppm] 8.11 (d, J=1.7, 1H), 8.08 (dd, J=8.7, 1.9, 1H), 7.89 (d, J=8.6, 1H), 7.54 (t, J=9.8, 1H), 7.43 (dd, J=10.9, 8.3, 2H), 7.33 (dt, J=18.3, 7.2, 2H), 7.26 (d, J=7.3, 1H), 5.06 (s, 2H), 4.95 (s, 2H), 4.89 (s, 2H), 1.31 (s, 6H), 1.29 (s, 9H).

2-[2-Amino-4-(1,3-dihydroisoindole-2-carbonyl)quinazolin-6-yl]-4,5-difluorobenzyl 2-amino-2-methylpropionate dihydrochloride ("A81")

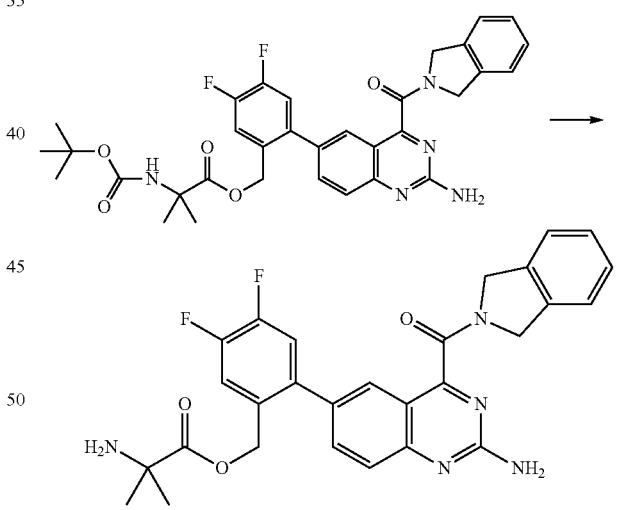

2.4 ml of 4N HCl in dioxane are added to 250 mg of 2-[2-amino-4-(1,3-dihydroisoindole-2-carbonyl)quinazolin-6-yl]-4,5-difluorobenzyl (2-tert-butoxycarbonylamino-2-methylpropionate in 5 ml of dichloromethane with ice-cooling. The mixture is subsequently stirred at 25° C. for a further 1 h, the precipitate is filtered off with suction and washed with 4 ml of dichloromethane. The residue is recrystallised from isopropanol.

Yield: 175 mg (73%) of 2-[2-amino-4-(1,3-dihydroisoindole-2-carbonyl)quinazolin-6-yl]-4,5-difluorobenzyl 2-amino-2-methylpropionate dihydrochloride; LC-MS retention time: 1.69 min;

¹H NMR (500 MHz, DMSO-d₆/TFA-d₁) δ [ppm] 8.12 (d, J=1.7, 1H), 8.07 (dd, J=8.6, 1.8, 1H), 7.88 (d, J=8.6, 1H), 7.68 (dd, J=11.5, 8.2, 1H), 7.49 (dd, J=10.9, 8.0, 1H), 7.44 (d, J=7.5, 1H), 7.34 (dt, J=15.2, 7.2, 2H), 7.27 (d, J=7.3, 1H), 5.13 (s, 2H), 5.04 (s, 2H), 4.89 (s, 2H), 1.42 (s, 6H).

2-[2-Amino-4-(1,3-dihydroisoindole-2-carbonyl)quinazolin-6-yl]-4,5-difluorobenzyl acetate ("A82")

2-[2-Amino-4-(1,3-dihydroisoindole-2-carbonyl)quinazolin-6-yl]-4,5-difluorobenzyl 6-tert-butoxycarbonylaminohexanoate ("A83")

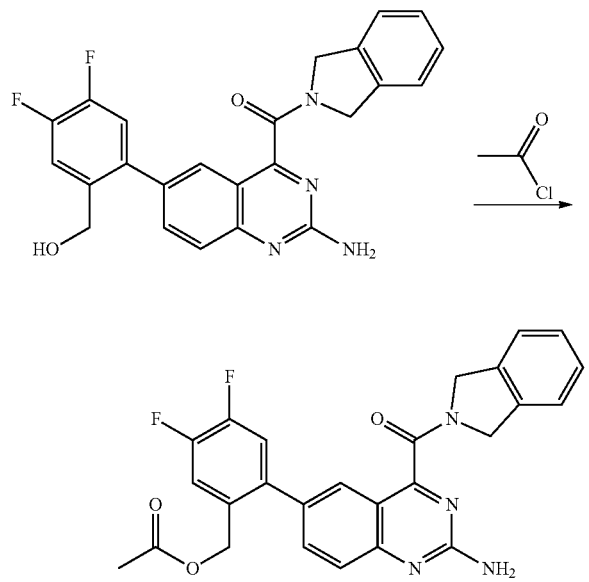

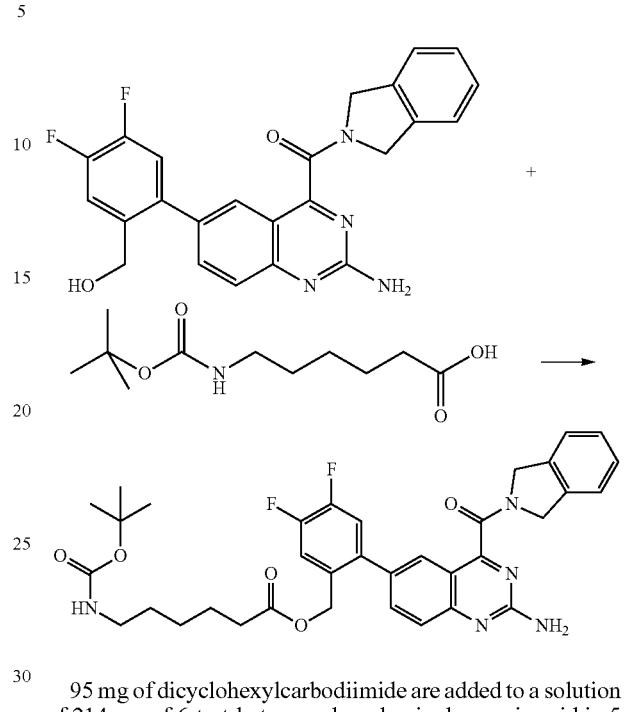

27 μl of acetyl chloride are added to a solution of 150 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 5 ml of dimethylformamide, and the mixture is stirred at 80° C. for 16 h. 8 ml of ethyl acetate and 8 ml of water are added, the organic phase is separated off and evaporated to dryness in vacuo. The residue is dissolved in 1 ml of dimethyl sulfoxide and purified by chromatography (reversed phase HPLC).

Yield: 31 mg (19%) of 2-[2-amino-4-(1,3-dihydroisoindole-2-carbonyl)quinazolin-6-yl]-4,5-difluorobenzyl acetate;

LC-MS retention time: 2.26 min;

¹H NMR (500 MHz, DMSO-d₆/TFA-d₁) δ [ppm] 8.07 (dd, J=15.5, 5.2, 2H), 7.87 (d, J=8.6, 1H), 7.58 (d, J=8.3, 1H), 7.44 (d, J=6.2, 2H), 7.38-7.27 (m, 2H), 7.26 (s, 1H), 5.03 (s, 2H), 4.89 (s, 2H), 4.86 (s, 2H), 1.97 (s, 3H).

95 mg of dicyclohexylcarbodiimide are added to a solution of 214 mg of 6-tert-butoxycarbonylaminohexanoic acid in 5 ml of dichloromethane, and the mixture is stirred at 25° C. for 1 h. The precipitate is filtered off, and the filtrate is added to a solution of 200 mg of [2-amino-6-(4,5-difluoro-2-hydroxymethylphenyl)quinazolin-4-yl]-(1,3-dihydroisoindol-2-yl)methanone and 3 mg of 4-(dimethylamino)pyridine (DMAP) in 5 ml of tetrahydrofuran. The mixture is stirred at 25° C. for 48 h, undissolved material is filtered off, and the filtrate is evaporated to dryness. The residue is purified by normal-phase chromatography.

Yield: 44 mg (15%) of 2-[2-amino-4-(1,3-dihydroisoindole-2-carbonyl)quinazolin-6-yl]-4,5-difluorobenzyl 6-tert-butoxycarbonylaminohexanoate;

LC-MS retention time: 2.61 min;

¹H NMR (500 MHz, DMSO-d₆) δ [ppm] 8.03 (d, J=1.7, 1H), 7.97 (dd, J=8.6, 1.8, 1H), 7.81 (d, J=8.8, 1H), 7.45 (dd, J=11.4, 8.3, 1H), 7.37-7.29 (m, 2H), 7.25 (dt, J=18.9, 7.3, 2H), 7.17 (d, J=7.3, 1H), 4.97 (s, 2H), 4.84 (s, 2H), 4.80 (s, 2H), 2.85 (t, J=7.1, 2H), 2.17 (t, J=7.4, 2H), 1.42-1.35 (m, 2H), 1.34-1.25 (m, 11H), 1.17-1.09 (m, 2H).

2-[2-Amino-4-(1,3-dihydroisoindole-2-carbonyl)quinazolin-6-yl]-4,5-difluorobenzyl 6-aminohexanoate dihydrochloride ("A84")

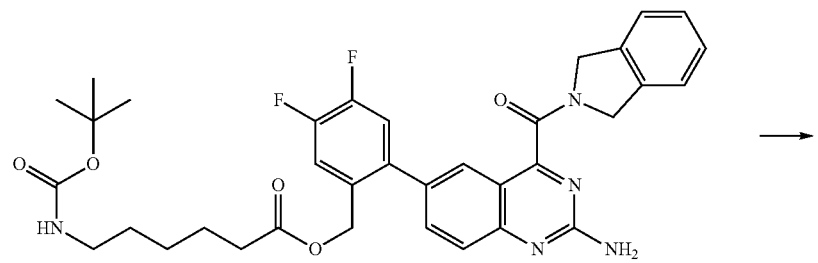

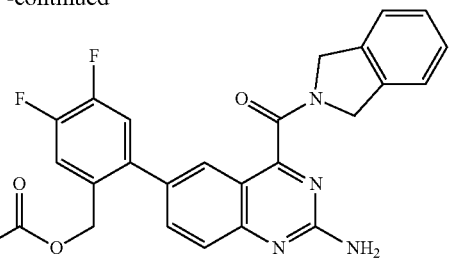

2.4 ml of 4N HCl in dioxane are added to 300 mg of 2-[2-amino-4-(1,3-dihydroisoindole-2-carbonyl)quinazolin-6-yl]-4,5-difluorobenzyl (2-tert-butoxycarbonylamino-2-methylpropionate in 5 ml of dichloromethane with ice-cooling. The mixture is subsequently stirred at 25° C. for a further 1 h, the precipitate is filtered off with suction and washed with 4 ml of dichloromethane.

Yield: 85 mg (32%) of 2-[2-amino-4-(1,3-dihydroisoindole-2-carbonyl)quinazolin-6-yl]-4,5-difluorobenzy 6-aminohexanoate dihydrochloride;

LC-MS retention time: 1.74 min;
$^1$H NMR (400 MHz, DMSO-d$_6$/TFA-d$_1$) δ [ppm] 8.06 (d, J=9.8, 2H), 7.88 (d, J=8.2, 1H), 7.59 (dd, J=10.9, 8.5, 1H), 7.52-7.42 (m, 2H), 7.34 (dt, J=15.0, 7.3, 2H), 7.26 (d, J=7.2, 1H), 5.03 (s, 2H), 4.92 (s, 2H), 4.86 (s, 2H), 2.76 (t, J=7.5, 2H), 2.29 (t, J=7.4, 2H), 1.60-1.50 (m, 2H), 1.46 (dd, J=15.5, 7.9, 2H), 1.32-1.21 (m, 2H).

2-[2-Amino-4-(1,3-dihydroisoindole-2-carbonyl)quinazolin-6-yl]-4,5-difluorobenzyl 5-tert-butoxycarbonylaminopentanoate ("A85")

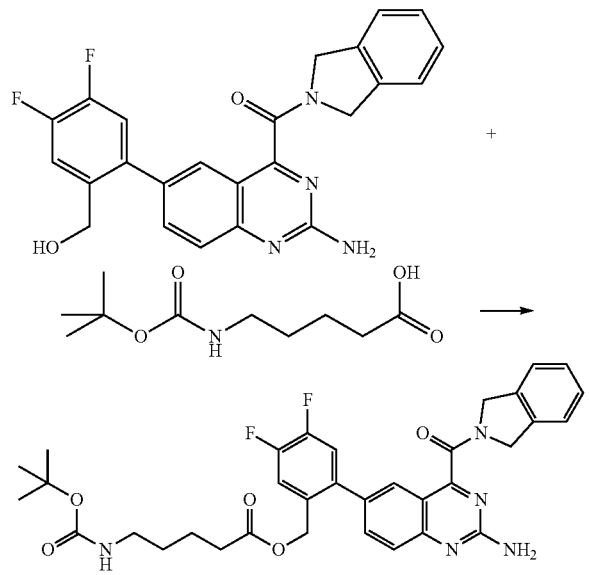

191 mg of dicyclohexylcarbodiimide are added to a solution of 402 mg of 6-tert-butoxycarbonylaminopentanoic acid in 10 ml of dichloromethane, and the mixture is stirred at 25° C. for 1 h. The precipitate is filtered off, and the filtrate is added to a solution of 400 mg of [2-amino-6-(4,5-difluoro-2-hydroxymethylphenyl)quinazolin-4-yl]-(1,3-dihydroisoindol-2-yl)methanone and 6 mg of 4-(dimethylamino)pyridine (DMAP) in 10 ml of tetrahydrofuran. The mixture is stirred at 25° C. for 48 h, undissolved material is filtered off, and the filtrate is evaporated to dryness. The residue is purified by normal-phase chromatography.

Yield: 580 mg (99%) of 2-[2-amino-4-(1,3-dihydroisoindole-2-carbonyl)quinazolin-6-yl]-4,5-difluorobenzy 5-tert-butoxycarbonylaminopentanoate; LC-MS retention time: 2.53 min;
$^1$H NMR (500 MHz, DMSO-d$_6$/TFA-d$_1$) δ [ppm] 8.03 (d, J=1.7, 1H), 7.97 (dd, J=8.6, 1.8, 1H), 7.81 (d, J=8.8, 1H), 7.45 (dd, J=11.4, 8.3, 1H), 7.35 (d, J=7.3, 1H), 7.31 (dd, J=10.8, 8.1, 1H), 7.25 (dt, J=18.9, 7.3, 2H), 7.17 (d, J=7.3, 1H), 4.97 (s, 2H), 4.84 (s, 2H), 4.80 (s, 2H), 2.85 (t, J=7.1, 2H), 2.17 (t, J=7.4, 2H), 1.42-1.34 (m, 2H), 1.31 (s, 9H), 1.30-1.24 (m, 2H), 1.18-1.09 (m, 2H).

2-[2-Amino-4-(1,3-dihydroisoindole-2-carbonyl)quinazolin-6-yl]-4,5-difluorobenzyl 5-aminopentanoate dihydrochloride ("A86")

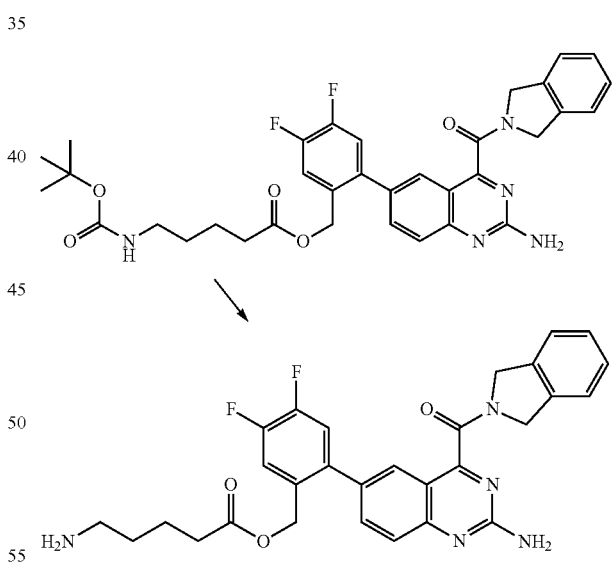

1.8 ml of 4N HCl in dioxane are added to 230 mg of 2-[2-amino-4-(1,3-dihydroisoindole-2-carbonyl)quinazolin-6-yl]-4,5-difluorobenzyl (2-tert-butoxycarbonylamino-2-methylpropionate in 3 ml of dichloromethane with ice-cooling. The mixture is subsequently stirred at 25° C. for a further 1 h, the precipitate is filtered off with suction and washed with 2 ml of dichloromethane.

Yield: 168 mg (76%) of 2-[2-amino-4-(1,3-dihydroisoindole-2-carbonyl)quinazolin-6-yl]-4,5-difluorobenzy 5-aminopentanoate dihydrochloride;

LC-MS retention time: 1.75 min;

$^1$H NMR (500 MHz, DMSO-d$_6$/TFA-d$_1$) δ [ppm] 8.09-8.04 (m, 2H), 7.87 (d, J=9.0, 1H), 7.59 (dd, J=11.4, 8.3, 1H), 7.50-7.43 (m, 2H), 7.33 (dt, J=15.2, 7.3, 2H), 7.26 (d, J=7.5, 1H), 5.03 (s, 2H), 4.92 (s, 2H), 4.86 (s, 2H), 2.79 (t, J=6.7, 2H), 2.35 (t, J=6.8, 2H), 1.63-1.47 (m, 4H).

2-{2-[2-Amino-4-(1,3-dihydroisoindole-2-carbonyl)quinazolin-6-yl]-4,5-difluorobenzyl}1-tert-butyl (S)-pyrrolidine-1,2-dicarboxylate ("A87")

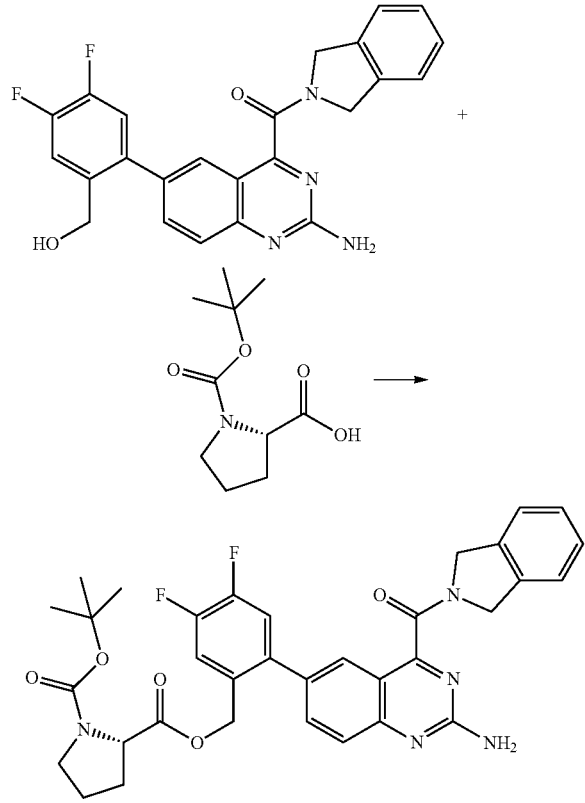

1 g of dicyclohexylcarbodiimide is added to a solution of 2.1 g of 1-tert-butyl (S)-pyrrolidine-1,2-dicarboxylate in 25 ml of dichloromethane, and the mixture is stirred at 25° C. for 1 h. The precipitate is filtered off, and the filtrate is added to a solution of 1 g of [2-amino-6-(4,5-difluoro-2-hydroxymethylphenyl)quinazolin-4-yl]-(1,3-dihydroisoindol-2-yl)methanone and 14 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 1.5 g (100%) of 2-{2-[2-amino-4-(1,3-dihydroisoindole-2-carbonyl)quinazolin-6-yl]-4,5-difluorobenzyl}1-tert-butyl (S)-pyrrolidine-1,2-dicarboxylate;

LC-MS retention time: 2.53 min;

$^1$H NMR (500 MHz, DMSO-d$_6$/TFA-d$_1$) δ [ppm] 8.03 (d, J=4.2, 1H), 7.95 (dd, J=8.6, 1.8, 1H), 7.79 (t, J=7.8, 1H), 7.43 (t, J=9.4, 1H), 7.34-7.17 (m, 4H), 7.13 (t, J=7.2, 1H), 5.01-4.75 (m, 6H), 4.09-3.96 (m, 1H), 3.28-3.14 (m, 2H), 2.04-1.91 (m, 1H), 1.72-1.56 (m, 3H), 1.31-1.04 (m, 9H).

2-[2-Amino-4-(1,3-dihydroisoindole-2-carbonyl)quinazolin-6-yl]-4,5-difluorobenzyl (S)-pyrrolidine-2-carboxylate ("A88")

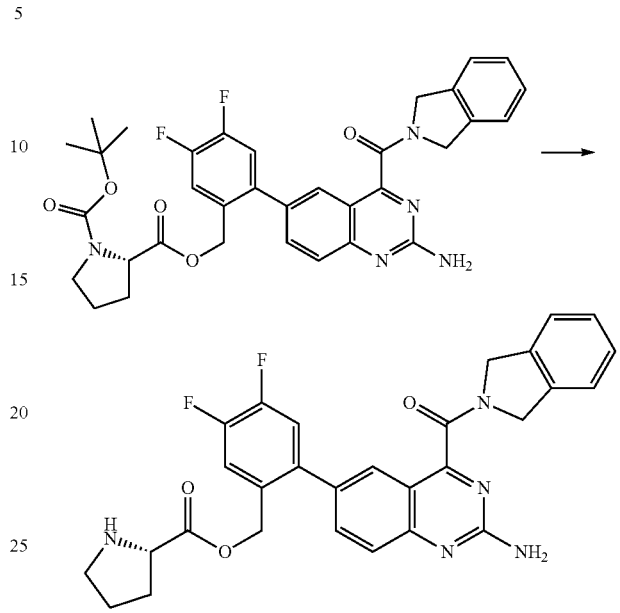

10 ml of trifluoroacetic acid are added to 1.5 g of 2-{2-[2-amino-4-(1,3-dihydroisoindole-2-carbonyl)quinazolin-6-yl]-4,5-difluorobenzyl}1-tert-butyl (S)-pyrrolidine-1,2-dicarboxylate in 50 ml of dichloromethane with ice-cooling. The mixture is subsequently stirred at 25° C. for a further 1 h, 10 ml of n-heptane are added, and the mixture is evaporated to dryness in vacuo. The residue is suspended in 100 ml of acetonitrile/water 3:1, neutralised using bicarbonate (~pH 8), and the precipitated material is filtered off with suction. The product is recrystallised from 100 ml of acetonitrile.

Yield: 900 mg (71%) of 2-[2-amino-4-(1,3-dihydroisoindole-2-carbonyl)quinazolin-6-yl]-4,5-difluorobenzyl (S)-pyrrolidine-2-carboxylate;

LC-MS retention time: 1.72 min;

$^1$H NMR (500 MHz, DMSO-d$_6$/TFA-d$_1$) δ [ppm] 8.12 (d, J=1.8, 1H), 8.08 (dd, J=8.6, 1.8, 1H), 7.88 (d, J=8.6, 1H), 7.70 (dd, J=11.4, 8.1, 1H), 7.50 (dd, J=10.9, 8.0, 1H), 7.44 (d, J=7.3, 1H), 7.34 (dt, J=14.9, 7.2, 2H), 7.27 (d, J=7.3, 1H), 5.09 (s, 2H), 5.04 (s, 2H), 4.88 (s, 2H), 4.51 (dd, J=8.3, 7.1, 1H), 3.33-3.21 (m, 2H), 2.34-2.22 (m, 1H), 2.02-1.84 (m, 3H).

2-[2-Amino-4-(1,3-dihydroisoindole-2-carbonyl)quinazolin-6-yl]-4,5-difluorobenzyl 4-tert-butoxycarbonylaminobutyrate ("A89")

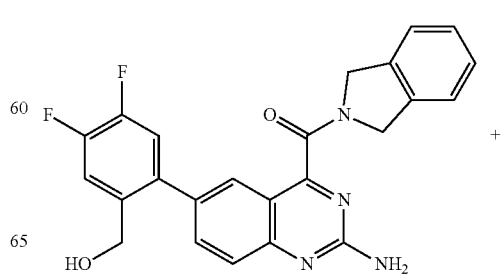

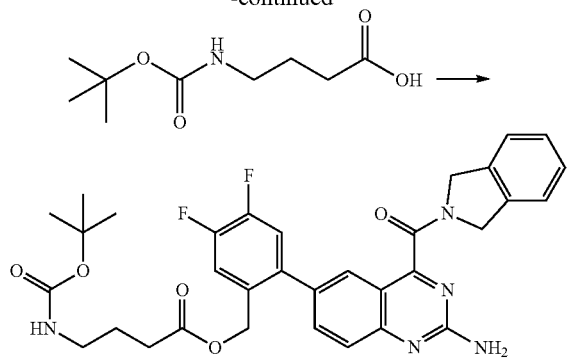

954 mg of dicyclohexylcarbodiimide are added to a solution of 1.88 g of 4-tert-butoxycarbonylaminobutyric acid in 50 ml of dichloromethane, and the mixture is stirred at 25° C. for 1 h. The precipitate is filtered off, and the filtrate is added to a solution of 1 g of [2-amino-6-(4,5-difluoro-2-hydroxymethylphenyl)quinazolin-4-yl]-(1,3-dihydroisoindol-2-yl) methanone and 14 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 1.2 g (84%) of 2-[2-amino-4-(1,3-dihydroisoindole-2-carbonyl)quinazolin-6-yl]-4,5-difluorobenzyl 4-tert-butoxycarbonylaminobutyrate;

LC-MS retention time: 2.48 min.

2-[2-Amino-4-(1,3-dihydroisoindole-2-carbonyl) quinazolin-6-yl]-4,5-difluorobenzyl 4-aminobutyrate dihydrochloride ("A90")

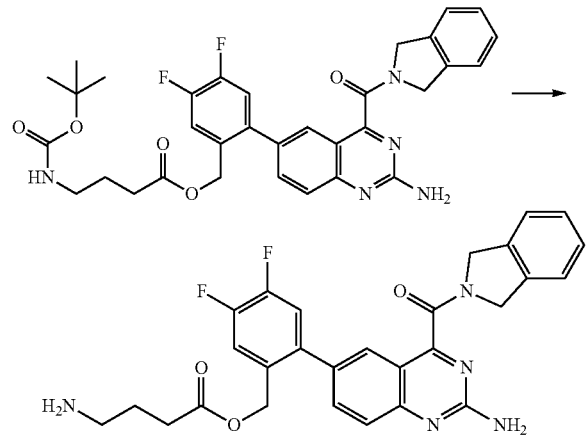

250 µl of 4N HCl in dioxane are added to 300 mg of 2-[2-amino-4-(1,3-dihydroisoindole-2-carbonyl)quinazolin-6-yl]-4,5-difluorobenzyl 4-tert-butoxycarbonylaminobutyrate in 5 ml of dichloromethane with ice-cooling. The mixture is subsequently stirred at 25° C. for a further 1 h, the precipitate is filtered off with suction and washed with 2 ml of dichloromethane.

Yield: 256 mg (89%) of 2-[2-amino-4-(1,3-dihydroisoindole-2-carbonyl)quinazolin-6-yl]-4,5-difluorobenzyl 4-aminobutyrate dihydrochloride LC-MS retention time: 1.70 min;

$^1$H NMR (400 MHz, DMSO-$d_6$/TFA-$d_1$) δ [ppm] 8.09-8.03 (m, 2H), 7.91-7.86 (m, 1H), 7.61 (dd, J=11.4, 8.2, 1H), 7.52-7.47 (m, 1H), 7.45 (d, J=8.8, 1H), 7.33 (td, J=13.2, 6.7, 2H), 7.26 (d, J=6.9, 1H), 5.02 (s, 2H), 4.93 (s, 2H), 4.85 (s, 2H), 2.82-2.77 (m, 2H), 2.44 (t, J=7.3, 2H), 1.82-1.73 (m, 2H).

2-[2-Amino-4-(1,3-dihydroisoindole-2-carbonyl) quinazolin-6-yl]-4,5-difluorobenzyl 3-(tert-butoxycarbonylmethylamino)propionate ("A91")

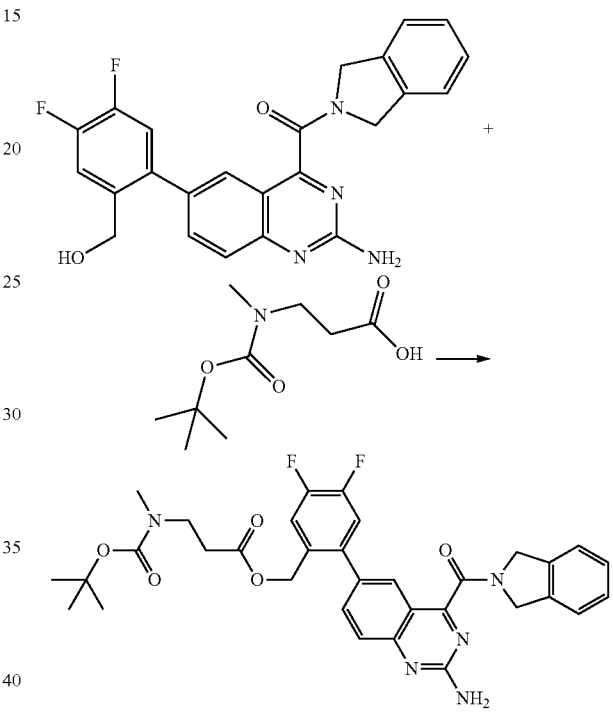

954 mg of dicyclohexylcarbodiimide are added to a solution of 1.88 g of 4-tert-butoxycarbonylaminopropionic acid in 50 ml of dichloromethane, and the mixture is stirred at 25° C. for 1 h. The precipitate is filtered off, and the filtrate is added to a solution of 1 g of [2-amino-6-(4,5-difluoro-2-hydroxymethylphenyl)-quinazolin-4-yl]-(1,3-dihydroisoindol-2-yl)methanone and 14 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 840 mg (59%) of 2-[2-amino-4-(1,3-dihydroisoindole-2-carbonyl)quinazolin-6-yl]-4,5-difluorobenzyl 3-(tert-butoxycarbonylmethylamino)propionate;

LC-MS retention time: 2.54 min;

$^1$H NMR (400 MHz, DMSO-$d_6$/TFA-$d_1$) δ [ppm] 8.11 (d, J=1.9, 1H), 8.08-8.03 (m, 1H), 7.88 (d, J=8.7, 1H), 7.62-7.52 (m, 1H), 7.43 (dd, J=12.8, 6.2, 2H), 7.32 (dt, J=14.5, 7.3, 2H), 7.25 (d, J=7.3, 1H), 5.04 (s, 2H), 4.93 (s, 2H), 4.87 (s, 2H), 3.35 (t, J=7.0, 2H), 2.74 (s, 3H), 2.54-2.44 (m, 2H), 1.36 (d, J=6.7, 9H).

2-[2-Amino-4-(1,3-dihydroisoindole-2-carbonyl) quinazolin-6-yl]-4,5-difluorobenzyl 3-methylaminopropionate dihydrochloride ("A92")

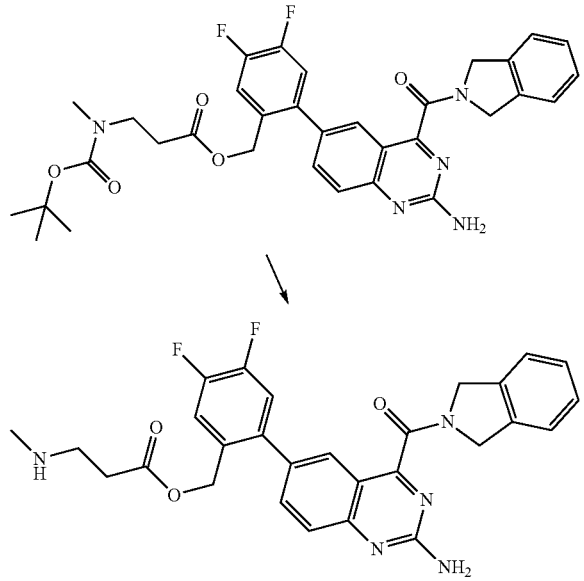

242 µl of 4N HCl in dioxane are added to 300 mg of 2-[2-amino-4-(1,3-dihydroisoindole-2-carbonyl)quinazolin-6-yl]-4,5-difluorobenzyl 3-(tert-butoxycarbonylmethylamino)propionate in 5 ml of dichloromethane with ice-cooling. The mixture is subsequently stirred at 25° C. for a further 1 h, the precipitate is filtered off with suction and washed with 2 ml of dichloromethane.

Yield: 260 mg (97%) of 2-[2-amino-4-(1,3-dihydroisoindole-2-carbonyl)quinazolin-6-yl]-4,5-difluorobenzyl 3-methylaminopropionate dihydrochloride; LC-MS retention time: 1.64 min;

$^1$H NMR (400 MHz, DMSO-$d_6$/TFA-$d_1$) δ [ppm] 8.10 (d, J=1.9, 1H), 8.07 (dd, J=8.7, 1.9, 1H), 7.90 (d, J=8.7, 1H), 7.63 (dd, J=11.4, 8.3, 1H), 7.44 (d, J=7.6, 2H), 7.33 (dt, J=14.5, 7.3, 2H), 7.26 (d, J=7.3, 1H), 5.05 (s, 2H), 4.98 (s, 2H), 4.88 (s, 2H), 3.15 (t, J=7.0, 2H), 2.80 (t, J=7.0, 2H), 2.61 (s, 3H).

2-[2-Amino-4-(1,3-dihydroisoindole-2-carbonyl) quinazolin-6-yl]-4,5-difluorobenzyl (R)-3-tert-butoxy-2-tert-butoxycarbonylaminopropionate ("A93")

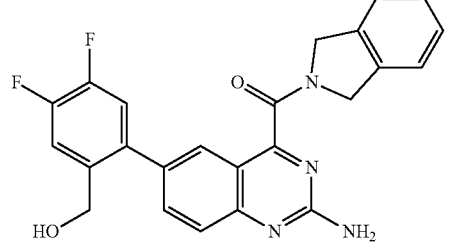

+

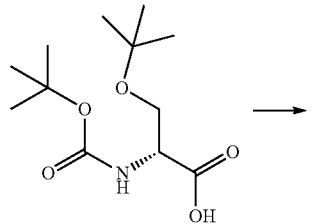

→

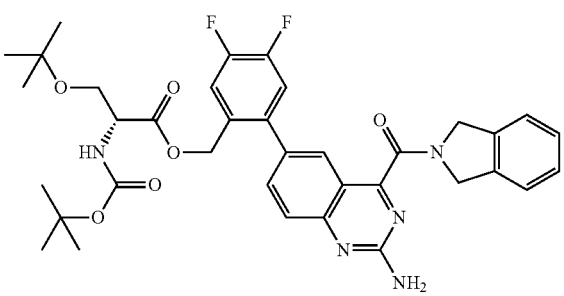

954 mg of dicyclohexylcarbodiimide are added to a solution of 2.4 g of (R)-3-tert-butoxy-2-tert-butoxycarbonylaminopropionic acid in 50 ml of dichloromethane, and the mixture is stirred at 25° C. for 1 h. The precipitate is filtered off, and the filtrate is added to a solution of 1 g of [2-amino-6-(4,5-difluoro-2-hydroxymethylphenyl)quinazolin-4-yl]-(1,3-dihydroisoindol-2-yl)methanone and 14 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 1.2 g (79%) of 2-[2-amino-4-(1,3-dihydroisoindole-2-carbonyl)quinazolin-6-yl]-4,5-difluorobenzyl (R)-3-tert-butoxy-2-tert-butoxycarbonylaminopropionate; LC-MS retention time: 2.79 min.

The following are obtained analogously:

2-[2-Amino-4-(1,3-dihydroisoindole-2-carbonyl) quinazolin-6-yl]benzyl (R)-3-tert-butoxy-2-tert-butoxycarbonylaminopropionate ("A94")

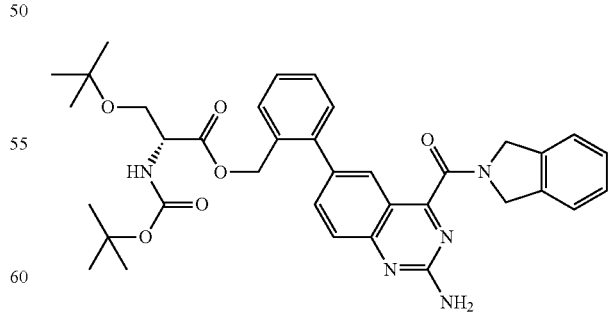

Yield: 1.6 g (66%) of 2-[2-amino-4-(1,3-dihydroisoindole-2-carbonyl)quinazolin-6-yl]benzyl (R)-3-tert-butoxy-2-tert-butoxycarbonylaminopropionate; LC-MS retention time: 2.04 min.

2-[2-Amino-4-(1,3-dihydroisoindole-2-carbonyl)quinazolin-6-yl]-4-fluorobenzyl (R)-3-tert-butoxy-2-tert-butoxycarbonylaminopropionate ("A95")

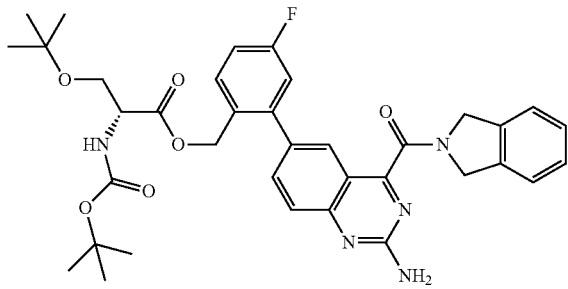 [SMILES: CC(C)(C)OC[C@@H](NC(=O)OC(C)(C)C)C(=O)OCc1ccc(F)cc1-c1ccc2nc(N)nc(C(=O)N3Cc4ccccc4C3)c2c1]

Yield: 1.4 g (61%) of 2-[2-amino-4-(1,3-dihydroisoindole-2-carbonyl)quinazolin-6-yl]-4-fluorobenzyl (R)-3-tert-butoxy-2-tert-butoxycarbonylaminopropionate;
LC-MS retention time: 2.44 min.
$^1$H NMR (500 MHz, DMSO-$d_6$/TFA-$d_1$) δ [ppm] 8.08 (s, 1H), 8.00 (d, J=8.1, 1H), 7.80 (d, J=8.7, 1H), 7.55-7.49 (m, 1H), 7.33 (d, J=7.2, 1H), 7.29-7.19 (m, 2H), 7.18-7.13 (m, 2H), 7.13-7.08 (m, 1H), 4.98 (s, 2H), 4.94 (dd, J=24.8, 14.0, 2H), 4.80 (s, 2H), 3.99 (t, J=4.7, 1H), 3.48 (dd, J=9.2, 5.0, 1H), 3.37 (dd, J=9.1, 4.4, 1H), 1.28 (s, 9H), 0.92 (s, 9H).

2-[2-Amino-4-(1,3-dihydroisoindole-2-carbonyl)quinazolin-6-yl]-4,5-difluorobenzyl (R)-2-amino-3-hydroxypropionate dihydrochloride ("A96")

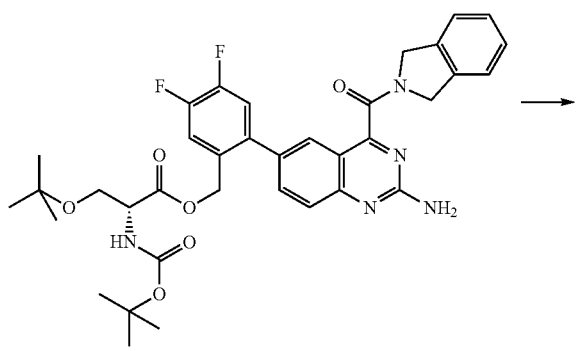

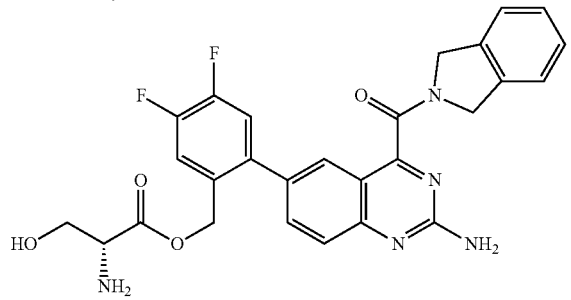

1.26 ml of 4N HCl in dioxane are added to 850 mg of 2-[2-amino-4-(1,3-dihydroisoindole-2-carbonyl)quinazolin-6-yl]-4,5-difluorobenzyl 3-(tert-butoxycarbonylmethylamino)propionate in 20 ml of dichloromethane with ice-cooling. The mixture is subsequently stirred at 25° C. for a further 1 h, evaporated to dryness in vacuo and recrystallised from ethanol.

Yield: 400 mg (54%) of 2-[2-amino-4-(1,3-dihydroisoindole-2-carbonyl)quinazolin-6-yl]-4,5-difluorobenzyl (R)-2-amino-3-hydroxypropionate dihydrochloride; LC-MS retention time: 1.60 min;
$^1$H NMR (400 MHz, DMSO-$d_6$/TFA-$d_1$) δ [ppm] 8.14 (d, J=1.5, 1H), 8.09 (dd, J=8.7, 2.0, 1H), 7.88 (d, J=8.7, 1H), 7.72 (dd, J=11.4, 8.2, 1H), 7.50 (dd, J=11.0, 7.9, 1H), 7.44 (d, J=7.0, 1H), 7.34 (dt, J=13.4, 6.6, 2H), 7.27 (d, J=7.0, 1H), 5.10 (q, J=12.7, 2H), 5.04 (s, 2H), 4.88 (s, 2H), 4.27 (t, J=3.5, 1H), 3.84 (ddd, J=34.3, 11.7, 3.6, 2H).

The following are obtained analogously:

2-[2-Amino-4-(1,3-dihydroisoindole-2-carbonyl)quinazolin-6-yl]benzyl (R)-2-amino-3-hydroxypropionate ("A97")

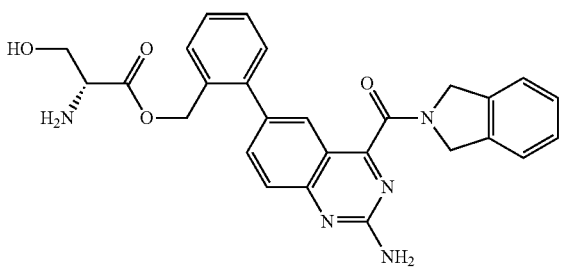 [SMILES: Nc1nc(C(=O)N2Cc3ccccc3C2)c2cc(-c3ccccc3COC(=O)[C@H](N)CO)ccc2n1]

Yield: 1.26 g (91%) of 2-[2-amino-4-(1,3-dihydroisoindole-2-carbonyl)quinazolin-6-yl]benzyl (R)-2-amino-3-hydroxypropionate;
LC-MS retention time: 1.53 min;
$^1$H NMR (400 MHz, DMSO-$d_6$/TFA-$d_1$) δ [ppm] 8.17 (d, J=1.7, 1H), 8.10 (dd, J=8.6, 1.9, 1H), 7.91 (d, J=8.7, 1H), 7.65 (dd, J=8.2, 4.9, 1H), 7.52-7.47 (m, 2H), 7.44-7.38 (m, 2H), 7.33 (dt, J=14.0, 7.2, 2H), 7.26 (d, J=6.9, 1H), 5.15 (q, J=12.2, 2H), 5.05 (s, 2H), 4.90 (s, 2H), 4.25 (t, J=3.6, 1H), 3.85 (ddd, J=25.2, 11.7, 3.6, 2H).

2-[2-Amino-4-(1,3-dihydroisoindole-2-carbonyl)quinazolin-6-yl]-4-fluorobenzyl (R)-2-amino-3-hydroxypropionate ("A98")

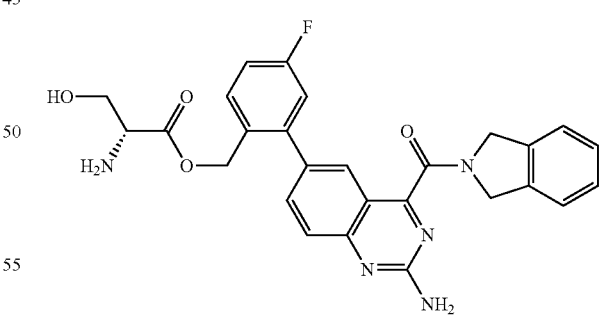

Yield: 490 mg (80%) of 2-[2-amino-4-(1,3-dihydroisoindole-2-carbonyl)quinazolin-6-yl]-4-fluorobenzyl (R)-2-amino-3-hydroxypropionate;
LC-MS retention time: 1.61 min;
$^1$H NMR (500 MHz, DMSO-$d_6$/TFA-$d_1$) δ [ppm] 8.17 (d, J=1.8, 1H), 8.11 (dd, J=8.6, 1.9, 1H), 7.89 (d, J=8.7, 1H), 7.70 (dd, J=8.6, 5.8, 1H), 7.43 (d, J=7.4, 1H), 7.38-7.23 (m, 5H), 5.10 (dd, J=22.6, 12.2, 2H), 5.06 (s, 2H), 4.89 (s, 2H), 4.25 (t, J=3.5, 1H), 3.89-3.75 (m, 2H).

2-[2-Amino-4-(1,3-dihydroisoindole-2-carbonyl)quinazolin-6-yl]-4-fluorobenzyl 2-tert-butoxycarbonylamino-2-methylpropionate ("A99")

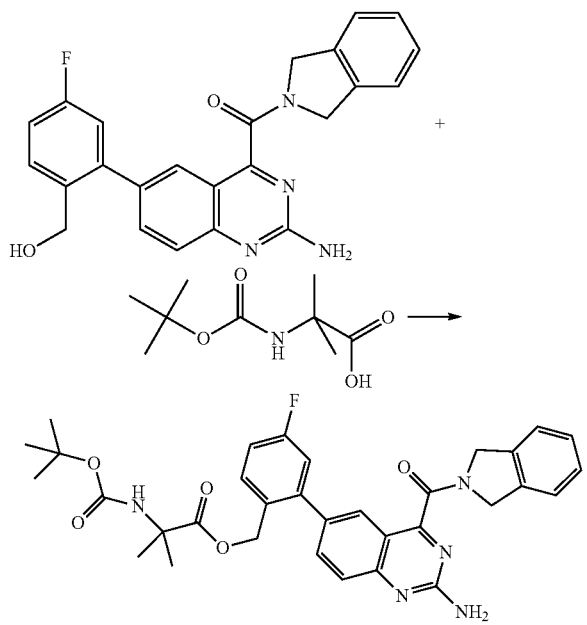

2.3 g of dicyclohexylcarbodiimide are added to a solution of 1.5 g of 2-tert-butoxycarbonylamino-2-methylpropionic acid in 70 ml of dichloromethane, and the mixture is stirred at 25° C. for 1 h. The precipitate is filtered off, and the filtrate is added to a solution of 1.5 g of [2-amino-6-(4-fluoro-2-hydroxymethylphenyl)quinazolin-4-yl]-(1,3-dihydroisoindol-2-yl)methanone and 20 mg of 4-(dimethylamino)pyridine (DMAP) in 50 ml of tetrahydrofuran. The mixture is stirred at 25° C. for 48 h, undissolved material is filtered off, and the filtrate is evaporated to dryness. The residue is purified by normal-phase chromatography.

Yield: 1.1 g (51%) of 2-[2-amino-4-(1,3-dihydroisoindole-2-carbonyl)quinazolin-6-yl]-4-fluorobenzyl 2-tert-butoxycarbonylamino-2-methylpropionate; LC-MS retention time: 2.45 min;

$^1$H NMR (500 MHz, DMSO-d$_6$/TFA-d$_1$) δ [ppm] 8.13 (d, J=1.6, 1H), 8.10 (dd, J=8.7, 1.9, 1H), 7.89 (d, J=8.6, 1H), 7.58 (dd, J=8.5, 5.8, 1H), 7.44 (d, J=7.3, 1H), 7.33 (dt, J=15.3, 7.1, 2H), 7.28-7.22 (m, 2H), 7.20 (dd, J=9.3, 2.6, 1H), 5.06 (s, 2H), 4.95 (s, 2H), 4.90 (s, 2H), 1.29 (s, 6H), 1.27 (s, 9H).

The following is obtained analogously:

2-[2-Amino-4-(1,3-dihydroisoindole-2-carbonyl)quinazolin-6-yl]benzyl 2-tert-butoxycarbonylamino-2-methylpropionate ("A100")

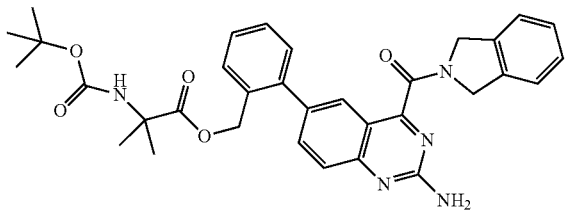 [SMILES: CC(C)(C)OC(=O)NC(C)(C)C(=O)OCc1ccccc1-c1ccc2nc(N)nc(C(=O)N3Cc4ccccc4C3)c2c1]

Yield: 1.1 g (50%) of 2-[2-amino-4-(1,3-dihydroisoindole-2-carbonyl)quinazolin-6-yl]benzyl 2-tert-butoxycarbonylamino-2-methylpropionate;

LC-MS retention time: 2.38 min;

$^1$H NMR (400 MHz, DMSO-d$_6$/TFA-d$_1$) δ [ppm] 8.12 (d, J=1.5, 1H), 8.09 (dd, J=8.6, 1.8, 1H), 7.89 (d, J=8.7, 1H), 7.55 (dd, J=5.6, 3.5, 1H), 7.44 (dt, J=13.2, 7.0, 3H), 7.37-7.27 (m, 3H), 7.25 (d, J=6.9, 1H), 5.06 (s, 2H), 5.00 (s, 2H), 4.90 (s, 2H), 1.98 (s, 6H), 1.29 (s, 9H).

2-[2-Amino-4-(1,3-dihydroisoindole-2-carbonyl)quinazolin-6-yl]-4-fluorobenzylamino-2-methylpropionate dihydrochloride ("A101")

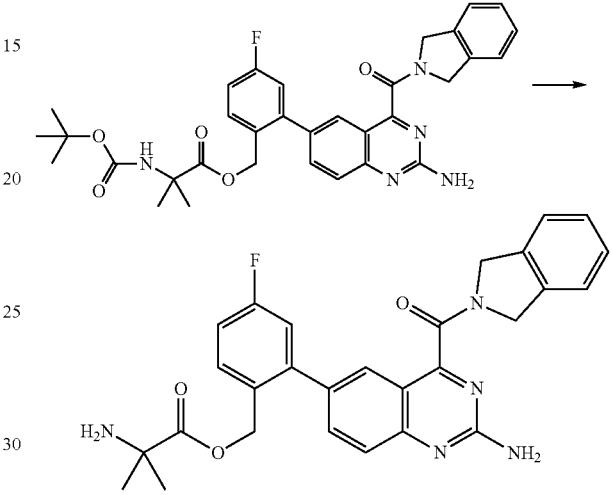

3 ml of 4N HCl in dioxane are added to 500 mg of 2-[2-amino-4-(1,3-dihydroisoindole-2-carbonyl)quinazolin-6-yl]-4-fluorobenzyl 2-tert-butoxycarbonyl-amino-2-methylpropionate in 20 ml of dichloromethane with ice-cooling. The mixture is subsequently stirred at 25° C. for a further 1 h, the precipitate is filtered off and recrystallised from isopropanol.

Yield: 230 mg (48%) of 2-[2-amino-4-(1,3-dihydroisoindole-2-carbonyl)quinazolin-6-yl]-4-fluorobenzyl 2-amino-2-methylpropionate dihydrochloride; LC-MS retention time: 1.63 min;

$^1$H NMR (400 MHz, DMSO-d$_6$/TFA-d$_1$) δ [ppm] 8.17 (d, J=1.9, 1H), 8.08 (dd, J=8.7, 1.8, 1H), 7.91 (d, J=8.7, 1H), 7.66 (dd, J=8.7, 5.7, 1H), 7.42 (d, J=7.0, 1H), 7.38-7.18 (m, 5H), 5.16 (s, 2H), 5.06 (s, 2H), 4.92 (s, 2H), 1.43 (s, 6H).

The following is obtained analogously:

2-[2-Amino-4-(1,3-dihydroisoindole-2-carbonyl)quinazolin-6-yl]benzyl 2-amino-2-methylpropionate ("A102")

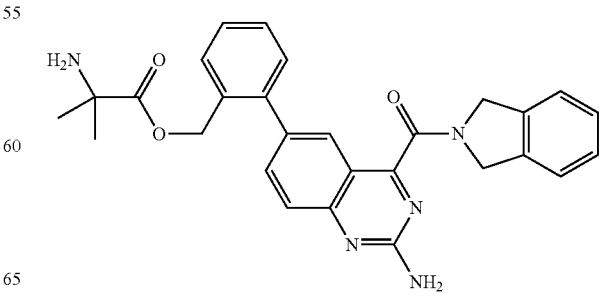

Yield: 280 mg (53%) of 2-[2-amino-4-(1,3-dihydroisoindole-2-carbonyl)quinazolin-6-yl]benzyl 2-amino-2-methylpropionate;

LC-MS retention time: 1.56 min;

$^1$H NMR (400 MHz, DMSO-$d_6$/TFA-$d_1$) δ [ppm] 8.09-8.02 (m, 2H), 7.83 (d, J=8.7, 1H), 7.56 (dd, J=5.9, 3.3, 1H), 7.46-7.42 (m, 2H), 7.37 (t, J=5.8, 1H), 7.36-7.32 (m, 1H), 7.27 (dt, J=14.8, 6.6, 2H), 7.21 (d, J=7.0, 1H), 5.14 (s, 2H), 4.98 (s, 2H), 4.83 (s, 2H), 1.33 (d, J=9.9, 6H).

2-[2-Amino-4-(1,3-dihydroisoindole-2-carbonyl)quinazolin-6-yl]-4-fluorobenzyl 2-tert-butoxycarbonylaminoacetate ("A103")

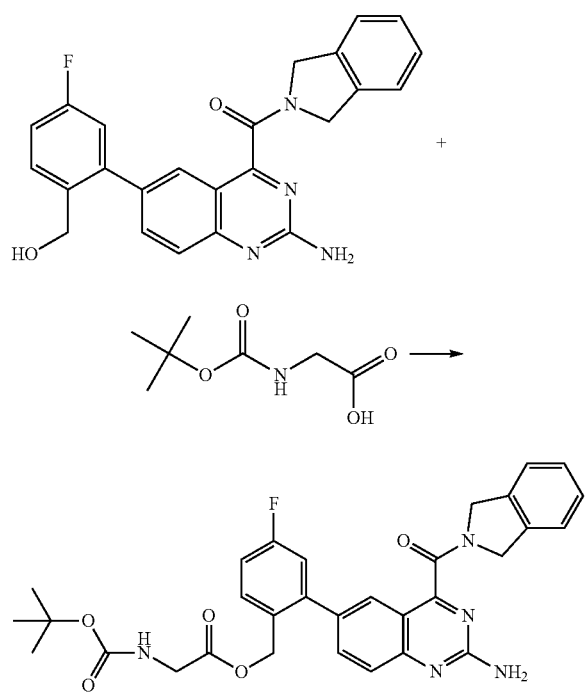

1.5 g of dicyclohexylcarbodiimide are added to a solution of 2.5 g of 2-tert-butoxycarbonylaminoacetic acid in 50 ml of dichloromethane, and the mixture is stirred at 25° C. for 1 h. The precipitate is filtered off, and the filtrate is added to a solution of 1.5 g of [2-amino-6-(4-fluoro-2-hydroxymethylphenyl)quinazolin-4-yl]-(1,3-dihydroisoindol-2-yl)methanone and 22 mg of 4-(dimethylamino)pyridine (DMAP) in 50 ml of tetrahydrofuran. The mixture is stirred at 25° C. for 4 h, undissolved material is filtered off, and the filtrate is evaporated to dryness. The residue is purified by normal-phase chromatography.

Yield: 2.0 g (97%) of 2-[2-amino-4-(1,3-dihydroisoindole-2-carbonyl)quinazolin-6-yl]-4-fluorobenzyl 2-tert-butoxycarbonylaminoacetate;

LC-MS retention time: 2.36 min;

$^1$H NMR (500 MHz, DMSO-$d_6$) δ [ppm] 7.77-7.72 (m, 2H), 7.59-7.53 (m, 2H), 7.41 (d, J=7.3, 1H), 7.33-7.15 (m, 5H), 4.95 (d, J=8.0, 2H), 4.94 (d, J=5.1, 2H), 4.73 (s, 2H), 3.67 (d, J=6.1, 2H), 1.33 (d, J=10.8, 9H).

2-[2-Amino-4-(1,3-dihydroisoindole-2-carbonyl)quinazolin-6-yl]-4-fluorobenzyl aminoacetate dihydrochloride ("A104")

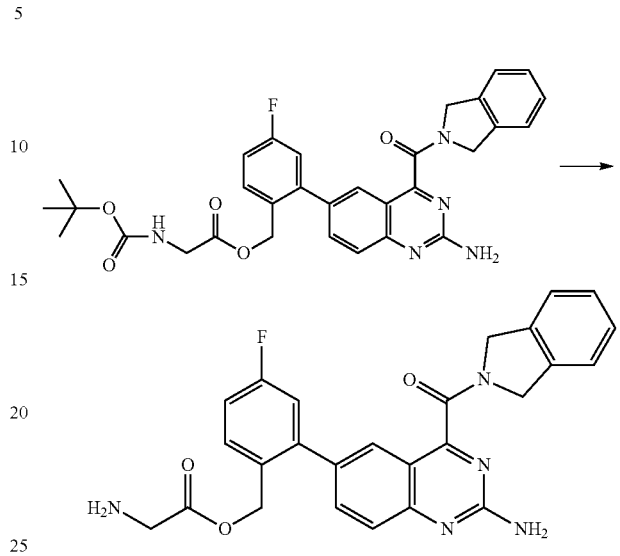

5 ml of 4N HCl in dioxane are added to 1 g of 2-[2-amino-4-(1,3-dihydroisoindole-2-carbonyl)quinazolin-6-yl]-4-fluorobenzyl 2-tert-butoxycarbonylaminoacetate in 50 ml of dichloromethane with ice-cooling. The mixture is subsequently stirred at 25° C. for a further 1 h, the precipitate is filtered off and rinsed with 5 ml of dichloromethane.

Yield: 717 mg (75%) of 2-[2-amino-4-(1,3-dihydroisoindole-2-carbonyl)quinazolin-6-yl]-4-fluorobenzyl aminoacetate dihydrochloride;

LC-MS retention time: 1.61 min;

$^1$H NMR (400 MHz, DMSO-$d_6$/TFA-$d_1$) δ [ppm] 8.13 (d, J=1.4, 1H), 8.10 (dd, J=8.6, 1.9, 1H), 7.89 (d, J=8.7, 1H), 7.61 (dd, J=5.9, 3.3, 1H), 7.52-7.48 (m, 2H), 7.46-7.37 (m, 1H), 7.33 (dt, J=14.8, 6.6, 2H), 7.26 (d, J=6.9, 1H), 5.20 (s, 2H), 5.04 (s, 2H), 4.90 (s, 2H), 3.60 (s, 2H).

2-[2-Amino-4-(1,3-dihydroisoindole-2-carbonyl)quinazolin-6-yl]-4,5-difluorobenzyl (tert-butoxycarbonylmethylamino)acetate ("A105")

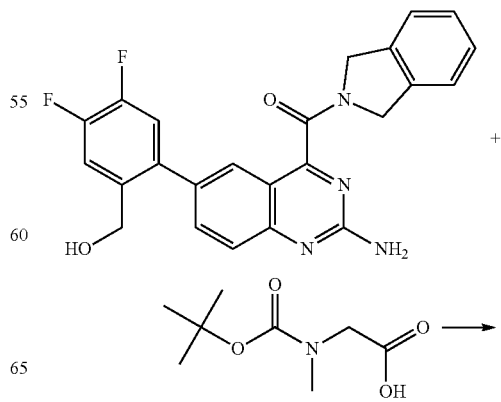

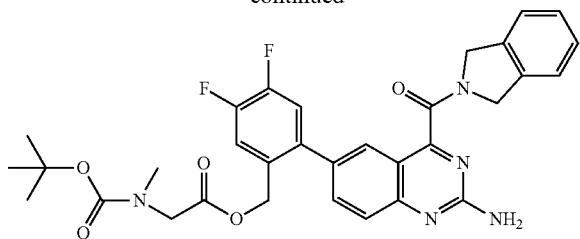

1.43 g of dicyclohexylcarbodiimide are added to a solution of 2.625 g of (tertbutoxycarbonylmethylamino)acetic acid in 100 ml of dichloromethane, and the mixture is stirred at 25° C. for 1 h. The precipitate is filtered off, and the filtrate is added to a solution of 1.5 g of [2-amino-6-(4,5-difluoro-2-hydroxymethylphenyl)quinazolin-4-yl]-(1,3-dihydroisoindol-2-yl)methanone and 14 mg of 4-(dimethylamino)pyridine (DMAP) in 100 ml of tetrahydrofuran. The mixture is stirred at 25° C. for 48 h, undissolved material is filtered off, and the filtrate is evaporated to dryness. The residue is purified by normal-phase chromatography.

Yield: 1.0 g (48%) of 2-[2-amino-4-(1,3-dihydroisoindole-2-carbonyl)quinazolin-6-yl]-4,5-difluorobenzyl (tert-butoxycarbonylmethylamino)acetate; LC-MS retention time: 2.49 min;

$^1$H NMR (500 MHz, DMSO-$d_6$/TFA-$d_1$) δ [ppm] 8.11 (d, J=2.1, 1H), 8.08-8.04 (m, 1H), 7.88 (dd, J=8.6, 4.2, 1H), 7.60 (ddd, J=22.1, 11.2, 8.2, 1H), 7.46 (dd, J=12.8, 7.9, 2H), 7.33 (dt, J=17.5, 7.2, 2H), 7.25 (t, J=6.1, 1H), 5.05 (s, 2H), 5.01 (s, 2H), 4.87 (d, J=8.3, 2H), 3.96-3.83 (m, 2H), 2.79 (m, 3H), 1.43-1.23 (m, 9H).

The following are obtained analogously:

2-[2-Amino-4-(1,3-dihydroisoindole-2-carbonyl)quinazolin-6-yl]benzyl (tertbutoxycarbonylmethylamino)acetate ("A106")

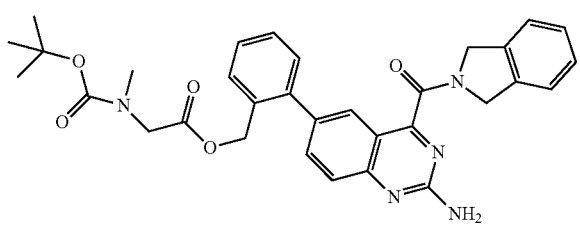 [SMILES: CN(CC(=O)OCc1ccccc1-c1ccc2nc(N)nc(C(=O)N3Cc4ccccc4C3)c2c1)C(=O)OC(C)(C)C]

Yield: 0.8 g (75%) of 2-[2-amino-4-(1,3-dihydroisoindole-2-carbonyl)quinazolin-6-yl]benzyl (tert-butoxycarbonylmethylamino)acetate;

LC-MS retention time: 2.38 min;

$^1$H NMR (400 MHz, DMSO-$d_6$/TFA-$d_1$) δ [ppm] 8.11 (d, J=1.6, 1H), 8.06 (d, J=8.5, 1H), 7.88 (d, J=8.5, 1H), 7.55 (d, J=4.4, 1H), 7.49-7.21 (m, 7H), 5.07 (s, 1H), 5.05 (s, 2H), 4.88 (s, 1H), 3.82 (m, 2H), 2.79 (m, 3H), 1.40 (s, 9H).

2-[2-Amino-4-(1,3-dihydroisoindole-2-carbonyl)quinazolin-6-yl]-4-fluorobenzyl (tert-butoxycarbonylmethylamino)acetate ("A107")

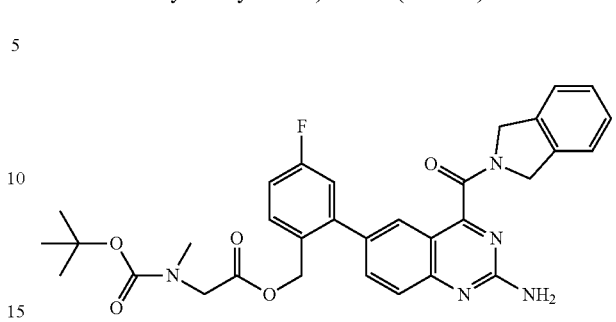

Yield: 1.2 g (75%) of 2-[2-amino-4-(1,3-dihydroisoindole-2-carbonyl)quinazolin-6-yl]-4-fluorobenzyl (tert-butoxycarbonylmethylamino)acetate;

LC-MS retention time: 2.14 min;

$^1$H NMR (400 MHz, DMSO-$d_6$/TFA-$d_1$) δ [ppm] 8.04 (s, 1H), 7.98-7.92 (m, 1H), 7.81-7.76 (m, 1H), 7.49 (dd, J=14.4, 6.2, 1H), 7.31 (d, J=7.0, 1H), 7.21 (m, 2H), 7.10 (dd, J=20.4, 5.7, 3H), 4.95 (s, 2H), 4.94 (s, 2H), 4.78 (s, 2H), 3.79 (s, 2H), 2.69 (s, 3H), 1.29 (s, 9H).

2-[2-Amino-4-(1,3-dihydroisoindole-2-carbonyl)quinazolin-6-yl]-4,5-difluorobenzyl methylaminoacetate dihydrochloride ("A108")

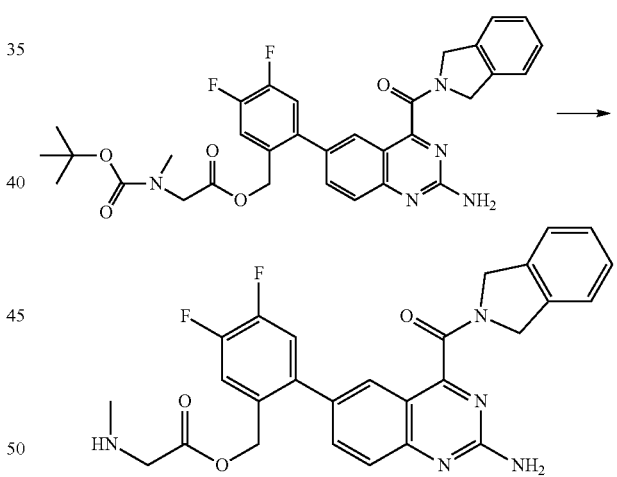

3.3 ml of 4N HCl in dioxane are added to 1 g of 2-[2-amino-4-(1,3-dihydroisoindole-2-carbonyl)quinazolin-6-yl]-4,5-difluorobenzyl (tert-butoxycarbonylmethylamino)acetate in 20 ml of dichloromethane with ice-cooling. The mixture is subsequently stirred at 25° C. for a further 1 h, the precipitate is filtered off and rinsed with 3 ml of dichloromethane.

Yield: 940 mg (98%) of 2-[2-amino-4-(1,3-dihydroisoindole-2-carbonyl)quinazolin-6-yl]-4,5-difluorobenzyl methylaminoacetate dihydrochloride;

LC-MS retention time: 1.65 min;

$^1$H NMR (400 MHz, DMSO-$d_6$/TFA-$d_1$) δ [ppm] 8.15 (s, 1H), 8.05 (d, J=8.7, 1H), 7.91 (d, J=8.7, 1H), 7.70-7.61 (m, 1H), 7.49-7.28 (m, 4H), 7.25 (d, J=7.3, 1H), 5.07 (s, 2H), 5.06 (s, 2H), 4.90 (s, 2H), 4.08 (s, 2H), 2.68 (s, 3H).

The following are obtained analogously:

2-[2-Amino-4-(1,3-dihydroisoindole-2-carbonyl)quinazolin-6-yl]benzyl methylaminoacetate dihydrochloride ("A109")

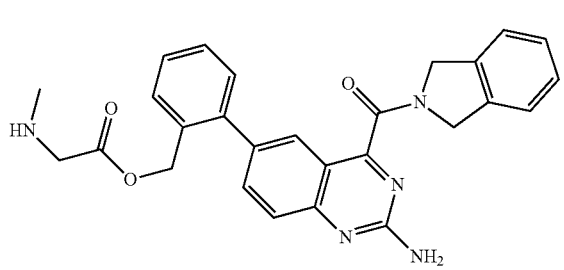 [SMILES: CNCC(=O)OCc1ccccc1-c1ccc2nc(N)nc(C(=O)N3Cc4ccccc4C3)c2c1]

Yield: 274 mg (72%) of 2-[2-amino-4-(1,3-dihydroisoindole-2-carbonyl)quinazolin-6-yl]benzyl methylaminoacetate dihydrochloride;

LC-MS retention time: 1.57 min;

$^1$H NMR (400 MHz, DMSO-$d_6$/TFA-$d_1$) δ [ppm] 7.83 (d, J=6.9, 2H), 7.68 (d, J=9.2, 1H), 7.60-7.56 (m, 1H), 7.49-7.45 (m, 2H), 7.44-7.24 (m, 5H), 5.07 (s, 2H), 4.97 (s, 2H), 4.77 (s, 2H), 4.02 (t, J=5.8, 2H), 2.57 (t, J=5.3, 3H).

2-[2-Amino-4-(1,3-dihydroisoindole-2-carbonyl)quinazolin-6-yl]-4-fluorobenzyl methylaminoacetate dihydrochloride ("A110")

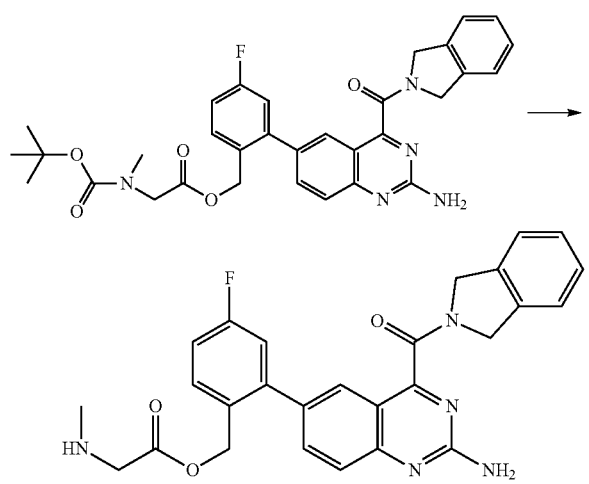

Yield: 524 mg (92%) of 2-[2-amino-4-(1,3-dihydroisoindole-2-carbonyl)quinazolin-6-yl]-4-fluorobenzyl methylaminoacetate dihydrochloride;

LC-MS retention time: 1.62 min;

$^1$H NMR (400 MHz, DMSO-$d_6$/TFA-$d_1$) δ [ppm] 8.10 (d, J=1.5, 1H), 8.01 (dd, J=8.6, 1.9, 1H), 7.83 (d, J=8.7, 1H), 7.61 (dd, J=8.5, 5.8, 1H), 7.38-7.14 (m, 6H), 4.99 (s, 4H), 4.82 (s, 2H), 4.01 (s, 2H), 2.59 (s, 3H).

2-[2-Amino-4-(1,3-dihydroisoindole-2-carbonyl)quinazolin-6-yl]-4-fluorobenzyl dimethylaminoacetate dihydrochloride ("A111")

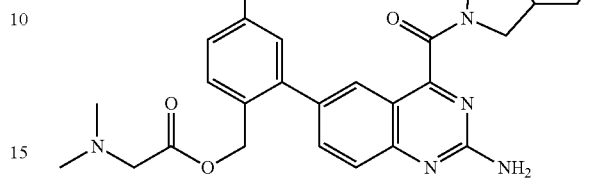

500 mg of dimethylaminoacetyl chloride hydrochloride are added to a solution of 959 mg of [2-amino-6-(4-fluoro-2-hydroxymethylphenyl)quinazolin-4-yl]-(1,3-dihydroisoindol-2-yl)methanone in 20 ml of pyridine, and the mixture is stirred at 25° C. After 18 h, 10 ml of methanol are added, the mixture is evaporated to dryness in vacuo and purified by normal-phase chromatography.

Yield: 390 mg (29%) of 2-[2-amino-4-(1,3-dihydroisoindole-2-carbonyl)quinazolin-6-yl]-4-fluorobenzyl dimethylaminoacetate dihydrochloride; LC-MS retention time: 1.70 min;

$^1$H NMR (500 MHz, DMSO-$d_6$/TFA-$d_1$) δ [ppm] 8.15 (d, J=1.7, 1H), 8.09 (dd, J=8.7, 1.9, 1H), 7.90 (d, J=8.6, 1H), 7.69 (dd, J=8.6, 5.8, 1H), 7.44 (d, J=7.3, 1H), 7.38-7.22 (m, 5H), 5.07 (d, J=3.7, 2H), 5.06 (s, 2H), 4.89 (s, 2H), 4.30 (s, 2H), 2.90 (s, 6H).

The following are obtained analogously:

2-[2-Amino-4-(1,3-dihydroisoindole-2-carbonyl)quinazolin-6-yl]-4,5-difluorobenzyl dimethylaminoacetate dihydrochloride ("A112")

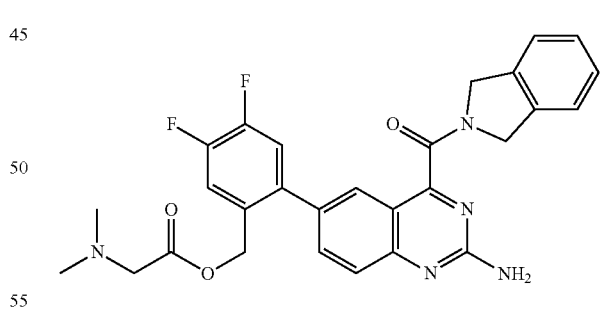

Yield: 390 mg (29%) of 2-[2-amino-4-(1,3-dihydroisoindole-2-carbonyl)quinazolin-6-yl]-4,5-difluorobenzyl dimethylaminoacetate dihydrochloride; LC-MS retention time: 1.71 min;

$^1$H NMR (400 MHz, DMSO-$d_6$/TFA-$d_1$) δ [ppm] 8.07 (d, J=1.7, 1H), 8.02 (dd, J=8.6, 1.9, 1H), 7.85 (d, J=8.7, 1H), 7.66 (dd, J=11.4, 8.2, 1H), 7.46 (dd, J=11.0, 8.1, 1H), 7.40 (d, J=7.2, 1H), 7.29 (dt, J=14.5, 7.2, 2H), 7.21 (d, J=7.0, 1H), 5.02 (s, 2H), 5.00 (s, 2H), 4.83 (s, 2H), 4.25 (s, 2H), 2.84 (s, 6H).

2-[2-Amino-4-(1,3-dihydroisoindole-2-carbonyl)quinazolin-6-yl]benzyl dimethylaminoacetate dihydrochloride ("A113")

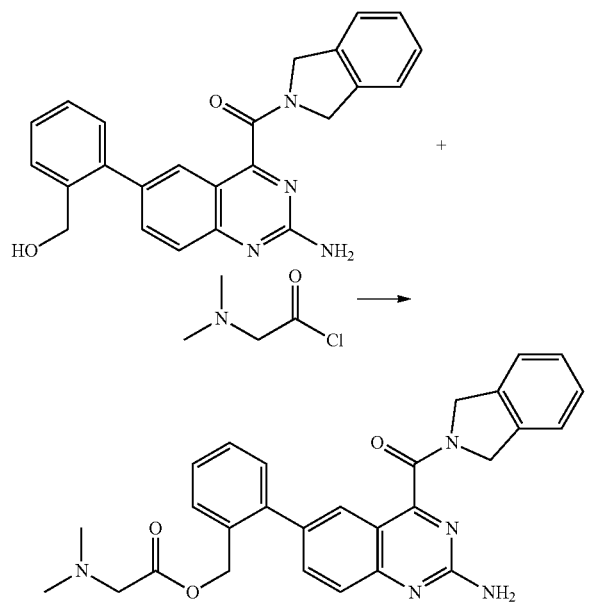

Yield: 300 mg (29%) of 2-[2-amino-4-(1,3-dihydroisoindole-2-carbonyl)quinazolin-6-yl]benzyl dimethylaminoacetate dihydrochloride;

LC-MS retention time: 1.60 min;

$^1$H NMR (400 MHz, DMSO-d$_6$/TFA-d$_1$) δ [ppm] 8.06 (d, J=1.5, 1H), 7.97 (dd, J=8.6, 1.9, 1H), 7.81 (d, J=8.7, 1H), 7.54 (dd, J=5.9, 3.1, 1H), 7.43-7.38 (m, 2H), 7.36-7.28 (m, 2H), 7.23 (dt, J=15.0, 6.6, 2H), 7.16 (d, J=7.0, 1H), 5.02 (s, 2H), 4.98 (s, 2H), 4.80 (s, 2H), 4.22 (s, 2H), 2.82 (d, J=6.7, 6H).

2-[2-Amino-4-(1,3-dihydroisoindole-2-carbonyl)quinazolin-6-yl]-4,5-difluorobenzyl dimethylcarbamate ("A114")

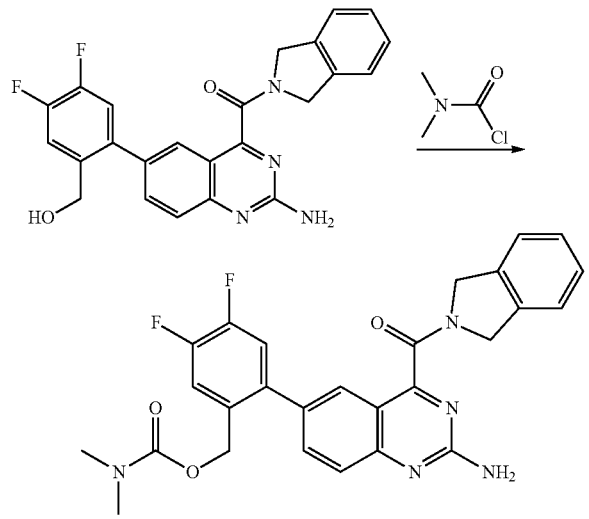

20 μl of dimethylcarbamoyl chloride are added to a solution of 100 mg of [2-amino-6-(4,5-difluoro-2-hydroxymethylphenyl)quinazolin-4-yl]-(1,3-dihydroisoindol-2-yl)methanone and 2 mg of 4-(dimethylamino)pyridine (DMAP) in 5 ml of dimethylformamide (DMF), and the mixture is heated at 80° C. for 18 h. After 18 h, 10 ml of methanol are added, the mixture is evaporated to dryness in vacuo and purified by normal-phase chromatography.

Yield: 26 mg (22%) of 2-[2-amino-4-(1,3-dihydroisoindole-2-carbonyl)quinazolin-6-yl]-4,5-difluorobenzyl dimethylcarbamate;

LC-MS retention time: 2.23 min;

$^1$H NMR (500 MHz, DMSO-d$_6$) δ [ppm] 8.07 (dd, J=15.5, 5.2, 2H), 7.87 (d, J=8.6, 1H), 7.58 (d, J=8.3, 1H), 7.44 (d, J=6.2, 2H),), 7.38-7.27 (m, 2H), 7.21 (d, J=7.2, 1H), 4.98 (s, 2H), 4.86 (s, 2H), 4.82 (s, 2H), 2.73 (s, 3H), 2.66 (s, 3H).

2-[2-Amino-4-(1,3-dihydroisoindole-2-carbonyl)quinazolin-6-yl]-4,5-difluorobenzyl (2-dimethylaminoethyl)carbamate ("A115")

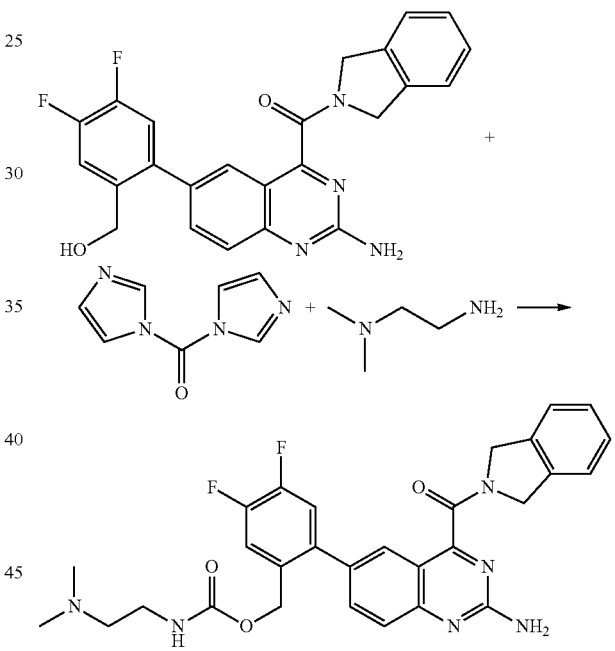

400 mg of 1,1'-carbonyldiimidazole are dissolved in 10 ml of pyridine and cooled to 0° C. A solution of 1.0 g of [2-amino-6-(4,5-difluoro-2-hydroxymethylphenyl)quinazolin-4-yl]-(1,3-dihydroisoindol-2-yl)methanone dissolved in 10 ml of pyridine is added. The mixture is subsequently stirred at 0° C. for 2 h and at 25° C. for 2 h. 300 μl of N,N-dimethylethylenediamine are then added, and the mixture is stirred at 25° C. for a further 18 h. The mixture is added to 250 ml of 1 N HCl, neutralised using bicarbonate solution and washed 3 times with 150 ml of dichloromethane each time. The organic phases are washed twice with 50 ml of water each time, dried over sodium sulfate, filtered and evaporated to dryness in vacuo. The residue is dissolved in 1 ml of dimethyl sulfoxide and purified by chromatography (reversed phase).

Yield: 366 mg (29%) of 2-[2-amino-4-(1,3-dihydroisoindole-2-carbonyl)quinazolin-6-yl]-4,5-difluorobenzyl (2-dimethylaminoethyl)carbamate;

LC-MS retention time: 1.72 min;

$^1$H NMR (500 MHz, DMSO-d$_6$/TFA-d$_1$) δ [ppm] 8.00 (s, 1H), 7.95 (dd, J=8.6, 1.8, 1H), 7.79 (d, J=8.6, 1H), 7.43 (dd, J=18.2, 8.5, 1H), 7.32 (d, J=7.3, 1H), 7.29-7.18 (m, 3H), 7.14 (d, J=7.3, 1H), 4.97 (s, 2H), 4.82 (s, 2H), 4.79 (s, 2H), 3.25 (t, J=5.9, 2H), 3.07 (t, J=6.0, 2H), 2.73 (s, 6H).

2-[2-Amino-4-(1,3-dihydroisoindole-2-carbonyl)
quinazolin-6-yl]-4,5-difluorobenzyl 4-methylpipera-
zine-1-carboxylate ("A116")

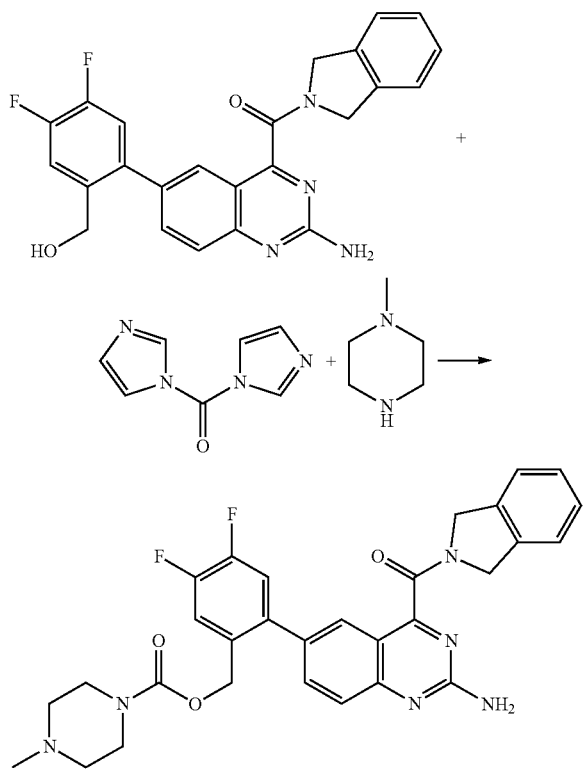

400 mg of 1,1'-carbonyldiimidazole are dissolved in 10 ml of pyridine and cooled to 0° C. A solution of 1.0 g of [2-amino-6-(4,5-difluoro-2-hydroxymethylphenyl)quinazolin-4-yl]-(1,3-dihydroisoindol-2-yl)methanone dissolved in 10 ml of pyridine is added. The mixture is subsequently stirred at 0° C. for 2 h and at 25° C. for 2 h. 300 µl of N-methylpiperazine are then added, and the mixture is stirred at 25° C. for a further 18 h. The mixture is added to 250 ml of 1 N HCl, neutralised using bicarbonate solution and washed 3 times with 150 ml of dichloromethane each time. The organic phases are washed twice with 50 ml of water each time, dried over sodium sulfate, filtered and evaporated to dryness in vacuo. The residue is dissolved in 1 ml of dimethyl sulfoxide and purified by chromatography (reversed phase).

Yield: 352 mg (27%) of 2-[2-amino-4-(1,3-dihydroisoindole-2-carbonyl)quinazolin-6-yl]-4,5-difluorobenzyl 4-methylpiperazine-1-carboxylate;

LC-MS retention time: 1.73 min;

$^1$H NMR (500 MHz, DMSO-d$_6$) δ [ppm] 7.75-7.71 (m, 1H), 7.58-7.51 (m, 2H), 7.48-7.40 (m, 2H), 7.32 (t, J=7.2, 1H), 7.27 (q, J=7.3, 2H), 7.17 (s, 1H), 4.95 (s, 2H), 4.94 (s, 2H), 4.73 (s, 2H), 3.39-3.16 (m, 3H), 3.18 (dd, J=8.2, 4.9, 4H), 2.11 (s, 4H).

2-[2-Amino-4-(1,3-dihydroisoindole-2-carbonyl)
quinazolin-6-yl]-4,5-difluorobenzyl (2-aminoethyl)
carbamate ("A117")

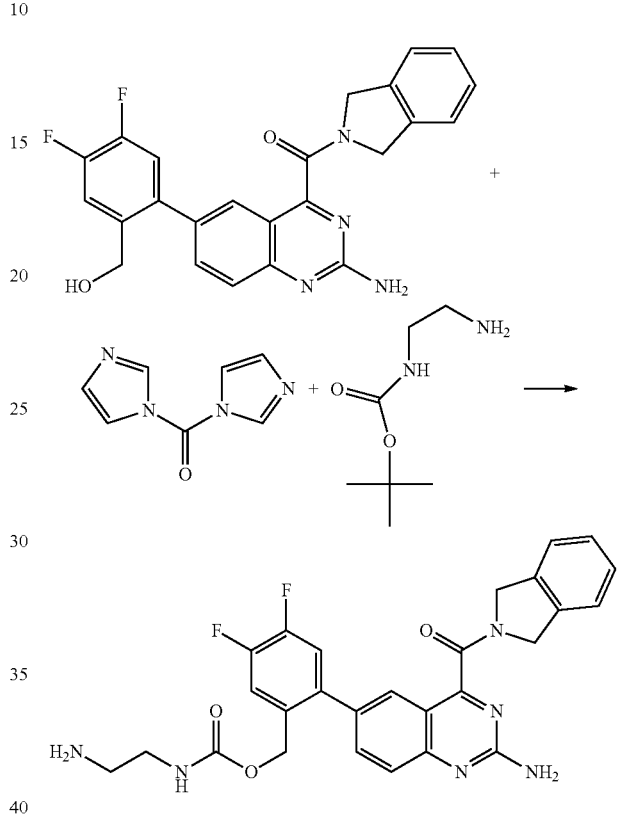

400 mg of 1,1'-carbonyldiimidazole are dissolved in 10 ml of pyridine and cooled to 0° C. A solution of 1.0 g of [2-amino-6-(4,5-difluoro-2-hydroxymethylphenyl)quinazolin-4-yl]-(1,3-dihydroisoindol-2-yl)methanone dissolved in 10 ml of pyridine is added. The mixture is subsequently stirred at 0° C. for 2 h and at 25° C. for 2 h. 400 mg of N-Boc-ethylenediamine are then added, and the mixture is stirred at 25° C. for a further 18 h. The mixture is added to 250 ml of 1 N HCl and stirred at 25° C. for 3 h, neutralised using bicarbonate solution and washed 3 times with 150 ml of dichloromethane each time. The organic phases are washed twice with 50 ml of water each time, dried over sodium sulfate, filtered and evaporated to dryness in vacuo. The residue is dissolved in 1 ml of dimethyl sulfoxide and purified by chromatography (reversed phase).

Yield: 286 mg (44%) of 2-[2-amino-4-(1,3-dihydroisoindole-2-carbonyl)quinazolin-6-yl]-4,5-difluorobenzyl (2-aminoethyl)carbamate;

LC-MS retention time: 1.65 min, $^1$H NMR (400 MHz, DMSO-d$_6$/TFA-d$_1$) δ [ppm] 8.09-8.03 (m, 2H), 7.84 (d, J=8.7, 1H), 7.57 (t, J=9.9, 1H), 7.49 (d, J=9.8, 1H), 7.44 (d, J=7.8, 1H), 7.33 (dt, J=14.7, 7.3, 2H), 7.26 (d, J=7.3, 1H), 5.02 (s, 2H), 4.88 (s, 2H), 4.85 (s, 2H), 3.20 (t, J=6.3, 2H), 2.85 (t, J=6.2, 2H).

2-[2-Amino-4-(1,3-dihydroisoindole-2-carbonyl)quinazolin-6-yl]-4,5-difluorobenzyl 2-tert-butoxycarbonylaminoethyl carboxylate ("A118")

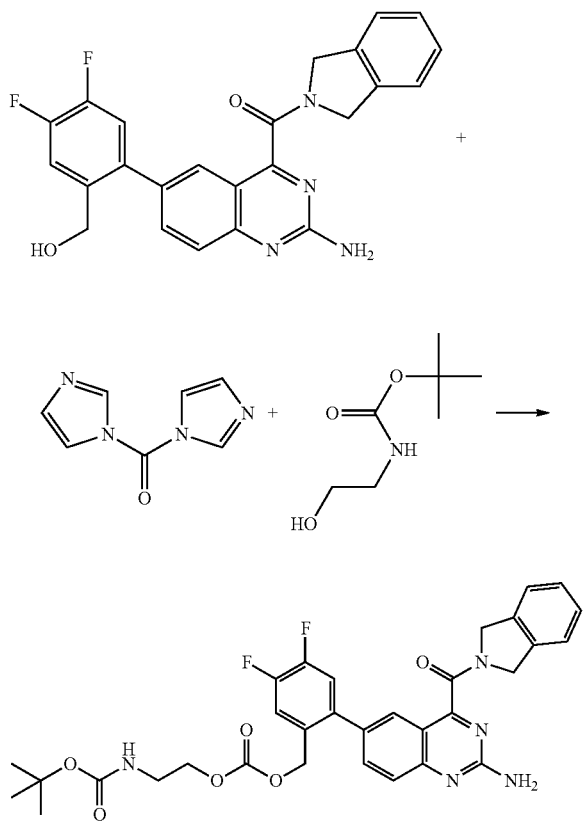

400 mg of 1,1'-carbonyldiimidazole are dissolved in 10 ml of pyridine and cooled to 0° C. A solution of 1.0 g of [2-amino-6-(4,5-difluoro-2-hydroxymethylphenyl)quinazolin-4-yl]-(1,3-dihydroisoindol-2-yl)methanone dissolved in 10 ml of pyridine is added. The mixture is subsequently stirred at 0° C. for 2 h and at 25° C. for 2 h. 400 mg of tert-butyl N-(2-hydroxyethyl)carbamate and 400 µl of 1,8-diazabicyclo[5.4.0]undec-7-ene are then added, and the mixture is stirred at 25° C. for a further 18 h. The mixture is added to 250 ml of 1 N HCl, neutralised using bicarbonate solution and washed 3 times with 150 ml of dichloromethane each time. The organic phases are washed twice with 50 ml of water each time, dried over sodium sulfate, filtered and evaporated to dryness in vacuo. The residue is dissolved in 1 ml of dimethyl sulfoxide and purified by chromatography (reversed phase).

Yield: 286 mg (44%) of 2-[2-amino-4-(1,3-dihydroisoindole-2-carbonyl)quinazolin-6-yl]-4,5-difluorobenzyl 2-tert-butoxycarbonylaminoethyl carboxylate.

LC-MS retention time: 2.43 min;

$^1$H NMR (400 MHz, DMSO-$d_6$/TFA-$d_1$) δ [ppm] 8.08-8.01 (m, 1H), 7.91 (d, J=8.7, 1H), 7.55 (dd, J=18.6, 10.2, 1H), 7.50-7.26 (m, 5H), 7.23 (d, J=7.5, 1H), 5.07 (s, 2H), 4.98 (s, 2H), 4.88 (s, 2H), 4.02 (t, J=5.4, 2H), 3.21 (t, J=5.5, 2H), 1.40 (s, 9H).

2-[2-Amino-4-(1,3-dihydroisoindole-2-carbonyl)quinazolin-6-yl]-4,5-difluorobenzyl 2-aminoethyl carboxylate ("A119")

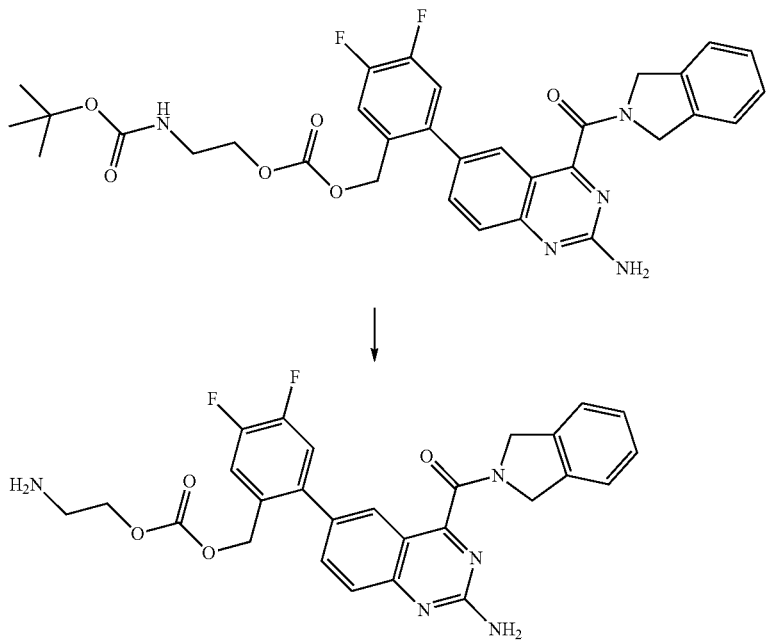

2 ml of trifluoroacetic acid are added to 371 mg of 2-[2-amino-4-(1,3-dihydroisoindole-2-carbonyl)quinazolin-6-yl]-4,5-difluorobenzyl 2-tert-butoxycarbonylaminoethyl carboxylate in 4 ml of dichloromethane with ice-cooling. The mixture is subsequently stirred at 25° C. for a further 2 h, 5 ml of n-heptane are added, and the mixture is evaporated to dryness in vacuo. The residue is dissolved in 500 µl of dimethyl sulfoxide and purified by chromatography (reversed phase).

Yield: 267 mg (86%) of 2-[2-amino-4-(1,3-dihydroisoindole-2-carbonyl)quinazolin-6-yl]-4,5-difluorobenzyl 2-aminoethyl carboxylate;

LC-MS retention time: 1.68 min;

$^1$H NMR (400 MHz, DMSO-$d_6$/TFA-$d_1$) δ [ppm] 8.10 (s, 1H), 8.06 (dd, J=8.7, 1.9, 1H), 7.90 (d, J=8.7, 1H), 7.59 (dd, J=11.3, 8.2, 1H), 7.48-7.39 (m, 2H), 7.38-7.28 (m, 2H), 7.25 (d, J=7.0, 1H), 5.06 (s, 2H), 5.05 (s, 2H), 4.89 (s, 2H), 4.30-4.24 (m, 2H), 3.17-3.11 (m, 2H).

2-[2-Amino-4-(1,3-dihydroisoindole-2-carbonyl)quinazolin-6-yl]-4,5-difluorobenzyl 2-dimethylaminoethyl carboxylate ("A120")

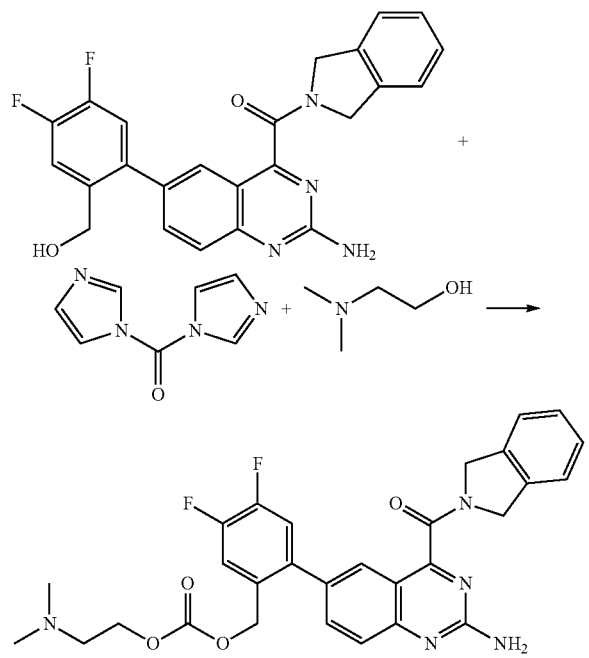

200 mg of 1,1'-carbonyldiimidazole are dissolved in 10 ml of pyridine and cooled to 0° C. A solution of 500 mg of [2-amino-6-(4,5-difluoro-2-hydroxymethylphenyl)quinazolin-4-yl]-(1,3-dihydroisoindol-2-yl)methanone dissolved in 10 ml of pyridine is added. The mixture is subsequently stirred at 0° C. for 2 h and at 25° C. for 2 h. 200 mg of 2-(dimethylamino)ethanol and 200 µl of 1,8-diazabicyclo[5.4.0]undec-7-ene are then added, and the mixture is stirred at 25° C. for a further 18 h. The mixture is added to 250 ml of 1 N HCl, neutralised using bicarbonate solution and washed 3 times with 150 ml of dichloromethane each time. The organic phases are washed twice with 50 ml of water each time, dried over sodium sulfate, filtered and evaporated to dryness in vacuo. The residue is dissolved in 1 ml of dimethyl sulfoxide and purified by chromatography (reversed phase).

Yield: 90 mg (14%) of 2-[2-amino-4-(1,3-dihydroisoindole-2-carbonyl)quinazolin-6-yl]-4,5-difluorobenzyl 2-dimethylaminoethyl carboxylate.

LC-MS retention time: 1.71 min;

$^1$H NMR (400 MHz, DMSO-$d_6$/TFA-$d_1$) δ [ppm] 8.05 (m, 2H), 7.85 (d, J=9.4, 1H), 7.66-7.58 (m, 1H), 7.56-7.48 (m, 1H), 7.45 (d, J=7.2, 1H), 7.39-7.28 (m, 2H), 7.26 (d, J=6.9, 1H), 5.04 (s, 2H), 5.02 (s, 2H), 4.85 (s, 2H), 4.38-4.34 (m, 2H), 3.44-3.38 (m, 2H), 2.54 (s, 6H).

[2-[2-Amino-4-(isoindoline-2-carbonyl)quinazolin-6-yl]-4,5-difluorophenyl]-methyl di-tert-butyl phosphate ("A121")

a) Di-tert-butyl phosphate

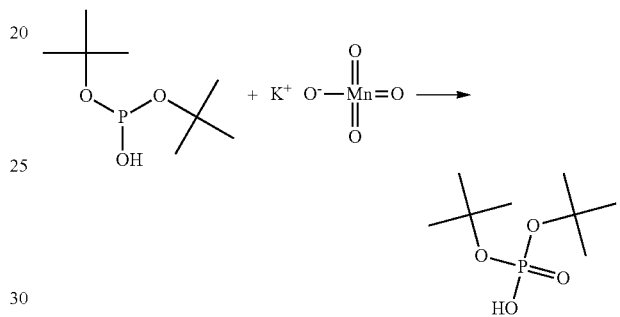

5.6 g of potassium permanganate are added in portions to a solution of 10 ml of di-tert-butyl phosphite and 3 g of potassium hydrogencarbonate in 50 ml of water at 0° C. The mixture is then allowed to warm to 25° C. and is stirred for 1 h. The mixture is subsequently heated at 60° C. for 15 min, and the precipitate is filtered off. The product is precipitated out by acidification of the filtrate by dropwise addition of concentrated hydrochloric acid with ice-cooling. The product is filtered off, washed with 5 ml of water and dried over phosphorus pentoxide in vacuo; yield: 6.3 g (63%) of di-tert-butyl phosphate.

b) Tetrabutylammonium di-tert-butylphosphate

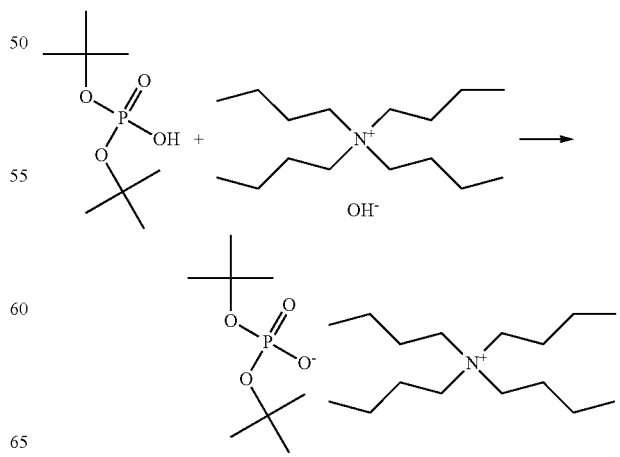

41.9 ml of tetra-n-butylammonium hydroxide (20% solution in water) dissolved in 50 ml of water, and 6.8 g of di-tert-butyl phosphate (75%), dissolved in 5 ml of acetone, added dropwise with stirring and ice-cooling. The solution obtained is lyophilised; yield: 14.6 g (99%) of tetrabutylammonium di-tert-butylphosphate (content about 40%).

c) [2-Amino-6-(2-chloromethyl-4,5-difluorophenyl)quinazolin-4-yl]-(1,3-dihydroisoindol-2-yl)methanone

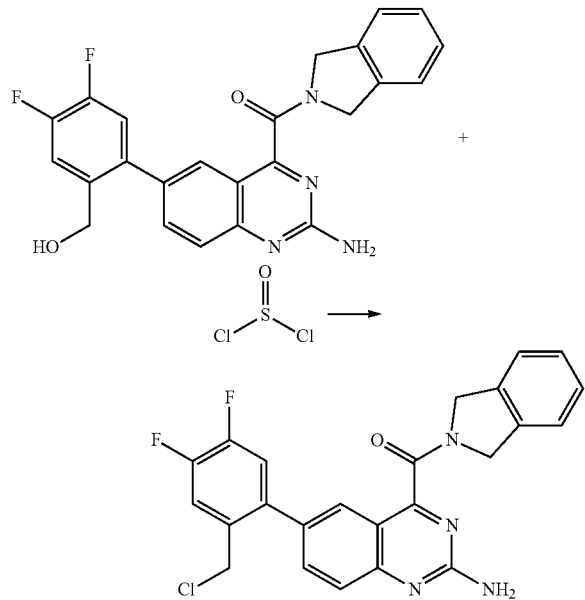

50 ml of thionyl chloride are added to 2 g of [2-amino-6-(4,5-difluoro-2-hydroxymethylphenyl)quinazolin-4-yl]-(1,3-dihydroisoindol-2-yl)methanone, and the mixture is stirred at 25° C. for 1 h. The mixture is subsequently evaporated to dryness in vacuo, the residue is taken up a further twice with 50 ml of dichloromethane each time, and the mixture is again evaporated to dryness in vacuo.

Yield: 2.2 g (97%) of [2-amino-6-(2-chloromethyl-4,5-difluorophenyl)quinazolin-4-yl]-(1,3-dihydroisoindol-2-yl)methanone;

LC-MS retention time: 2.33 min.

d) [2-[2-Amino-4-(isoindoline-2-carbonyl)quinazolin-6-yl]-4,5-difluorophenyl]methyl di-tert-butyl phosphate

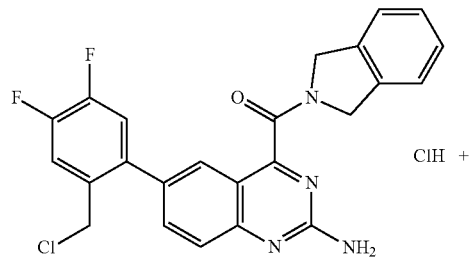

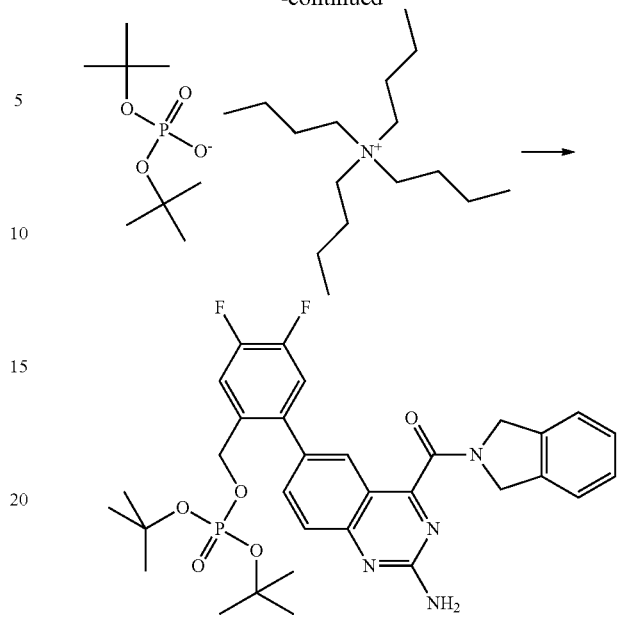

800 mg of tetrabutylammonium di-tert-butylphosphate are added to 270 mg of [2-amino-6-(2-chloromethyl-4,5-difluorophenyl)quinazolin-4-yl]-(1,3-dihydroisoindol-2-yl)methanone dissolved in 20 ml of acetonitrile, and the solution obtained is heated at 80° C. for 2 h. After cooling to 25° C., undissolved material is filtered off, and the filtrate is evaporated to dryness in vacuo. The residue is dissolved in 1 ml of dimethyl sulfoxide and purified by chromatography (reversed phase).

Yield: 1.3 g (46%) of [2-[2-amino-4-(isoindoline-2-carbonyl)quinazolin-6-yl]-4,5-difluorophenyl]methyl di-tert-butyl phosphate;

LC-MS retention time: 2.47 min;

$^1$H NMR (500 MHz, DMSO-$d_6$/TFA-$d_1$) δ [ppm] 8.13 (d, J=1.8, 1H), 8.07 (dd, J=8.6, 1.8, 1H), 7.89 (dd, J=8.9, 2.8, 1H), 7.55 (dd, J=11.4, 8.3, 1H), 7.46-7.39 (m, 2H), 7.32 (dt, J=14.7, 7.1, 2H), 7.24 (d, J=7.3, 1H), 5.06 (s, 2H), 4.84 (dd, J=21.2, 12.6, 4H), 1.31 (s, 18H).

[2-[2-Amino-4-(isoindoline-2-carbonyl)quinazolin-6-yl]-4,5-difluorophenyl]-methyl dihydrogenphosphate ("A122")

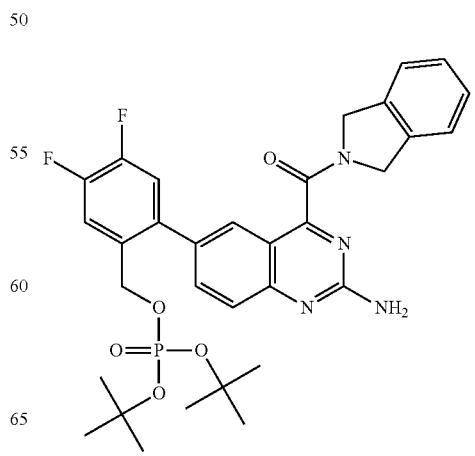

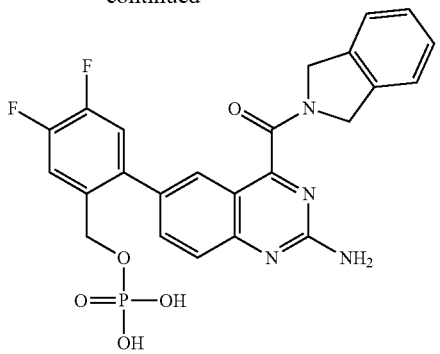

1.3 g of [2-[2-amino-4-(isoindoline-2-carbonyl)quinazolin-6-yl]-4,5-difluorophenyl]methyl di-tert-butyl phosphate are stirred at 25° C. for 1 h in 20 ml of trifluoroacetic acid. The mixture is evaporated at 25° C. in vacuo, and the residue is taken up in 100 ml of water. The pH is adjusted to 6 using bicarbonate solution, and the precipitate formed is filtered off. Drying at 40° C. in vacuo gives product.

Yield: 1.3 g (46%) of [2-[2-amino-4-(isoindoline-2-carbonyl)quinazolin-6-yl]-4,5-difluorophenyl]methyl dihydrogenphosphate;

LC-MS retention time: 2.47 min;

$^1$H NMR (500 MHz, DMSO-$d_6$/TFA-$d_1$) δ [ppm] 8.04 (d, J=1.8, 1H), 8.01-7.97 (m, 1H), 7.81 (d, J=8.6, 1H), 7.51 (dd, J=11.2, 8.4, 1H), 7.34 (dd, J=11.4, 7.9, 2H), 7.29-7.20 (m, 2H), 7.18 (d, J=7.3, 1H), 4.98 (s, 2H), 4.83 (s, 2H), 4.75 (d, J=7.3, 2H).

2-[2-Amino-4-(isoindoline-2-carbonyl)quinazolin-6-yl]-4,5-difluorophenyl]methyl diethyl phosphate ("A123")

a) Tetrabutylammonium diethylphosphate

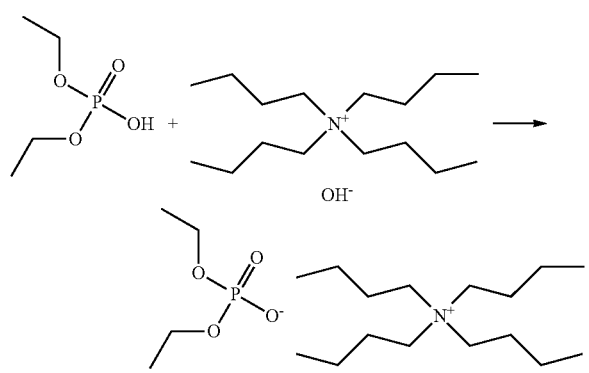

12.8 ml of tetra-n-butylammonium hydroxide (20% solution in water) is dissolved in 20 ml of water, and 1 g of diethyl phosphate (75%), dissolved in 2 ml of acetone, is added dropwise with stirring and ice-cooling. The solution obtained is lyophilised.

Yield: 3.3 g of tetrabutylammonium diethylphosphate (content about 40%).

b) [2-[2-Amino-4-(isoindoline-2-carbonyl)quinazolin-6-yl]-4,5-difluorophenyl]methyl diethyl phosphate

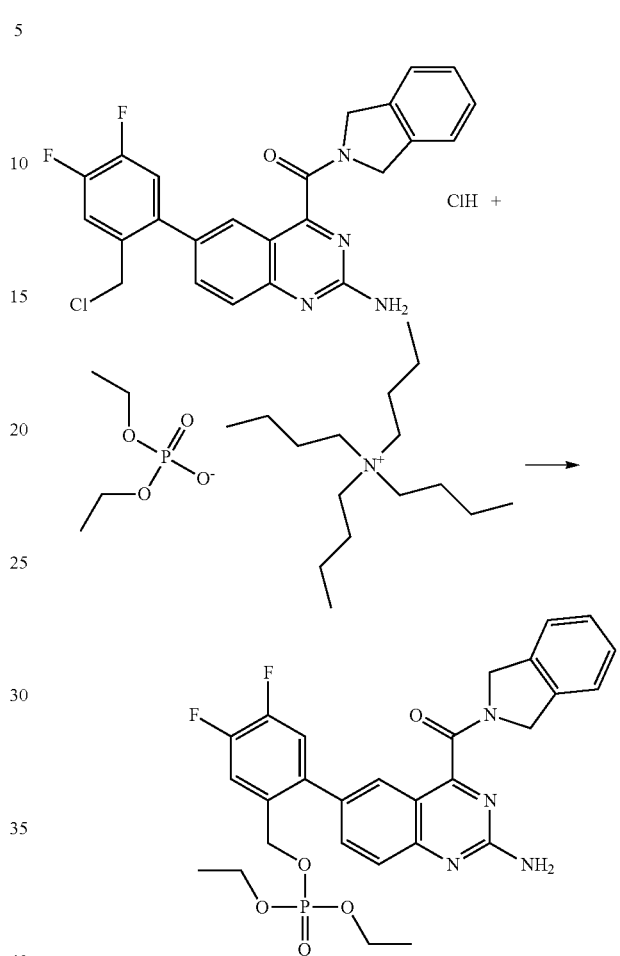

800 mg of tetrabutylammonium diethylphosphate are added to 270 mg of [2-amino-6-(2-chloromethyl-4,5-difluorophenyl)quinazolin-4-yl]-(1,3-dihydroisoindol-2-yl)methanone dissolved in 20 ml of acetonitrile, and the solution obtained is heated at 80° C. for 2 h. After cooling to 25° C., undissolved material is filtered off, and the filtrate is evaporated to dryness in vacuo. The residue is dissolved in 1 ml of dimethyl sulfoxide and purified by chromatography (reversed phase).

Yield: 109 mg (32%) of [2-[2-amino-4-(isoindoline-2-carbonyl)quinazolin-6-yl]-4,5-difluorophenyl]methyl diethyl phosphate;

LC-MS retention time: 2.00 min;

$^1$H NMR (500 MHz, DMSO-$d_6$/TFA-$d_1$) δ [ppm] 8.05 (d, J=1.5, 1H), 7.99 (d, J=8.6, 1H), 7.82 (d, J=8.6, 1H), 7.52 (dd, J=11.2, 8.1, 1H), 7.40-7.32 (m, 2H), 7.25 (dt, J=18.5, 7.2, 2H), 7.18 (d, J=7.2, 1H), 4.98 (s, 2H), 4.82 (s, 4H), 3.86-3.75 (m, 4H), 1.06 (t, J=7.1, 6H).

The following examples relate to pharmaceutical compositions:

EXAMPLE A

Injection Vials

A solution of 100 g of an active ingredient according to the invention and g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed in a conventional manner to give tablets in such a way that each tablet contains mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. A compound selected from the following compounds:

| Compound No. | Name and/or structure |
| --- | --- |
| "A1" | [2-Amino-6-[2-(hydroxymethyl)phenyl]quinazolin-4-yl]-isoindolin-2-ylmethanone |
| "A2" | [2-Amino-6-[5-fluoro-2-(hydroxymethyl)phenyl]quinazolin-4-yl]isoindolin-2-ylmethanone |
| "A3" | [2-Amino-6-[2-(methylaminomethyl)phenyl]quinazolin-4-yl]-isoindolin-2-ylmethanone |
| "A4" | [2-Amino-6-[4-fluoro-2-(hydroxymethyl)phenyl]quinazolin-4-yl]isoindolin-2-ylmethanone |
| "A5" | [2-Amino-6-[5-fluoro-2-(hydroxymethyl)phenyl]quinazolin-4-yl]isoindolin-2-ylmethanone |
| "A6" | [2-Amino-6-[4,5-difluoro-2-(hydroxymethyl)phenyl]quinazolin-4-yl]isoindolin-2-ylmethanone |
| "A7" | [2-Amino-6-[2-(hydroxymethyl)-4,5-dimethoxy-phenyl]quinazolin-4-yl]isoindolin-2-ylmethanone |
| "A8" | [2-Amino-6-[2-(2-dimethylaminoethoxymethyl)-4,5-difluoro-phenyl]quinazolin-4-yl]isoindolin-2-ylmethanone |
| "A9" | [2-Amino-6-[2-(3-dimethylaminoproproxymethyl)-4,5-difluorophenyl]quinazolin-4-yl]isoindolin-2-ylmethanone |
| "A10" | (2-Amino-6-{2-[(ethylmethylamino)methyl]phenyl}quinazolin-4-yl)-(1,3-dihydroisoindol-2-yl)methanone |
| "A11" | (2-Amino-6-{2-[(ethylmethylamino)methyl]-5-fluorophenyl}-quinazolin-4-yl)-(1,3-dihydroisoindol-2-yl)methanone |
| "A12" | [2-Amino-6-(2-diethylaminomethylphenyl)quinazolin-4-yl]-(1,3-dihydroisoindol-2-yl)methanone |
| "A13" | [2-Amino-6-(2-{[(2-hydroxyethyl)methylamino]methyl}phenyl)-quinazolin-4-yl]-(1,3-dihydroisoindol-2-yl)methanone |
| "A14" | [2-Amino-6-(2-{[(2-hydroxyethyl)ethylamino]methyl}phenyl)-quinazolin-4-yl]-(1,3-dihydroisoindol-2-yl)methanone |
| "A15" | [2-Amino-6-(2-{[ethyl-(2-hydroxyethyl)amino]methyl}-5-fluorophenyl)quinazolin-4-yl]-(1,3-dihydroisoindol-2-yl)-methanone |
| "A16" | [2-Amino-6-(2-{[ethyl-(2-hydroxyethyl)amino]methyl}-4-fluorophenyl)quinazolin-4-yl]-(1,3-dihydroisoindol-2-yl)-methanone |
| "A17" | [2-Amino-6-(2-{[bis-(2-hydroxyethyl)amino]methyl}phenyl)-quinazolin-4-yl]-(1,3-dihydroisoindol-2-yl)methanone |
| "A18" | {2-Amino-6-[2-(tert-butylaminomethyl)phenyl]quinazolin-4-yl}-(1,3-dihydroisoindol-2-yl)methanone |
| "A19" | {2-Amino-6-[2-(tert-butylaminomethyl)-4-fluorophenyl]-quinazolin-4-yl}-(1,3-dihydroisoindol-2-yl)methanone |
| "A20" | {2-Amino-6-[2-(tert-butylaminomethyl)-5-fluorophenyl]-quinazolin-4-yl}-(1,3-dihydroisoindol-2-yl)methanone |
| "A21" | {2-Amino-6-[6-(tert-butylaminomethyl)benzo-1,3-dioxol-5-yl]-quinazolin-4-yl}-(1,3-dihydroisoindol-2-yl)methanone |
| "A22" | 2-{2-[2-Amino-4-(1,3-dihydroisoindole-2-carbonyl)quinazolin-6-yl]benzylamino}acetamide |
| "A23" | [2-Amino-6-(2-cyclopropylaminomethylphenyl)quinazolin-4-yl]-(1,3-dihydroisoindol-2-yl)methanone |
| "A24" | [2-Amino-6-(2-cyclobutylaminomethylphenyl)quinazolin-4-yl]-(1,3-dihydroisoindol-2-yl)methanone |
| "A25" | [2-Amino-6-(2-pyrrolidin-1-ylmethylphenyl)quinazolin-4-yl]-(1,3-dihydroisoindol-2-yl)methanone |
| "A26" | {2-Amino-6-[2-(2-methylpyrrolidin-1-ylmethyl)phenyl]-quinazolin-4-yl}-(1,3-dihydroisoindol-2-yl)methanone |
| "A27" | {2-Amino-6-[2-(2-hydroxymethylpyrrolidin-1-ylmethyl)phenyl]-quinazolin-4-yl}-(1,3-dihydroisoindol-2-yl)methanone |
| "A28" | {2-Amino-6-[2-(3-hydroxypyrrolidin-1-ylmethyl)phenyl]-quinazolin-4-yl}-(1,3-dihydroisoindol-2-yl)methanone |
| "A29" | {2-Amino-6-[2-(3-aminopyrrolidin-1-ylmethyl)phenyl]-quinazolin-4-yl}-(1,3-dihydroisoindol-2-yl)methanone |
| "A30" | {2-Amino-6-[2-(2,5-dimethylpyrrolidin-1-ylmethyl)phenyl]-quinazolin-4-yl}-(1,3-dihydroisoindol-2-yl)methanone |
| "A31" | {2-Amino-6-[2-(3,3-difluoropyrrolidin-1-ylmethyl)phenyl]-quinazolin-4-yl}-(1,3-dihydroisoindol-2-yl)methanone |
| "A32" | {2-Amino-6-[2-((S)-3-fluoropyrrolidin-1-ylmethyl)phenyl]-quinazolin-4-yl}-(1,3-dihydroisoindol-2-yl)methanone |
| "A33" | {2-Amino-6-[2-((S)-2-methylpyrrolidin-1-ylmethyl)phenyl]-quinazolin-4-yl}-(1,3-dihydroisoindol-2-yl)methanone |

-continued

| Compound No. | Name and/or structure |
|---|---|
| "A34" | {2-Amino-6-[2-((R)-2-methylpyrrolidin-1-ylmethyl)phenyl]-quinazolin-4-yl}-(1,3-dihydroisoindol-2-yl)methanone |
| "A35" | {2-Amino-6-[4-fluoro-2-(2-methylpyrrolidin-1-ylmethyl)phenyl]-quinazolin-4-yl}-(1,3-dihydroisoindol-2-yl)methanone |
| "A36" | {2-Amino-6-[5-fluoro-2-(2-methylpyrrolidin-1-ylmethyl)phenyl]-quinazolin-4-yl}-(1,3-dihydroisoindol-2-yl)methanone |
| "A37" | Methyl 1-{2-[2-amino-4-(1,3-dihydroisoindole-2-carbonyl)-quinazolin-6-yl]benzyl}pyrrolidine-2-carboxylate |
| "A38" | 1-{2-[2-Amino-4-(1,3-dihydroisoindole-2-carbonyl)quinazolin-6-yl]benzyl}pyrrolidine-2-carboxylic acid |
| "A39" | N-Methyl-1-{2-[2-amino-4-(1,3-dihydroisoindole-2-carbonyl)-quinazolin-6-yl]benzyl}pyrrolidine-2-carboxamide |
| "A40" | N-(2-Hydroxyethyl)-1-{2-[2-amino-4-(1,3-dihydroisoindole-2-carbonyl)quinazolin-6-yl]benzyl}pyrrolidine-2-carboxamide |
| "A41" | {2-Amino-6-[2-(4-hydroxypiperidin-1-ylmethyl)phenyl]-quinazolin-4-yl}-(1,3-dihydroisoindol-2-yl)methanone |
| "A42" | {2-Amino-6-[5-fluoro-2-(4-methylpiperazin-1-ylmethyl)phenyl]-quinazolin-4-yl}-(1,3-dihydroisoindol-2-yl)methanone |
| "A43" | {2-Amino-6-[4-fluoro-2-(4-methylpiperazin-1-ylmethyl)phenyl]-quinazolin-4-yl}-(1,3-dihydroisoindol-2-yl)methanone |
| "A44" | {2-Amino-6-[2-(methylethylaminomethyl)-4,5-difluorophenyl]-quinazolin-4-yl}-(1,3-dihydroisoindol-2-yl)methanone |
| "A45" | {2-Amino-6-[2-(diethylaminomethyl)-4,5-difluorophenyl]-quinazolin-4-yl}-(1,3-dihydroisoindol-2-yl)methanone |
| "A46" | {2-Amino-6-[2-(tert-butylaminomethyl)-4,5-difluorophenyl]-quinazolin-4-yl}-(1,3-dihydroisoindol-2-yl)methanone |
| "A47" | (2-Amino-6-{2-[(tert-butylmethylamino)methyl]-4,5-difluoro-phenyl}quinazolin-4-yl)-(1,3-dihydroisoindol-2-yl)methanone |
| "A48" | [2-Amino-6-(4,5-difluoro-2-pyrrolidin-1-ylmethylphenyl)-quinazolin-4-yl]-(1,3-dihydroisoindol-2-yl)methanone |
| "A49" | {2-Amino-6-[4,5-difluoro-2-(2-methylpyrrolidin-1-ylmethyl)-phenyl]quinazolin-4-yl}-(1,3-dihydroisoindol-2-yl)methanone |
| "A50" | {2-Amino-6-[2-(2,5-dimethylpyrrolidin-1-ylmethyl)4,5-difluorophenyl]quinazolin-4-yl}-(1,3-dihydroisoindol-2-yl)-methanone |
| "A51" | (2-Amino-6-{2-[(cyclopropylmethylamino)methyl]phenyl}-quinazolin-4-yl)-(1,3-dihydroisoindol-2-yl)methanone |
| "A52" | {2-Amino-6-[4,5-difluoro-2-(4-methylpiperazin-1-ylmethyl)-phenyl]quinazolin-4-yl}-(1,3-dihydroisoindol-2-yl)methanone |
| "A53" | tert-Butyl {2-[2-amino-4-(1,3-dihydroisoindole-2-carbonyl)-quinazolin-6-yl]-4,5-difluorobenzyl}bis-carbamate |
| "A54" | [2-Amino-6-(2-aminomethyl-4,5-difluorophenyl)quinazolin-4-yl]-(1,3-dihydroisoindol-2-yl)methanone |
| "A55" | 3-Amino-N-{2-[2-amino-4-(1,3-dihydroisoindole-2-carbonyl)-quinazolin-6-yl]-4,5-difluorobenzyl}propionamide |
| "A56" | N-{2-[2-Amino-4-(1,3-dihydroisoindole-2-carbonyl)quinazolin-6-yl]-4,5-difluorobenzyl}-3-dimethylaminopropionamide |
| "A57" | [2-Amino-6-(2-diethylaminomethyl-5-fluorophenyl)quinazolin-4-yl]-(1,3-dihydroisoindol-2-yl)methanone |
| "A58" | {2-Amino-6-[5-fluoro-2-(4-hydroxypiperidin-1-ylmethyl)-phenyl]quinazolin-4-yl}-(1,3-dihydroisoindol-2-yl)methanone |
| "A59" | {2-Amino-6-[4,5-difluoro-2-(2-hydroxyethoxymethyl)phenyl]-quinazolin-4-yl}-(1,3-dihydroisoindol-2-yl)methanone |
| "A60" | [2-Amino-6-(4,5-difluoro-2-{2-[2-(2-hydroxyethoxy)ethoxy]-ethoxymethyl}phenyl)quinazolin-4-yl]-(1,3-dihydroisoindol-2-yl)methanone |
| "A61" | (2-Amino-6-{4,5-difluoro-2-[2-(2-hydroxyethoxy)ethoxymethyl]-phenyl}quinazolin-4-yl)-(1,3-dihydroisoindol-2-yl)methanone |
| "A62" | {2-Amino-6-[4,5-difluoro-2-(2-{2-[2-(2-hydroxyethoxy)ethoxy]-ethoxy}ethoxymethyl)phenyl]quinazolin-4-yl}-(1,3-dihydroisoindol-2-yl)methanone |
| "A63" | [2-Amino-6-(2-aminoxymethyl-4,5-difluorophenyl)quinazolin-4-yl]-(1,3-dihydroisoindol-2-yl)methanone |
| "A64" | [2-Amino-6-(4,5-difluoro-2-hydroxymethylphenyl)quinazolin-4-yl]-(1,3-dihydroisoindol-2-yl)methanone |
| "A65" | 2-[2-Amino-4-(1,3-dihydroisoindole-2-carbonyl)quinazolin-6-yl]-4,5-difluorobenzyl 3-aminopropionate |
| "A66" | 2-[2-Amino-4-(1,3-dihydroisoindole-2-carbonyl)quinazolin-6-yl]-4,5-difluorobenzyl(S)-2,5-diaminopentanoate |
| "A67" | 2-[2-Amino-4-(1,3-dihydroisoindole-2-carbonyl)quinazolin-6-yl]-4,5-difluorobenzyl 3-dimethylaminopropionate |
| "A68" | 2-[2-Amino-4-(1,3-dihydroisoindole-2-carbonyl)quinazolin-6-yl]-4,5-difluorobenzyl(S)-2,6-bis-tert-butoxycarbonylamino-hexanoate |
| "A69" | 2-[2-Amino-4-(1,3-dihydroisoindole-2-carbonyl)quinazolin-6-yl]-benzyl(S)-2,6-bis-tert-butoxycarbonylaminohexanoate |
| "A70" | 2-[2-Amino-4-(1,3-dihydroisoindole-2-carbonyl)quinazolin-6-yl]-4-fluorobenzyl(S)-2,6-bis-tert-butoxycarbonylaminohexanoate |
| "A70a" | 2-[2-Amino-4-(1,3-dihydroisoindole-2-carbonyl)quinazolin-6-yl]-4,5-difluorobenzyl(S)-2-tert-butoxycarbonylamino-6-dimethylaminohexanoate |
| "A71" | 2-[2-Amino-4-(1,3-dihydroisoindole-2-carbonyl)quinazolin-6-yl]-4,5-difluorobenzyl(S)-2,6-diaminohexanoate |
| "A72" | 2-[2-Amino-4-(1,3-dihydroisoindole-2-carbonyl)quinazolin-6-yl]-4-fluorobenzyl(S)-2,6-diaminohexanoate |
| "A73" | 2-[2-Amino-4-(1,3-dihydroisoindole-2-carbonyl)quinazolin-6-yl]-benzyl(S)-2,6-diaminohexanoate |
| "A73a" | 2-[2-Amino-4-(1,3-dihydroisoindole-2-carbonyl)quinazolin-6-yl]-4,5-difluorobenzyl(S)-2-amino-6-dimethylaminohexanoate |
| "A74" | 2-[2-Amino-4-(1,3-dihydroisoindole-2-carbonyl)quinazolin-6-yl]-4,5-difluorobenzyl 2-amino-4-methylpentanoate |
| "A75" | 2-[2-Amino-4-(1,3-dihydroisoindole-2-carbonyl)quinazolin-6-yl]-4,5-difluorobenzyl(S)-2-tert-butoxycarbonylaminopropionate |
| "A76" | 2-[2-Amino-4-(1,3-dihydroisoindole-2-carbonyl)quinazolin-6-yl]-4,5-difluorobenzyl(S)-2-aminopropionate |
| "A77" | 2-[2-Amino-4-(1,3-dihydroisoindole-2-carbonyl)quinazolin-6-yl]-4,5-difluorobenzyl 2,2-dimethylpropionate |
| "A78" | 2-[2-Amino-4-(1,3-dihydroisoindole-2-carbonyl)quinazolin-6-yl]-4,5-difluorobenzyl isobutyrate |
| "A79" | 2-[2-Amino-4-(1,3-dihydroisoindole-2-carbonyl)quinazolin-6-yl]-4,5-difluorobenzyl propionate |
| "A80" | 2-[2-Amino-4-(1,3-dihydroisoindole-2-carbonyl)quinazolin-6-yl]-4,5-difluorobenzyl 2-tert-butoxycarbonylamino-2-methylpropionate |
| "A81" | 2-[2-Amino-4-(1,3-dihydroisoindole-2-carbonyl)quinazolin-6-yl]-4,5-difluorobenzyl 2-amino-2-methylpropionate |
| "A82" | 2-[2-Amino-4-(1,3-dihydroisoindole-2-carbonyl)quinazolin-6-yl]-4,5-difluorobenzyl acetate |
| "A83" | 2-[2-Amino-4-(1,3-dihydroisoindole-2-carbonyl)quinazolin-6-yl]-4,5-difluorobenzyl 6-tert-butoxycarbonylaminohexanoate |
| "A84" | 2-[2-Amino-4-(1,3-dihydroisoindole-2-carbonyl)quinazolin-6-yl]-4,5-difluorobenzyl 6-aminohexanoate |
| "A85" | 2-[2-Amino-4-(1,3-dihydroisoindole-2-carbonyl)quinazolin-6-yl]-4,5-difluorobenzyl 5-tert-butoxycarbonylaminopentanoate |
| "A86" | 2-[2-Amino-4-(1,3-dihydroisoindole-2-carbonyl)quinazolin-6-yl]-4,5-difluorobenzyl 5-aminopentanoate |
| "A87" | 2-{2-[2-Amino-4-(1,3-dihydroisoindole-2-carbonyl)quinazolin-6-yl]-4,5-difluorobenzyl}1-tert-butyl(S)-pyrrolidine-1,2-dicarboxylate |
| "A88" | 2-[2-Amino-4-(1,3-dihydroisoindole-2-carbonyl)quinazolin-6-yl]-4,5-difluorobenzyl(S)-pyrrolidine-2-carboxylate |
| "A89" | 2-[2-Amino-4-(1,3-dihydroisoindole-2-carbonyl)quinazolin-6-yl]-4,5-difluorobenzyl 4-tert-butoxycarbonylaminobutyrate |
| "A90" | 2-[2-Amino-4-(1,3-dihydroisoindole-2-carbonyl)quinazolin-6-yl]-4,5-difluorobenzyl 4-aminobutyrate dihydrochloride |
| "A91" | 2-[2-Amino-4-(1,3-dihydroisoindole-2-carbonyl)quinazolin-6-yl]-4,5-difluorobenzyl 3-(tert-butoxycarbonylmethylamino)-propionate |
| "A92" | 2-[2-Amino-4-(1,3-dihydroisoindole-2-carbonyl)quinazolin-6-yl]-4,5-difluorobenzyl 3-methylaminopropionate |

| Compound No. | Name and/or structure |
|---|---|
| "A93" | 2-[2-Amino-4-(1,3-dihydroisoindole-2-carbonyl)quinazolin-6-yl]-4,5-difluorobenzyl(R)-3-tert-butoxy-2-tert-butoxycarbonylaminopropionate |
| "A94" | 2-[2-Amino-4-(1,3-dihydroisoindole-2-carbonyl)quinazolin-6-yl]-benzyl(R)-3-tert-butoxy-2-tert-butoxycarbonylaminopropionate |
| "A95" | 2-[2-Amino-4-(1,3-dihydroisoindole-2-carbonyl)quinazolin-6-yl]-4-fluorobenzyl(R)-3-tert-butoxy-2-tert-butoxycarbonylaminopropionate |
| "A96" | 2-[2-Amino-4-(1,3-dihydroisoindole-2-carbonyl)quinazolin-6-yl]-4,5-difluorobenzyl(R)-2-amino-3-hydroxypropionate |
| "A97" | 2-[2-Amino-4-(1,3-dihydroisoindole-2-carbonyl)quinazolin-6-yl]-benzyl(R)-2-amino-3-hydroxypropionate |
| "A98" | 2-[2-Amino-4-(1,3-dihydroisoindole-2-carbonyl)quinazolin-6-yl]-4-fluorobenzyl(R)-2-amino-3-hydroxypropionate |
| "A99" | 2-[2-Amino-4-(1,3-dihydroisoindole-2-carbonyl)quinazolin-6-yl]-4-fluorobenzyl 2-tert-butoxycarbonylamino-2-methylpropionate |
| "A100" | 2-[2-Amino-4-(1,3-dihydroisoindole-2-carbonyl)quinazolin-6-yl]-benzyl 2-tert-butoxycarbonylamino-2-methylpropionate |
| "A101" | 2-[2-Amino-4-(1,3-dihydroisoindole-2-carbonyl)quinazolin-6-yl]-4-fluorobenzyl 2-amino-2-methylpropionate |
| "A102" | 2-[2-Amino-4-(1,3-dihydroisoindole-2-carbonyl)quinazolin-6-yl]-benzyl 2-amino-2-methylpropionate |
| "A103" | 2-[2-Amino-4-(1,3-dihydroisoindole-2-carbonyl)quinazolin-6-yl]-4-fluorobenzyl 2-tert-butoxycarbonylaminoacetate |
| "A104" | 2-[2-Amino-4-(1,3-dihydroisoindole-2-carbonyl)quinazolin-6-yl]-4-fluorobenzyl aminoacetate |
| "A105" | 2-[2-Amino-4-(1,3-dihydroisoindole-2-carbonyl)quinazolin-6-yl]-4,5-difluorobenzyl(tert-butoxycarbonylmethylamino)acetate |
| "A106" | 2-[2-Amino-4-(1,3-dihydroisoindole-2-carbonyl)quinazolin-6-yl]-benzyl(tert-butoxycarbonylmethylamino)acetate |
| "A107" | 2-[2-Amino-4-(1,3-dihydroisoindole-2-carbonyl)quinazolin-6-yl]-4-fluorobenzyl(tert-butoxycarbonylmethylamino)acetate |
| "A108" | 2-[2-Amino-4-(1,3-dihydroisoindole-2-carbonyl)quinazolin-6-yl]-4,5-difluorobenzyl methylaminoacetate |
| "A109" | 2-[2-Amino-4-(1,3-dihydroisoindole-2-carbonyl)quinazolin-6-yl]-benzyl methylaminoacetate |
| "A110" | 2-[2-Amino-4-(1,3-dihydroisoindole-2-carbonyl)quinazolin-6-yl]-4-fluorobenzyl methylaminoacetate |
| "A111" | 2-[2-Amino-4-(1,3-dihydroisoindole-2-carbonyl)quinazolin-6-yl]-4-fluorobenzyl dimethylaminoacetate |
| "A112" | 2-[2-Amino-4-(1,3-dihydroisoindole-2-carbonyl)quinazolin-6-yl]-4,5-difluorobenzyl dimethylaminoacetate |
| "A113" | 2-[2-Amino-4-(1,3-dihydroisoindole-2-carbonyl)quinazolin-6-yl]-benzyl dimethylaminoacetate |
| "A114" | 2-[2-Amino-4-(1,3-dihydroisoindole-2-carbonyl)quinazolin-6-yl]-4,5-difluorobenzyl dimethylcarbamate |
| "A115" | 2-[2-Amino-4-(1,3-dihydroisoindole-2-carbonyl)quinazolin-6-yl]-4,5-difluorobenzyl(2-dimethylaminoethyl)carbamate |
| "A116" | 2-[2-Amino-4-(1,3-dihydroisoindole-2-carbonyl)quinazolin-6-yl]-4,5-difluorobenzyl 4-methylpiperazine-1-carboxylate |
| "A117" | 2-[2-Amino-4-(1,3-dihydroisoindole-2-carbonyl)quinazolin-6-yl]-4,5-difluorobenzyl(2-aminoethyl)carbamate |
| "A118" | 2-[2-Amino-4-(1,3-dihydroisoindole-2-carbonyl)quinazolin-6-yl]-4,5-difluorobenzyl 2-tert-butoxycarbonylaminoethyl carboxylate |
| "A119" | 2-[2-Amino-4-(1,3-dihydroisoindole-2-carbonyl)quinazolin-6-yl]-4,5-difluorobenzyl 2-aminoethyl carboxylate |
| "A120" | 2-[2-Amino-4-(1,3-dihydroisoindole-2-carbonyl)quinazolin-6-yl]-4,5-difluorobenzyl 2-dimethylaminoethyl carboxylate |
| "A121" | [2-[2-Amino-4-(isoindoline-2-carbonyl)quinazolin-6-yl]-4,5-difluorophenyl]methyl di-tert-butyl phosphate |
| "A122" | [2-[2-Amino-4-(isoindoline-2-carbonyl)quinazolin-6-yl]-4,5-difluorophenyl]methyl dihydrogenphosphate |
| "A123" | 2-[2-Amino-4-(isoindoline-2-carbonyl)quinazolin-6-yl]-4,5-difluorophenyl]methyl diethyl phosphate | or a pharmaceutically usable salt, tautomer or stereoisomer thereof, including mixtures thereof in all ratios.

2. A pharmaceutical composition comprising at least one compound according to claim 1 or a pharmaceutically usable salt, tautomer or stereoisomer thereof, including mixtures thereof in all ratios, and at least one excipient or adjuvant.

* * * * *